(12) United States Patent
Boettcher et al.

(10) Patent No.: US 10,669,323 B2
(45) Date of Patent: Jun. 2, 2020

(54) METHODS OF TREATING METABOLIC DISORDERS WITH DUAL FUNCTION FIBROBLAST GROWTH FACTOR 21 PROTEINS

(71) Applicants: Brian R. Boettcher, Winchester, MA (US); Shari Lynn Caplan, Lunenburg, MA (US); Susan E. Cellitti, San Diego, CA (US); Douglas S. Daniels, New Haven, CT (US); Norio Hamamatsu, Belmont, MA (US); Bernhard Hubert Geierstanger, Solana Beach, CA (US); Stuart Licht, Cambridge, MA (US); Andreas Loew, Somerville, MA (US); Stephen Craig Weldon, Leominster, MA (US)

(72) Inventors: Brian R. Boettcher, Winchester, MA (US); Shari Lynn Caplan, Lunenburg, MA (US); Susan E. Cellitti, San Diego, CA (US); Douglas S. Daniels, New Haven, CT (US); Norio Hamamatsu, Belmont, MA (US); Bernhard Hubert Geierstanger, Solana Beach, CA (US); Stuart Licht, Cambridge, MA (US); Andreas Loew, Somerville, MA (US); Stephen Craig Weldon, Leominster, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/248,712

(22) Filed: Aug. 26, 2016

(65) Prior Publication Data
US 2017/0166621 A1   Jun. 15, 2017

Related U.S. Application Data

(62) Division of application No. 13/626,207, filed on Sep. 25, 2012, now Pat. No. 9,458,214.

(Continued)

(51) Int. Cl.
*A61K 38/18* (2006.01)
*A61K 38/26* (2006.01)
(Continued)

(52) U.S. Cl.
CPC ............ *C07K 14/605* (2013.01); *C07K 14/50* (2013.01); *C07K 2319/00* (2013.01); *C07K 2319/30* (2013.01); *C07K 2319/75* (2013.01)

(58) Field of Classification Search
None
See application file for complete search history.

(56) References Cited

U.S. PATENT DOCUMENTS 6,268,343 B1   7/2001   Knudsen et al.
8,188,040 B2   5/2012   Belouski et al.
(Continued)

FOREIGN PATENT DOCUMENTS

CN   1723220        1/2006
CN   101993496 A    3/2011
(Continued)

OTHER PUBLICATIONS

Koyama et al., "A novel procedure for the preparation of biologically active recombinant peptides using a cyanylation reaction", Journal of Biotechnology 32(3)273-281 (Feb. 29, 1994).
(Continued)

*Primary Examiner* — Christine J Saoud
(74) *Attorney, Agent, or Firm* — Yichen Liu

(57) ABSTRACT

The present invention relates to the identification of dual function fusion proteins comprising fibroblast growth factor
(Continued)

21 (FGF21) and Exenatide, Exendin-4, or GLP-1. Also disclosed are methods for treating metabolic, cardiovascular, and endocrine conditions related to glucose and/or lipid homeostasis.

15 Claims, 17 Drawing Sheets

Specification includes a Sequence Listing.

Related U.S. Application Data

(60) Provisional application No. 61/539,290, filed on Sep. 26, 2011.

(51) Int. Cl.
    *C07K 14/605*     (2006.01)
    *C07K 14/50*     (2006.01)

(56) References Cited

U.S. PATENT DOCUMENTS

| | | | |
|---|---|---|---|
| 8,557,771 B2 | 10/2013 | Fan et al. | |
| 9,006,400 B2 | 4/2015 | Boettcher et al. | |
| 9,023,791 B2 | 5/2015 | Boettcher et al. | |
| 9,266,935 B2 | 2/2016 | Boettcher et al. | |
| 9,458,214 B2 | 10/2016 | Boettcher et al. | |
| 2009/0118190 A1 | 5/2009 | Beals et al. | |
| 2010/0216715 A1 | 8/2010 | Tagmose et al. | |
| 2011/0034373 A1 | 2/2011 | Coskun et al. | |
| 2011/0195895 A1 | 8/2011 | Walker et al. | |
| 2012/0052069 A1 | 3/2012 | Belouski et al. | |
| 2012/0129766 A1 | 5/2012 | Boettcher et al. | |
| 2012/0238496 A1 | 9/2012 | Fan et al. | |
| 2016/0051628 A1 | 2/2016 | Boettcher et al. | |
| 2016/0193297 A1 | 7/2016 | Boettcher et al. | |
| 2017/0065678 A1 | 3/2017 | Diener et al. | |

FOREIGN PATENT DOCUMENTS

| | | |
|---|---|---|
| EP | 2468858 A1 | 6/2012 |
| WO | 9808871 A1 | 3/1998 |
| WO | WO2005047337 | 5/2005 |
| WO | 2005061712 A1 | 7/2005 |
| WO | 2006036834 A2 | 4/2006 |
| WO | 2008121563 A2 | 10/2008 |
| WO | 2010065439 A1 | 6/2010 |
| WO | 2010142665 A1 | 12/2010 |
| WO | 2011020319 A1 | 2/2011 |
| WO | 2011089203 A1 | 7/2011 |
| WO | 2012066075 A1 | 5/2012 |
| WO | 2013/049247 A1 | 4/2013 |
| WO | 2015/138278 A1 | 9/2015 |

OTHER PUBLICATIONS

Geneseq Database, Jul. 19, 2012 "Human fibroblast growth factor 21 polypeptide variant 76, Seq. 39", XP002699914, EBI accession no GSP AZW46640, Database Accession No. AZW46640 sequence.
"Human Fibroblast Growth Factor 21 Mutein Q153E" Sep. 8, 2005. Database Accession No. AEB19076.
Micanovic, et al., "Different roles of N- and C- termini in the functional activity of FGF21", J. Cell Physiol. May 2009, 219(2)227-34.
Yie et al., "FGF21 N- and C- termini play different roles in receptor interaction and activation", FEBS Lett. Jan. 5, 2009 583(1):19-24.
Soltani, N. et al., "In vivo expression of GLP-1/IgG-Fc fusion protein enhances beta-cell mass and protects against streptozotocin-induced diabetes", Gene Therapy, 14:981-988, (2007).
Database Genseq [Online] Jan. 20, 2011 (Jan. 20, 2011), "Human Fc-(G5)-FGF21 fusion protein, SEQ ID 107 of WO2010129600," retrieved from EBI accession No. GSP:AYM23795.

```
                        SEQUENCE LISTING

<160> NUMBER OF SEQ ID NOS: 188

<210> SEQ ID NO 1
<211> LENGTH: 209
<212> TYPE: PRT
<213> ORGANISM: Homo sapiens

<400> SEQUENCE: 1

Met Asp Ser Asp Glu Thr Gly Phe Glu His Ser Gly Leu Trp Val Ser
 1               5                  10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190
```

```
    Pro Leu Ser Met Val Gly Pro Ser Gln Gly Arg Ser Pro Ser Tyr Ala
            195                 200                 205

Ser

<210> SEQ ID NO 2
<211> LENGTH: 940
<212> TYPE: DNA
<213> ORGANISM: Homo sapiens

<400> SEQUENCE: 2
ctgtcagctg aggatccagc cgaaagagga gccaggcact caggccacct gagtctactc      60
acctggacaa ctggaatctg gcaccaattc taaaccactc agcttctccg agctcacacc     120
ccggagatca cctgaggacc cgagccattg atggactcgg acgagaccgg gttcgagcac     180
tcaggactgt gggtttctgt gctggctggt cttctgctgg gagcctgcca ggcacacccc     240
atccctgact ccagtcctct cctgcaattc gggggccaag tccggcagcg gtacctctac     300
acagatgatg cccagcagac agaagcccac ctggagatca ggaggatggg acggtgggg      360 ggcgctgctg accagagccc cgaaagtctc ctgcagctga aagccttgaa gccgggagtt     420
attcaaatct gggagtcaa gacatccagg ttcctgtgcc agcggccaga tggggccctg      480
tatggatcgc tccactttga ccctgaggcc tgcagcttcc gggagctgct tcttgaggac     540
ggatacaatg tttaccagtc gaagcccac ggcctcccgc tgcacctgcc agggaacaag      600
tccccacacc gggaccctgc accccgagga ccagctcgct tcctgccact accaggcctg     660
ccccccgcac tcccggagcc acccggaatc ctggcccccc agcccccga tgtgggctcc      720 tcggaccctc tgagcatggt gggaccttcc cagggccgaa gccccagcta cgcttcctga     780
agccagaggc tgtttactat gacatctcct ctttatttat taggttattt atcttattta     840
tttttttatt tttcttactt gagataataa agagttccag aggagaaaaa aaaaaaaaaa     900
aaaaaaaaaa aaaaaaaaaa aaaaaaaaaa aaaaaaaaaa                           940

<210> SEQ ID NO 3
<211> LENGTH: 181
<212> TYPE: PRT
<213> ORGANISM: Homo sapiens

<400> SEQUENCE: 3

His Pro Ile Pro Asp Ser Ser Pro Leu Leu Gln Phe Gly Gly Gln Val
    1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
    65                  70                  75                  80

Ala Leu Tyr Gly Ser Leu His Phe Asp Pro Glu Ala Cys Ser Phe Arg
                    85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140
```

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 4
<211> LENGTH: 546
<212> TYPE: DNA
<213> ORGANISM: Homo sapiens

<400> SEQUENCE: 4

| | | | | | |
|---|---|---|---|---|---|
| cacccatcc | ctgactccag | tcctctcctg | caattcgggg | gccaagtccg | gcagcggtac | 60 |
| ctctacacag | atgatgccca | gcagacagaa | gcccacctgg | agatcaggga | ggatgggacg | 120 |
| gtgggggcg | ctgctgacca | gagccccgaa | agtctcctgc | agctgaaagc | cttgaagccg | 180 |
| ggagttattc | aaatcttggg | agtcaagaca | tccaggttcc | tgtgccagcg | gccagatggg | 240 |
| gccctgtatg | gatcgctcca | ctttgaccct | gaggcctgca | gcttccggga | gctgcttctt | 300 |
| gaggacggat | acaatgttta | ccagtccgaa | gcccacggcc | tcccgctgca | cctgccaggg | 360 |
| aacaagtccc | cacaccggga | ccctgcaccc | cgaggaccag | ctcgcttcct | gccactacca | 420 |
| ggcctgcccc | ccgcactccc | ggagccaccc | ggaatcctgg | ccccccagcc | cccgatgtg | 480 |
| ggctcctcgg | accctctgag | catggtggga | ccttcccagg | gccgaagccc | cagctacgct | 540 |
| tcctga | | | | | 546 |

<210> SEQ ID NO 5
<211> LENGTH: 180
<212> TYPE: PRT
<213> ORGANISM: Homo sapiens

<400> SEQUENCE: 5

Met Lys Ser Ile Tyr Phe Val Ala Gly Leu Phe Val Met Leu Val Gln
1               5                   10                  15

Gly Ser Trp Gln Arg Ser Leu Gln Asp Thr Glu Glu Lys Ser Arg Ser
                20                  25                  30

Phe Ser Ala Ser Gln Ala Asp Pro Leu Ser Asp Pro Asp Gln Met Asn
            35                  40                  45

Glu Asp Lys Arg His Ser Gln Gly Thr Phe Thr Ser Asp Tyr Ser Lys
50                  55                  60

Tyr Leu Asp Ser Arg Arg Ala Gln Asp Phe Val Gln Trp Leu Met Asn
65                  70                  75                  80

Thr Lys Arg Asn Arg Asn Asn Ile Ala Lys Arg His Asp Glu Phe Glu
                85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
        115                 120                 125

Arg Arg Asp Phe Pro Glu Glu Val Ala Ile Val Glu Glu Leu Gly Arg
130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg Lys
        180

<210> SEQ ID NO 6
<211> LENGTH: 1298
<212> TYPE: DNA
<213> ORGANISM: Homo sapiens

<400> SEQUENCE: 6

| | | | | | |
|---|---|---|---|---|---|
| gcatagaatg | cagatgagca | aagtgagtgg | gagagggaag | tcatttgtaa | caaaaactca | 60 |
| ttatttacag | atgagaaatt | tatattgtca | gcgtaatatc | tgtgaggcta | aacagagctg | 120 |
| gagagtatat | aaaagcagtg | cgccttggtg | cagaagtaca | gagcttagga | cacagagcac | 180 |
| atcaaaagtt | cccaaagagg | gcttgctctc | tcttcacctg | ctctgttcta | cagcacacta | 240 |
| ccagaagaca | gcagaaatga | aaagcattta | ctttgtggct | ggattatttg | taatgctggt | 300 |
| acaaggcagc | tggcaacgtt | cccttcaaga | cacagaggag | aaatccagat | cattctcagc | 360 |
| ttcccaggca | gacccactca | gtgatcctga | tcagatgaac | gaggacaagc | gccattcaca | 420 |
| gggcacattc | accagtgact | acagcaagta | tctggactcc | aggcgtgccc | aagattttgt | 480 |
| gcagtggttg | atgaatacca | agaggaacag | gaataacatt | gccaaacgtc | acgatgaatt | 540 |
| tgagagacat | gctgaaggga | cctttaccag | tgatgtaagt | tcttatttgg | aaggccaagc | 600 |
| tgccaaggaa | ttcattgctt | ggctggtgaa | aggccgagga | aggcgagatt | cccagaaga | 660 |
| ggtcgccatt | gttgaagaac | ttggccgcag | acatgctgat | ggttctttct | ctgatgagat | 720 |
| gaacaccatt | cttgataatc | ttgccgccag | ggactttata | aactggttga | ttcagaccaa | 780 |
| aatcactgac | aggaaataac | tatatcacta | ttcaagatca | tcttcacaac | atcacctgct | 840 |
| agccacgtgg | gatgtttgaa | atgttaagtc | ctgtaaattt | aagaggtgta | ttctgaggcc | 900 |
| acattgcttt | gcatgccaat | aaataaattt | tcttttagtg | ttgtgtagcc | aaaaattaca | 960 |
| aatggaataa | agtttttatca | aaatattgct | aaaatatcag | ctttaaaata | tgaaagtgct | 1020 |
| agattctgtt | attttcttct | tattttggat | gaagtacccc | aacctgttta | catttagcga | 1080 |
| taaaattatt | tttctatgat | ataatttgta | aatgtaaatt | attccgatct | gacatatctg | 1140 |
| cattataata | ataggagaat | agaagaactg | gtagccacag | tggtgaaatt | ggaaagagaa | 1200 |
| ctttcttcct | gaaacctttg | tcttaaaaat | actcagcttt | caatgtatca | agatacaat | 1260 |
| taaataaaat | tttcaagctt | ctttaccaaa | aaaaaaaa | | | 1298 |

<210> SEQ ID NO 7
<211> LENGTH: 39
<212> TYPE: PRT
<213> ORGANISM: Homo sapiens

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Gly Gly Gly Gly Ser Gly Gly Gly Ser Gly Gly Gly Ser
1               5                   10                  15

<210> SEQ ID NO 9
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
                20                  25                  30

Gly Gly Gly Ser Gly Gly Gly Asp Ser Ser Pro Leu Leu Gln Phe Gly
            35                  40                  45

Gly Gln Val Arg Gln Arg Tyr Leu Tyr Thr Asp Asp Ala Gln Glu Thr
        50                  55                  60

Glu Ala His Leu Glu Ile Arg Glu Asp Gly Thr Val Gly Gly Ala Ala
65                  70                  75                  80

His Gln Ser Pro Glu Ser Leu Leu Glu Leu Lys Ala Leu Lys Pro Gly
                85                  90                  95

Val Ile Gln Ile Leu Gly Val Lys Thr Ser Arg Phe Leu Cys Gln Lys
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Arg Ser Pro His
145                 150                 155                 160

Cys Asp Pro Ala Pro Gln Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ala Met Val Gly Pro Ser Gln
        195                 200                 205

Gly Arg Ser Pro Ser Tyr Ala Ser
    210                 215

<210> SEQ ID NO 10
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
cattctgaag gcactttac tagcgatgtt tctagctacc tggaaggcca ggctgcgaaa        60
gaattcatcg cgtggctggt taaaggcggt tctggtggtg gtggttctgg cggtggcgat      120
agcagcccgc tgctgcagtt tggcggccag gtgcgtcagc gttatctgta taccgatgat      180
gcgcaggaaa ccgaagcgca tctggaaatt cgtgaagatg gcaccgtggg cggtgcggcg      240

```
catcagagcc cggaaagcct gctggaactg aaagcgctga aaccgggcgt gattcagatt      300
ctgggcgtga aaccagccg ttttctgtgc cagaaaccgg atggcgcgct gtatggcagc      360
ctgcattttg atccggaagc gtgcagcttt cgtgaactgc tgctggaaga tggctataac     420
gtgtatcaga gcgaagcgca tggcctgccg ctgcatctgc cgggcaaccg tagcccgcat     480
tgcgatccgg caccgcaggg tccggcgcgt tttctgccgc tgccgggtct gccgccggca     540
ctgccggaac cgccgggtat tctggccccg cagccgccgg atgttggtag cagcgatccg     600
ctggcgatgg tgggtccgag ccagggtcgt agcccgagct atgcgagcta a              651
```

<210> SEQ ID NO 11
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Ser Gly
            20                  25                  30

Gly Gly Gly Ser Gly Gly Gly Ser Gly Gly Gly Ser Gly Gly
        35                  40                  45

Gly Gly Asp Ser Ser Pro Leu Leu Gln Phe Gly Gly Gln Val Arg Gln
    50                  55                  60

Arg Tyr Leu Tyr Thr Asp Ala Gln Glu Thr Glu Ala His Leu Glu
65                  70                  75                  80

Ile Arg Glu Asp Gly Thr Val Gly Gly Ala Ala His Gln Ser Pro Glu
                85                  90                  95

Ser Leu Leu Glu Leu Lys Ala Leu Lys Pro Gly Val Ile Gln Ile Leu
            100                 105                 110

Gly Val Lys Thr Ser Arg Phe Leu Cys Gln Lys Pro Asp Gly Ala Leu
        115                 120                 125

Tyr Gly Ser Leu His Phe Asp Pro Glu Ala Cys Ser Phe Arg Glu Leu
    130                 135                 140

Leu Leu Glu Asp Gly Tyr Asn Val Tyr Gln Ser Glu Ala His Gly Leu
145                 150                 155                 160

Pro Leu His Leu Pro Gly Asn Arg Ser Pro His Cys Asp Pro Ala Pro
                165                 170                 175

Gln Gly Pro Ala Arg Phe Leu Pro Leu Pro Gly Leu Pro Pro Ala Leu
            180                 185                 190

Pro Glu Pro Pro Gly Ile Leu Ala Pro Gln Pro Pro Asp Val Gly Ser
        195                 200                 205

Ser Asp Pro Leu Ala Met Val Gly Pro Ser Gln Gly Arg Ser Pro Ser
    210                 215                 220

Tyr Ala Ser
225
```

<210> SEQ ID NO 12
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 12
catggtgagg gtacgtttac ttctgatctg tctaaacaga tggaagaaga agctgttcgc      60
ctgttcattg aatggctgaa aaatggtggt tctggtggtg gtggttctgg cggtggcggt     120
tctggcggcg gtggtagcgg tggcggcggt gatagcagcc cgctgctgca gtttggcggc     180
caggtgcgtc agcgttatct gtataccgat gatgcgcagg aaaccgaagc gcatctggaa     240
attcgtgaag atggcaccgt gggcggtgcg gcgcatcaga gcccggaaag cctgctggaa     300
ctgaaagcgc tgaaaccggg cgtgattcag attctgggcg tgaaaaccag ccgtttcctg     360
tgccagaaac cggatggcgc gctgtatggc agcctgcatt ttgatccgga agcgtgcagc     420
tttcgtgaac tgctgctgga agatggctat aacgtgtatc agagcgaagc gcatggcctg     480
ccgctgcatc tgccgggcaa ccgtagcccg cattgcgatc cggcaccgca gggtccggcg     540
cgttttctgc cgctgccggg tctgccgccg gcactgccgg aaccgccggg tattctggcc     600
ccgcagccgc cggatgttgg tagcagcgat ccgctggcga tggtgggtcc gagccagggt     660
cgtagcccga gctatgcgag ctaa                                           684

<210> SEQ ID NO 13
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

```
<210> SEQ ID NO 14
<211> LENGTH: 630
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
cattctgaag gcactttac tagcgatgtt tctagctacc tggaaggcca ggctgcgaaa      60
gaattcatcg cgtggctggt taaaggcggt tctggtgata gcagcccgct gctgcagttt     120
ggcggccagg tgcgtcagcg ttatctgtat accgatgatg cgcagcagac cgaagcgcat     180
ctggaaattc gtgaagatgg caccgtgggc ggtgcggcgg atcagagccc ggaaagcctg     240
ctgcagctga aagcgctgaa accgggcgtg attcagattc tgggcgtgaa aaccagccgt     300
tttctgtgcc agcgtccgga tggcgcgctg tatggcagcc tgcattttga tccggaagcg     360
tgcagctttc gtgaactgct gctggaagat ggctataacg tgtatcagag cgaagcgcat     420
ggcctgccgc tgcatctgcc gggcaacaaa agcccgcatc gtgatccggc accgcgtggt     480
ccggcgcgtt ttctgccgct gccgggtctg ccgccggcac tgccggaacc gccgggtatt     540
ctggccccgc agccgccgga tgttggtagc agcgatccgc tgtctatggt gggtccgagc     600
cagggtcgta gcccgagcta tgcgagctaa                                      630

<210> SEQ ID NO 15
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
        50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
        130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190
```

```
                    Pro Leu Ser Met Val Gly Pro Ser Gln Gly Arg Ser Pro Ser Tyr Ala
                            195                 200                 205

Ser

<210> SEQ ID NO 16
<211> LENGTH: 630
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
catgcggaag gcacttttac tagcgatgtt tctagctacc tggaaggcca ggctgcgaaa        60
gaattcatcg cgtggctggt taaaggcggt tctggtgata gcagcccgct gctgcagttt      120
ggcggccagg tgcgtcagcg ttatctgtat accgatgatg cgcagcagac cgaagcgcat      180
ctggaaattc gtgaagatgg caccgtgggc ggtgcggcgg atcagagccc ggaaagcctg      240
ctgcagctga aagcgctgaa accgggcgtg attcagattc tgggcgtgaa aaccagccgt      300
tttctgtgcc agcgtccgga tggcgcgctg tatggcagcc tgcattttga tccggaagcg      360
tgcagctttc gtgaactgct gctggaagat ggctataacg tgtatcagag cgaagcgcat      420
ggcctgccgc tgcatctgcc gggcaacaaa agcccgcatc gtgatccggc accgcgtggt      480
ccggcgcgtt ttctgccgct gccgggtctg ccgccggcac tgccggaacc gccgggtatt      540
ctggccccgc agccgccgga tgttggtagc agcgatccgc tgtctatggt gggtccgagc      600
cagggtcgta gcccgagcta tgcgagctaa                                        630

<210> SEQ ID NO 17
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

His Gly Glu Gly Thr Phe Thr Ser Asp Leu Ser Lys Gln Met Glu Glu
1                   5                  10                  15

Glu Ala Val Arg Leu Phe Ile Glu Trp Leu Lys Asn Gly Gly Pro Ser
                20                  25                  30

Ser Gly Ala Pro Pro Pro Ser Gly Gly Asp Ser Ser Pro Leu Leu
            35                  40                  45

Gln Phe Gly Gly Gln Val Arg Gln Arg Tyr Leu Tyr Thr Asp Asp Ala
    50                  55                  60

Gln Gln Thr Glu Ala His Leu Glu Ile Arg Glu Asp Gly Thr Val Gly
65                  70                  75                  80

Gly Ala Ala Asp Gln Ser Pro Glu Ser Leu Leu Gln Leu Lys Ala Leu
                85                  90                  95

Lys Pro Gly Val Ile Gln Ile Leu Gly Val Lys Thr Ser Arg Phe Leu
            100                 105                 110

Cys Gln Arg Pro Asp Gly Ala Leu Tyr Gly Ser Leu His Phe Asp Pro
        115                 120                 125

Glu Ala Cys Ser Phe Arg Glu Leu Leu Leu Glu Asp Gly Tyr Asn Val
    130                 135                 140

Tyr Gln Ser Glu Ala His Gly Leu Pro Leu His Leu Pro Gly Asn Lys
145                 150                 155                 160
```

```
Ser Pro His Arg Asp Pro Ala Pro Arg Gly Pro Ala Arg Phe Leu Pro
            165                 170                 175

Leu Pro Gly Leu Pro Pro Ala Leu Pro Glu Pro Pro Gly Ile Leu Ala
        180                 185                 190

Pro Gln Pro Pro Asp Val Gly Ser Ser Asp Pro Leu Ser Met Val Gly
        195                 200                 205

Pro Ser Gln Gly Arg Ser Pro Ser Tyr Ala Ser
    210                 215
```

<210> SEQ ID NO 18
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
catggtgagg gtacgtttac ttctgatctg tctaaacaga tggaagaaga agctgttcgc      60
ctgttcattg aatggctgaa aaatggtggt ccgtcctccg gcgctcctcc gccttctggt     120
ggtggcgact cgagcccgct gctgcagttt ggcggccagg tgcgtcagcg ttatctgtat     180
accgatgatg cgcagcagac cgaagcgcat ctggaaattc gtgaagatgg caccgtgggc     240
ggtgcggcgg atcagagccc ggaaagcctg ctgcagctga aagcgctgaa accgggcgtg     300
attcagattc tgggcgtgaa aaccagccgt tttctgtgcc agcgtccgga tggcgcgctg     360
tatggcagcc tgcatttga tccggaagcg tgcagctttc gtgaactgct gctggaagat     420
ggctataacg tgtatcagag cgaagcgcat ggcctgccgc tgcatctgcc gggcaacaaa     480
agcccgcatc gtgatccggc accgcgtggt ccggcgcgtt ttctgccgct gccgggtctg     540
ccgccggcac tgccggaacc gccgggtatt ctggccccgc agccgccgga tgttggtagc     600
agcgatccgc tgtctatggt gggtccgagc cagggtcgta gcccgagcta tgcgagctaa     660
```

<210> SEQ ID NO 19
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125
```

```
Ser Phe Arg Glu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Arg Asp Pro Ala Pro Arg Gly Pro Ala Arg Phe Leu Pro Leu Pro Gly
            165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
        210                 215
```

<210> SEQ ID NO 20
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
cattctgaag gcactttac tagcgatgtt tctagctacc tggaaggcca ggctgcgaaa    60
gaattcatcg cgtggctggt taaaggcggt tctggtggtg gtggttctgg cggtggcgac   120
tcgagcccgc tgctgcagtt tggcggccag gtgcgtcagc gttatctgta taccgatgat   180
gcgcagcaga ccgaagcgca tctggaaatt cgtgaagatg gcaccgtggg cggtgcggcg   240
gatcagagcc cggaaagcct gctgcagctg aaagcgctga accgggcgt gattcagatt   300 ctgggcgtga aaccagccg ttttctgtgc cagcgtccgg atggcgcgct gtatggcagc   360
ctgcattttg atccggaagc gtgcagcttt cgtgaactgc tgctggaaga tggctataac   420
gtgtatcaga gcgaagcgca tggcctgccg ctgcatctgc cgggcaacaa aagcccgcat   480
cgtgatccgg caccgcgtgg tccggcgcgt tttctgccgc tgccgggtct gccgccggca   540
ctgccggaac cgccgggtat tctggccccg cagccgccgg atgttggtag cagcgatccg   600
ctgtctatgg tgggtccgag ccagggtcgt agcccgagct atgcgagcta a            651
```

<210> SEQ ID NO 21
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
```

```
                85                  90                  95
Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Arg Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
    210                 215

<210> SEQ ID NO 22
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
catgcggaag gcacttttac tagcgatgtt tctagctacc tggaaggcca ggctgcgaaa      60
gaattcatcg cgtggctggt taaaggcggt tctggtggtg gtggttctgg cggtggcgac     120
tcgagcccgc tgctgcagtt tggcggccag gtgcgtcagc gttatctgta taccgatgat     180
gcgcagcaga ccgaagcgca tctggaaatt cgtgaagatg gcaccgtggg cggtgcgggc     240
gatcagagcc ggaaagcct gctgcagctg aaagcgctga accgggcgt gattcagatt      300 ctgggcgtga aaaccagccg tttttctgtgc cagcgtccgg atggcgcgct gtatggcagc     360
ctgcattttg atccggaagc gtgcagcttt cgtgaactgc tgctggaaga tggctataac     420
gtgtatcaga gcgaagcgca tggcctgccg ctgcatctgc cgggcaacaa aagcccgcat     480
cgtgatccgg caccgcgtgg tccggcgcgt tttctgccgc tgccgggtct gccgccggca     540
ctgccggaac cgccgggtat tctggccccg cagccgccgg atgttggtag cagcgatccg     600
ctgtctatgg tgggtccgag ccagggtcgt agcccgagct atgcgagcta a             651

<210> SEQ ID NO 23
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Ser Gly Gly Gly Asp
        35                  40                  45
```

| | | | | | | | | | | | | | | |
|---|---|---|---|---|---|---|---|---|---|---|---|---|---|---|
| Ser | Ser<br>50 | Pro | Leu | Leu | Gln<br>55 | Phe | Gly | Gly | Gln<br>60 | Val | Arg | Gln | Arg | Tyr Leu |

Tyr Thr Asp Asp Ala Gln Gln Thr Glu Ala His Leu Glu Ile Arg Glu
65              70                75                  80

Asp Gly Thr Val Gly Gly Ala Ala Asp Gln Ser Pro Glu Ser Leu Leu
                85                  90                  95

Gln Leu Lys Ala Leu Lys Pro Gly Val Ile Gln Ile Leu Gly Val Lys
            100                 105                 110

Thr Ser Arg Phe Leu Cys Gln Arg Pro Asp Gly Ala Leu Tyr Gly Ser
            115                 120                 125

Leu His Phe Asp Pro Glu Ala Cys Ser Phe Arg Glu Leu Leu Leu Glu
        130                 135                 140

Asp Gly Tyr Asn Val Tyr Gln Ser Glu Ala His Gly Leu Pro Leu His
145                 150                 155                 160

Leu Pro Gly Asn Lys Ser Pro His Arg Asp Pro Ala Pro Arg Gly Pro
                165                 170                 175

Ala Arg Phe Leu Pro Leu Pro Gly Leu Pro Ala Leu Pro Glu Pro
            180                 185                 190

Pro Gly Ile Leu Ala Pro Gln Pro Pro Asp Val Gly Ser Ser Asp Pro
            195                 200                 205

Leu Ser Met Val Gly Pro Ser Gln Gly Arg Ser Pro Ser Tyr Ala Ser
210                 215                 220

<210> SEQ ID NO 24
<211> LENGTH: 675
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
catggtgagg gtacgtttac ttctgatctg tctaaacaga tggaagaaga agctgttcgc    60
ctgttcattg aatggctgaa aaatggtggt ccgtcctccg gcgctcctcc gccttctggt   120
ggtggtggtt ctggcggtgg cgactcgagc ccgctgctgc agtttggcgg ccaggtgcgt   180
cagcgttatc tgtataccga tgatgcgcag cagaccgaag cgcatctgga aattcgtgaa   240
gatggcaccg tggcggtgc ggcggatcag agcccggaaa gcctgctgca gctgaaagcg   300
ctgaaaccgg gcgtgattca gattctgggc gtgaaaacca gccgttttct gtgccagcgt   360
ccggatggcg cgctgtatgg cagcctgcat tttgatccgg aagcgtgcag ctttcgtgaa   420
ctgctgctgg aagatggcta taacgtgtat cagagcgaag cgcatggcct gccgctgcat   480
ctgccgggca acaaaagccc gcatcgtgat ccggcaccgc gtggtccggc cgttttctg   540
ccgctgccgg gtctgccgcc ggcactgccg gaaccgccgg gtattctggc cccgcagccg   600
ccggatgttg gtagcagcga tccgctgtct atggtgggtc cgagccaggg tcgtagcccg   660
agctatgcga gctaa                                                   675
```

<210> SEQ ID NO 25
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

-continued

```
His Ser Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Gly Ser Gly
            20                  25                  30
Gly Gly Gly Ser Gly Gly Gly Ser Gly Gly Gly Gly Ser Ala Asp
        35                  40                  45
Lys Thr His Thr Cys Pro Pro Cys Pro Ala Pro Glu Ala Ala Gly Gly
50                  55                  60
Pro Ser Val Phe Leu Phe Pro Pro Lys Pro Lys Asp Thr Leu Met Ile
65                  70                  75                  80
Ser Arg Thr Pro Glu Val Thr Cys Val Val Val Asp Val Ser His Glu
                85                  90                  95
Asp Pro Glu Val Lys Phe Asn Trp Tyr Val Asp Gly Val Glu Val His
            100                 105                 110
Asn Ala Lys Thr Lys Pro Arg Glu Glu Gln Tyr Asn Ser Thr Tyr Arg
            115                 120                 125
Val Val Ser Val Leu Thr Val Leu His Gln Asp Trp Leu Asn Gly Lys
        130                 135                 140
Glu Tyr Lys Cys Lys Val Ser Asn Lys Ala Leu Pro Ala Pro Ile Glu
145                 150                 155                 160
Lys Thr Ile Ser Lys Ala Lys Gly Gln Pro Arg Glu Pro Gln Val Tyr
                165                 170                 175
Thr Leu Pro Pro Ser Arg Glu Glu Met Thr Lys Asn Gln Val Ser Leu
            180                 185                 190
Thr Cys Leu Val Lys Gly Phe Tyr Pro Ser Asp Ile Ala Val Glu Trp
            195                 200                 205
Glu Ser Asn Gly Gln Pro Glu Asn Asn Tyr Lys Thr Thr Pro Pro Val
        210                 215                 220
Leu Asp Ser Asp Gly Ser Phe Phe Leu Tyr Ser Lys Leu Thr Val Asp
225                 230                 235                 240
Lys Ser Arg Trp Gln Gln Gly Asn Val Phe Ser Cys Ser Val Met His
                245                 250                 255
Glu Ala Leu His Asn His Tyr Thr Gln Lys Ser Leu Ser Leu Ser Pro
            260                 265                 270
Gly Lys Gly Gly Gly Gly Ser Gly Gly Gly Gly Ser Gly Gly Gly Gly
            275                 280                 285
Ser Asp Ser Ser Pro Leu Leu Gln Phe Gly Gly Gln Val Arg Gln Arg
        290                 295                 300
Tyr Leu Tyr Thr Asp Asp Ala Cys Gln Thr Glu Ala His Leu Glu Ile
305                 310                 315                 320
Arg Glu Asp Gly Thr Val Gly Gly Ala Ala Asp Gln Ser Pro Glu Ser
                325                 330                 335
Leu Leu Gln Leu Lys Ala Leu Lys Pro Gly Val Ile Gln Ile Leu Gly
            340                 345                 350
Val Lys Thr Ser Arg Phe Leu Cys Gln Lys Pro Asp Gly Ala Leu Tyr
            355                 360                 365
Gly Ser Leu His Phe Asp Pro Glu Ala Cys Ser Phe Arg Glu Leu Leu
        370                 375                 380
Leu Glu Asp Gly Tyr Asn Val Tyr Gln Ser Glu Ala His Gly Leu Pro
385                 390                 395                 400
Leu His Leu Pro Cys Asn Arg Ser Pro His Arg Asp Pro Ala Ser Arg
                405                 410                 415
Gly Pro Ala Arg Phe Leu Pro Leu Pro Gly Leu Pro Pro Ala Leu Pro
```

```
                    420              425                430
Glu Pro Pro Gly Ile Leu Ala Pro Gln Pro Pro Asp Val Gly Ser Ser
            435                440                445

Asp Pro Leu Ala Met Val Gly Gly Ser Gln Ala Arg Ser Pro Ser Tyr
        450                455                460

Ala Ser
465

<210> SEQ ID NO 26
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Ser Gly Gly Gly Ser Ala Asp
        35                  40                  45

Lys Thr His Thr Cys Pro Pro Cys Pro Ala Pro Glu Ala Ala Gly Gly
50                  55                  60

Pro Ser Val Phe Leu Phe Pro Pro Lys Pro Lys Asp Thr Leu Met Ile
65                  70                  75                  80

Ser Arg Thr Pro Glu Val Thr Cys Val Val Val Asp Val Ser His Glu
                85                  90                  95

Asp Pro Glu Val Lys Phe Asn Trp Tyr Val Asp Gly Val Glu Val His
            100                 105                 110

Asn Ala Lys Thr Lys Pro Arg Glu Glu Gln Tyr Asn Ser Thr Tyr Arg
        115                 120                 125

Val Val Ser Val Leu Thr Val Leu His Gln Asp Trp Leu Asn Gly Lys
130                 135                 140

Glu Tyr Lys Cys Lys Val Ser Asn Lys Ala Leu Pro Ala Pro Ile Glu
145                 150                 155                 160

Lys Thr Ile Ser Lys Ala Lys Gly Gln Pro Arg Glu Pro Gln Val Tyr
                165                 170                 175

Thr Leu Pro Pro Ser Arg Glu Glu Met Thr Lys Asn Gln Val Ser Leu
            180                 185                 190

Thr Cys Leu Val Lys Gly Phe Tyr Pro Ser Asp Ile Ala Val Glu Trp
        195                 200                 205

Glu Ser Asn Gly Gln Pro Glu Asn Asn Tyr Lys Thr Thr Pro Pro Val
210                 215                 220

Leu Asp Ser Asp Gly Ser Phe Phe Leu Tyr Ser Lys Leu Thr Val Asp
225                 230                 235                 240

Lys Ser Arg Trp Gln Gln Gly Asn Val Phe Ser Cys Ser Val Met His
                245                 250                 255

Glu Ala Leu His Asn His Tyr Thr Gln Lys Ser Leu Ser Leu Ser Pro
            260                 265                 270

Gly Lys Gly Gly Gly Gly Ser Gly Gly Gly Gly Ser Gly Gly Gly Gly
        275                 280                 285

Ser Asp Ser Ser Pro Leu Leu Gln Phe Gly Gly Gln Val Arg Gln Arg
290                 295                 300
```

```
Tyr Leu Tyr Thr Asp Asp Ala Cys Gln Thr Glu Ala His Leu Glu Ile
305                 310                 315                 320

Arg Glu Asp Gly Thr Val Gly Gly Ala Ala Asp Gln Ser Pro Glu Ser
            325                 330                 335

Leu Leu Gln Leu Lys Ala Leu Lys Pro Gly Val Ile Gln Ile Leu Gly
            340                 345                 350

Val Lys Thr Ser Arg Phe Leu Cys Gln Lys Pro Asp Gly Ala Leu Tyr
        355                 360                 365

Gly Ser Leu His Phe Asp Pro Glu Ala Cys Ser Phe Arg Glu Leu Leu
    370                 375                 380

Leu Glu Asp Gly Tyr Asn Val Tyr Gln Ser Glu Ala His Gly Leu Pro
385                 390                 395                 400

Leu His Leu Pro Cys Asn Arg Ser Pro His Arg Asp Pro Ala Ser Arg
                405                 410                 415

Gly Pro Ala Arg Phe Leu Pro Leu Pro Gly Leu Pro Pro Ala Leu Pro
            420                 425                 430

Glu Pro Pro Gly Ile Leu Ala Pro Gln Pro Pro Asp Val Gly Ser Ser
        435                 440                 445

Asp Pro Leu Ala Met Val Gly Pro Ser Gln Ala Arg Ser Pro Ser Tyr
450                 455                 460

Glu Ser
465

<210> SEQ ID NO 27
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Gly Ser Gly Gly Gly Gly Ser Ala Asp
        35                  40                  45

Lys Thr His Thr Cys Pro Pro Cys Pro Ala Pro Glu Ala Ala Gly Gly
    50                  55                  60

Pro Ser Val Phe Leu Phe Pro Pro Lys Pro Lys Asp Thr Leu Met Ile
65                  70                  75                  80

Ser Arg Thr Pro Glu Val Thr Cys Val Val Val Asp Val Ser His Glu
                85                  90                  95

Asp Pro Glu Val Lys Phe Asn Trp Tyr Val Asp Gly Val Glu Val His
            100                 105                 110

Asn Ala Lys Thr Lys Pro Arg Glu Glu Gln Tyr Asn Ser Thr Tyr Arg
        115                 120                 125

Val Val Ser Val Leu Thr Val Leu His Gln Asp Trp Leu Asn Gly Lys
    130                 135                 140

Glu Tyr Lys Cys Lys Val Ser Asn Lys Ala Leu Pro Ala Pro Ile Glu
145                 150                 155                 160

Lys Thr Ile Ser Lys Ala Lys Gly Gln Pro Arg Glu Pro Gln Val Tyr
                165                 170                 175

Thr Leu Pro Pro Ser Arg Glu Glu Met Thr Lys Asn Gln Val Ser Leu
            180                 185                 190
```

```
Thr Cys Leu Val Lys Gly Phe Tyr Pro Ser Asp Ile Ala Val Glu Trp
            195                 200                 205

Glu Ser Asn Gly Gln Pro Glu Asn Asn Tyr Lys Thr Thr Pro Pro Val
    210                 215                 220

Leu Asp Ser Asp Gly Ser Phe Phe Leu Tyr Ser Lys Leu Thr Val Asp
225                 230                 235                 240

Lys Ser Arg Trp Gln Gln Gly Asn Val Phe Ser Cys Ser Val Met His
            245                 250                 255

Glu Ala Leu His Asn His Tyr Thr Gln Lys Ser Leu Ser Leu Ser Pro
        260                 265                 270

Gly Lys Gly Gly Gly Gly Ser Gly Gly Gly Ser Gly Gly Gly Gly
            275                 280                 285

Ser Asp Ser Ser Pro Leu Leu Gln Phe Gly Gly Gln Val Arg Gln Arg
    290                 295                 300

Tyr Leu Tyr Thr Asp Asp Ala Cys Gln Thr Glu Ala His Leu Glu Ile
305                 310                 315                 320

Arg Glu Asp Gly Thr Val Gly Gly Ala Ala Asp Gln Ser Pro Glu Ser
            325                 330                 335

Leu Leu Gln Leu Lys Ala Leu Lys Pro Gly Val Ile Gln Ile Leu Gly
        340                 345                 350

Val Lys Thr Ser Arg Phe Leu Cys Gln Lys Pro Asp Gly Ala Leu Tyr
    355                 360                 365

Gly Ser Leu His Phe Asp Pro Glu Ala Cys Ser Phe Arg Glu Leu Leu
370                 375                 380

Leu Glu Asp Gly Tyr Asn Val Tyr Gln Ser Glu Ala His Gly Leu Pro
385                 390                 395                 400

Leu His Leu Pro Cys Asn Arg Ser Pro His Arg Asp Pro Ala Ser Arg
            405                 410                 415

Gly Pro Ala Arg Phe Leu Pro Leu Pro Gly Leu Pro Pro Ala Leu Pro
            420                 425                 430

Glu Pro Pro Gly Ile Leu Ala Pro Gln Pro Pro Asp Val Gly Ser Ser
        435                 440                 445

Asp Pro Leu Ala Met Val Gly Pro Ser Gln Ala Arg Ser Pro Ser Tyr
    450                 455                 460

Asp Ser
465

<210> SEQ ID NO 28
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Glu Thr
    50                  55                  60

Glu Ala His Leu Glu Ile Arg Glu Asp Gly Thr Val Gly Gly Ala Ala
```

```
                65                  70                  75                  80
His Gln Ser Pro Glu Ser Leu Leu Glu Leu Lys Ala Leu Lys Pro Gly
                    85                  90                  95

Val Ile Gln Ile Leu Gly Val Lys Thr Ser Arg Phe Leu Cys Gln Lys
                100                 105                 110

Pro Asp Gly Ala Leu Tyr Gly Ser Leu His Phe Asp Pro Glu Ala Cys
                115                 120                 125

Ser Phe Arg Glu Leu Leu Leu Glu Asp Gly Tyr Asn Val Tyr Gln Ser
130                 135                 140

Glu Ala His Gly Leu Pro Leu His Leu Pro Gly Asn Arg Ser Pro His
145                 150                 155                 160

Cys Asp Pro Ala Pro Gln Gly Pro Ala Arg Phe Leu Pro Leu Pro Gly
                165                 170                 175

Leu Pro Pro Ala Leu Pro Glu Pro Gly Ile Leu Ala Pro Gln Pro
                180                 185                 190

Pro Asp Val Gly Ser Ser Asp Pro Leu Ala Met Val Gly Pro Ser Gln
                195                 200                 205

Gly Arg Ser Pro Ser Tyr Ala Ser
210                 215

<210> SEQ ID NO 29
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
catggtgaag gcacttttac tagcgatgtt tctagctacc tggaaggcca ggctgcgaaa      60
gaattcatcg cgtggctggt taaaggcggt tctggtggtg gtggttctgg cggtggcgat     120
agcagcccgc tgctgcagtt tggcggccag gtgcgtcagc gttatctgta taccgatgat     180
gcgcaggaaa ccgaagcgca tctggaaatt cgtgaagatg gcaccgtggg cggtgcggcg     240
catcagagcc cggaaagcct gctggaactg aaagcgctga accgggcgt gattcagatt     300 ctgggcgtga aaccagccg ttttctgtgc cagaaaccgg atggcgcgct gtatggcagc     360 ctgcatttg atccggaagc gtgcagcttt cgtgaactgc tgctggaaga tggctataac     420
gtgtatcaga gcgaagcgca tggcctgccg ctgcatctgc cgggcaaccg tagcccgcat     480
tgcgatccgg caccgcaggg tccggcgcgt tttctgccgc tgccgggtct gccgccggca     540
ctgccggaac cgccgggtat tctggccccg cagccgccgg atgttggtag cagcgatccg     600
ctggcgatgg tgggtccgag ccagggtcgt agcccgagct atgcgagcta a              651

<210> SEQ ID NO 30
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
                20                  25                  30
```

```
<210> SEQ ID NO 31
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31
```

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Asp Lys Thr His Thr Cys Pro Pro Cys
        35                  40                  45

Pro Ala Pro Glu Ala Ala Gly Gly Pro Ser Val Phe Leu Phe Pro Pro
    50                  55                  60

Lys Pro Lys Asp Thr Leu Met Ile Ser Arg Thr Pro Glu Val Thr Cys
65                  70                  75                  80

Val Val Val Asp Val Ser His Glu Asp Pro Glu Val Lys Phe Asn Trp
                85                  90                  95

Tyr Val Asp Gly Val Glu Val His Asn Ala Lys Thr Lys Pro Arg Glu
            100                 105                 110

Glu Gln Tyr Asn Ser Thr Tyr Arg Val Val Ser Val Leu Thr Val Leu
        115                 120                 125

His Gln Asp Trp Leu Asn Gly Lys Glu Tyr Lys Cys Lys Val Ser Asn
130                 135                 140

Lys Ala Leu Pro Ala Pro Ile Glu Lys Thr Ile Ser Lys Ala Lys Gly
145                 150                 155                 160

Gln Pro Arg Glu Pro Gln Val Tyr Thr Leu Pro Pro Ser Arg Glu Glu
                165                 170                 175

Met Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn
        195                 200                 205

Asn Tyr Lys Thr Thr Pro Pro Val Leu Asp Ser Asp Gly Ser Phe Phe
210                 215                 220

Leu Tyr Ser Lys Leu Thr Val Asp Lys Ser Arg Trp Gln Gln Gly Asn
225                 230                 235                 240

Val Phe Ser Cys Ser Val Met His Glu Ala Leu His Asn His Tyr Thr
                245                 250                 255

Gln Lys Ser Leu Ser Leu Ser Pro Gly Lys Asp Ser Ser Pro Leu Leu
            260                 265                 270

Gln Phe Gly Gly Gln Val Arg Gln Arg Tyr Leu Tyr Thr Asp Asp Ala
        275                 280                 285

Cys Gln Thr Glu Ala His Leu Glu Ile Arg Glu Asp Gly Thr Val Gly
290                 295                 300

Gly Ala Ala Asp Gln Ser Pro Glu Ser Leu Leu Gln Leu Lys Ala Leu
305                 310                 315                 320

Lys Pro Gly Val Ile Gln Ile Leu Gly Val Lys Thr Ser Arg Phe Leu
                325                 330                 335

Cys Gln Lys Pro Asp Gly Ala Leu Tyr Gly Ser Leu His Phe Asp Pro
            340                 345                 350

Glu Ala Cys Ser Phe Arg Glu Leu Leu Leu Glu Asp Gly Tyr Asn Val
        355                 360                 365

```
Tyr Gln Ser Glu Ala His Gly Leu Pro Leu His Leu Pro Cys Asn Arg
        370                 375                 380

Ser Pro His Arg Asp Pro Ala Ser Arg Gly Pro Ala Arg Phe Leu Pro
385                 390                 395                 400

Leu Pro Gly Leu Pro Pro Ala Leu Pro Glu Pro Pro Gly Ile Leu Ala
                405                 410                 415

Pro Gln Pro Pro Asp Val Gly Ser Ser Asp Pro Leu Ala Met Val Gly
        420                 425                 430

Gly Ser Gln Ala Arg Ser Pro Ser Tyr Ala Ser
        435                 440

<210> SEQ ID NO 32
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Asp Lys Thr His Thr Cys Pro Pro Cys
        35                  40                  45

Pro Ala Pro Glu Ala Ala Gly Gly Pro Ser Val Phe Leu Phe Pro Pro
50                  55                  60

Lys Pro Lys Asp Thr Leu Met Ile Ser Arg Thr Pro Glu Val Thr Cys
65                  70                  75                  80

Val Val Val Asp Val Ser His Glu Asp Pro Glu Val Lys Phe Asn Trp
                85                  90                  95

Tyr Val Asp Gly Val Glu Val His Asn Ala Lys Thr Lys Pro Arg Glu
            100                 105                 110

Glu Gln Tyr Asn Ser Thr Tyr Arg Val Val Ser Val Leu Thr Val Leu
        115                 120                 125

His Gln Asp Trp Leu Asn Gly Lys Glu Tyr Lys Cys Lys Val Ser Asn
130                 135                 140

Lys Ala Leu Pro Ala Pro Ile Glu Lys Thr Ile Ser Lys Ala Lys Gly
145                 150                 155                 160

Gln Pro Arg Glu Pro Gln Val Tyr Thr Leu Pro Pro Ser Arg Glu Glu
                165                 170                 175

Met Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn
        195                 200                 205

Asn Tyr Lys Thr Thr Pro Pro Val Leu Asp Ser Asp Gly Ser Phe Phe
210                 215                 220

Leu Tyr Ser Lys Leu Thr Val Asp Lys Ser Arg Trp Gln Gln Gly Asn
225                 230                 235                 240

Val Phe Ser Cys Ser Val Met His Glu Ala Leu His Asn His Tyr Thr
                245                 250                 255

Gln Lys Ser Leu Ser Leu Ser Pro Gly Lys Gly Ser Asp Ser Ser Pro
            260                 265                 270

Leu Leu Gln Phe Gly Gly Gln Val Arg Gln Arg Tyr Leu Tyr Thr Asp
```

```
            275                 280                 285
Asp Ala Cys Gln Thr Glu Ala His Leu Glu Ile Arg Glu Asp Gly Thr
    290                 295                 300

Val Gly Gly Ala Ala Asp Gln Ser Pro Glu Ser Leu Leu Gln Leu Lys
305                 310                 315                 320

Ala Leu Lys Pro Gly Val Ile Gln Ile Leu Gly Val Lys Thr Ser Arg
                325                 330                 335

Phe Leu Cys Gln Arg Pro Asp Gly Thr Leu Tyr Gly Ser Leu His Phe
            340                 345                 350

Asp Pro Glu Ala Cys Ser Phe Arg Glu Leu Leu Leu Glu Asp Gly Tyr
        355                 360                 365

Asn Val Tyr Gln Ser Glu Ala His Gly Leu Pro Leu His Leu Pro Cys
    370                 375                 380

Asn Arg Ser Pro His Arg Asp Pro Ala Ser Arg Gly Pro Ala Arg Phe
385                 390                 395                 400

Leu Pro Leu Pro Gly Leu Pro Pro Ala Leu Pro Glu Pro Pro Gly Ile
                405                 410                 415

Leu Ala Pro Gln Pro Pro Asp Val Gly Ser Ser Asp Pro Leu Ala Met
            420                 425                 430

Val Gly Gly Ser Gln Ala Arg Ser Pro Ser Tyr Ala Ser
        435                 440                 445

<210> SEQ ID NO 33
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
cacggagaag gcacctttac atcggacttg tcgaagcaga tggaggaaga agcggtgagg    60
ctcttcatcg agtggctcaa gaatggagga ccctcaagcg gagcgcctcc tccttccgac   120
aaaacccata catgtccgcc ttgtcccgca ccagaagcag cgggtgggcc ctcggtgttc   180
ctgttcccgc caaaaccgaa ggacacactt atgatttcac gcacaccgga agtgacttgc   240
gtcgtggtgg atgtatcgca cgaggacccc gaggtcaaat tcaactggta tgtcgatgga   300
gtggaggtgc acaatgcaaa gaccaagccg agggaagaac aatacaatag cacgtaccga   360
gtcgtgtccg tcttgacggt cctttaccag gactggctga acggaaagga gtacaagtgc   420
aaagtgagca ataaggccct ccctgccccg attgagaaaa ccatttccaa ggccaaaggt   480
cagcctagag aacctcaagt gtatactctt ccgccctcac gcgaagagat gacgaaaaac   540
caagtgtcgc ttacgtgtct tgtcaaaggt ttctacccct cggacatcgc cgtagagtgg   600
gagtcgaacg gccagccgga gaacaactac aagaccacgc ccctgtcttg gatagcgac    660 ggatcgtttt tcctctactc gaaactcaca gtagataagt cccgatggca cagggtaat    720 gtctttagct gcagcgtgat gcacgaggcg cttcacaatc attacacaca aaaatcactg   780
tcgcttagcc cgggaaaggg ttcagattcg tcgcccctgt tgcagtttgg tggacaggtc   840
agacagcgct acctttacac ggatgacgcc tgccagacag aggcacacct cgaaatcaga   900
gaggacggta cggtcggggg tgcggccgat cagagccccg agtcgcttct ccagttgaag   960
gcccttaagc caggagtcat ccagattttg ggagtaaaga cctcacggtt tctctgtcag  1020
cgtccagatg ggacactgta cggctcattg catttcgatc ccgaagcgtg ctcgttccgg  1080
```

```
gagttgctgc ttgaggacgg atataacgtc tatcagagcg aagcgcatgg cctccccctt    1140
cacctcccgt gtaacaggtc gccgcatcgg gatccggcct cgaggggtcc cgcgagattt    1200
cttccgttgc ccgggttgcc tcccgcgctg cccgagcctc ccgggatcct cgcgccacag    1260
cctcctgatg tagggtcctc ggacccttttg gcgatggtag gtggatcaca agcacggtcc    1320
ccgagctatg catca                                                     1335
```

<210> SEQ ID NO 34
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (161)..(161)
<223> OTHER INFORMATION: Any amino acid

<400> SEQUENCE: 34

```
His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Xaa Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
    210                 215
```

<210> SEQ ID NO 35
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
cattctgaag gcacttttac tagcgatgtt tctagctacc tggaaggcca ggctgcgaaa      60
```

```
gaattcatcg cgtggctggt taaaggcggt tctggtggtg gtggttctgg cggtggcgac      120
tcgagcccgc tgctgcagtt tggcggccag gtgcgtcagc gttatctgta taccgatgat      180
gcgcagcaga ccgaagcgca tctggaaatt cgtgaagatg caccgtggg cggtgcggcg       240 gatcagagcc ggaaagcct gctgcagctg aaagcgctga aaccgggcgt gattcagatt       300
ctgggcgtga aaccagccg ttttctgtgc cagcgtccgg atggcgcgct gtatggcagc       360
ctgcattttg atccggaagc gtgcagctttt cgtgaactgc tgctggaaga tggctataac    420
gtgtatcaga gcgaagcgca tggcctgccg ctgcatctgc cgggcaacaa aagcccgcat      480
taggatccgg caccgcgtgg tccggcgcgt tttctgccgc tgcccgggtct gccgccggca    540 ctgccggaac cgccgggtat tctggccccg cagccgccgg atgttggtag cagcgatccg      600
ctgtctatgg tgggtccgag ccagggtcgt agcccgagct atgcgagcta a               651
```

<210> SEQ ID NO 36
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Ser Gly Gly Gly Gly
        35                  40                  45

Ser Gly Gly Gly Gly Ser Asp Lys Thr His Thr Cys Pro Pro Cys Pro
    50                  55                  60

Ala Pro Glu Ala Ala Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser His Glu Asp Pro Glu Val Lys Phe Asn Trp Tyr
            100                 105                 110

Val Asp Gly Val Glu Val His Asn Ala Lys Thr Lys Pro Arg Glu Glu
        115                 120                 125

Gln Tyr Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Ala Leu Pro Ala Pro Ile Glu Lys Thr Ile Ser Lys Ala Lys Gly Gln
                165                 170                 175

Pro Arg Glu Pro Gln Val Tyr Thr Leu Pro Pro Ser Arg Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Lys Leu Thr Val Asp Lys Ser Arg Trp Gln Gln Gly Asn Val
                245                 250                 255
```

Phe Ser Cys Ser Val Met His Glu Ala Leu His Asn His Tyr Thr Gln
            260                 265                 270

Lys Ser Leu Ser Leu Ser Pro Gly Lys Gly Ser Asp Ser Ser Pro Leu
        275                 280                 285

Leu Gln Phe Gly Gly Gln Val Arg Gln Arg Tyr Leu Tyr Thr Asp Asp
    290                 295                 300

Ala Cys Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Arg Pro Asp Gly Thr Leu Tyr Gly Ser Leu His Phe Asp
        355                 360                 365

Pro Glu Ala Cys Ser Phe Arg Glu Leu Leu Leu Glu Asp Gly Tyr Asn
    370                 375                 380

Val Tyr Gln Ser Glu Ala His Gly Leu Pro Leu His Leu Pro Cys Asn
385                 390                 395                 400

Arg Ser Pro His Arg Asp Pro Ala Ser Arg Gly Pro Ala Arg Phe Leu
                405                 410                 415

Pro Leu Pro Gly Leu Pro Pro Ala Leu Pro Glu Pro Gly Ile Leu
            420                 425                 430

Ala Pro Gln Pro Pro Asp Val Gly Ser Ser Asp Pro Leu Ala Met Val
        435                 440                 445

Gly Gly Ser Gln Ala Arg Ser Pro Ser Tyr Ala Ser
    450                 455                 460

<210> SEQ ID NO 37
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
cacggagaag gcacctttac atcggacttg tcgaagcaga tggaggaaga agcggtgagg    60
ctcttcatcg agtggctcaa gaatggagga ccctcaagcg agcgcctcc tccttccgga   120 ggaggtgggt cgggcggtgg aggctccgga gggggaggga gcgacaaaac ccatacatgt   180
ccgccttgtc ccgcaccaga agcagcgggt gggccctcgg tgttcctgtt cccgccaaaa   240
ccgaaggaca cacttatgat ttcacgcaca ccggaagtga cttgcgtcgt ggtggatgta   300
tcgcacgagg accccgaggt caaattcaac tggtatgtcg atggagtgga ggtgcacaat   360
gcaaagacca agccgaggga agaacaatac aatagcacgt accgagtcgt gtccgtcttg   420
acggtccttc accaggactg gctgaacgga aggagtacaa gtgcaaagt gagcaataag   480 gccctccctg ccccgattga gaaaaccatt tccaaggcca aaggtcagcc tagagaacct   540
caagtgtata ctcttccgcc ctcacgcgaa gagatgacga aaaaccaagt gtcgcttacg   600
tgtcttgtca aaggtttcta ccccctcgga catcgccgtag agtgggagtc gaacggccag   660
ccggagaaca actacaagac cacgcccct gtcttggata gcgacggatc gttttttcctc   720 tactcgaaac tcacagtaga taagtcccga tggcaacagg gtaatgtctt tagctgcagc   780
gtgatgcacg aggcgcttca caatcattac acacaaaaat cactgtcgct tagcccggga   840

```
aagggttcag attcgtcgcc cctgttgcag tttggtggac aggtcagaca gcgctacctt      900
tacacggatg acgcctgcca gacagaggca cacctcgaaa tcagagagga cggtacggtc      960
gggggtgcgg ccgatcagag ccccgagtcg cttctccagt tgaaggccct taagccagga     1020
gtcatccaga ttttgggagt aaagacctca cggtttctct gtcagcgtcc agatgggaca     1080
ctgtacggct cattgcattt cgatcccgaa gcgtgctcgt tccgggagtt gctgcttgag     1140
gacggatata acgtctatca gagcgaagcg catggcctcc cccttcacct cccgtgtaac     1200
aggtcgccgc atcgggatcc ggcctcgagg gtcccgcga gatttcttcc gttgcccggg     1260
ttgcctcccg cgctgcccga gcctcccggg atcctcgcgc acagcctcc tgatgtaggg     1320 tcctcggacc ctttggcgat ggtaggtgga tcacaagcac ggtccccgag ctatgcatca     1380
```

<210> SEQ ID NO 38
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (169)..(169)
<223> OTHER INFORMATION: Any amino acid

<400> SEQUENCE: 38

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Ser Gly Gly Gly Asp
        35                  40                  45

Ser Ser Pro Leu Leu Gln Phe Gly Gly Gln Val Arg Gln Arg Tyr Leu
    50                  55                  60

Tyr Thr Asp Asp Ala Gln Gln Thr Glu Ala His Leu Glu Ile Arg Glu
65                  70                  75                  80

Asp Gly Thr Val Gly Gly Ala Ala Asp Gln Ser Pro Glu Ser Leu Leu
                85                  90                  95

Gln Leu Lys Ala Leu Lys Pro Gly Val Ile Gln Ile Leu Gly Val Lys
            100                 105                 110

Thr Ser Arg Phe Leu Cys Gln Arg Pro Asp Gly Ala Leu Tyr Gly Ser
        115                 120                 125

Leu His Phe Asp Pro Glu Ala Cys Ser Phe Arg Glu Leu Leu Leu Glu
    130                 135                 140

Asp Gly Tyr Asn Val Tyr Gln Ser Glu Ala His Gly Leu Pro Leu His
145                 150                 155                 160

Leu Pro Gly Asn Lys Ser Pro His Xaa Asp Pro Ala Pro Arg Gly Pro
                165                 170                 175

Ala Arg Phe Leu Pro Leu Pro Gly Leu Pro Ala Leu Pro Glu Pro
            180                 185                 190

Pro Gly Ile Leu Ala Pro Gln Pro Pro Asp Val Gly Ser Ser Asp Pro
        195                 200                 205

Leu Ser Met Val Gly Pro Ser Gln Gly Arg Ser Pro Ser Tyr Ala Ser
    210                 215                 220

<210> SEQ ID NO 39
<211> LENGTH: 675
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 39

```
catggtgagg gtacgtttac ttctgatctg tctaaacaga tggaagaaga agctgttcgc      60
ctgttcattg aatggctgaa aaatggtggt ccgtcctccg gcgctcctcc gccttctggt     120
ggtggtggtt ctggcggtgg cgactcgagc ccgctgctgc agtttggcgg ccaggtgcgt     180
cagcgttatc tgtataccga tgatgcgcag cagaccgaag cgcatctgga aattcgtgaa     240
gatggcaccg tgggcggtgc ggcggatcag agcccggaaa gcctgctgca gctgaaagcg     300
ctgaaaccgg gcgtgattca gattctgggc gtgaaaacca gccgttttct gtgccagcgt     360
ccggatggcg cgctgtatgg cagcctgcat tttgatccgg aagcgtgcag ctttcgtgaa     420
ctgctgctgg aagatggcta taacgtgtat cagagcgaag cgcatggcct gccgctgcat     480
ctgccgggca acaaaagccc gcattaggat ccggcaccgc gtggtccggc gcgttttctg     540
ccgctgccgg tcctgccgcc ggcactgccg gaaccgccgg gtattctggc cccgcagccg     600
ccggatgttg gtagcagcga tccgctgtct atggtgggtc cgagccaggg tcgtagcccg     660
agctatgcga gctaa                                                      675
```

<210> SEQ ID NO 40
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Cys Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
```

```
                    195                 200                 205
Gly Arg Ser Pro Ser Tyr Ala Ser
    210             215

<210> SEQ ID NO 41
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
cattctgaag gcacttttac tagcgatgtt tctagctacc tggaaggcca ggctgcgaaa      60
gaattcatcg cgtggctggt taaaggcggt tctggtggtg gtggttctgg cggtggcgac     120
tcgagcccgc tgctgcagtt tggcggccag gtgcgtcagc gttatctgta taccgatgat     180
gcgcagcaga ccgaagcgca tctggaaatt cgtgaagatg gcaccgtggg cggtgcggcg     240
gatcagagcc cggaaagcct gctgcagctg aaagcgctga aaccgggcgt gattcagatt     300
ctgggcgtga aaaccagccg tttttctgtgc cagcgtccgg atggcgcgct gtatggcagc     360
ctgcattttg atccggaagc gtgcagcttt cgtgaactgc tgctggaaga tggctataac     420
gtgtatcaga gcgaagcgca tggcctgccg ctgcatctgc cgggcaacaa aagcccgcat     480
tgcgatccgg caccgcgtgg tccggcgcgt tttctgccgc tgccgggtct gccgccggca     540
ctgccggaac cgccgggtat tctggccccg cagccgccgg atgttggtag cagcgatccg     600
ctgtctatgg tgggtccgag ccagggtcgt agcccgagct atgcgagcta a              651

<210> SEQ ID NO 42
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160
```

Cys Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
    210                 215

<210> SEQ ID NO 43
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
catgcggaag gcacttttac tagcgatgtt tctagctacc tggaaggcca ggctgcgaaa      60
gaattcatcg cgtggctggt taaaggcggt tctggtggtg gtggttctgg cggtggcgac     120
tcgagcccgc tgctgcagtt tggcggccag gtgcgtcagc gttatctgta taccgatgat     180
gcgcagcaga ccgaagcgca tctggaaatt cgtgaagatg gcaccgtggg cggtgcggcg     240
gatcagagcc cggaaagcct gctgcagctg aaagcgctga accgggcgt gattcagatt     300 ctgggcgtga aaccagccg tttttctgtgc agcgtccgg atggcgcgct gtatggcagc     360
ctgcattttg atccggaagc gtgcagcttt cgtgaactgc tgctggaaga tggctataac     420
gtgtatcaga gcgaagcgca tggcctgccg ctgcatctgc gggcaacaa aagcccgcat     480 tgcgatccgg caccgcgtgg tccggcgcgt tttctgccgc tgccgggtct gccgccggca     540
ctgccggaac cgccgggtat tctggccccg cagccgccgg atgttggtag cagcgatccg     600
ctgtctatgg tgggtccgag ccagggtcgt agcccgagct atgcgagcta a              651

<210> SEQ ID NO 44
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Ser Gly Gly Gly Gly Asp
        35                  40                  45

Ser Ser Pro Leu Leu Gln Phe Gly Gly Gln Val Arg Gln Arg Tyr Leu
    50                  55                  60

Tyr Thr Asp Asp Ala Gln Gln Thr Glu Ala His Leu Glu Ile Arg Glu
65                  70                  75                  80

Asp Gly Thr Val Gly Gly Ala Ala Asp Gln Ser Pro Glu Ser Leu Leu
                85                  90                  95

Gln Leu Lys Ala Leu Lys Pro Gly Val Ile Gln Ile Leu Gly Val Lys
            100                 105                 110

Thr Ser Arg Phe Leu Cys Gln Arg Pro Asp Gly Ala Leu Tyr Gly Ser
        115                 120                 125

Leu His Phe Asp Pro Glu Ala Cys Ser Phe Arg Glu Leu Leu Leu Glu
    130                 135                 140

Asp Gly Tyr Asn Val Tyr Gln Ser Glu Ala His Gly Leu Pro Leu His
145                 150                 155                 160

Leu Pro Gly Asn Lys Ser Pro His Cys Asp Pro Ala Pro Arg Gly Pro
                165                 170                 175

Ala Arg Phe Leu Pro Leu Pro Gly Leu Pro Ala Leu Pro Glu Pro
            180                 185                 190

Pro Gly Ile Leu Ala Pro Gln Pro Pro Asp Val Gly Ser Ser Asp Pro
            195                 200                 205

Leu Ser Met Val Gly Pro Ser Gln Gly Arg Ser Pro Ser Tyr Ala Ser
    210                 215                 220

<210> SEQ ID NO 45
<211> LENGTH: 675
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
catggtgagg gtacgtttac ttctgatctg tctaaacaga tggaagaaga agctgttcgc      60
ctgttcattg aatggctgaa aaatggtggt ccgtcctccg cgctcctcc gccttctggt     120 ggtggtggtt ctggcggtgg cgactcgagc ccgctgctgc agtttggcgg ccaggtgcgt    180
cagcgttatc tgtataccga tgatgcgcag cagaccgaag cgcatctgga aattcgtgaa    240
gatggcaccg tgggcggtgc ggcggatcag agcccggaaa gcctgctgca gctgaaagcg    300
ctgaaaccgg cgtgattca gattctgggc gtgaaaacca gccgttttct gtgccagcgt     360
ccggatggcg cgctgtatgg cagcctgcat tttgatccgg aagcgtgcag cttcgtgaa     420 ctgctgctgg aagatggcta taacgtgtat cagagcgaag cgcatggcct gccgctgcat    480
ctgccgggca acaaaagccc gcattgcgat ccggcaccgc gtggtccggc cgttttctg     540 ccgctgccgg gtctgccgcc ggcactgccg gaaccgccgg gtattctggc cccgcagccg    600
ccggatgttg gtagcagcga tccgctgtct atggtgggtc cgagccaggg tcgtagcccg    660
agctatgcga gctaa                                                     675

<210> SEQ ID NO 46
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

His Ala Pro Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
            35                  40                  45

Gly Gln Val Arg Gln Arg Tyr Leu Tyr Thr Asp Asp Ala Gln Gln Thr
        50                  55                  60

Glu Ala His Leu Glu Ile Arg Glu Asp Gly Thr Val Gly Gly Ala Ala
65                  70                  75                  80

```
Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
130                 135                 140

Glu Ala His Gly Leu Pro Leu His Leu Pro Gly Asn Lys Ser Pro His
145                 150                 155                 160

Cys Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
    210                 215

<210> SEQ ID NO 47
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
catgcgccgg gcacttttac tagcgatgtt tctagctacc tggaaggcca ggctgcgaaa      60
gaattcatcg cgtggctggt taaaggcggt tctggtggtg gtggttctgg cggtggcgac     120
tcgagcccgc tgctgcagtt tggcggccag gtgcgtcagc gttatctgta taccgatgat     180
gcgcagcaga ccgaagcgca tctggaaatt cgtgaagatg gcaccgtggg cggtgcggcg     240
gatcagagcc cggaaagcct gctgcagctg aaagcgctga accgggcgt gattcagatt     300 ctgggcgtga aaccagccg tttttctgtgc agcgtccgg atgcgcgct gtatggcagc      360 ctgcattttg atccggaagc gtgcagcttt cgtgaactgc tgctggaaga tggctataac     420
gtgtatcaga gcgaagcgca tggcctgccg ctgcatctgc cgggcaacaa aagcccgcat     480
tgcgatccgg caccgcgtgg tccggcgcgt tttctgccgc tgccgggtct gccgccggca     540
ctgccggaac cgccgggtat tctggccccg cagccgccgg atgttggtag cagcgatccg     600
ctgtctatgg tgggtccgag ccagggtcgt agcccgagct atgcgagcta a              651

<210> SEQ ID NO 48
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Gly Ser
            20                  25                  30

Gly Gly Gly Gly Ser Gly Gly Gly Asp Ser Ser Pro Leu Leu Gln Phe
```

```
                35                  40                  45
Gly Gly Gln Val Arg Gln Arg Tyr Leu Tyr Thr Asp Asp Ala Gln Gln
 50                  55                  60

Thr Glu Ala His Leu Glu Ile Arg Glu Asp Gly Thr Val Gly Gly Ala
 65                  70                  75                  80

Ala Asp Gln Ser Pro Glu Ser Leu Leu Gln Leu Lys Ala Leu Lys Pro
                 85                  90                  95

Gly Val Ile Gln Ile Leu Gly Val Lys Thr Ser Arg Phe Leu Cys Gln
            100                 105                 110

Arg Pro Asp Gly Ala Leu Tyr Gly Ser Leu His Phe Asp Pro Glu Ala
        115                 120                 125

Cys Ser Phe Arg Glu Leu Leu Leu Glu Asp Gly Tyr Asn Val Tyr Gln
    130                 135                 140

Ser Glu Ala His Gly Leu Pro Leu His Leu Pro Gly Asn Lys Ser Pro
145                 150                 155                 160

His Cys Asp Pro Ala Pro Arg Gly Pro Ala Arg Phe Leu Pro Leu Pro
                165                 170                 175

Gly Leu Pro Pro Ala Leu Pro Glu Pro Pro Gly Ile Leu Ala Pro Gln
            180                 185                 190

Pro Pro Asp Val Gly Ser Ser Asp Pro Leu Ser Met Val Gly Pro Ser
        195                 200                 205

Gln Gly Arg Ser Pro Ser Tyr Ala Ser
    210                 215
```

<210> SEQ ID NO 49
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49

```
ggtcatgcgg aaggcacttt tactagcgat gtttctagct acctggaagg ccaggctgcg    60
aaagaattca tcgcgtggct ggttaaaggc ggttctggtg gtggtggttc tggcggtggc   120
gactcgagcc cgctgctgca gtttggcggc caggtgcgtc agcgttatct gtataccgat   180
gatgcgcagc agaccgaagc gcatctggaa attcgtgaag atggcaccgt gggcggtgcg   240
gcggatcaga gcccggaaag cctgctgcag ctgaaagcgc tgaaaccggg cgtgattcag   300
attctgggcg tgaaaaccag ccgttttctg tgccagcgtc cggatggcgc gctgtatggc   360
agcctgcatt ttgatccgga agcgtgcagc tttcgtgaac tgctgctgga agatggctat   420
aacgtgtatc agagcgaagc gcatggcctg ccgctgcatc tgccgggcaa caaaagcccg   480
cattgcgatc cggcaccgcg tggtccggcg cgttttctgc cgctgccggg tctgccgccg   540
gcactgccgg aaccgccggg tattctggcc ccgcagccgc cggatgttgg tagcagcgat   600
ccgctgtcta tggtgggtcc gagccagggt cgtagcccga gctatgcgag ctaa         654
```

<210> SEQ ID NO 50
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
His Ser Glu Gly Thr Phe Thr Ala Asp Ala Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Cys Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
    210                 215

<210> SEQ ID NO 51
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
cattctgaag gcacttttac tgctgatgct tctagctacc tggaaggcca ggctgcgaaa      60
gaattcatcg cgtggctggt taaaggcggt tctggtggtg gtggttctgg cggtggcgac     120
tcgagcccgc tgctgcagtt tggcggccag gtgcgtcagc gttatctgta taccgatgat     180
gcgcagcaga ccgaagcgca tctggaaatt cgtgaagatg gcaccgtggg cggtgcggcg     240
gatcagagcc cggaaagcct gctgcagctg aaagcgctga aaccgggcgt gattcagatt     300
ctgggcgtga aaaccagccg ttttctgtgc cagcgtccgg atggcgcgct gtatggcagc     360
ctgcattttg atccggaagc gtgcagcttt cgtgaactgc tgctggaaga tggctataac     420
gtgtatcaga gcgaagcgca tggcctgccg ctgcatctgc cgggcaacaa aagcccgcat     480
tgcgatccgg caccgcgtgg tccggcgcgt tttctgccgc tgccgggtct gccgccggca     540
ctgccggaac cgccgggtat tctggccccg cagccgccgg atgttggtag cagcgatccg     600
ctgtctatgg tgggtccgag ccagggtcgt agcccgagct atgcgagcta a              651

<210> SEQ ID NO 52
<211> LENGTH: 216
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 52

```
His Ser Glu Gly Thr Phe Thr Ser Asp Ala Ala Tyr Leu Glu Gly
1               5                   10                  15
Gln Ala Ala Lys Glu Phe Ile Ala Trp Leu Val Lys Gly Gly Ser Gly
            20                  25                  30
Gly Gly Gly Ser Gly Gly Gly Asp Ser Ser Pro Leu Leu Gln Phe Gly
        35                  40                  45
Gly Gln Val Arg Gln Arg Tyr Leu Tyr Thr Asp Asp Ala Gln Gln Thr
    50                  55                  60
Glu Ala His Leu Glu Ile Arg Glu Asp Gly Thr Val Gly Gly Ala Ala
65                  70                  75                  80
Asp Gln Ser Pro Glu Ser Leu Leu Gln Leu Lys Ala Leu Lys Pro Gly
                85                  90                  95
Val Ile Gln Ile Leu Gly Val Lys Thr Ser Arg Phe Leu Cys Gln Arg
            100                 105                 110
Pro Asp Gly Ala Leu Tyr Gly Ser Leu His Phe Asp Pro Glu Ala Cys
        115                 120                 125
Ser Phe Arg Glu Leu Leu Leu Glu Asp Gly Tyr Asn Val Tyr Gln Ser
    130                 135                 140
Glu Ala His Gly Leu Pro Leu His Leu Pro Gly Asn Lys Ser Pro His
145                 150                 155                 160
Cys Asp Pro Ala Pro Arg Gly Pro Ala Arg Phe Leu Pro Leu Pro Gly
                165                 170                 175
Leu Pro Pro Ala Leu Pro Glu Pro Pro Gly Ile Leu Ala Pro Gln Pro
            180                 185                 190
Pro Asp Val Gly Ser Ser Asp Pro Leu Ser Met Val Gly Pro Ser Gln
        195                 200                 205
Gly Arg Ser Pro Ser Tyr Ala Ser
    210                 215
```

<210> SEQ ID NO 53
<211> LENGTH: 651
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

```
cattctgaag gcactttac tagcgatgct gctgcttacc tggaaggcca ggctgcgaaa    60
gaattcatcg cgtggctggt taaaggcggt tctggtggtg gtggttctgg cggtggcgac   120
tcgagcccgc tgctgcagtt tggcggccag gtgcgtcagc gttatctgta taccgatgat   180
gcgcagcaga ccgaagcgca tctggaaatt cgtgaagatg gcaccgtggg cggtgcggcg   240
gatcagagcc cggaaagcct gctgcagctg aaagcgctga accgggcgt gattcagatt   300
ctgggcgtga aaaccagccg tttttctgtgc cagcgtccgg atggcgcgct gtatggcagc   360
ctgcattttg atccggaagc gtgcagcttt cgtgaactgc tgctggaaga tggctataac   420
gtgtatcaga gcgaagcgca tggcctgccg ctgcatctgc cgggcaacaa aagcccgcat   480
tgcgatccgg caccgcgtgg tccggcgcgt tttctgccgc tgccgggtct gccgccggca   540
ctgccggaac cgccgggtat tctggccccg cagccgccgg atgttggtag cagcgatccg   600
```
ctgtctatgg tgggtccgag ccagggtcgt agcccgagct atgcgagcta a            651

<210> SEQ ID NO 54
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

His Ser Glu Gly Thr Phe Thr Ser Asp Val Ser Ser Tyr Ala Glu Gly
1               5                   10                  15

Ala Ala Ala Lys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Cys Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
    210                 215

<210> SEQ ID NO 55
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
cattctgaag gcacttttac tagcgatgtt tctagctacg ctgaaggcgc tgctgcgaaa       60
gaattcatcg cgtggctggt taaaggcggt tctggtggtg gtggttctgg cggtggcgac      120
tcgagcccgc tgctgcagtt tggcggccag gtgcgtcagc gttatctgta taccgatgat      180
gcgcagcaga ccgaagcgca tctggaaatt cgtgaagatg gcaccgtggg cggtgcggcg      240
gatcagagcc cggaaagcct gctgcagctg aaagcgctga aacccgggcgt gattcagatt      300 ctgggcgtga aaaccagccg ttttctgtgc cagcgtccgg atggcgcgct gtatggcagc      360

| | |
|---|---|
| ctgcattttg atccggaagc gtgcagcttt cgtgaactgc tgctggaaga tggctataac | 420 |
| gtgtatcaga gcgaagcgca tggcctgccg ctgcatctgc cgggcaacaa aagcccgcat | 480 |
| tgcgatccgg caccgcgtgg tccggcgcgt tttctgccgc tgccgggtct gccgccggca | 540 |
| ctgccggaac cgccgggtat tctggccccg cagccgccgg atgttggtag cagcgatccg | 600 |
| ctgtctatgg tgggtccgag ccagggtcgt agcccgagct atgcgagcta a | 651 |

<210> SEQ ID NO 56
<211> LENGTH: 1335
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 56

| | |
|---|---|
| cacggagaag gcacctttac atcggacttg tcgaagcaga tggaggaaga agcggtgagg | 60 |
| ctcttcatcg agtggctcaa gaatggagga ccctcaagcg gagcgcctcc tccttccgac | 120 |
| aaaacccata catgtccgcc ttgtcccgca ccagaagcag cgggtgggcc ctcggtgttc | 180 |
| ctgttcccgc caaaaccgaa ggacacactt atgatttcac gcacaccgga agtgacttgc | 240 |
| gtcgtggtgg atgtatcgca cgaggacccc gaggtcaaat tcaactggta tgtcgatgga | 300 |
| gtggaggtgc acaatgcaaa gaccaagccg agggaagaac aatacaatag cacgtaccga | 360 |
| gtcgtgtccg tcttgacggt ccttcaccag gactggctga acggaaagga gtacaagtgc | 420 |
| aaagtgagca ataaggccct ccctgccccg attgagaaaa ccatttccaa ggccaaaggt | 480 |
| cagcctagag aacctcaagt gtatactctt ccgccctcac gcgaagagat gacgaaaaac | 540 |
| caagtgtcgc ttacgtgtct tgtcaaaggt ttctaccccct cggacatcgc cgtagagtgg | 600 |
| gagtcgaacg gccagccgga gaacaactac aagaccacgc cccctgtctt ggatagcgac | 660 |
| ggatcgtttt tcctctactc gaaactcaca gtagataagt cccgatggca acagggtaat | 720 |
| gtctttagct gcagcgtgat gcacgaggcg cttcacaatc attacacaca aaaatcactg | 780 |
| tcgcttagcc cggaaagggg ttcagattcg tcgcccctgt tgcagtttgg tggacaggtc | 840 |
| agacagcgct acctttacac ggatgacgcc tgccagacag aggcacacct cgaaatcaga | 900 |
| gaggacggta cggtcggggg tgcggccgat cagagccccg agtcgcttct ccagttgaag | 960 |
| gcccttaagc caggagtcat ccagattttg ggagtaaaga cctcacggtt tctctgtcag | 1020 |
| aaaccagatg gggcactgta cggctcattg catttcgatc ccgaagcgtg ctcgttccgg | 1080 |
| gagttgctgc ttgaggacgg atataacgtc tatcagagcg aagcgcatgg cctcccccctt | 1140 |
| cacctcccgt gtaacaggtc gccgcatcgg gatccggcct cgaggggtcc cgcgagattt | 1200 |
| cttccgttgc ccgggttgcc tcccgcgctg cccgagcctc ccgggatcct cgcgccacag | 1260 |
| cctcctgatg tagggtcctc ggacccttg gcgatggtag gtggatcaca agcacggtcc | 1320 |
| ccgagctatg catca | 1335 |

<210> SEQ ID NO 57
<211> LENGTH: 1380
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 57

| | |
|---|---|
| cacggagaag gcacctttac atcggacttg tcgaagcaga tggaggaaga agcggtgagg | 60 |

```
ctcttcatcg agtggctcaa gaatggagga ccctcaagcg gagcgcctcc tccttccgga    120
ggaggtgggt cgggcggtgg aggctccgga gggggaggga gcgacaaaac ccatacatgt    180
ccgccttgtc ccgcaccaga agcagcgggt gggccctcgg tgttcctgtt cccgccaaaa    240
ccgaaggaca cacttatgat ttcacgcaca ccggaagtga cttgcgtcgt ggtggatgta    300
tcgcacgagg accccgaggt caaattcaac tggtatgtcg atggagtgga ggtgcacaat    360
gcaaagacca agccgaggga agaacaatac aatagcacgt accgagtcgt gtccgtcttg    420
acggtccttc accaggactg gctgaacgga aaggagtaca agtgcaaagt gagcaataag    480
gccctccctg ccccgattga gaaaaccatt tccaaggcca aggtcagcc tagagaacct     540 caagtgtata ctcttccgcc ctcacgcgaa gagatgacga aaaaccaagt gtcgcttacg    600
tgtcttgtca aaggtttcta cccctcggac atcgccgtag agtgggagtc gaacggccag    660
ccggagaaca actacaagac cacgccccct gtcttggata gcgacggatc gttttcctc    720 tactcgaaac tcacagtaga taagtcccga tggcaacagg gtaatgtctt tagctgcagc    780
gtgatgcacg aggcgcttca caatcattac acacaaaaat cactgtcgct tagcccggga    840
aagggttcag attcgtcgcc cctgttgcag tttggtggac aggtcagaca gcgctacctt    900
tacacggatg acgcctgcca gacagaggca cacctcgaaa tcagagagga cggtacggtc    960
gggggtgcgg ccgatcagag ccccgagtcg cttctccagt tgaaggccct taagccagga   1020
gtcatccaga ttttgggagt aaagacctca cggtttctct gtcagaaacc agatggggca   1080
ctgtacggct cattgcattt cgatcccgaa gcgtgctcgt tccgggagtt gctgcttgag   1140
gacggatata acgtctatca gagcgaagcg catggcctcc cccttcacct cccgtgtaac   1200
aggtcgccgc atcgggatcc ggcctcgagg ggtcccgcga gatttcttcc gttgcccggg   1260
ttgcctcccg cgctgcccga gcctcccggg atcctcgcgc acagcctcc tgatgtaggg   1320 tcctcggacc ctttggcgat ggtaggtgga tcacaagcac ggtccccgag ctatgcatca   1380
```

<210> SEQ ID NO 58
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
His Ser Glu Gly Thr Phe Thr Ser Asp Ser Pro Leu Leu Gln Phe
1               5                   10                  15

Gly Gly Gln Val Arg Gln Arg Tyr Leu Tyr Thr Asp Asp Ala Gln Gln
            20                  25                  30

Thr Glu Ala His Leu Glu Ile Arg Glu Asp Gly Thr Val Gly Gly Ala
        35                  40                  45

Ala Asp Gln Ser Pro Glu Ser Leu Leu Gln Leu Lys Ala Leu Lys Pro
    50                  55                  60

Gly Val Ile Gln Ile Leu Gly Val Lys Thr Ser Arg Phe Leu Cys Gln
65                  70                  75                  80

Arg Pro Asp Gly Ala Leu Tyr Gly Ser Leu His Phe Asp Pro Glu Ala
                85                  90                  95

Cys Ser Phe Arg Glu Leu Leu Leu Glu Asp Gly Tyr Asn Val Tyr Gln
            100                 105                 110

Ser Glu Ala His Gly Leu Pro Leu His Leu Pro Gly Asn Lys Ser Pro
        115                 120                 125
```

His Cys Asp Pro Ala Pro Arg Gly Pro Ala Arg Phe Leu Pro Leu Pro
    130                 135                 140

Gly Leu Pro Pro Ala Leu Pro Glu Pro Pro Gly Ile Leu Ala Pro Gln
145                 150                 155                 160

Pro Pro Asp Val Gly Ser Ser Asp Pro Leu Ser Met Val Gly Pro Ser
                165                 170                 175

Gln Gly Arg Ser Pro Ser Tyr Ala Ser
            180                 185

<210> SEQ ID NO 59
<211> LENGTH: 558
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
cattctgaag gcactttac tagcgatagc agcccgctgc tgcagtttgg cggccaggtg      60
cgtcagcgtt atctgtatac cgatgatgcg cagcagaccg aagcgcatct ggaaattcgt    120
gaagatggca ccgtgggcgg tgcggcggat cagagcccgg aaagcctgct gcagctgaaa    180
gcgctgaaac cgggcgtgat tcagattctg ggcgtgaaaa ccagccgttt tctgtgccag    240
cgtccggatg gcgcgctgta tggcagcctg cattttgatc cggaagcgtg cagctttcgt    300
gaactgctgc tggaagatgg ctataacgtg tatcagagcg aagcgcatgg cctgccgctg    360
catctgccgg gcaacaaaag cccgcattgc gatccggcac cgcgtggtcc ggcgcgtttt    420
ctgccgctgc cgggtctgcc gccggcactg ccggaaccgc cgggtattct ggccccgcag    480
ccgccggatg ttggtagcag cgatccgctg tctatggtgg gtccgagcca gggtcgtagc    540
ccgagctatg cgagctaa                                                   558

<210> SEQ ID NO 60
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

His Ser Glu Gly Thr Phe Thr Ser Asp Val Ser Ser Gly Gly Gly Gly
1               5                   10                  15

Ser Gly Gly Gly Asp Ser Ser Pro Leu Leu Gln Phe Gly Gly Gln Val
            20                  25                  30

Arg Gln Arg Tyr Leu Tyr Thr Asp Asp Ala Gln Gln Thr Glu Ala His
        35                  40                  45

Leu Glu Ile Arg Glu Asp Gly Thr Val Gly Gly Ala Ala Asp Gln Ser
    50                  55                  60

Pro Glu Ser Leu Leu Gln Leu Lys Ala Leu Lys Pro Gly Val Ile Gln
65                  70                  75                  80

Ile Leu Gly Val Lys Thr Ser Arg Phe Leu Cys Gln Arg Pro Asp Gly
                85                  90                  95

Ala Leu Tyr Gly Ser Leu His Phe Asp Pro Glu Ala Cys Ser Phe Arg
            100                 105                 110

Glu Leu Leu Leu Glu Asp Gly Tyr Asn Val Tyr Gln Ser Glu Ala His
        115                 120                 125

Gly Leu Pro Leu His Leu Pro Gly Asn Lys Ser Pro His Cys Asp Pro
        130                 135                 140

Ala Pro Arg Gly Pro Ala Arg Phe Leu Pro Leu Pro Gly Leu Pro Pro
145                 150                 155                 160

Ala Leu Pro Glu Pro Pro Gly Ile Leu Ala Pro Gln Pro Pro Asp Val
                165                 170                 175

Gly Ser Ser Asp Pro Leu Ser Met Val Gly Pro Ser Gln Gly Arg Ser
            180                 185                 190

Pro Ser Tyr Ala Ser
        195

<210> SEQ ID NO 61
<211> LENGTH: 594
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
cattctgaag gcactttac tagcgatgtt tcttctggtg gtggtggttc tggcggtggc    60
gactcgagcc cgctgctgca gtttggcggc caggtgcgtc agcgttatct gtataccgat   120
gatgcgcagc agaccgaagc gcatctggaa attcgtgaag atggcaccgt gggcggtgcg   180
gcggatcaga gcccggaaag cctgctgcag ctgaaagcgc tgaaaccggg cgtgattcag   240
attctgggcg tgaaaaccag ccgttttctg tgccagcgtc cggatggcgc gctgtatggc   300
agcctgcatt ttgatccgga agcgtgcagc tttcgtgaac tgctgctgga agatggctat   360
aacgtgtatc agagcgaagc gcatggcctg ccgctgcatc tgccgggcaa caaaagcccg   420
cattgcgatc cggcaccgcg tggtccggcg cgttttctgc cgctgccggg tctgccgccg   480
gcactgccgg aaccgccggg tattctggcc ccgcagccgc cggatgttgg tagcagcgat   540
ccgctgtcta tggtgggtcc gagccagggt cgtagcccga gctatgcgag ctaa         594

<210> SEQ ID NO 62
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

His Ser Glu Gly Thr Phe Thr Ser Asp Val Ser Ser Tyr Leu Glu Ser
1               5                   10                  15

Gly Gly Gly Gly Ser Gly Gly Gly Asp Ser Ser Pro Leu Leu Gln Phe
            20                  25                  30

Gly Gly Gln Val Arg Gln Arg Tyr Leu Tyr Thr Asp Asp Ala Gln Gln
        35                  40                  45

Thr Glu Ala His Leu Glu Ile Arg Glu Asp Gly Thr Val Gly Gly Ala
    50                  55                  60

Ala Asp Gln Ser Pro Glu Ser Leu Leu Gln Leu Lys Ala Leu Lys Pro
65                  70                  75                  80

Gly Val Ile Gln Ile Leu Gly Val Lys Thr Ser Arg Phe Leu Cys Gln
                85                  90                  95

Arg Pro Asp Gly Ala Leu Tyr Gly Ser Leu His Phe Asp Pro Glu Ala
            100                 105                 110

Cys Ser Phe Arg Glu Leu Leu Leu Glu Asp Gly Tyr Asn Val Tyr Gln

| | 115 | | | 120 | | | | 125 | | | |
|---|---|---|---|---|---|---|---|---|---|---|---|

Ser Glu Ala His Gly Leu Pro Leu His Leu Pro Gly Asn Lys Ser Pro
130                 135                 140

His Cys Asp Pro Ala Pro Arg Gly Pro Ala Arg Phe Leu Pro Leu Pro
145                 150                 155                 160

Gly Leu Pro Pro Ala Leu Pro Glu Pro Pro Gly Ile Leu Ala Pro Gln
            165                 170                 175

Pro Pro Asp Val Gly Ser Ser Asp Pro Leu Ser Met Val Gly Pro Ser
        180                 185                 190

Gln Gly Arg Ser Pro Ser Tyr Ala Ser
        195                 200

<210> SEQ ID NO 63
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
cattctgaag gcactttac tagcgatgtt tctagctacc tggaatctgg tggtggtggt        60
tctggcggtg cgactcgag cccgctgctg cagtttggcg ccaggtgcg tcagcgttat       120 ctgtataccg atgatgcgca gcagaccgaa gcgcatctgg aaattcgtga agatggcacc     180
gtgggcggtg cggcggatca gagcccggaa agcctgctgc agctgaaagc gctgaaaccg     240
ggcgtgattc agattctggg cgtgaaaacc agccgttttc tgtgccagcg tccggatggc     300
gcgctgtatg cagcctgca ttttgatccg gaagcgtgca gctttcgtga actgctgctg     360
gaagatggct ataacgtgta tcagagcgaa gcgcatggcc tgccgctgca tctgccgggc     420
aacaaaagcc cgcattgcga tccggcaccg cgtggtccgg cgcgtttctt gccgctgccg     480
ggtctgccgc cggcactgcc ggaaccgccg ggtattctgg ccccgcagcc gccggatgtt     540
ggtagcagcg atccgctgtc tatggtgggt ccgagccagg gtcgtagccc gagctatgcg     600
agctaa                                                                  606

<210> SEQ ID NO 64
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
cactccgaag gaacattcac ttccgatgta agctcgtatt tggaagggca ggcggctaag        60
gagtttatcg catggttggt caaaggtggt ggaggtgggt cgggcggtgg aggctccgga       120
gggggaggga gcgacaaaac ccatacatgt ccgccttgtc ccgcaccaga agcagcgggt       180
gggccctcgg tgttcctgtt cccgccaaaa ccgaaggaca cacttatgat ttcacgcaca       240
ccggaagtga cttgcgtcgt ggtggatgta tcgcacgagg accccgaggt caaattcaac       300
tggtatgtcg atggagtgga ggtgcacaat gcaaagacca gccgaggga gaacaatac       360 aatagcacgt accgagtcgt gtccgtcttg acggtccttc accaggactg gctgaacgga     420
aaggagtaca gtgcaaagt gagcaataag gccctccctg ccccgattga gaaaaccatt       480
tccaaggcca aggtcagcc tagagaacct caagtgtata ctcttccgcc ctcacgcgaa       540

```
gagatgacga aaaccaagt  gtcgcttacg tgtcttgtca aaggtttcta cccctcggac    600
atcgccgtag agtgggagtc gaacggccag ccggagaaca actacaagac cacgccccct    660
gtcttggata gcgacggatc gttttcctc  tactcgaaac tcacagtaga taagtcccga    720
tggcaacagg gtaatgtctt tagctgcagc gtgatgcacg aggcgcttca caatcattac    780
acacaaaaat cactgtcgct tagcccggga aagggttcag attcgtcgcc cctgttgcag    840
tttggtggac aggtcagaca gcgctacctt tacacggatg acgcctgcca gacagaggca    900
cacctcgaaa tcagagagga cggtacggtc gggggtgcgg ccgatcagag ccccgagtcg    960
cttctccagt tgaaggccct taagccagga gtcatccaga ttttgggagt aaagacctca   1020
cggtttctct gtcagcgtcc agatgggaca ctgtacggct cattgcattt cgatcccgaa   1080
gcgtgctcgt tccgggagtt gctgcttgag gacggatata acgtctatca gagcgaagcg   1140
catggcctcc cccttcacct cccgtgtaac aggtcgccgc atcgggatcc ggcctcgagg   1200
ggtcccgcga gatttcttcc gttgcccggg ttgcctcccg cgctgcccga gcctcccggg   1260
atcctcgcgc cacagcctcc tgatgtaggg tcctcggacc ctttggcgat ggtaggtgga   1320
tcacaagcac ggtccccgag ctatgcatca                                    1350
```

<210> SEQ ID NO 65
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
cactccgaag gaacattcac ttccgatgta agctcgtatt tggaagggca ggcggctaag     60
gagtttatcg catggttggt caaaggtggt ggaggtgggt cgggcggtgg aggctccgga    120
gggggaggga gcgacaaaac ccatacatgt ccgccttgtc ccgcaccaga agcagcgggt    180
gggccctcgg tgttcctgtt cccgccaaaa ccgaaggaca cacttatgat ttcacgcaca    240
ccggaagtga cttgcgtcgt ggtggatgta tcgcacgagg accccgaggt caaattcaac    300
tggtatgtcg atggagtgga ggtgcacaat gcaaagacca gccgaggga  agaacaatac    360 aatagcacgt accgagtcgt gtccgtcttg acggtccttc accaggactg gctgaacgga    420
aaggagtaca agtgcaaagt gagcaataag gccctccctg ccccgattga gaaaaccatt    480
tccaaggcca aggtcagcc  tagagaacct caagtgtata ctcttccgcc ctcacgcgaa    540
gagatgacga aaaccaagt  gtcgcttacg tgtcttgtca aggtttcta  cccctcggac    600 atcgccgtag agtgggagtc gaacggccag ccggagaaca actacaagac cacgccccct    660
gtcttggata gcgacggatc gttttcctc  tactcgaaac tcacagtaga taagtcccga    720
tggcaacagg gtaatgtctt tagctgcagc gtgatgcacg aggcgcttca caatcattac    780
acacaaaaat cactgtcgct tagcccggga aagggttcag attcgtcgcc cctgttgcag    840
tttggtggac aggtcagaca gcgctacctt tacacggatg acgcctgcca gacagaggca    900
cacctcgaaa tcagagagga cggtacggtc gggggtgcgg ccgatcagag ccccgagtcg    960
cttctccagt tgaaggccct taagccagga gtcatccaga ttttgggagt aaagacctca   1020
cggtttctct gtcagaaacc agatgggca  ctgtacggct cattgcattt cgatcccgaa   1080
gcgtgctcgt tccgggagtt gctgcttgag gacggatata acgtctatca gagcgaagcg   1140
catggcctcc cccttcacct cccgtgtaac aggtcgccgc atcgggatcc ggcctcgagg   1200
```

```
ggtcccgcga gatttcttcc gttgcccggg ttgcctcccg cgctgcccga gcctcccggg    1260
atcctcgcgc cacagcctcc tgatgtaggg tcctcggacc ctttggcgat ggtaggtgga    1320
tcacaagcac ggtccccgag ctatgcatca                                     1350
```

<210> SEQ ID NO 66
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
His Ser Glu Gly Thr Phe Thr Ser Asp Val Ser Ser Tyr Leu Glu Gly
1               5                   10                  15

Gln Ala Ala Lys Glu Phe Ile Ser Gly Gly Gly Ser Gly Gly Gly
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Cys Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 67
<211> LENGTH: 630
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
cattctgaag gcacttttac tagcgatgtt tctagctacc tggaaggcca ggctgcgaaa     60
gaattcatct ctggtggtgg tggttctggc ggtggcgact cgagcccgct gctgcagttt    120
ggcggccagg tgcgtcagcg ttatctgtat accgatgatg cgcagcagac cgaagcgcat    180
ctggaaattc gtgaagatgg caccgtgggc ggtgcggcgg atcagagccc ggaaagcctg    240
ctgcagctga aagcgctgaa accgggcgtg attcagattc tgggcgtgaa aaccagccgt    300
```

```
tttctgtgcc agcgtccgga tggcgcgctg tatggcagcc tgcattttga tccggaagcg    360
tgcagctttc gtgaactgct gctggaagat ggctataacg tgtatcagag cgaagcgcat    420
ggcctgccgc tgcatctgcc gggcaacaaa agcccgcatt gcgatccggc accgcgtggt    480
ccggcgcgtt ttctgccgct gccgggtctg ccgccggcac tgccggaacc gccgggtatt    540
ctggccccgc agccgccgga tgttggtagc agcgatccgc tgtctatggt gggtccgagc    600
cagggtcgta gcccgagcta tgcgagctaa                                    630
```

```
<210> SEQ ID NO 68
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

His Ser Glu Gly Thr Phe Thr Ser Asp Val Ser Ser Tyr Leu Glu Gly
1               5                   10                  15

Gln Ala Ala Lys Glu Phe Ile Ala Trp Leu Ser Gly Gly Gly Gly Ser
            20                  25                  30

Gly Gly Gly Asp Ser Ser Pro Leu Leu Gln Phe Gly Gly Gln Val Arg
        35                  40                  45

Gln Arg Tyr Leu Tyr Thr Asp Asp Ala Gln Gln Thr Glu Ala His Leu
    50                  55                  60

Glu Ile Arg Glu Asp Gly Thr Val Gly Gly Ala Ala Asp Gln Ser Pro
65                  70                  75                  80

Glu Ser Leu Leu Gln Leu Lys Ala Leu Lys Pro Gly Val Ile Gln Ile
                85                  90                  95

Leu Gly Val Lys Thr Ser Arg Phe Leu Cys Gln Arg Pro Asp Gly Ala
            100                 105                 110

Leu Tyr Gly Ser Leu His Phe Asp Pro Glu Ala Cys Ser Phe Arg Glu
        115                 120                 125

Leu Leu Leu Glu Asp Gly Tyr Asn Val Tyr Gln Ser Glu Ala His Gly
    130                 135                 140

Leu Pro Leu His Leu Pro Gly Asn Lys Ser Pro His Cys Asp Pro Ala
145                 150                 155                 160

Pro Arg Gly Pro Ala Arg Phe Leu Pro Leu Pro Gly Leu Pro Pro Ala
                165                 170                 175

Leu Pro Glu Pro Pro Gly Ile Leu Ala Pro Gln Pro Pro Asp Val Gly
            180                 185                 190

Ser Ser Asp Pro Leu Ser Met Val Gly Pro Ser Gln Gly Arg Ser Pro
        195                 200                 205

Ser Tyr Ala Ser
        210
```

```
<210> SEQ ID NO 69
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
cattctgaag gcactttttac tagcgatgtt tctagctacc tggaaggcca ggctgcgaaa    60
gaattcatcg cgtggctgtc tggtggtggt ggttctggcg gtggcgactc gagcccgctg    120
```

```
ctgcagtttg gcggccaggt gcgtcagcgt tatctgtata ccgatgatgc gcagcagacc    180
gaagcgcatc tggaaattcg tgaagatggc accgtgggcg gtgcggcgga tcagagcccg    240
gaaagcctgc tgcagctgaa agcgctgaaa ccgggcgtga ttcagattct gggcgtgaaa    300
accagccgtt ttctgtgcca gcgtccggat ggcgcgctgt atggcagcct gcattttgat    360
ccggaagcgt gcagctttcg tgaactgctg ctggaagatg gctataacgt gtatcagagc    420
gaagcgcatg gcctgccgct gcatctgccg ggcaacaaaa gcccgcattg cgatccggca    480
ccgcgtggtc cggcgcgttt tctgccgctg ccgggtctgc cgccggcact gccggaaccg    540
ccgggtattc tggccccgca gccgccggat gttggtagca gcgatccgct gtctatggtg    600
ggtccgagcc agggtcgtag cccgagctat gcgagctaa                           639
```

<210> SEQ ID NO 70
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
His Ser Glu Gly Thr Phe Thr Ser Asp Val Cys Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Arg Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
    210                 215
```

<210> SEQ ID NO 71
<211> LENGTH: 651
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
cattctgaag gcacttttac tagcgatgtt tgtagctacc tggaaggcca ggctgcgaaa      60
gaattcatcg cgtggctggt taaaggcggt tctggtggtg gtggttctgg cggtggcgac     120
tcgagcccgc tgctgcagtt tggcggccag gtgcgtcagc gttatctgta taccgatgat     180
gcgcagcaga ccgaagcgca tctggaaatt cgtgaagatg gcaccgtggg cggtgcggcg     240
gatcagagcc cggaaagcct gctgcagctg aaagcgctga accgggcgt gattcagatt      300
ctgggcgtga aaaccagccg tttttctgtgc cagcgtccgg atggcgcgct gtatggcagc     360
ctgcattttg atccggaagc gtgcagcttt cgtgaactgc tgctggaaga tggctataac     420
gtgtatcaga gcgaagcgca tggcctgccg ctgcatctgc cgggcaacaa aagcccgcat     480
cgtgatccgg caccgcgtgg tccggcgcgt tttctgccgc tgccgggtct gccgccggca     540
ctgccggaac cgccgggtat tctggccccg cagccgccgg atgttggtag cagcgatccg     600
ctgtctatgg tgggtccgag ccagggtcgt agcccgagct atgcgagcta a              651
```

<210> SEQ ID NO 72
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
His Ser Glu Gly Thr Phe Thr Ser Asp Val Ser Ser Tyr Leu Glu Gly
  1               5                  10                  15
Cys Ala Ala Lys Glu Phe Ile Ala Trp Leu Val Lys Gly Gly Ser Gly
             20                  25                  30
Gly Gly Gly Ser Gly Gly Gly Asp Ser Ser Pro Leu Leu Gln Phe Gly
         35                  40                  45
Gly Gln Val Arg Gln Arg Tyr Leu Tyr Thr Asp Asp Ala Gln Gln Thr
     50                  55                  60
Glu Ala His Leu Glu Ile Arg Glu Asp Gly Thr Val Gly Gly Ala Ala
 65                  70                  75                  80
Asp Gln Ser Pro Glu Ser Leu Leu Gln Leu Lys Ala Leu Lys Pro Gly
                 85                  90                  95
Val Ile Gln Ile Leu Gly Val Lys Thr Ser Arg Phe Leu Cys Gln Arg
            100                 105                 110
Pro Asp Gly Ala Leu Tyr Gly Ser Leu His Phe Asp Pro Glu Ala Cys
        115                 120                 125
Ser Phe Arg Glu Leu Leu Leu Glu Asp Gly Tyr Asn Val Tyr Gln Ser
    130                 135                 140
Glu Ala His Gly Leu Pro Leu His Leu Pro Gly Asn Lys Ser Pro His
145                 150                 155                 160
Arg Asp Pro Ala Pro Arg Gly Pro Ala Arg Phe Leu Pro Leu Pro Gly
                165                 170                 175
Leu Pro Pro Ala Leu Pro Glu Pro Pro Gly Ile Leu Ala Pro Gln Pro
            180                 185                 190
Pro Asp Val Gly Ser Ser Asp Pro Leu Ser Met Val Gly Pro Ser Gln
        195                 200                 205
Gly Arg Ser Pro Ser Tyr Ala Ser
    210                 215
```

<210> SEQ ID NO 73
<211> LENGTH: 651
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73

```
cattctgaag gcacttttac tagcgatgtt tctagctacc tggaaggctg tgctgcgaaa      60
gaattcatcg cgtggctggt taaaggcggt tctggtggtg gtggttctgg cggtggcgac     120
tcgagcccgc tgctgcagtt tggcggccag gtgcgtcagc gttatctgta taccgatgat     180
gcgcagcaga ccgaagcgca tctggaaatt cgtgaagatg gcaccgtggg cggtgcggcg     240
gatcagagcc cggaaagcct gctgcagctg aaagcgctga accgggcgt gattcagatt      300
ctgggcgtga aaccagccg ttttctgtgc cagcgtccgg atggcgcgct gtatggcagc      360
ctgcattttg atccggaagc gtgcagcttt cgtgaactgc tgctggaaga tggctataac      420
gtgtatcaga gcgaagcgca tggcctgccg ctgcatctgc cgggcaacaa aagcccgcat      480
cgtgatccgg caccgcgtgg tccggcgcgt tttctgccgc tgccgggtct gccgccggca      540
ctgccggaac cgccgggtat tctggccccg cagccgccgg atgttggtag cagcgatccg      600
ctgtctatgg tgggtccgag ccagggtcgt agcccgagct atgcgagcta a               651
```

<210> SEQ ID NO 74
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
His Ser Glu Gly Thr Phe Thr Ser Asp Val Ser Ser Tyr Leu Glu Gly
1               5                   10                  15

Gln Ala Ala Cys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Arg Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190
```

Pro Asp Val Gly Ser Ser Asp Pro Leu Ser Met Val Gly Pro Ser Gln
        195                 200                 205

Gly Arg Ser Pro Ser Tyr Ala Ser
    210                 215

<210> SEQ ID NO 75
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
cattctgaag gcacttttac tagcgatgtt tctagctacc tggaaggcca ggctgcgtgt    60
gaattcatcg cgtggctggt taaaggcggt tctggtggtg gtggttctgg cggtggcgac   120
tcgagcccgc tgctgcagtt tggcggccag gtgcgtcagc gttatctgta taccgatgat   180
gcgcagcaga ccgaagcgca tctggaaatt cgtgaagatg gcaccgtggg cggtgcggcg   240
gatcagagcc cggaaagcct gctgcagctg aaagcgctga accgggcgt gattcagatt   300 ctgggcgtga aaccagccg ttttctgtgc cagcgtccgg atggcgcgct gtatggcagc   360
ctgcattttg atccggaagc gtgcagcttt cgtgaactgc tgctggaaga tggctataac   420
gtgtatcaga gcgaagcgca tggcctgccg ctgcatctgc cgggcaacaa aagcccgcat   480
cgtgatccgg caccgcgtgg tccggcgcgt tttctgccgc tgccgggtct gccgccggca   540
ctgccggaac cgccgggtat tctggccccg cagccgccgg atgttggtag cagcgatccg   600
ctgtctatgg tgggtccgag ccagggtcgt agcccgagct atgcgagcta a             651

<210> SEQ ID NO 76
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

His Ser Glu Gly Thr Phe Thr Ser Asp Val Ser Ser Tyr Leu Glu Gly
1               5                  10                  15

Gln Ala Ala Lys Cys Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Lys Ser Pro His

```
                    145                 150                 155                 160
Arg Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
    210                 215

<210> SEQ ID NO 77
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
cattctgaag gcacttttac tagcgatgtt tctagctacc tggaaggcca ggctgcgaaa      60
tgtttcatcg cgtggctggt taaaggcggt tctggtggtg gtggttctgg cggtggcgac     120
tcgagcccgc tgctgcagtt tggcggccag gtgcgtcagc gttatctgta taccgatgat     180
gcgcagcaga ccgaagcgca tctggaaatt cgtgaagatg gcaccgtggg cggtgcggcg     240
gatcagagcc cggaaagcct gctgcagctg aaagcgctga accgggcgt gattcagatt      300 ctgggcgtga aaaccagccg ttttctgtgc cagcgtccgg atggcgcgct gtatggcagc     360
ctgcattttg atccggaagc gtgcagcttt cgtgaactgc tgctggaaga tggctataac     420
gtgtatcaga gcgaagcgca tggcctgccg ctgcatctgc cggcaacaa aagcccgcat      480 cgtgatccgg caccgcgtgg tccggcgcgt tttctgccgc tgccgggtct gccgccggca     540
ctgccggaac cgccgggtat tctgccccg cagccgccgg atgttggtag cagcgatccg      600
ctgtctatgg tgggtccgag ccagggtcgt agcccgagct atgcgagcta a              651

<210> SEQ ID NO 78
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Cys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110
```

```
Pro Asp Gly Ala Leu Tyr Gly Ser Leu His Phe Asp Pro Glu Ala Cys
            115                 120                 125

Ser Phe Arg Glu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Arg Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
                180                 185                 190

Pro Asp Val Gly Ser Ser Asp Pro Leu Ser Met Val Gly Pro Ser Gln
                195                 200                 205

Gly Arg Ser Pro Ser Tyr Ala Ser
    210                 215
```

<210> SEQ ID NO 79
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
cattctgaag gcacttttac tagcgatgtt tctagctacc tggaaggcca ggctgcgaaa      60
gaattcatcg cgtggctggt ttgtggcggt tctggtggtg gtggttctgg cggtggcgac     120
tcgagcccgc tgctgcagtt tggcggccag gtgcgtcagc gttatctgta taccgatgat     180
gcgcagcaga ccgaagcgca tctggaaatt cgtgaagatg gcaccgtggg cggtgcggcg     240
gatcagagcc cggaaagcct gctgcagctg aaagcgctga accgggcgt gattcagatt     300
ctgggcgtga aaaccagccg ttttctgtgc cagcgtccgg atggcgcgct gtatggcagc     360
ctgcattttg atccggaagc gtgcagcttt cgtgaactgc tgctggaaga tggctataac     420
gtgtatcaga gcgaagcgca tggcctgccg ctgcatctgc cgggcaacaa aagcccgcat     480
cgtgatccgg caccgcgtgg tccggcgcgt tttctgccgc tgccgggtct gccgccggca     540
ctgccggaac cgccgggtat tctggccccg cagccgccgg atgttggtag cagcgatccg     600
ctgtctatgg tgggtccgag ccagggtcgt agcccgagct atgcgagcta a             651
```

<210> SEQ ID NO 80
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Cys Gly Gly Gly Asp Ser Ser Pro Leu Leu Gln Phe Gly
            35                  40                  45

Gly Gln Val Arg Gln Arg Tyr Leu Tyr Thr Asp Asp Ala Gln Gln Thr
        50                  55                  60

Glu Ala His Leu Glu Ile Arg Glu Asp Gly Thr Val Gly Gly Ala Ala
65                  70                  75                  80
```

```
Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Arg Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
    210                 215

<210> SEQ ID NO 81
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
cattctgaag gcacttttac tagcgatgtt tctagctacc tggaaggcca ggctgcgaaa      60
gaattcatcg cgtggctggt taaaggcggt tctggtggtg gtggttgtgg cggtggcgac     120
tcgagcccgc tgctgcagtt tggcggccag gtgcgtcagc gttatctgta taccgatgat     180
gcgcagcaga ccgaagcgca tctggaaatt cgtgaagatg gcaccgtggg cggtgcggcg     240
gatcagagcc cggaaagcct gctgcagctg aaagcgctga accgggcgt gattcagatt      300 ctgggcgtga aaccagccg ttttctgtgc cagcgtccgg atggcgcgct gtatggcagc      360
ctgcattttg atccggaagc gtgcagcttt cgtgaactgc tgctggaaga tggctataac      420
gtgtatcaga gcgaagcgca tggcctgccg ctgcatctgc cgggcaacaa aagcccgcat     480
cgtgatccgg caccgcgtgg tccggcgcgt tttctgccgc tgccgggtct gccgccggca     540
ctgccggaac cgccgggtat tctggccccg cagccgccgg atgttggtag cagcgatccg     600
ctgtctatgg tgggtccgag ccagggtcgt agcccgagct atgcgagcta a              651

<210> SEQ ID NO 82
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

His Ala Glu Gly Thr Phe Thr Ser Asp Val Ser Ser Tyr Leu Glu Gly
1               5                   10                  15

Gln Ala Ala Cys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
```

-continued

```
                35                  40                  45
Gly Gln Val Arg Gln Arg Tyr Leu Tyr Thr Asp Asp Ala Gln Gln Thr
 50                  55                  60

Glu Ala His Leu Glu Ile Arg Glu Asp Gly Thr Val Gly Gly Ala Ala
 65                  70                  75                  80

Asp Gln Ser Pro Glu Ser Leu Leu Gln Leu Lys Ala Leu Lys Pro Gly
                 85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
130                 135                 140

Glu Ala His Gly Leu Pro Leu His Leu Pro Gly Asn Lys Ser Pro His
145                 150                 155                 160

Arg Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
210                 215
```

<210> SEQ ID NO 83
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

```
catgcggaag gcactttac tagcgatgtt ctagctacc tggaaggcca ggctgcgtgt      60
gaattcatcg cgtggctggt taaaggcggt tctggtggtg gtggttctgg cggtggcgac    120
tcgagcccgc tgctgcagtt tggcggccag gtgcgtcagc gttatctgta taccgatgat    180
gcgcagcaga ccgaagcgca tctggaaatt cgtgaagatg gcaccgtggg cggtgcggcg    240
gatcagagcc cggaaagcct gctgcagctg aaagcgctga aaccgggcgt gattcagatt    300
ctgggcgtga aaccagccg ttttctgtgc cagcgtccgg atggcgcgct gtatggcagc    360
ctgcattttg atccggaagc gtgcagcttt cgtgaactgc tgctggaaga tggctataac    420
gtgtatcaga gcgaagcgca tggcctgccg ctgcatctgc cgggcaacaa aagcccgcat    480
cgtgatccgg caccgcgtgg tccggcgcgt tttctgccgc tgccgggtct gccgccggca    540
ctgccggaac cgccgggtat tctggccccg cagccgccgg atgttggtag cagcgatccg    600
ctgtctatgg tgggtccgag ccagggtcgt agcccgagct atgcgagcta a              651
```

<210> SEQ ID NO 84
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Cys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
            115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Arg Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
            195                 200                 205

Gly Arg Ser Pro Ser Tyr Ala Ser
    210                 215

<210> SEQ ID NO 85
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
catgcggaag gcacttttac tagcgatgtt tctagctacc tggaaggcca ggctgcgaaa      60
gaattcatcg cgtggctggt ttgtggcggt tctggtggtg gtggttctgg cggtggcgac     120
tcgagcccgc tgctgcagtt tggcggccag gtgcgtcagc gttatctgta taccgatgat     180
gcgcagcaga ccgaagcgca tctggaaatt cgtgaagatg gcaccgtggg cggtgcggcg     240
gatcagagcc cggaaagcct gctgcagctg aaagcgctga aaccgggcgt gattcagatt     300
ctgggcgtga aaaccagccg ttttctgtgc cagcgtccgg atggcgcgct gtatggcagc     360
ctgcattttg atccggaagc gtgcagcttt cgtgaactgc tgctggaaga tggctataac     420
gtgtatcaga gcgaagcgca tggcctgccg ctgcatctgc cgggcaacaa aagcccgcat     480
cgtgatccgg caccgcgtgg tccggcgcgt tttctgccgc tgccgggtct gccgccggca     540
ctgccggaac cgccgggtat tctggccccg cagccgccgg atgttggtag cagcgatccg     600
ctgtctatgg tgggtccgag ccagggtcgt agcccgagct atgcgagcta a              651

<210> SEQ ID NO 86
<211> LENGTH: 216
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 86

```
His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Gly Ser Gly
            20                  25                  30
Gly Gly Gly Cys Gly Gly Gly Asp Ser Ser Pro Leu Leu Gln Phe Gly
        35                  40                  45
Gly Gln Val Arg Gln Arg Tyr Leu Tyr Thr Asp Asp Ala Gln Gln Thr
    50                  55                  60
Glu Ala His Leu Glu Ile Arg Glu Asp Gly Thr Val Gly Gly Ala Ala
65                  70                  75                  80
Asp Gln Ser Pro Glu Ser Leu Leu Gln Leu Lys Ala Leu Lys Pro Gly
                85                  90                  95
Val Ile Gln Ile Leu Gly Val Lys Thr Ser Arg Phe Leu Cys Gln Arg
            100                 105                 110
Pro Asp Gly Ala Leu Tyr Gly Ser Leu His Phe Asp Pro Glu Ala Cys
        115                 120                 125
Ser Phe Arg Glu Leu Leu Leu Glu Asp Gly Tyr Asn Val Tyr Gln Ser
    130                 135                 140
Glu Ala His Gly Leu Pro Leu His Leu Pro Gly Asn Lys Ser Pro His
145                 150                 155                 160
Arg Asp Pro Ala Pro Arg Gly Pro Ala Arg Phe Leu Pro Leu Pro Gly
                165                 170                 175
Leu Pro Pro Ala Leu Pro Glu Pro Pro Gly Ile Leu Ala Pro Gln Pro
            180                 185                 190
Pro Asp Val Gly Ser Ser Asp Pro Leu Ser Met Val Gly Pro Ser Gln
        195                 200                 205
Gly Arg Ser Pro Ser Tyr Ala Ser
    210                 215
```

<210> SEQ ID NO 87
<211> LENGTH: 651
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

```
catgcggaag gcacttttac tagcgatgtt tctagctacc tggaaggcca ggctgcgaaa      60
gaattcatcg cgtggctggt taaaggcggt tctggtggtg gtggttgtgg cggtggcgac     120
tcgagcccgc tgctgcagtt tggcggccag gtgcgtcagc gttatctgta taccgatgat     180
gcgcagcaga ccgaagcgca tctggaaatt cgtgaagatg gcaccgtggg cggtgcggcg     240
gatcagagcc cggaaagcct gctgcagctg aaagcgctga aaccgggcgt gattcagatt     300
ctgggcgtga aaaccagccg ttttctgtgc cagcgtccgg atggcgcgct gtatggcagc     360
ctgcattttg atccggaagc gtgcagcttt cgtgaactgc tgctggaaga tggctataac     420
gtgtatcaga gcgaagcgca tggcctgccg ctgcatctgc cgggcaacaa aagcccgcat     480
cgtgatccgg caccgcgtgg tccggcgcgt tttctgccgc tgccgggtct gccgccggca     540
ctgccggaac cgccgggtat tctggccccg cagccgccgg atgttggtag cagcgatccg     600
```
ctgtctatgg tgggtccgag ccagggtcgt agcccgagct atgcgagcta a       651

<210> SEQ ID NO 88
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Ser Gly
                20                  25                  30

Gly Gly Gly Ser Gly Gly Gly Asp Ser Ser Pro Leu Leu Gln Phe Gly
            35                  40                  45

Gly Gln Val Arg Gln Arg Tyr Leu Tyr Thr Asp Asp Ala Gln Gln Thr
        50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
                100                 105                 110

Pro Asp Gly Ala Leu Tyr Gly Ser Leu His Phe Asp Pro Glu Ala Cys
            115                 120                 125

Ser Phe Arg Glu Leu Leu Leu Glu Asp Gly Tyr Asn Val Tyr Gln Ser
        130                 135                 140

Glu Ala His Gly Leu Pro Leu His Leu Pro Gly Asn Lys Ser Pro His
145                 150                 155                 160

Cys Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
    210                 215

<210> SEQ ID NO 89
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
catggtgagg gtacgtttac ttctgatctg tctaaacaga tggaagaaga agctgttcgc       60
ctgttcattg aatggctgaa aaatggtggt tctggtggtg gtggttctgg cggtggcgac      120
tcgagcccgc tgctgcagtt tggcggccag gtgcgtcagc gttatctgta taccgatgat      180
gcgcagcaga ccgaagcgca tctggaaatt cgtgaagatg gcaccgtggg cggtgcggcg      240
gatcagagcc cggaaagcct gctgcagctg aaagcgctga aacccggcgt gattcagatt      300
ctgggcgtga aaaccagccg ttttctgtgc cagcgtccgg atggcgcgct gtatggcagc      360

```
ctgcattttg atccggaagc gtgcagcttt cgtgaactgc tgctggaaga tggctataac    420
gtgtatcaga gcgaagcgca tggcctgccg ctgcatctgc cgggcaacaa aagcccgcat    480
tgcgatccgg caccgcgtgg tccggcgcgt tttctgccgc tgccgggtct gccgccggca    540
ctgccggaac cgccgggtat tctggccccg cagccgccgg atgttggtag cagcgatccg    600
ctgtctatgg tgggtccgag ccagggtcgt agcccgagct atgcgagcta a             651
```

<210> SEQ ID NO 90
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
His Gly Glu Gly Thr Phe Thr Ser Asp Leu Ser Lys Gln Met Glu Gly
1               5                   10                  15

Gln Ala Val Arg Leu Phe Ile Glu Trp Leu Lys Asn Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Cys Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
    210                 215
```

<210> SEQ ID NO 91
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

```
catggtgagg gtacgtttac ttctgatctg tctaaacaga tggaagggca agctgttcgc    60
ctgttcattg aatggctgaa aaatggtggt tctggtggtg gtggttctgg cggtggcgac    120
tcgagcccgc tgctgcagtt tggcggccag gtgcgtcagc gttatctgta taccgatgat    180
```

```
gcgcagcaga ccgaagcgca tctggaaatt cgtgaagatg gcaccgtggg cggtgcggcg    240
gatcagagcc cggaaagcct gctgcagctg aaagcgctga accgggcgt gattcagatt     300 ctgggcgtga aaaccagccg ttttctgtgc cagcgtccgg atggcgcgct gtatggcagc    360
ctgcattttg atccggaagc gtgcagcttt cgtgaactgc tgctggaaga tggctataac    420
gtgtatcaga gcgaagcgca tggcctgccg ctgcatctgc cgggcaacaa aagcccgcat    480
tgcgatccgg caccgcgtgg tccggcgcgt tttctgccgc tgccgggtct gccgccggca    540
ctgccggaac cgccgggtat tctggccccg cagccgccgg atgttggtag cagcgatccg    600
ctgtctatgg tgggtccgag ccagggtcgt agcccgagct atgcgagcta a            651
```

<210> SEQ ID NO 92
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (161)..(161)
<223> OTHER INFORMATION: Any amino acid

<400> SEQUENCE: 92

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Cys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Xaa Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
    210                 215

<210> SEQ ID NO 93
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

```
cattctgaag gcacttttac tagcgatgtt tctagctacc tggaaggcca ggctgcgaaa    60
gaattcatcg cgtggctggt ttgtggcggt tctggtggtg gtggttctgg cggtggcgac   120
tcgagcccgc tgctgcagtt tggcggccag gtgcgtcagc gttatctgta taccgatgat   180
gcgcagcaga ccgaagcgca tctggaaatt cgtgaagatg gcaccgtggg cggtgcggcg   240
gatcagagcc cggaaagcct gctgcagctg aaagcgctga accgggcgt gattcagatt   300
ctgggcgtga aaccagccg ttttctgtgc cagcgtccgg atggcgcgct gtatggcagc   360
ctgcattttg atccggaagc gtgcagcttt cgtgaactgc tgctggaaga tggctataac   420
gtgtatcaga gcgaagcgca tggcctgccg ctgcatctgc cgggcaacaa aagcccgcat   480
taggatccgg caccgcgtgg tccggcgcgt tttctgccgc tgccgggtct gccgccggca   540
ctgccggaac cgccgggtat tctggccccg cagccgccgg atgttggtag cagcgatccg   600
ctgtctatgg tgggtccgag ccagggtcgt agcccgagct atgcgagcta a            651
```

<210> SEQ ID NO 94
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (161)..(161)
<223> OTHER INFORMATION: Any amino acid

<400> SEQUENCE: 94

```
His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Cys Gly Gly Ser Gly
                20                  25                  30
Gly Gly Gly Ser Gly Gly Gly Asp Ser Ser Pro Leu Leu Gln Phe Gly
            35                  40                  45
Gly Gln Val Arg Gln Arg Tyr Leu Tyr Thr Asp Asp Ala Gln Gln Thr
        50                  55                  60
Glu Ala His Leu Glu Ile Arg Glu Asp Gly Thr Val Gly Gly Ala Ala
65                  70                  75                  80
Asp Gln Ser Pro Glu Ser Leu Leu Gln Leu Lys Ala Leu Lys Pro Gly
                85                  90                  95
Val Ile Gln Ile Leu Gly Val Lys Thr Ser Arg Phe Leu Cys Gln Arg
            100                 105                 110
Pro Asp Gly Ala Leu Tyr Gly Ser Leu His Phe Asp Pro Glu Ala Cys
        115                 120                 125
Ser Phe Arg Glu Leu Leu Leu Glu Asp Gly Tyr Asn Val Tyr Gln Ser
    130                 135                 140
Glu Ala His Gly Leu Pro Leu His Leu Pro Gly Asn Lys Ser Pro His
145                 150                 155                 160
Xaa Asp Pro Ala Pro Arg Gly Pro Ala Arg Phe Leu Pro Leu Pro Gly
                165                 170                 175
Leu Pro Pro Ala Leu Pro Glu Pro Pro Gly Ile Leu Ala Pro Gln Pro
            180                 185                 190
```

Pro Asp Val Gly Ser Ser Asp Pro Leu Ser Met Val Gly Pro Ser Gln
            195                 200                 205

Gly Arg Ser Pro Ser Tyr Ala Ser
    210                 215

<210> SEQ ID NO 95
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
catgcggaag gcactttac tagcgatgtt tctagctacc tggaaggcca ggctgcgaaa       60
gaattcatcg cgtggctggt tgtggcggt tctggtggtg gtggttctgg cggtggcgac      120
tcgagcccgc tgctgcagtt tggcggccag gtgcgtcagc gttatctgta taccgatgat    180
gcgcagcaga ccgaagcgca tctggaaatt cgtgaagatg gcaccgtggg cggtgcggcg    240
gatcagagcc cggaaagcct gctgcagctg aaagcgctga accgggcgt gattcagatt    300 ctgggcgtga aaccagccg ttttctgtgc cagcgtccgg atggcgcgct gtatggcagc    360
ctgcattttg atccggaagc gtgcagctt cgtgaactgc tgctggaaga tggctataac    420
gtgtatcaga gcaagcgca tggcctgccg ctgcatctgc cggcaacaa aagcccgcat     480 taggatccgg caccgcgtgg tccggcgcgt tttctgccgc tgccgggtct gccgccggca    540
ctgccggaac cgccgggtat tctggccccg cagccgccgg atgttggtag cagcgatccg    600
ctgtctatgg tgggtccgag ccagggtcgt agcccgagct atgcgagcta a              651

<210> SEQ ID NO 96
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Any amino acid

<400> SEQUENCE: 96

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Xaa Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser

```
                130                 135                 140

Glu Ala His Gly Leu Pro Leu His Leu Pro Gly Asn Lys Ser Pro His
145                 150                 155                 160

Cys Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
                195                 200                 205

Gly Arg Ser Pro Ser Tyr Ala Ser
            210                 215
```

<210> SEQ ID NO 97
<211> LENGTH: 651
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97

```
cattctgaag gcactttac tagcgatgtt tctagctacc tggaaggcca ggctgcgaaa      60
gaattcatcg cgtggctggt ttagggcggt tctggtggtg gtggttctgg cggtggcgac    120
tcgagcccgc tgctgcagtt tggcggccag gtgcgtcagc gttatctgta taccgatgat    180
gcgcagcaga ccgaagcgca tctggaaatt cgtgaagatg gcaccgtggg cggtgcggcg    240
gatcagagcc cggaaagcct gctgcagctg aaagcgctga accgggcgt gattcagatt     300 ctgggcgtga aaccagccg ttttctgtgc cagcgtccgg atggcgcgct gtatggcagc    360
ctgcattttg atccggaagc gtgcagcttt cgtgaactgc tgctggaaga tggctataac    420
gtgtatcaga gcgaagcgca tggcctgccg ctgcatctgc cgggcaacaa aagcccgcat    480
tgcgatccgg caccgcgtgg tccggcgcgt tttctgccgc tgccgggtct gccgccggca    540
ctgccggaac cgccgggtat tctggccccg cagccgccgg atgttggtag cagcgatccg    600
ctgtctatgg tgggtccgag ccagggtcgt agcccgagct atgcgagcta a             651
```

<210> SEQ ID NO 98
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

```
His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
                20                  25                  30

Gly Gly Gly Ser Gly Gly Gly Asp Ser Ser Pro Leu Leu Gln Phe Gly
            35                  40                  45

Gly Gln Val Arg Gln Arg Tyr Leu Tyr Thr Asp Asp Ala Gln Glu Thr
        50                  55                  60

Glu Ala His Leu Glu Ile Arg Glu Asp Gly Thr Val Gly Gly Ala Ala
65                  70                  75                  80

His Gln Ser Pro Glu Ser Leu Leu Glu Leu Lys Ala Leu Lys Pro Gly
                85                  90                  95
```

Val Ile Gln Ile Leu Gly Val Lys Thr Ser Arg Phe Leu Cys Gln Lys
                100                 105                 110

Pro Asp Gly Ala Leu Tyr Gly Ser Leu His Phe Asp Pro Glu Ala Cys
            115                 120                 125

Ser Phe Arg Glu Leu Leu Leu Glu Asp Gly Tyr Asn Val Tyr Gln Ser
130                 135                 140

Glu Ala His Gly Leu Pro Leu His Leu Pro Gly Asn Arg Ser Pro His
145                 150                 155                 160

Arg Asp Pro Ala Pro Gln Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ala Met Val Gly Pro Ser Gln
                195                 200                 205

Gly Arg Ser Pro Ser Tyr Ala Ser
210                 215

<210> SEQ ID NO 99
<211> LENGTH: 651
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99
cattctgaag gcacttttac tagcgatgtt tctagctacc tggaaggcca ggctgcgaaa    60
gaattcatcg cgtggctggt taaaggcggt tctggtggtg gtggttctgg cggtggcgac   120
tcgagcccgc tgctgcagtt tggcggccag gtgcgtcagc gttatctgta taccgatgat   180
gcgcaggaaa ccgaagcgca tctggaaatt cgtgaagatg gcaccgtggg cggtgcggcg   240
catcagagcc cggaaagcct gctggaactg aaagcgctga accgggcgt gattcagatt   300 ctgggcgtga aaccagccg ttttctgtgc cagaaaccgg atggcgcgct gtatggcagc   360
ctgcattttg atccggaagc gtgcagcttt cgtgaactgc tgctggaaga tggctataac   420
gtgtatcaga gcgaagcgca tggcctgccg ctgcatctgc cgggcaaccg tagcccgcat   480
cgtgatccgg caccgcaggg tccggcgcgt tttctgccgc tgccgggtct gccgccggca   540
ctgccggaac cgccgggtat tctggccccg cagccgccgg atgttggtag cagcgatccg   600
ctggcgatgg tgggtccgag ccagggtcgt agcccgagct atgcgagcta a            651

<210> SEQ ID NO 100
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Glu Thr
    50                  55                  60

Glu Ala His Leu Glu Ile Arg Glu Asp Gly Thr Val Gly Gly Ala Ala
65                  70                  75                  80

His Gln Ser Pro Glu Ser Leu Leu Glu Leu Lys Ala Leu Lys Pro Gly
            85                  90                  95

Val Ile Gln Ile Leu Gly Val Lys Thr Ser Arg Phe Leu Cys Gln Lys
        100                 105                 110

Pro Asp Gly Ala Leu Tyr Gly Ser Leu His Phe Asp Pro Glu Ala Cys
    115                 120                 125

Ser Phe Arg Glu Leu Leu Leu Glu Glu Gly Tyr Asn Val Tyr Gln Ser
130                 135                 140

Glu Ala His Gly Leu Pro Leu His Leu Pro Gly Asn Arg Ser Pro His
145                 150                 155                 160

Arg Asp Pro Ala Pro Gln Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ala Met Val Gly Pro Ser Gln
        195                 200                 205

Gly Arg Ser Pro Ser Tyr Ala Ser
    210                 215

<210> SEQ ID NO 101
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
cattctgaag gcacttttac tagcgatgtt tctagctacc tggaaggcca ggctgcgaaa      60
gaattcatcg cgtggctggt taaaggcggt tctggtggtg gtggttctgg cggtggcgac     120
tcgagcccgc tgctgcagtt tggcggccag gtgcgtcagc gttatctgta taccgatgat     180
gcgcaggaaa ccgaagcgca tctggaaatt cgtgaagatg gcaccgtggg cggtgcggcg     240
catcagagcc cggaaagcct gctggaactg aaagcgctga accgggcgt gattcagatt      300 ctgggcgtga aaaccagccg ttttctgtgc cagaaaccgg atggcgcgct gtatggcagc     360
ctgcattttg atccggaagc gtgcagcttt cgtgaactgc tgctggaaga aggctataac     420
gtgtatcaga gcgaagcgca tggcctgccg ctgcatctgc cgggcaaccg tagcccgcat     480
cgtgatccgg caccgcaggg tccggcgcgt tttctgccgc tgccgggtct gccgccggca     540
ctgccggaac cgccgggtat tctggccccg cagccgccgg atgttggtag cagcgatccg     600
ctggcgatgg tgggtccgag ccagggtcgt agcccgagct atgcgagcta a             651

<210> SEQ ID NO 102
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Cys Gly Gly Ser Gly

```
                20                  25                  30
Gly Gly Gly Ser Gly Gly Gly Asp Ser Ser Pro Leu Leu Gln Phe Gly
            35                  40                  45

Gly Gln Val Arg Gln Arg Tyr Leu Tyr Thr Asp Asp Ala Gln Glu Thr
 50                  55                  60

Glu Ala His Leu Glu Ile Arg Glu Asp Gly Thr Val Gly Gly Ala Ala
 65                  70                  75                  80

His Gln Ser Pro Glu Ser Leu Leu Glu Leu Lys Ala Leu Lys Pro Gly
                85                  90                  95

Val Ile Gln Ile Leu Gly Val Lys Thr Ser Arg Phe Leu Cys Gln Lys
            100                 105                 110

Pro Asp Gly Ala Leu Tyr Gly Ser Leu His Phe Asp Pro Glu Ala Cys
            115                 120                 125

Ser Phe Arg Glu Leu Leu Leu Glu Glu Gly Tyr Asn Val Tyr Gln Ser
    130                 135                 140

Glu Ala His Gly Leu Pro Leu His Leu Pro Gly Asn Arg Ser Pro His
145                 150                 155                 160

Arg Asp Pro Ala Pro Gln Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ala Met Val Gly Pro Ser Gln
            195                 200                 205

Gly Arg Ser Pro Ser Tyr Ala Ser
    210                 215
```

<210> SEQ ID NO 103
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
cattctgaag gcacttttac tagcgatgtt tctagctacc tggaaggcca ggctgcgaaa      60
gaattcatcg cgtggctggt ttgtggcggt tctggtggtg gtggttctgg cggtggcgac     120
tcgagcccgc tgctgcagtt tggcggccag gtgcgtcagc gttatctgta taccgatgat     180
gcgcaggaaa ccgaagcgca tctggaaatt cgtgaagatg gcaccgtggg cggtgcggcg     240
catcagagcc cggaaagcct gctggaactg aaagcgctga aaccgggcgt gattcagatt     300
ctgggcgtga aaaccagccg ttttctgtgc cagaaaccgg atggcgcgct gtatggcagc     360
ctgcattttg atccggaagc gtgcagcttt cgtgaactgc tgctggaaga aggctataac     420
gtgtatcaga gcgaagcgca tggcctgccg ctgcatctgc cgggcaaccg tagcccgcat     480
cgtgatccgg caccgcaggg tccggcgcgt tttctgccgc tgccgggtct gccgccggca     540
ctgccggaac cgccgggtat tctggccccg cagccgccgg atgttggtag cagcgatccg     600
ctggcgatgg tgggtccgag ccagggtcgt agcccgagct atgcgagcta a              651
```

<210> SEQ ID NO 104
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
His Ser Glu Gly Thr Phe Thr Ser Asp Val Ser Ser Tyr Leu Glu Gly
1               5                   10                  15
Gln Ala Ala Lys Glu Phe Ile Ala Trp Leu Val Cys Gly Gly Ser Gly
            20                  25                  30
Gly Gly Gly Ser Gly Gly Gly Asp Ser Ser Pro Leu Leu Gln Phe Gly
        35                  40                  45
Gly Gln Val Arg Gln Arg Tyr Leu Tyr Thr Asp Asp Ala Gln Glu Thr
    50                  55                  60
Glu Ala His Leu Glu Ile Arg Glu Asp Gly Thr Val Gly Gly Ala Ala
65                  70                  75                  80
His Gln Ser Pro Glu Ser Leu Leu Glu Leu Lys Ala Leu Lys Pro Gly
                85                  90                  95
Val Ile Gln Ile Leu Gly Val Lys Thr Ser Arg Phe Leu Cys Gln Lys
            100                 105                 110
Pro Asp Gly Ala Leu Tyr Gly Ser Leu His Phe Asp Pro Glu Ala Cys
        115                 120                 125
Ser Phe Arg Glu Leu Leu Leu Glu Asp Gly Tyr Asn Val Tyr Gln Ser
130                 135                 140
Glu Ala His Gly Leu Pro Leu His Leu Pro Gly Asn Arg Ser Pro His
145                 150                 155                 160
Arg Asp Pro Ala Pro Gln Gly Pro Ala Arg Phe Leu Pro Leu Pro Gly
                165                 170                 175
Leu Pro Pro Ala Leu Pro Glu Pro Pro Gly Ile Leu Ala Pro Gln Pro
            180                 185                 190
Pro Asp Val Gly Ser Ser Asp Pro Leu Ala Met Val Gly Pro Ser Gln
        195                 200                 205
Ala Arg Ser Pro Ser Tyr Ala Ser
    210                 215
```

<210> SEQ ID NO 105
<211> LENGTH: 651
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105

```
cattctgaag gcactttttac tagcgatgtt tctagctacc tggaaggcca ggctgcgaaa      60
gaattcatcg cgtggctggt ttgtggcggt tctggtggtg gtggttctgg cggtggcgac     120
tcgagcccgc tgctgcagtt tggcggccag gtgcgtcagc gttatctgta taccgatgat     180
gcgcaggaaa ccgaagcgca tctggaaatt cgtgaagatg gcaccgtggg cggtgcggcg     240
catcagagcc cggaaagcct gctggaactg aaagcgctga aaccgggcgt gattcagatt     300
ctgggcgtga aaaccagccg ttttctgtgc cagaaaccgg atggcgcgct gtatggcagc     360
ctgcattttg atccggaagc gtgcagcttt cgtgaactgc tgctggaaga tggctataac     420
gtgtatcaga gcgaagcgca tggcctgccg ctgcatctgc cgggcaaccg tagcccgcat     480
cgtgatccgg caccgcaggg tccggcgcgt tttctgccgc tgccgggtct gccgccggca     540
ctgccggaac cgccgggtat tctggccccg cagccgccgg atgttggtag cagcgatccg     600
ctggcgatgg tgggtccgag ccaggcgcgt agcccgagct atgcgagcta a             651
```

<210> SEQ ID NO 106
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 106

```
cactccgaag gaacattcac ttccgatgta agctcgtatt tggaagggca ggcggctaag      60
gagtttatcg catggttggt caaaggtggt ggaggtgggt cgggcggtgg aggctccgga     120
gggggaggga gcgacaaaac ccatacatgt ccgccttgtc ccgcaccaga agcagcgggt     180
gggccctcgg tgttcctgtt cccgccaaaa ccgaaggaca cacttatgat ttcacgcaca     240
ccggaagtga cttgcgtcgt ggtggatgta tcgcacgagg accccgaggt caaattcaac     300
tggtatgtcg atggagtgga ggtgcacaat gcaaagacca gccgaggga  agaacaatac     360
aatagcacgt accgagtcgt gtccgtcttg acggtccttc accaggactg gctgaacgga     420
aaggagtaca agtgcaaagt gagcaataag gccctccctg ccccgattga gaaaaccatt     480
tccaaggcca aggtcagcc tagagaacct caagtgtata ctcttccgcc ctcacgcgaa      540
gagatgacga aaaccaagt gtcgcttacg tgtcttgtca aggtttctac ccctcggac       600
atcgccgtag agtgggagtc gaacggccag ccggagaaca actacaagac cacgcccct      660
gtcttggata gcgacggatc gttttttcctc tactcgaaac tcacagtaga taagtcccga    720
tggcaacagg gtaatgtctt tagctgcagc gtgatgcacg aggcgcttca caatcattac     780
acacaaaaat cactgtcgct tagcccggga aaggattcgt cgcccctgtt gcagtttggt     840
ggacaggtca gcagcgcta cctttacacg gatgacgcct gccagacaga ggcacacctc      900
gaaatcagag aggacggtac ggtcgggggt gcggccgatc agagccccga gtcgcttctc     960
cagttgaagg cccttaagcc aggagtcatc cagatttggg gagtaaagac ctcacggttt    1020
ctctgtcaga aaccagatgg ggcactgtac ggctcattgc atttcgatcc cgaagcgtgc    1080
tcgttccggg agttgctgct tgaggacgga tataacgtct atcagagcga agcgcatggc    1140
ctcccccttc acctccggtg taacaggtcg ccgcatcggg atccggcctc gaggggtccc    1200
gcgagatttc ttccgttgcc cgggttgcct cccgcgctgc ccgagcctcc cgggatcctc    1260
gcgccacagc ctcctgatgt agggtcctcg gaccctttgg cgatggtagg tggatcacaa    1320
gcacggtccc cgagctatgc atca                                           1344
```

<210> SEQ ID NO 107
<211> LENGTH: 281
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

```
His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser Gly Gly Gly Ser Gly Gly Gly Gly
         35                  40                  45

Ser Gly Gly Gly Gly Ser Asp Lys Thr His Thr Cys Pro Pro Cys Pro
     50                  55                  60
```

```
Ala Pro Glu Ala Ala Gly Gly Pro Ser Val Phe Leu Phe Pro Pro Lys
 65                  70                  75                  80

Pro Lys Asp Thr Leu Met Ile Ser Arg Thr Pro Glu Val Thr Cys Val
                 85                  90                  95

Val Val Asp Val Ser His Glu Asp Pro Glu Val Lys Phe Asn Trp Tyr
            100                 105                 110

Val Asp Gly Val Glu Val His Asn Ala Lys Thr Lys Pro Arg Glu Glu
        115                 120                 125

Gln Tyr Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Ala Leu Pro Ala Pro Ile Glu Lys Thr Ile Ser Lys Ala Lys Gly Gln
                165                 170                 175

Pro Arg Glu Pro Gln Val Tyr Thr Leu Pro Pro Ser Arg Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Lys Leu Thr Val Asp Lys Ser Arg Trp Gln Gln Gly Asn Val
                245                 250                 255

Phe Ser Cys Ser Val Met His Glu Ala Leu His Asn His Tyr Thr Gln
            260                 265                 270

Lys Ser Leu Ser Leu Ser Pro Gly Lys
        275                 280

<210> SEQ ID NO 108
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Ser Gly
                 20                  25                  30

Gly Gly Gly Ser Gly Gly Gly Asp Ser Ser Pro Leu Leu Gln Phe Gly
             35                  40                  45

Gly Gln Val Arg Gln Arg Tyr Leu Tyr Thr Asp Asp Ala Gln Glu Thr
         50                  55                  60

Glu Ala His Leu Glu Ile Arg Glu Asp Gly Thr Val Gly Gly Ala Ala
 65                  70                  75                  80

His Gln Ser Pro Glu Ser Leu Leu Glu Leu Lys Ala Leu Lys Pro Gly
                 85                  90                  95

Val Ile Gln Ile Leu Gly Val Lys Thr Ser Arg Phe Leu Cys Gln Lys
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Glu Gly Tyr Asn Val Tyr Gln Ser
    130                 135                 140
```

Glu Ala His Gly Leu Pro Leu His Leu Pro Gly Asn Arg Ser Pro His
145                 150                 155                 160

Arg Asp Pro Ala Pro Gln Gly Pro Ala Arg Phe Leu Pro Leu Pro Gly
            165                 170                 175

Leu Pro Pro Ala Leu Pro Glu Pro Pro Gly Ile Leu Ala Pro Gln Pro
        180                 185                 190

Pro Asp Val Gly Ser Ser Asp Pro Leu Ala Met Val Gly Pro Ser Gln
    195                 200                 205

Gly Arg Ser Pro Ser Tyr Ala Ser
210                 215

<210> SEQ ID NO 109
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
catggtgagg gtacgtttac ttctgatctg tctaaacaga tggaagaaga agctgttcgc    60
ctgttcattg aatggctgaa aaatggtggt tctggtggtg gtggttctgg cggtggcgac   120
tcgagcccgc tgctgcagtt tggcggccag gtgcgtcagc gttatctgta taccgatgat   180
gcgcaggaaa ccgaagcgca tctggaaatt cgtgaagatg gcaccgtggg cggtgcggcg   240
catcagagcc cggaaagcct gctggaactg aaagcgctga accgggcgt gattcagatt   300 ctgggcgtga aaccagccg ttttctgtgc cagaaaccgg atggcgcgct gtatggcagc   360
ctgcattttg atccggaagc gtgcagcttt cgtgaactgc tgctggaaga aggctataac   420
gtgtatcaga gcgaagcgca tggcctgccg ctgcatctgc cgggcaaccg tagcccgcat   480
cgtgatccgg caccgcaggg tccggcgcgt tttctgccgc tgccgggtct gccgccggca   540
ctgccggaac cgccgggtat tctggccccg cagccgccgg atgttggtag cagcgatccg   600
ctggcgatgg tgggtccgag ccagggtcgt agcccgagct atgcgagcta a            651

<210> SEQ ID NO 110
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

His Gly Glu Gly Thr Phe Thr Ser Asp Leu Ser Lys Gln Met Glu Glu
1               5                   10                  15

Glu Ala Val Arg Leu Phe Ile Glu Trp Leu Cys Asn Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Glu Thr
    50                  55                  60

Glu Ala His Leu Glu Ile Arg Glu Asp Gly Thr Val Gly Gly Ala Ala
65                  70                  75                  80

His Gln Ser Pro Glu Ser Leu Leu Glu Leu Lys Ala Leu Lys Pro Gly
                85                  90                  95

Val Ile Gln Ile Leu Gly Val Lys Thr Ser Arg Phe Leu Cys Gln Lys

```
                    100                 105                 110
Pro Asp Gly Ala Leu Tyr Gly Ser Leu His Phe Asp Pro Glu Ala Cys
            115                 120                 125

Ser Phe Arg Glu Leu Leu Leu Glu Glu Gly Tyr Asn Val Tyr Gln Ser
        130                 135                 140

Glu Ala His Gly Leu Pro Leu His Leu Pro Gly Asn Arg Ser Pro His
145                 150                 155                 160

Arg Asp Pro Ala Pro Gln Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ala Met Val Gly Pro Ser Gln
        195                 200                 205

Gly Arg Ser Pro Ser Tyr Ala Ser
        210                 215

<210> SEQ ID NO 111
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
catggtgagg gtacgtttac ttctgatctg tctaaacaga tggaagaaga agctgttcgc      60
ctgttcattg aatggctgtg taatggtggt tctggtggtg gtggttctgg cggtggcgac     120
tcgagcccgc tgctgcagtt tggcggccag gtgcgtcagc gttatctgta taccgatgat     180
gcgcaggaaa ccgaagcgca tctggaaatt cgtgaagatg gcaccgtggg cggtgcggcg     240
catcagagcc cggaaagcct gctggaactg aaagcgctga accgggcgt gattcagatt     300
ctgggcgtga aaccagccg ttttctgtgc cagaaaccgg atggcgcgct gtatggcagc     360
ctgcattttg atccggaagc gtgcagcttt cgtgaactgc tgctggaaga aggctataac     420
gtgtatcaga gcgaagcgca tggcctgccg ctgcatctgc cggcaaccg tagcccgcat     480
cgtgatccgg caccgcaggg tccggcgcgt tttctgccgc tgccgggtct gccgccggca     540
ctgccggaac cgccgggtat tctggccccg cagccgccgg atgttggtag cagcgatccg     600
ctggcgatgg tgggtccgag ccagggtcgt agcccgagct atgcgagcta a              651

<210> SEQ ID NO 112
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Cys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Glu Thr
    50                  55                  60
```

```
Glu Ala His Leu Glu Ile Arg Glu Asp Gly Thr Val Gly Gly Ala Ala
 65                  70                  75                  80

His Gln Ser Pro Glu Ser Leu Leu Glu Leu Lys Ala Leu Lys Pro Gly
                 85                  90                  95

Val Ile Gln Ile Leu Gly Val Lys Thr Ser Arg Phe Leu Cys Gln Lys
            100                 105                 110

Pro Asp Gly Ala Leu Tyr Gly Ser Leu His Phe Asp Pro Glu Ala Cys
        115                 120                 125

Ser Phe Arg Glu Leu Leu Glu Gly Tyr Asn Val Tyr Gln Ser
    130                 135                 140

Glu Ala His Gly Leu Pro Leu His Leu Pro Gly Asn Arg Ser Pro His
145                 150                 155                 160

Arg Asp Pro Ala Pro Gln Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ala Met Val Gly Pro Ser Gln
        195                 200                 205

Gly Arg Ser Pro Ser Tyr Ala Ser
    210                 215
```

<210> SEQ ID NO 113
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

```
catggtgagg gtacgtttac ttctgatctg tctaaacaga tggaagaaga agctgttcgc    60
ctgttcattg aatggctgaa atgtggtggt tctggtggtg gtggttctgg cggtggcgac   120
tcgagcccgc tgctgcagtt tggcggccag gtgcgtcagc gttatctgta taccgatgat   180
gcgcaggaaa ccgaagcgca tctggaaatt cgtgaagatg gcaccgtggg cggtgcggcg   240
catcagagcc cggaaagcct gctggaactg aaagcgctga aaccgggcgt gattcagatt   300
ctgggcgtga aaaccagccg ttttctgtgc cagaaaccgg atggcgcgct gtatggcagc   360
ctgcattttg atccggaagc gtgcagcttt cgtgaactgc tgctggaaga aggctataac   420
gtgtatcaga gcgaagcgca tggcctgccg ctgcatctgc cgggcaaccg tagcccgcat   480
cgtgatccgg caccgcaggg tccggcgcgt tttctgccgc tgccgggtct gccgccggca   540
ctgccggaac cgccgggtat tctggccccg cagccgccgg atgttggtag cagcgatccg   600
ctggcgatgg tgggtccgag ccagggtcgt agcccgagct atgcgagcta a           651
```

<210> SEQ ID NO 114
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

```
His Gly Glu Gly Thr Phe Thr Ser Asp Leu Ser Lys Gln Met Glu Glu
  1               5                  10                  15

Glu Ala Val Arg Leu Phe Ile Glu Trp Leu Cys Asn Gly Gly Ser Gly
             20                  25                  30
```

Gly Gly Gly Ser Gly Gly Gly Asp Ser Ser Pro Leu Leu Gln Phe Gly
            35                  40                  45

Gly Gln Val Arg Gln Arg Tyr Leu Tyr Thr Asp Asp Ala Gln Glu Thr
        50                  55                  60

Glu Ala His Leu Glu Ile Arg Glu Asp Gly Thr Val Gly Gly Ala Ala
65                  70                  75                  80

His Gln Ser Pro Glu Ser Leu Leu Glu Leu Lys Ala Leu Lys Pro Gly
                85                  90                  95

Val Ile Gln Ile Leu Gly Val Lys Thr Ser Arg Phe Leu Cys Gln Lys
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Arg Ser Pro His
145                 150                 155                 160

Arg Asp Pro Ala Pro Gln Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ala Met Val Gly Pro Ser Gln
        195                 200                 205

Ala Arg Ser Pro Ser Tyr Ala Ser
    210                 215

<210> SEQ ID NO 115
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
catggtgagg gtacgtttac ttctgatctg tctaaacaga tggaagaaga agctgttcgc      60
ctgttcattg aatggctgtg taatggtggt tctggtggtg gtggttctgg cggtggcgac     120
tcgagcccgc tgctgcagtt tggcggccag gtgcgtcagc gttatctgta taccgatgat     180
gcgcaggaaa ccgaagcgca tctggaaatt cgtgaagatg gcaccgtggg cggtgcggcg     240
catcagagcc cggaaagcct gctggaactg aaagcgctga accgggcgt gattcagatt     300 ctgggcgtga aaaccagccg tttctgtgc cagaaaccgg atggcgcgct gtatggcagc     360
ctgcattttg atccggaagc gtgcagcttt cgtgaactgc tgctggaaga tggctataac     420
gtgtatcaga gcgaagcgca tggcctgccg ctgcatctgc cgggcaaccg tagcccgcat     480
cgtgatccgg caccgcaggg tccggcgcgt tttctgccgc tgccgggtct gccgccggca     540
ctgccggaac cgccgggtat tctggccccg cagccgccgg atgttggtag cagcgatccg     600
ctggcgatgg tgggtccgag ccaggcgcgt agcccgagct atgcgagcta a              651

<210> SEQ ID NO 116
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Cys Gly Gly Ser Gly
                20                  25                  30

Gly Gly Ser Gly Gly Gly Asp Ser Ser Pro Leu Leu Gln Phe Gly
            35                  40                  45

Gly Gln Val Arg Gln Arg Tyr Leu Tyr Thr Asp Ala Gln Glu Thr
    50                  55                  60

Glu Ala His Leu Glu Ile Arg Glu Asp Gly Thr Val Gly Gly Ala Ala
65                  70                  75                  80

His Gln Ser Pro Glu Ser Leu Leu Glu Leu Lys Ala Leu Lys Pro Gly
                85                  90                  95

Val Ile Gln Ile Leu Gly Val Lys Thr Ser Arg Phe Leu Cys Gln Lys
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Arg Ser Pro His
145                 150                 155                 160

Arg Asp Pro Ala Pro Gln Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ala Met Val Gly Pro Ser Gln
        195                 200                 205

Ala Arg Ser Pro Ser Tyr Ala Ser
    210                 215
```

<210> SEQ ID NO 117
<211> LENGTH: 651
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 117

```
catggtgagg gtacgtttac ttctgatctg tctaaacaga tggaagaaga agctgttcgc      60
ctgttcattg aatggctgaa atgtggtggt tctggtggtg gtggttctgg cggtggcgac     120
tcgagcccgc tgctgcagtt tggcggccag gtgcgtcagc gttatctgta taccgatgat     180
gcgcaggaaa ccgaagcgca tctggaaatt cgtgaagatg gcaccgtggg cggtgcggcg     240
catcagagcc cggaaagcct gctggaactg aaagcgctga aaccgggcgt gattcagatt     300
ctgggcgtga aaaccagccg ttttctgtgc cagaaaccgg atggcgcgct gtatggcagc     360
ctgcattttg atccggaagc gtgcagcttt cgtgaactgc tgctggaaga tggctataac     420
gtgtatcaga gcgaagcgca tggcctgccg ctgcatctgc cgggcaaccg tagcccgcat     480
cgtgatccgg caccgcaggg tccggcgcgt tttctgccgc tgccgggtct gccgccggca     540
ctgccggaac cgccgggtat tctggccccg cagccgccgg atgttggtag cagcgatccg     600
ctggcgatgg tgggtccgag ccaggcgcgt agcccgagct atgcgagcta a              651
```

<210> SEQ ID NO 118

```
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118
```

| His Ser Glu Gly Thr Phe Thr Ser Asp Val Ser Ser Tyr Leu Glu Gly |
|---|
| 1               5                   10                  15 |

| Gln Ala Ala Lys Glu Phe Ile Ala Trp Leu Val Lys Gly Gly Gly Ser |
|---|
|             20                  25                  30 |

| Gly Gly Gly Gly Ser Gly Gly Gly Ser Gly Gly Gly Gly Ser Gly |
|---|
|         35                  40                  45 |

| Gly Gly Asp Ser Ser Pro Leu Leu Gln Phe Gly Gly Gln Val Arg Gln |
|---|
|     50                  55                  60 |

| Arg Tyr Leu Tyr Thr Asp Asp Ala Gln Glu Thr Glu Ala His Leu Glu |
|---|
| 65                  70                  75                  80 |

| Ile Arg Glu Asp Gly Thr Val Gly Gly Ala Ala His Gln Ser Pro Glu |
|---|
|                 85                  90                  95 |

| Ser Leu Leu Glu Leu Lys Ala Leu Lys Pro Gly Val Ile Gln Ile Leu |
|---|
|             100                 105                 110 |

| Gly Val Lys Thr Ser Arg Phe Leu Cys Gln Lys Pro Asp Gly Ala Leu |
|---|
|         115                 120                 125 |

| Tyr Gly Ser Leu His Phe Asp Pro Glu Ala Cys Ser Phe Arg Glu Leu |
|---|
|     130                 135                 140 |

| Leu Leu Glu Asp Gly Tyr Asn Val Tyr Gln Ser Glu Ala His Gly Leu |
|---|
| 145                 150                 155                 160 |

| Pro Leu His Leu Pro Gly Asn Arg Ser Pro His Cys Asp Pro Ala Pro |
|---|
|                 165                 170                 175 |

| Gln Gly Pro Ala Arg Phe Leu Pro Leu Pro Gly Leu Pro Pro Ala Leu |
|---|
|             180                 185                 190 |

| Pro Glu Pro Pro Gly Ile Leu Ala Pro Gln Pro Pro Asp Val Gly Ser |
|---|
|         195                 200                 205 |

| Ser Asp Pro Leu Ala Met Val Gly Pro Ser Gln Gly Arg Ser Pro Ser |
|---|
|     210                 215                 220 |

| Tyr Ala Ser |
|---|
| 225 |

```
<210> SEQ ID NO 119
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 119
cattctgaag gcacttttac tagcgatgtt tctagctacc tggaaggcca ggctgcgaaa      60
gaattcatcg cgtggctggt taaaggcggt ggtagcggtg cggcggttc tggtggtggt     120 ggttctggcg gtggcggtag cggtggcggc gatagcagcc cgctgctgca gtttggcggc     180
caggtgcgtc agcgttatct gtataccgat gatgcgcagg aaaccgaagc gcatctggaa     240
attcgtgaag atggcaccgt gggcggtgcg gcgcatcaga gcccggaaag cctgctggaa     300
ctgaaagcgc tgaaaccggg cgtgattcag attctgggcg tgaaaaccag ccgttttctg     360
tgccagaaac cggatggcgc gctgtatggc agcctgcatt ttgatccgga agcgtgcagc     420
```

```
tttcgtgaac tgctgctgga agatggctat aacgtgtatc agagcgaagc gcatggcctg    480
ccgctgcatc tgccgggcaa ccgtagcccg cattgcgatc cggcaccgca gggtccggcg    540
cgttttctgc cgctgccggg tctgccgccg gcactgccgg aaccgccggg tattctggcc    600
ccgcagccgc cggatgttgg tagcagcgat ccgctggcga tggtgggtcc gagccagggt    660
cgtagcccga gctatgcgag ctaa                                           684
```

<210> SEQ ID NO 120
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
            20                  25                  30

Gly Gly Ser Asp Lys Thr His Thr Cys Pro Pro Cys Pro Ala Pro Glu
        35                  40                  45

Ala Ala Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Glu Glu Met Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys Gly Gly Gly Ser Gly Gly Gly Gly Ser
            260                 265                 270

Gly Gly Gly Gly Ser Asp Ser Ser Pro Leu Leu Gln Phe Gly Gly Gln
        275                 280                 285

Val Arg Gln Arg Tyr Leu Tyr Thr Asp Ala Cys Gln Thr Glu Ala
    290                 295                 300

His Leu Glu Ile Arg Glu Asp Gly Thr Val Gly Gly Ala Ala Asp Gln
```

```
                305                 310                 315                 320

Ser Pro Glu Ser Leu Leu Gln Leu Lys Ala Leu Lys Pro Gly Val Ile
                        325                 330                 335

Gln Ile Leu Gly Val Lys Thr Ser Arg Phe Leu Cys Gln Lys Pro Asp
                        340                 345                 350

Gly Ala Leu Tyr Gly Ser Leu His Phe Asp Pro Glu Ala Cys Ser Phe
                        355                 360                 365

Arg Glu Leu Leu Leu Glu Asp Gly Tyr Asn Val Tyr Gln Ser Glu Ala
                        370                 375                 380

His Gly Leu Pro Leu His Leu Pro Cys Asn Arg Ser Pro His Arg Asp
        385                 390                 395                 400

Pro Ala Ser Arg Gly Pro Ala Arg Phe Leu Pro Leu Pro Gly Leu Pro
                        405                 410                 415

Pro Ala Leu Pro Glu Pro Pro Gly Ile Leu Ala Pro Gln Pro Pro Asp
                        420                 425                 430

Val Gly Ser Ser Asp Pro Leu Ala Met Val Gly Gly Ser Gln Ala Arg
                        435                 440                 445

Ser Pro Ser Tyr Ala Ser
                450

<210> SEQ ID NO 121
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

His Gly Glu Gly Thr Phe Thr Ser Asp Leu Ser Lys Gln Met Glu Glu
        1               5                   10                  15

Glu Ala Val Arg Leu Phe Ile Glu Trp Leu Lys Asn Gly Gly Gly Gly
                        20                  25                  30

Gly Ser Gly Gly Gly Gly Ser Gly Gly Gly Gly Ser Asp Lys Thr
                    35                  40                  45

His Thr Cys Pro Pro Cys Pro Ala Pro Glu Ala Ala Gly Gly Pro Ser
            50                  55                  60

Val Phe Leu Phe Pro Pro Lys Pro Lys Asp Thr Leu Met Ile Ser Arg
        65                  70                  75                  80

Thr Pro Glu Val Thr Cys Val Val Asp Val Ser His Glu Asp Pro
                        85                  90                  95

Glu Val Lys Phe Asn Trp Tyr Val Asp Gly Val Glu Val His Asn Ala
                        100                 105                 110

Lys Thr Lys Pro Arg Glu Glu Gln Tyr Asn Ser Thr Tyr Arg Val Val
                        115                 120                 125

Ser Val Leu Thr Val Leu His Gln Asp Trp Leu Asn Gly Lys Glu Tyr
                        130                 135                 140

Lys Cys Lys Val Ser Asn Lys Ala Leu Pro Ala Pro Ile Glu Lys Thr
        145                 150                 155                 160

Ile Ser Lys Ala Lys Gly Gln Pro Arg Glu Pro Gln Val Tyr Thr Leu
                        165                 170                 175

Pro Pro Ser Arg Glu Glu Met Thr Lys Asn Gln Val Ser Leu Thr Cys
                        180                 185                 190

Leu Val Lys Gly Phe Tyr Pro Ser Asp Ile Ala Val Glu Trp Glu Ser
                        195                 200                 205
```

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

Gly Gly Gly Gly Ser Gly Gly Gly Gly Ser Gly Gly Gly Gly Ser Asp
            275                 280                 285

Ser Ser Pro Leu Leu Gln Phe Gly Gly Gln Val Arg Gln Arg Tyr Leu
    290                 295                 300

Tyr Thr Asp Asp Ala Cys Gln Thr Glu Ala His Leu Glu Ile Arg Glu
305                 310                 315                 320

Asp Gly Thr Val Gly Gly Ala Ala Asp Gln Ser Pro Glu Ser Leu Leu
                325                 330                 335

Gln Leu Lys Ala Leu Lys Pro Gly Val Ile Gln Ile Leu Gly Val Lys
            340                 345                 350

Thr Ser Arg Phe Leu Cys Gln Lys Pro Asp Gly Ala Leu Tyr Gly Ser
    355                 360                 365

Leu His Phe Asp Pro Glu Ala Cys Ser Phe Arg Glu Leu Leu Leu Glu
370                 375                 380

Asp Gly Tyr Asn Val Tyr Gln Ser Glu Ala His Gly Leu Pro Leu His
385                 390                 395                 400

Leu Pro Cys Asn Arg Ser Pro His Arg Asp Pro Ala Ser Arg Gly Pro
                405                 410                 415

Ala Arg Phe Leu Pro Leu Pro Gly Leu Pro Pro Ala Leu Pro Glu Pro
            420                 425                 430

Pro Gly Ile Leu Ala Pro Gln Pro Pro Asp Val Gly Ser Ser Asp Pro
            435                 440                 445

Leu Ala Met Val Gly Gly Ser Gln Ala Arg Ser Pro Ser Tyr Ala Ser
    450                 455                 460

<210> SEQ ID NO 122
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Ser Asp Lys Thr His
        35                  40                  45

Thr Cys Pro Pro Cys Pro Ala Pro Glu Ala Ala Gly Gly Pro Ser Val
50                  55                  60

Phe Leu Phe Pro Pro Lys Pro Lys Asp Thr Leu Met Ile Ser Arg Thr
65                  70                  75                  80

Pro Glu Val Thr Cys Val Val Val Asp Val Ser His Glu Asp Pro Glu
                85                  90                  95

Val Lys Phe Asn Trp Tyr Val Asp Gly Val Glu Val His Asn Ala Lys
            100                 105                 110

-continued

```
Thr Lys Pro Arg Glu Glu Gln Tyr Asn Ser Thr Tyr Arg Val Val Ser
    115                 120                 125
Val Leu Thr Val Leu His Gln Asp Trp Leu Asn Gly Lys Glu Tyr Lys
    130                 135                 140
Cys Lys Val Ser Asn Lys Ala Leu Pro Ala Pro Ile Glu Lys Thr Ile
145                 150                 155                 160
Ser Lys Ala Lys Gly Gln Pro Arg Glu Pro Gln Val Tyr Thr Leu Pro
                165                 170                 175
Pro Ser Arg Glu Glu Met Thr Lys Asn Gln Val Ser Leu Thr Cys Leu
            180                 185                 190
Val Lys Gly Phe Tyr Pro Ser Asp Ile Ala Val Glu Trp Glu Ser Asn
        195                 200                 205
Gly Gln Pro Glu Asn Asn Tyr Lys Thr Thr Pro Pro Val Leu Asp Ser
    210                 215                 220
Asp Gly Ser Phe Phe Leu Tyr Ser Lys Leu Thr Val Asp Lys Ser Arg
225                 230                 235                 240
Trp Gln Gln Gly Asn Val Phe Ser Cys Ser Val Met His Glu Ala Leu
                245                 250                 255
His Asn His Tyr Thr Gln Lys Ser Leu Ser Leu Ser Pro Gly Lys Gly
            260                 265                 270
Gly Gly Gly Ser Gly Gly Gly Ser Gly Gly Gly Ser Asp Ser
        275                 280                 285
Ser Pro Leu Leu Gln Phe Gly Gly Gln Val Arg Gln Arg Tyr Leu Tyr
    290                 295                 300
Thr Asp Asp Ala Cys Gln Thr Glu Ala His Leu Glu Ile Arg Glu Asp
305                 310                 315                 320
Gly Thr Val Gly Gly Ala Ala Asp Gln Ser Pro Glu Ser Leu Leu Gln
                325                 330                 335
Leu Lys Ala Leu Lys Pro Gly Val Ile Gln Ile Leu Gly Val Lys Thr
            340                 345                 350
Ser Arg Phe Leu Cys Gln Lys Pro Asp Gly Ala Leu Tyr Gly Ser Leu
        355                 360                 365
His Phe Asp Pro Glu Ala Cys Ser Phe Arg Glu Leu Leu Leu Glu Asp
    370                 375                 380
Gly Tyr Asn Val Tyr Gln Ser Glu Ala His Gly Leu Pro Leu His Leu
385                 390                 395                 400
Pro Cys Asn Arg Ser Pro His Arg Asp Pro Ala Ser Arg Gly Pro Ala
                405                 410                 415
Arg Phe Leu Pro Leu Pro Gly Leu Pro Pro Ala Leu Pro Glu Pro Pro
            420                 425                 430
Gly Ile Leu Ala Pro Gln Pro Pro Asp Val Gly Ser Ser Asp Pro Leu
        435                 440                 445
Ala Met Val Gly Gly Ser Gln Ala Arg Ser Pro Ser Tyr Ala Ser
    450                 455                 460
```

<210> SEQ ID NO 123
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

His Gly Glu Gly Thr Phe Thr Ser Asp Leu Ser Lys Gln Met Glu Glu

-continued

```
1               5                   10                  15
Glu Ala Val Arg Leu Phe Ile Glu Trp Leu Lys Asn Gly Gly Pro Ser
                20                  25                  30
Ser Gly Ala Pro Pro Ser Gly Gly Gly Ser Gly Gly Gly Gly
                35                  40                  45
Ser Gly Gly Gly Ser Asp Lys Thr His Thr Cys Pro Pro Cys Pro
    50                  55                  60
Ala Pro Glu Ala Ala Gly Gly Pro Ser Val Phe Leu Phe Pro Pro Lys
65                  70                  75                  80
Pro Lys Asp Thr Leu Met Ile Ser Arg Thr Pro Glu Val Thr Cys Val
                85                  90                  95
Val Val Asp Val Ser His Glu Asp Pro Glu Val Lys Phe Asn Trp Tyr
                100                 105                 110
Val Asp Gly Val Glu Val His Asn Ala Lys Thr Lys Pro Arg Glu Glu
                115                 120                 125
Gln Tyr Asn Ser Thr Tyr Arg Val Val Ser Val Leu Thr Val Leu His
                130                 135                 140
Gln Asp Trp Leu Asn Gly Lys Glu Tyr Lys Cys Lys Val Ser Asn Lys
145                 150                 155                 160
Ala Leu Pro Ala Pro Ile Glu Lys Thr Ile Ser Lys Ala Lys Gly Gln
                165                 170                 175
Pro Arg Glu Pro Gln Val Tyr Thr Leu Pro Pro Ser Arg Glu Glu Met
                180                 185                 190
Thr Lys Asn Gln Val Ser Leu Thr Cys Leu Val Lys Gly Phe Tyr Pro
                195                 200                 205
Ser Asp Ile Ala Val Glu Trp Glu Ser Asn Gly Gln Pro Glu Asn Asn
                210                 215                 220
Tyr Lys Thr Thr Pro Pro Val Leu Asp Ser Asp Gly Ser Phe Phe Leu
225                 230                 235                 240
Tyr Ser Lys Leu Thr Val Asp Lys Ser Arg Trp Gln Gln Gly Asn Val
                245                 250                 255
Phe Ser Cys Ser Val Met His Glu Ala Leu His Asn His Tyr Thr Gln
                260                 265                 270
Lys Ser Leu Ser Leu Ser Pro Gly Lys Gly Gly Gly Ser Gly Gly
                275                 280                 285
Gly Gly Ser Gly Gly Gly Ser Asp Ser Ser Pro Leu Leu Gln Phe
                290                 295                 300
Gly Gly Gln Val Arg Gln Arg Tyr Leu Tyr Thr Asp Asp Ala Cys Gln
305                 310                 315                 320
Thr Glu Ala His Leu Glu Ile Arg Glu Asp Gly Thr Val Gly Gly Ala
                325                 330                 335
Ala Asp Gln Ser Pro Glu Ser Leu Leu Gln Leu Lys Ala Leu Lys Pro
                340                 345                 350
Gly Val Ile Gln Ile Leu Gly Val Lys Thr Ser Arg Phe Leu Cys Gln
                355                 360                 365
Lys Pro Asp Gly Ala Leu Tyr Gly Ser Leu His Phe Asp Pro Glu Ala
                370                 375                 380
Cys Ser Phe Arg Glu Leu Leu Leu Glu Asp Gly Tyr Asn Val Tyr Gln
385                 390                 395                 400
Ser Glu Ala His Gly Leu Pro Leu His Leu Pro Cys Asn Arg Ser Pro
                405                 410                 415
His Arg Asp Pro Ala Ser Arg Gly Pro Ala Arg Phe Leu Pro Leu Pro
                420                 425                 430
```

```
Gly Leu Pro Pro Ala Leu Pro Glu Pro Pro Gly Ile Leu Ala Pro Gln
        435                 440                 445

Pro Pro Asp Val Gly Ser Ser Asp Pro Leu Ala Met Val Gly Gly Ser
450                 455                 460

Gln Ala Arg Ser Pro Ser Tyr Ala Ser
465                 470

<210> SEQ ID NO 124
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
            20                  25                  30

Gly Ser Asp Lys Thr His Thr Cys Pro Pro Cys Pro Ala Pro Glu Ala
        35                  40                  45

Ala Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Glu Glu Met Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
        195                 200                 205

Pro Pro Val Leu Asp Ser Asp Gly Ser Phe Phe Leu Tyr Ser Lys Leu
    210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys Gly Gly Gly Ser Gly Gly Gly Gly Ser Gly
            260                 265                 270

Gly Gly Ser Asp Ser Ser Pro Leu Leu Gln Phe Gly Gly Gln Val
        275                 280                 285

Arg Gln Arg Tyr Leu Tyr Thr Asp Asp Ala Cys Gln Thr Glu Ala His
    290                 295                 300

Leu Glu Ile Arg Glu Asp Gly Thr Val Gly Gly Ala Ala Asp Gln Ser
```

```
              305                 310                 315                 320
Pro Glu Ser Leu Leu Gln Leu Lys Ala Leu Lys Pro Val Ile Gln
                325                 330                 335

Ile Leu Gly Val Lys Thr Ser Arg Phe Leu Cys Gln Lys Pro Asp Gly
                340                 345                 350

Ala Leu Tyr Gly Ser Leu His Phe Asp Pro Glu Ala Cys Ser Phe Arg
                355                 360                 365

Glu Leu Leu Leu Glu Asp Gly Tyr Asn Val Tyr Gln Ser Glu Ala His
        370                 375                 380

Gly Leu Pro Leu His Leu Pro Cys Asn Arg Ser Pro His Arg Asp Pro
385                 390                 395                 400

Ala Ser Arg Gly Pro Ala Arg Phe Leu Pro Leu Pro Gly Leu Pro Pro
                405                 410                 415

Ala Leu Pro Glu Pro Pro Gly Ile Leu Ala Pro Gln Pro Pro Asp Val
                420                 425                 430

Gly Ser Ser Asp Pro Leu Ala Met Val Gly Ser Gln Ala Arg Ser
                435                 440                 445

Pro Ser Tyr Ala Ser
        450

<210> SEQ ID NO 125
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
                20                  25                  30

Gly Ser Gly Gly Gly Gly Ser Gly Gly Gly Gly Ser Asp Lys Thr His
        35                  40                  45

Thr Cys Pro Pro Cys Pro Ala Pro Glu Ala Ala Gly Gly Pro Ser Val
    50                  55                  60

Phe Leu Phe Pro Pro Lys Pro Lys Asp Thr Leu Met Ile Ser Arg Thr
65                  70                  75                  80

Pro Glu Val Thr Cys Val Val Asp Val Ser His Glu Asp Pro Glu
                85                  90                  95

Val Lys Phe Asn Trp Tyr Val Asp Gly Val Glu Val His Asn Ala Lys
                100                 105                 110

Thr Lys Pro Arg Glu Glu Gln Tyr Asn Ser Thr Tyr Arg Val Val Ser
            115                 120                 125

Val Leu Thr Val Leu His Gln Asp Trp Leu Asn Gly Lys Glu Tyr Lys
        130                 135                 140

Cys Lys Val Ser Asn Lys Ala Leu Pro Ala Pro Ile Glu Lys Thr Ile
145                 150                 155                 160

Ser Lys Ala Lys Gly Gln Pro Arg Glu Pro Gln Val Tyr Thr Leu Pro
                165                 170                 175

Pro Ser Arg Glu Glu Met Thr Lys Asn Gln Val Ser Leu Thr Cys Leu
                180                 185                 190

Val Lys Gly Phe Tyr Pro Ser Asp Ile Ala Val Glu Trp Glu Ser Asn
        195                 200                 205
```

Gly Gln Pro Glu Asn Asn Tyr Lys Thr Thr Pro Pro Val Leu Asp Ser
    210                 215                 220

Asp Gly Ser Phe Phe Leu Tyr Ser Lys Leu Thr Val Asp Lys Ser Arg
225                 230                 235                 240

Trp Gln Gln Gly Asn Val Phe Ser Cys Ser Val Met His Glu Ala Leu
                245                 250                 255

His Asn His Tyr Thr Gln Lys Ser Leu Ser Leu Ser Pro Gly Lys Gly
            260                 265                 270

Gly Gly Gly Ser Gly Gly Gly Ser Gly Gly Gly Ser Asp Ser
        275                 280                 285

Ser Pro Leu Leu Gln Phe Gly Gln Val Arg Gln Arg Tyr Leu Tyr
    290                 295                 300

Thr Asp Asp Ala Cys Gln Thr Glu Ala His Leu Glu Ile Arg Glu Asp
305                 310                 315                 320

Gly Thr Val Gly Gly Ala Ala Asp Gln Ser Pro Glu Ser Leu Leu Gln
                325                 330                 335

Leu Lys Ala Leu Lys Pro Gly Val Ile Gln Ile Leu Gly Val Lys Thr
                340                 345                 350

Ser Arg Phe Leu Cys Gln Lys Pro Asp Gly Ala Leu Tyr Gly Ser Leu
            355                 360                 365

His Phe Asp Pro Glu Ala Cys Ser Phe Arg Glu Leu Leu Leu Glu Asp
        370                 375                 380

Gly Tyr Asn Val Tyr Gln Ser Glu Ala His Gly Leu Pro Leu His Leu
385                 390                 395                 400

Pro Cys Asn Arg Ser Pro His Arg Asp Pro Ala Ser Arg Gly Pro Ala
                405                 410                 415

Arg Phe Leu Pro Leu Pro Gly Leu Pro Pro Ala Leu Pro Glu Pro Pro
            420                 425                 430

Gly Ile Leu Ala Pro Gln Pro Pro Asp Val Gly Ser Ser Asp Pro Leu
        435                 440                 445

Ala Met Val Gly Gly Ser Gln Ala Arg Ser Pro Ser Tyr Ala Ser
    450                 455                 460

<210> SEQ ID NO 126
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Ser Gly Gly Gly Gly
        35                  40                  45

Ser Gly Gly Gly Gly Ser Gly Gly Gly Gly Asp Ser Ser Pro Leu Leu
    50                  55                  60

Gln Phe Gly Gly Gln Val Arg Gln Arg Tyr Leu Tyr Thr Asp Asp Ala
65                  70                  75                  80

Gln Glu Thr Glu Ala His Leu Glu Ile Arg Glu Asp Gly Thr Val Gly
                85                  90                  95

Gly Ala Ala His Gln Ser Pro Glu Ser Leu Leu Glu Leu Lys Ala Leu
            100                 105                 110

Lys Pro Gly Val Ile Gln Ile Leu Gly Val Lys Thr Ser Arg Phe Leu
            115                 120                 125

Cys Gln Lys Pro Asp Gly Ala Leu Tyr Gly Ser Leu His Phe Asp Pro
        130                 135                 140

Glu Ala Cys Ser Phe Arg Glu Leu Leu Leu Glu Asp Gly Tyr Asn Val
145                 150                 155                 160

Tyr Gln Ser Glu Ala His Gly Leu Pro Leu His Leu Pro Gly Asn Arg
                165                 170                 175

Ser Pro His Cys Asp Pro Ala Pro Gln Gly Pro Ala Arg Phe Leu Pro
            180                 185                 190

Leu Pro Gly Leu Pro Pro Ala Leu Pro Glu Pro Pro Gly Ile Leu Ala
        195                 200                 205

Pro Gln Pro Pro Asp Val Gly Ser Ser Asp Pro Leu Ala Met Val Gly
    210                 215                 220

Pro Ser Gln Gly Arg Ser Pro Ser Tyr Ala Ser
225                 230                 235

<210> SEQ ID NO 127
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
catggtgagg gtacgtttac ttctgatctg tctaaacaga tggaagaaga agctgttcgc      60
ctgttcattg aatggctgaa aaatggtggt ccgtcctccg gcgctcctcc gccttctggt     120
ggtggtggtt ctggcggtgg cggttctggc ggcggtggta gcggtggcgg cggtgatagc     180
agcccgctgc tgcagtttgg cggccaggtg cgtcagcgtt atctgtatac cgatgatgcg     240
caggaaaccg aagcgcatct ggaaattcgt gaagatggca ccgtgggcgg tgcggcgcat     300
cagagcccgg aaagcctgct ggaactgaaa gcgctgaaac cgggcgtgat tcagattctg     360
ggcgtgaaaa ccagccgttt tctgtgccag aaaccggatg gcgcgctgta tggcagcctg     420
cattttgatc cggaagcgtg cagctttcgt gaactgctgc tggaagatgg ctataacgtg     480
tatcagagcg aagcgcatgg cctgccgctg catctgccgg gcaaccgtag cccgcattgc     540
gatccggcac cgcagggtcc ggcgcgtttt ctgccgctgc cgggtctgcc gccggcactg     600
ccggaaccgc cgggtattct ggccccgcag ccgccggatg ttggtagcag cgatccgctg     660
gcgatggtgg tgccgagcca gggtcgtagc ccgagctatg cgagctaa               708

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser Gly Gly Gly Gly Ser Gly Gly Gly
1               5

<210> SEQ ID NO 129
<211> LENGTH: 37
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 129

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 130
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Ser Ser Pro Leu Leu Gln Phe Gly Gly Gln Val Arg Gln Arg Tyr
1               5                   10                  15

Leu Tyr Thr Asp Asp Ala Gln Glu Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Glu Leu Lys Ala Leu Lys Pro Gly Val Ile Gln Ile Leu Gly Val
    50                  55                  60

Lys Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asp Gly Tyr Asn Val Tyr Gln Ser Glu Ala His Gly Leu Pro Leu
            100                 105                 110

His Leu Pro Gly Asn Arg Ser Pro His Cys Asp Pro Ala Pro Gln Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 131
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Asp Ser Ser Pro Leu Leu Gln Phe Gly Gly Gln Val Arg Gln Arg Tyr
1               5                   10                  15

Leu Tyr Thr Asp Asp Ala Gln Glu Thr Glu Ala His Leu Glu Ile Arg
            20                  25                  30

Glu Asp Gly Thr Val Gly Gly Ala Ala His Gln Ser Pro Glu Ser Leu
```

```
                    35                  40                  45
Leu Glu Leu Lys Ala Leu Lys Pro Gly Val Ile Gln Ile Leu Gly Val
                50                  55                  60
Lys Thr Ser Arg Phe Leu Cys Gln Lys Pro Asp Gly Ala Leu Tyr Gly
 65                  70                  75                  80
Ser Leu His Phe Asp Pro Glu Ala Cys Ser Phe Arg Glu Leu Leu Leu
                    85                  90                  95
Glu Glu Gly Tyr Asn Val Tyr Gln Ser Glu Ala His Gly Leu Pro Leu
               100                 105                 110
His Leu Pro Gly Asn Arg Ser Pro His Arg Asp Pro Ala Pro Gln Gly
               115                 120                 125
Pro Ala Arg Phe Leu Pro Leu Pro Gly Leu Pro Pro Ala Leu Pro Glu
               130                 135                 140
Pro Pro Gly Ile Leu Ala Pro Gln Pro Pro Asp Val Gly Ser Ser Asp
145                 150                 155                 160
Pro Leu Ala Met Val Gly Pro Ser Gln Gly Arg Ser Pro Ser Tyr Ala
                165                 170                 175
Ser

<210> SEQ ID NO 132
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Met Asp Ser Asp Glu Thr Gly Phe Glu His Ser Gly Leu Trp Val Ser
1               5                   10                  15
Val Leu Ala Gly Leu Leu Leu Gly Ala Cys Gln Ala
                20                  25

<210> SEQ ID NO 133
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Gly Gly Pro Ser
                20                  25                  30
Ser Gly Ala Pro Pro Pro Ser Asp Lys Thr His Thr Cys Pro Pro Cys
            35                  40                  45
Pro Ala Pro Glu Ala Ala Gly Gly Pro Ser Val Phe Leu Phe Pro Pro
        50                  55                  60
Lys Pro Lys Asp Thr Leu Met Ile Ser Arg Thr Pro Glu Val Thr Cys
65                  70                  75                  80
Val Val Val Asp Val Ser His Glu Asp Pro Glu Val Lys Phe Asn Trp
                    85                  90                  95
Tyr Val Asp Gly Val Glu Val His Asn Ala Lys Thr Lys Pro Arg Glu
                100                 105                 110
Glu Gln Tyr Asn Ser Thr Tyr Arg Val Val Ser Val Leu Thr Val Leu
            115                 120                 125
```

His Gln Asp Trp Leu Asn Gly Lys Glu Tyr Lys Cys Lys Val Ser Asn
        130                 135                 140

Lys Ala Leu Pro Ala Pro Ile Glu Lys Thr Ile Ser Lys Ala Lys Gly
145                 150                 155                 160

Gln Pro Arg Glu Pro Gln Val Tyr Thr Leu Pro Pro Ser Arg Glu Glu
                165                 170                 175

Met Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn
        195                 200                 205

Asn Tyr Lys Thr Thr Pro Pro Val Leu Asp Ser Asp Gly Ser Phe Phe
210                 215                 220

Leu Tyr Ser Lys Leu Thr Val Asp Lys Ser Arg Trp Gln Gln Gly Asn
225                 230                 235                 240

Val Phe Ser Cys Ser Val Met His Glu Ala Leu His Asn His Tyr Thr
                245                 250                 255

Gln Lys Ser Leu Ser Leu Ser Pro Gly Lys Gly Ser Asp Ser Ser Pro
            260                 265                 270

Leu Leu Gln Phe Gly Gly Gln Val Arg Gln Arg Tyr Leu Tyr Thr Asp
        275                 280                 285

Asp Ala Cys Gln Thr Glu Ala His Leu Glu Ile Arg Glu Asp Gly Thr
290                 295                 300

Val Gly Gly Ala Ala Asp Gln Ser Pro Glu Ser Leu Leu Gln Leu Lys
305                 310                 315                 320

Ala Leu Lys Pro Gly Val Ile Gln Ile Leu Gly Val Lys Thr Ser Arg
                325                 330                 335

Phe Leu Cys Gln Lys Pro Asp Gly Ala Leu Tyr Gly Ser Leu His Phe
            340                 345                 350

Asp Pro Glu Ala Cys Ser Phe Arg Glu Leu Leu Leu Glu Asp Gly Tyr
        355                 360                 365

Asn Val Tyr Gln Ser Glu Ala His Gly Leu Pro Leu His Leu Pro Cys
370                 375                 380

Asn Arg Ser Pro His Arg Asp Pro Ala Ser Arg Gly Pro Ala Arg Phe
385                 390                 395                 400

Leu Pro Leu Pro Gly Leu Pro Pro Ala Leu Pro Glu Pro Pro Gly Ile
                405                 410                 415

Leu Ala Pro Gln Pro Pro Asp Val Gly Ser Ser Asp Pro Leu Ala Met
            420                 425                 430

Val Gly Gly Ser Gln Ala Arg Ser Pro Ser Tyr Ala Ser
        435                 440                 445

<210> SEQ ID NO 134
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Ser Gly Gly Gly Gly

```
                35                  40                  45
Ser Gly Gly Gly Ser Asp Lys Thr His Thr Cys Pro Cys Pro
 50                  55                  60

Ala Pro Glu Ala Ala Gly Gly Pro Ser Val Phe Leu Phe Pro Pro Lys
 65                      70                  75                  80

Pro Lys Asp Thr Leu Met Ile Ser Arg Thr Pro Glu Val Thr Cys Val
                     85                  90                  95

Val Val Asp Val Ser His Glu Asp Pro Glu Val Lys Phe Asn Trp Tyr
                100                 105                 110

Val Asp Gly Val Glu Val His Asn Ala Lys Thr Lys Pro Arg Glu Glu
                115                 120                 125

Gln Tyr Asn Ser Thr Tyr Arg Val Val Ser Val Leu Thr Val Leu His
130                 135                 140

Gln Asp Trp Leu Asn Gly Lys Glu Tyr Lys Cys Lys Val Ser Asn Lys
145                 150                 155                 160

Ala Leu Pro Ala Pro Ile Glu Lys Thr Ile Ser Lys Ala Lys Gly Gln
                165                 170                 175

Pro Arg Glu Pro Gln Val Tyr Thr Leu Pro Pro Ser Arg Glu Glu Met
                180                 185                 190

Thr Lys Asn Gln Val Ser Leu Thr Cys Leu Val Lys Gly Phe Tyr Pro
                195                 200                 205

Ser Asp Ile Ala Val Glu Trp Glu Ser Asn Gly Gln Pro Glu Asn Asn
210                 215                 220

Tyr Lys Thr Thr Pro Pro Val Leu Asp Ser Asp Gly Ser Phe Phe Leu
225                 230                 235                 240

Tyr Ser Lys Leu Thr Val Asp Lys Ser Arg Trp Gln Gln Gly Asn Val
                245                 250                 255

Phe Ser Cys Ser Val Met His Glu Ala Leu His Asn His Tyr Thr Gln
                260                 265                 270

Lys Ser Leu Ser Leu Ser Pro Gly Lys Gly Ser Asp Ser Ser Pro Leu
                275                 280                 285

Leu Gln Phe Gly Gly Gln Val Arg Gln Arg Tyr Leu Tyr Thr Asp Asp
                290                 295                 300

Ala Cys Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
                340                 345                 350

Leu Cys Gln Lys Pro Asp Gly Ala Leu Tyr Gly Ser Leu His Phe Asp
                355                 360                 365

Pro Glu Ala Cys Ser Phe Arg Glu Leu Leu Leu Glu Asp Gly Tyr Asn
                370                 375                 380

Val Tyr Gln Ser Glu Ala His Gly Leu Pro Leu His Leu Pro Cys Asn
385                 390                 395                 400

Arg Ser Pro His Arg Asp Pro Ala Ser Arg Gly Pro Ala Arg Phe Leu
                405                 410                 415

Pro Leu Pro Gly Leu Pro Pro Ala Leu Pro Glu Pro Gly Ile Leu
                420                 425                 430

Ala Pro Gln Pro Pro Asp Val Gly Ser Ser Asp Pro Leu Ala Met Val
                435                 440                 445

Gly Gly Ser Gln Ala Arg Ser Pro Ser Tyr Ala Ser
450                 455                 460
```

<210> SEQ ID NO 135
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

```
His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
                20                  25                  30

Gly Ser Gly Gly Gly Ser Gly Gly Gly Ser Asp Lys Thr His
            35                  40                  45

Thr Cys Pro Pro Cys Pro Ala Pro Glu Ala Ala Gly Gly Pro Ser Val
        50                  55                  60

Phe Leu Phe Pro Pro Lys Pro Lys Asp Thr Leu Met Ile Ser Arg Thr
65                  70                  75                  80

Pro Glu Val Thr Cys Val Val Val Asp Val Ser His Glu Asp Pro Glu
                85                  90                  95

Val Lys Phe Asn Trp Tyr Val Asp Gly Val Glu Val His Asn Ala Lys
            100                 105                 110

Thr Lys Pro Arg Glu Glu Gln Tyr Asn Ser Thr Tyr Arg Val Val Ser
        115                 120                 125

Val Leu Thr Val Leu His Gln Asp Trp Leu Asn Gly Lys Glu Tyr Lys
    130                 135                 140

Cys Lys Val Ser Asn Lys Ala Leu Pro Ala Pro Ile Glu Lys Thr Ile
145                 150                 155                 160

Ser Lys Ala Lys Gly Gln Pro Arg Glu Pro Gln Val Tyr Thr Leu Pro
                165                 170                 175

Pro Ser Arg Glu Glu Met Thr Lys Asn Gln Val Ser Leu Thr Cys Leu
            180                 185                 190

Val Lys Gly Phe Tyr Pro Ser Asp Ile Ala Val Glu Trp Glu Ser Asn
        195                 200                 205

Gly Gln Pro Glu Asn Asn Tyr Lys Thr Thr Pro Pro Val Leu Asp Ser
    210                 215                 220

Asp Gly Ser Phe Phe Leu Tyr Ser Lys Leu Thr Val Asp Lys Ser Arg
225                 230                 235                 240

Trp Gln Gln Gly Asn Val Phe Ser Cys Ser Val Met His Glu Ala Leu
                245                 250                 255

His Asn His Tyr Thr Gln Lys Ser Leu Ser Leu Ser Pro Gly Lys Gly
            260                 265                 270

Ser Asp Ser Ser Pro Leu Leu Gln Phe Gly Gly Gln Val Arg Gln Arg
        275                 280                 285

Tyr Leu Tyr Thr Asp Asp Ala Cys Gln Thr Glu Ala His Leu Glu Ile
    290                 295                 300

Arg Glu Asp Gly Thr Val Gly Gly Ala Ala Asp Gln Ser Pro Glu Ser
305                 310                 315                 320

Leu Leu Gln Leu Lys Ala Leu Lys Pro Gly Val Ile Gln Ile Leu Gly
                325                 330                 335

Val Lys Thr Ser Arg Phe Leu Cys Gln Arg Pro Asp Gly Thr Leu Tyr
            340                 345                 350

Gly Ser Leu His Phe Asp Pro Glu Ala Cys Ser Phe Arg Glu Leu Leu
```

```
                    355                 360                 365
Leu Glu Asp Gly Tyr Asn Val Tyr Gln Ser Glu Ala His Gly Leu Pro
370                 375                 380

Leu His Leu Pro Cys Asn Arg Ser Pro His Arg Asp Pro Ala Ser Arg
385                 390                 395                 400

Gly Pro Ala Arg Phe Leu Pro Leu Pro Gly Leu Pro Pro Ala Leu Pro
                    405                 410                 415

Glu Pro Pro Gly Ile Leu Ala Pro Gln Pro Pro Asp Val Gly Ser Ser
                420                 425                 430

Asp Pro Leu Ala Met Val Gly Gly Ser Gln Ala Arg Ser Pro Ser Tyr
            435                 440                 445

Ala Ser
    450

<210> SEQ ID NO 136
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
                20                  25                  30

Gly Ser Gly Gly Gly Gly Ser Gly Gly Gly Gly Ser Asp Lys Thr His
            35                  40                  45

Thr Cys Pro Pro Cys Pro Ala Pro Glu Ala Ala Gly Gly Pro Ser Val
50                  55                  60

Phe Leu Phe Pro Pro Lys Pro Lys Asp Thr Leu Met Ile Ser Arg Thr
65                  70                  75                  80

Pro Glu Val Thr Cys Val Val Asp Val Ser His Glu Asp Pro Glu
                85                  90                  95

Val Lys Phe Asn Trp Tyr Val Asp Gly Val Glu Val His Asn Ala Lys
                100                 105                 110

Thr Lys Pro Arg Glu Glu Gln Tyr Asn Ser Thr Tyr Arg Val Val Ser
            115                 120                 125

Val Leu Thr Val Leu His Gln Asp Trp Leu Asn Gly Lys Glu Tyr Lys
130                 135                 140

Cys Lys Val Ser Asn Lys Ala Leu Pro Ala Pro Ile Glu Lys Thr Ile
145                 150                 155                 160

Ser Lys Ala Lys Gly Gln Pro Arg Glu Pro Gln Val Tyr Thr Leu Pro
                165                 170                 175

Pro Ser Arg Glu Glu Met Thr Lys Asn Gln Val Ser Leu Thr Cys Leu
            180                 185                 190

Val Lys Gly Phe Tyr Pro Ser Asp Ile Ala Val Glu Trp Glu Ser Asn
        195                 200                 205

Gly Gln Pro Glu Asn Asn Tyr Lys Thr Thr Pro Pro Val Leu Asp Ser
    210                 215                 220

Asp Gly Ser Phe Phe Leu Tyr Ser Lys Leu Thr Val Asp Lys Ser Arg
225                 230                 235                 240

Trp Gln Gln Gly Asn Val Phe Ser Cys Ser Val Met His Glu Ala Leu
                245                 250                 255
```

His Asn His Tyr Thr Gln Lys Ser Leu Ser Leu Ser Pro Gly Lys Gly
                260                 265                 270

Ser Asp Ser Ser Pro Leu Leu Gln Phe Gly Gly Gln Val Arg Gln Arg
            275                 280                 285

Tyr Leu Tyr Thr Asp Asp Ala Cys Gln Thr Glu Ala His Leu Glu Ile
        290                 295                 300

Arg Glu Asp Gly Thr Val Gly Gly Ala Ala Asp Gln Ser Pro Glu Ser
305                 310                 315                 320

Leu Leu Gln Leu Lys Ala Leu Lys Pro Gly Val Ile Gln Ile Leu Gly
                325                 330                 335

Val Lys Thr Ser Arg Phe Leu Cys Gln Lys Pro Asp Gly Ala Leu Tyr
            340                 345                 350

Gly Ser Leu His Phe Asp Pro Glu Ala Cys Ser Phe Arg Glu Leu Leu
        355                 360                 365

Leu Glu Asp Gly Tyr Asn Val Tyr Gln Ser Glu Ala His Gly Leu Pro
370                 375                 380

Leu His Leu Pro Cys Asn Arg Ser Pro His Arg Asp Pro Ala Ser Arg
385                 390                 395                 400

Gly Pro Ala Arg Phe Leu Pro Leu Pro Gly Leu Pro Pro Ala Leu Pro
                405                 410                 415

Glu Pro Pro Gly Ile Leu Ala Pro Gln Pro Pro Asp Val Gly Ser Ser
            420                 425                 430

Asp Pro Leu Ala Met Val Gly Ser Gln Ala Arg Ser Pro Ser Tyr
        435                 440                 445

Ala Ser
    450

<210> SEQ ID NO 137
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
            20                  25                  30

Gly Ser Gly Gly Gly Gly Ser Gly Gly Gly Gly Ser Asp Lys Thr His
        35                  40                  45

Thr Cys Pro Pro Cys Pro Ala Pro Glu Ala Ala Gly Gly Pro Ser Val
    50                  55                  60

Phe Leu Phe Pro Pro Lys Pro Lys Asp Thr Leu Met Ile Ser Arg Thr
65                  70                  75                  80

Pro Glu Val Thr Cys Val Val Val Asp Val Ser His Glu Asp Pro Glu
                85                  90                  95

Val Lys Phe Asn Trp Tyr Val Asp Gly Val Glu Val His Asn Ala Lys
            100                 105                 110

Thr Lys Pro Arg Glu Glu Gln Tyr Asn Ser Thr Tyr Arg Val Val Ser
        115                 120                 125

Val Leu Thr Val Leu His Gln Asp Trp Leu Asn Gly Lys Glu Tyr Lys
130                 135                 140

Cys Lys Val Ser Asn Lys Ala Leu Pro Ala Pro Ile Glu Lys Thr Ile
145                 150                 155                 160

```
Ser Lys Ala Lys Gly Gln Pro Arg Glu Pro Gln Val Tyr Thr Leu Pro
            165                 170                 175

Pro Ser Arg Glu Glu Met Thr Lys Asn Gln Val Ser Leu Thr Cys Leu
        180                 185                 190

Val Lys Gly Phe Tyr Pro Ser Asp Ile Ala Val Glu Trp Glu Ser Asn
        195                 200                 205

Gly Gln Pro Glu Asn Asn Tyr Lys Thr Thr Pro Pro Val Leu Asp Ser
    210                 215                 220

Asp Gly Ser Phe Phe Leu Tyr Ser Lys Leu Thr Val Asp Lys Ser Arg
225                 230                 235                 240

Trp Gln Gln Gly Asn Val Phe Ser Cys Ser Val Met His Glu Ala Leu
                245                 250                 255

His Asn His Tyr Thr Gln Lys Ser Leu Ser Leu Ser Pro Gly Lys Asp
            260                 265                 270

Ser Ser Pro Leu Leu Gln Phe Gly Gly Gln Val Arg Gln Arg Tyr Leu
        275                 280                 285

Tyr Thr Asp Asp Ala Cys Gln Thr Glu Ala His Leu Glu Ile Arg Glu
    290                 295                 300

Asp Gly Thr Val Gly Gly Ala Ala Asp Gln Ser Pro Glu Ser Leu Leu
305                 310                 315                 320

Gln Leu Lys Ala Leu Lys Pro Gly Val Ile Gln Ile Leu Gly Val Lys
                325                 330                 335

Thr Ser Arg Phe Leu Cys Gln Lys Pro Asp Gly Ala Leu Tyr Gly Ser
            340                 345                 350

Leu His Phe Asp Pro Glu Ala Cys Ser Phe Arg Glu Leu Leu Leu Glu
        355                 360                 365

Asp Gly Tyr Asn Val Tyr Gln Ser Glu Ala His Gly Leu Pro Leu His
    370                 375                 380

Leu Pro Cys Asn Arg Ser Pro His Arg Asp Pro Ala Ser Arg Gly Pro
385                 390                 395                 400

Ala Arg Phe Leu Pro Leu Pro Gly Leu Pro Pro Ala Leu Pro Glu Pro
                405                 410                 415

Pro Gly Ile Leu Ala Pro Gln Pro Pro Asp Val Gly Ser Ser Asp Pro
            420                 425                 430

Leu Ala Met Val Gly Gly Ser Gln Ala Arg Ser Pro Ser Tyr Ala Ser
        435                 440                 445

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ser Gly Gly Gly Gly Ser Gly Gly Gly Gly Ser Gly Gly Gly Gly Ser
1               5                   10                  15

Ala

<210> SEQ ID NO 139
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 139

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Ser Asp Lys Thr His
        35                  40                  45

Thr Cys Pro Pro Cys Pro Ala Pro Glu Ala Ala Gly Gly Pro Ser Val
50                  55                  60

Phe Leu Phe Pro Pro Lys Pro Lys Asp Thr Leu Met Ile Ser Arg Thr
65                  70                  75                  80

Pro Glu Val Thr Cys Val Val Val Asp Val Ser His Glu Asp Pro Glu
                85                  90                  95

Val Lys Phe Asn Trp Tyr Val Asp Gly Val Glu Val His Asn Ala Lys
            100                 105                 110

Thr Lys Pro Arg Glu Glu Gln Tyr Asn Ser Thr Tyr Arg Val Val Ser
        115                 120                 125

Val Leu Thr Val Leu His Gln Asp Trp Leu Asn Gly Lys Glu Tyr Lys
130                 135                 140

Cys Lys Val Ser Asn Lys Ala Leu Pro Ala Pro Ile Glu Lys Thr Ile
145                 150                 155                 160

Ser Lys Ala Lys Gly Gln Pro Arg Glu Pro Gln Val Tyr Thr Leu Pro
                165                 170                 175

Pro Ser Arg Glu Glu Met Thr Lys Asn Gln Val Ser Leu Thr Cys Leu
            180                 185                 190

Val Lys Gly Phe Tyr Pro Ser Asp Ile Ala Val Glu Trp Glu Ser Asn
        195                 200                 205

Gly Gln Pro Glu Asn Asn Tyr Lys Thr Thr Pro Pro Val Leu Asp Ser
210                 215                 220

Asp Gly Ser Phe Phe Leu Tyr Ser Lys Leu Thr Val Asp Lys Ser Arg
225                 230                 235                 240

Trp Gln Gln Gly Asn Val Phe Ser Cys Ser Val Met His Glu Ala Leu
                245                 250                 255

His Asn His Tyr Thr Gln Lys Ser Leu Ser Leu Ser Pro Gly Lys
            260                 265                 270
```

<210> SEQ ID NO 140
<211> LENGTH: 458
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 140

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Asp Lys Thr His Thr Cys Pro Cys
        35                  40                  45

Pro Ala Pro Glu Ala Ala Gly Gly Pro Ser Val Phe Leu Phe Pro Pro
50                  55                  60

Lys Pro Lys Asp Thr Leu Met Ile Ser Arg Thr Pro Glu Val Thr Cys
65                  70                  75                  80
```

Val Val Val Asp Val Ser His Glu Asp Pro Glu Val Lys Phe Asn Trp
            85                  90                  95

Tyr Val Asp Gly Val Glu Val His Asn Ala Lys Thr Lys Pro Arg Glu
        100                 105                 110

Glu Gln Tyr Asn Ser Thr Tyr Arg Val Val Ser Val Leu Thr Val Leu
    115                 120                 125

His Gln Asp Trp Leu Asn Gly Lys Glu Tyr Lys Cys Lys Val Ser Asn
130                 135                 140

Lys Ala Leu Pro Ala Pro Ile Glu Lys Thr Ile Ser Lys Ala Lys Gly
145                 150                 155                 160

Gln Pro Arg Glu Pro Gln Val Tyr Thr Leu Pro Pro Ser Arg Glu Glu
                165                 170                 175

Met Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn
        195                 200                 205

Asn Tyr Lys Thr Thr Pro Pro Val Leu Asp Ser Asp Gly Ser Phe Phe
    210                 215                 220

Leu Tyr Ser Lys Leu Thr Val Asp Lys Ser Arg Trp Gln Gln Gly Asn
225                 230                 235                 240

Val Phe Ser Cys Ser Val Met His Glu Ala Leu His Asn His Tyr Thr
                245                 250                 255

Gln Lys Ser Leu Ser Leu Ser Pro Gly Lys Gly Gly Gly Gly Ser Gly
            260                 265                 270

Gly Gly Gly Ser Gly Gly Gly Ser Asp Ser Ser Pro Leu Leu Gln
        275                 280                 285

Phe Gly Gly Gln Val Arg Gln Arg Tyr Leu Tyr Thr Asp Asp Ala Cys
    290                 295                 300

Gln Thr Glu Ala His Leu Glu Ile Arg Glu Asp Gly Thr Val Gly Gly
305                 310                 315                 320

Ala Ala Asp Gln Ser Pro Glu Ser Leu Leu Gln Leu Lys Ala Leu Lys
                325                 330                 335

Pro Gly Val Ile Gln Ile Leu Gly Val Lys Thr Ser Arg Phe Leu Cys
            340                 345                 350

Gln Lys Pro Asp Gly Ala Leu Tyr Gly Ser Leu His Phe Asp Pro Glu
        355                 360                 365

Ala Cys Ser Phe Arg Glu Leu Leu Leu Glu Asp Gly Tyr Asn Val Tyr
    370                 375                 380

Gln Ser Glu Ala His Gly Leu Pro Leu His Leu Pro Cys Asn Arg Ser
385                 390                 395                 400

Pro His Arg Asp Pro Ala Ser Arg Gly Pro Ala Arg Phe Leu Pro Leu
                405                 410                 415

Pro Gly Leu Pro Pro Ala Leu Pro Glu Pro Gly Ile Leu Ala Pro
            420                 425                 430

Gln Pro Pro Asp Val Gly Ser Ser Asp Pro Leu Ala Met Val Gly Gly
        435                 440                 445

Ser Gln Ala Arg Ser Pro Ser Tyr Ala Ser
    450                 455

<210> SEQ ID NO 141
<211> LENGTH: 447
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 141

```
His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Asp Lys Thr His
            20                  25                  30

Thr Cys Pro Pro Cys Pro Ala Pro Glu Ala Ala Gly Gly Pro Ser Val
        35                  40                  45

Phe Leu Phe Pro Pro Lys Pro Lys Asp Thr Leu Met Ile Ser Arg Thr
    50                  55                  60

Pro Glu Val Thr Cys Val Val Val Asp Val Ser His Glu Asp Pro Glu
65              70                  75                  80

Val Lys Phe Asn Trp Tyr Val Asp Gly Val Glu Val His Asn Ala Lys
                85                  90                  95

Thr Lys Pro Arg Glu Glu Gln Tyr Asn Ser Thr Tyr Arg Val Val Ser
            100                 105                 110

Val Leu Thr Val Leu His Gln Asp Trp Leu Asn Gly Lys Glu Tyr Lys
        115                 120                 125

Cys Lys Val Ser Asn Lys Ala Leu Pro Ala Pro Ile Glu Lys Thr Ile
    130                 135                 140

Ser Lys Ala Lys Gly Gln Pro Arg Glu Pro Gln Val Tyr Thr Leu Pro
145                 150                 155                 160

Pro Ser Arg Glu Glu Met Thr Lys Asn Gln Val Ser Leu Thr Cys Leu
                165                 170                 175

Val Lys Gly Phe Tyr Pro Ser Asp Ile Ala Val Glu Trp Glu Ser Asn
            180                 185                 190

Gly Gln Pro Glu Asn Asn Tyr Lys Thr Thr Pro Pro Val Leu Asp Ser
        195                 200                 205

Asp Gly Ser Phe Phe Leu Tyr Ser Lys Leu Thr Val Asp Lys Ser Arg
210                 215                 220

Trp Gln Gln Gly Asn Val Phe Ser Cys Ser Val Met His Glu Ala Leu
225                 230                 235                 240

His Asn His Tyr Thr Gln Lys Ser Leu Ser Leu Ser Pro Gly Lys Gly
                245                 250                 255

Gly Gly Gly Ser Gly Gly Gly Ser Gly Gly Gly Ser Asp Ser
            260                 265                 270

Ser Pro Leu Leu Gln Phe Gly Gly Gln Val Arg Gln Arg Tyr Leu Tyr
    275                 280                 285

Thr Asp Asp Ala Cys Gln Thr Glu Ala His Leu Glu Ile Arg Glu Asp
290                 295                 300

Gly Thr Val Gly Gly Ala Ala Asp Gln Ser Pro Glu Ser Leu Leu Gln
305                 310                 315                 320

Leu Lys Ala Leu Lys Pro Gly Val Ile Gln Ile Leu Gly Val Lys Thr
                325                 330                 335

Ser Arg Phe Leu Cys Gln Lys Pro Asp Gly Ala Leu Tyr Gly Ser Leu
            340                 345                 350

His Phe Asp Pro Glu Ala Cys Ser Phe Arg Glu Leu Leu Leu Glu Asp
        355                 360                 365

Gly Tyr Asn Val Tyr Gln Ser Glu Ala His Gly Leu Pro Leu His Leu
    370                 375                 380

Pro Cys Asn Arg Ser Pro His Arg Asp Pro Ala Ser Arg Gly Pro Ala
385                 390                 395                 400
```

Arg Phe Leu Pro Leu Pro Gly Leu Pro Pro Ala Leu Pro Glu Pro Pro
                405                 410                 415

Gly Ile Leu Ala Pro Gln Pro Pro Asp Val Gly Ser Ser Asp Pro Leu
            420                 425                 430

Ala Met Val Gly Gly Ser Gln Ala Arg Ser Pro Ser Tyr Ala Ser
        435                 440                 445

<210> SEQ ID NO 142
<211> LENGTH: 434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Asp Lys Thr His
            20                  25                  30

Thr Cys Pro Pro Cys Pro Ala Pro Glu Ala Ala Gly Gly Pro Ser Val
        35                  40                  45

Phe Leu Phe Pro Pro Lys Pro Lys Asp Thr Leu Met Ile Ser Arg Thr
    50                  55                  60

Pro Glu Val Thr Cys Val Val Asp Val Ser His Glu Asp Pro Glu
65                  70                  75                  80

Val Lys Phe Asn Trp Tyr Val Asp Gly Val Glu Val His Asn Ala Lys
                85                  90                  95

Thr Lys Pro Arg Glu Glu Gln Tyr Asn Ser Thr Tyr Arg Val Val Ser
            100                 105                 110

Val Leu Thr Val Leu His Gln Asp Trp Leu Asn Gly Lys Glu Tyr Lys
        115                 120                 125

Cys Lys Val Ser Asn Lys Ala Leu Pro Ala Pro Ile Glu Lys Thr Ile
    130                 135                 140

Ser Lys Ala Lys Gly Gln Pro Arg Glu Pro Gln Val Tyr Thr Leu Pro
145                 150                 155                 160

Pro Ser Arg Glu Glu Met Thr Lys Asn Gln Val Ser Leu Thr Cys Leu
                165                 170                 175

Val Lys Gly Phe Tyr Pro Ser Asp Ile Ala Val Glu Trp Glu Ser Asn
            180                 185                 190

Gly Gln Pro Glu Asn Asn Tyr Lys Thr Thr Pro Pro Val Leu Asp Ser
        195                 200                 205

Asp Gly Ser Phe Phe Leu Tyr Ser Lys Leu Thr Val Asp Lys Ser Arg
    210                 215                 220

Trp Gln Gln Gly Asn Val Phe Ser Cys Ser Val Met His Glu Ala Leu
225                 230                 235                 240

His Asn His Tyr Thr Gln Lys Ser Leu Ser Leu Ser Pro Gly Lys Gly
                245                 250                 255

Ser Asp Ser Ser Pro Leu Leu Gln Phe Gly Gly Gln Val Arg Gln Arg
            260                 265                 270

Tyr Leu Tyr Thr Asp Asp Ala Cys Gln Thr Glu Ala His Leu Glu Ile
        275                 280                 285

Arg Glu Asp Gly Thr Val Gly Gly Ala Ala Asp Gln Ser Pro Glu Ser
    290                 295                 300

Leu Leu Gln Leu Lys Ala Leu Lys Pro Gly Val Ile Gln Ile Leu Gly

```
                    305                 310                 315                 320
Val Lys Thr Ser Arg Phe Leu Cys Gln Arg Pro Asp Gly Thr Leu Tyr
                325                 330                 335

Gly Ser Leu His Phe Asp Pro Glu Ala Cys Ser Phe Arg Glu Leu Leu
                340                 345                 350

Leu Glu Asp Gly Tyr Asn Val Tyr Gln Ser Glu Ala His Gly Leu Pro
                355                 360                 365

Leu His Leu Pro Cys Asn Arg Ser Pro His Arg Asp Pro Ala Ser Arg
                370                 375                 380

Gly Pro Ala Arg Phe Leu Pro Leu Pro Gly Leu Pro Pro Ala Leu Pro
385                 390                 395                 400

Glu Pro Pro Gly Ile Leu Ala Pro Gln Pro Pro Asp Val Gly Ser Ser
                405                 410                 415

Asp Pro Leu Ala Met Val Gly Gly Ser Gln Ala Arg Ser Pro Ser Tyr
                420                 425                 430

Ala Ser

<210> SEQ ID NO 143
<211> LENGTH: 434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Asp Lys Thr His
                20                  25                  30

Thr Cys Pro Pro Cys Pro Ala Pro Glu Ala Ala Gly Gly Pro Ser Val
                35                  40                  45

Phe Leu Phe Pro Pro Lys Pro Lys Asp Thr Leu Met Ile Ser Arg Thr
            50                  55                  60

Pro Glu Val Thr Cys Val Val Val Asp Val Ser His Glu Asp Pro Glu
65              70                  75                  80

Val Lys Phe Asn Trp Tyr Val Asp Gly Val Glu Val His Asn Ala Lys
                85                  90                  95

Thr Lys Pro Arg Glu Glu Gln Tyr Asn Ser Thr Tyr Arg Val Val Ser
                100                 105                 110

Val Leu Thr Val Leu His Gln Asp Trp Leu Asn Gly Lys Glu Tyr Lys
                115                 120                 125

Cys Lys Val Ser Asn Lys Ala Leu Pro Ala Pro Ile Glu Lys Thr Ile
            130                 135                 140

Ser Lys Ala Lys Gly Gln Pro Arg Glu Pro Gln Val Tyr Thr Leu Pro
145                 150                 155                 160

Pro Ser Arg Glu Glu Met Thr Lys Asn Gln Val Ser Leu Thr Cys Leu
                165                 170                 175

Val Lys Gly Phe Tyr Pro Ser Asp Ile Ala Val Glu Trp Glu Ser Asn
                180                 185                 190

Gly Gln Pro Glu Asn Asn Tyr Lys Thr Thr Pro Pro Val Leu Asp Ser
                195                 200                 205

Asp Gly Ser Phe Phe Leu Tyr Ser Lys Leu Thr Val Asp Lys Ser Arg
            210                 215                 220

Trp Gln Gln Gly Asn Val Phe Ser Cys Ser Val Met His Glu Ala Leu
```

```
            225                 230                 235                 240
His Asn His Tyr Thr Gln Lys Ser Leu Ser Leu Ser Pro Gly Lys Gly
                245                 250                 255

Ser Asp Ser Ser Pro Leu Leu Gln Phe Gly Gly Gln Val Arg Gln Arg
            260                 265                 270

Tyr Leu Tyr Thr Asp Asp Ala Cys Gln Thr Glu Ala His Leu Glu Ile
                275                 280                 285

Arg Glu Asp Gly Thr Val Gly Gly Ala Ala Asp Gln Ser Pro Glu Ser
            290                 295                 300

Leu Leu Gln Leu Lys Ala Leu Lys Pro Gly Val Ile Gln Ile Leu Gly
305                 310                 315                 320

Val Lys Thr Ser Arg Phe Leu Cys Gln Lys Pro Asp Gly Ala Leu Tyr
                325                 330                 335

Gly Ser Leu His Phe Asp Pro Glu Ala Cys Ser Phe Arg Glu Leu Leu
                340                 345                 350

Leu Glu Asp Gly Tyr Asn Val Tyr Gln Ser Glu Ala His Gly Leu Pro
            355                 360                 365

Leu His Leu Pro Cys Asn Arg Ser Pro His Arg Asp Pro Ala Ser Arg
            370                 375                 380

Gly Pro Ala Arg Phe Leu Pro Leu Pro Gly Leu Pro Pro Ala Leu Pro
385                 390                 395                 400

Glu Pro Pro Gly Ile Leu Ala Pro Gln Pro Pro Asp Val Gly Ser Ser
                405                 410                 415

Asp Pro Leu Ala Met Val Gly Gly Ser Gln Ala Arg Ser Pro Ser Tyr
            420                 425                 430

Ala Ser

<210> SEQ ID NO 144
<211> LENGTH: 532
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser Gly Gly Gly Ser Gly Gly Gly Gly Gly
            35                  40                  45

Ser Gly Gly Gly Ser Thr Asp Thr Leu Leu Leu Trp Val Leu Leu
        50                  55                  60

Leu Trp Val Pro Gly Ser Thr Gly His Gly Glu Gly Thr Phe Thr Ser
65              70                  75                  80

Asp Leu Ser Lys Gln Met Glu Glu Glu Ala Val Arg Leu Phe Ile Glu
                85                  90                  95

Trp Leu Lys Asn Gly Gly Pro Ser Ser Gly Ala Pro Pro Pro Ser Gly
                100                 105                 110

Gly Gly Ser Gly Gly Gly Gly Ser Gly Gly Gly Gly Ser Asp Lys
            115                 120                 125

Thr His Thr Cys Pro Pro Cys Pro Ala Pro Glu Ala Ala Gly Gly Pro
            130                 135                 140

Ser Val Phe Leu Phe Pro Pro Lys Pro Lys Asp Thr Leu Met Ile Ser
```

```
            145                 150                 155                 160
Arg Thr Pro Glu Val Thr Cys Val Val Asp Val Ser His Glu Asp
                165                 170                 175

Pro Glu Val Lys Phe Asn Trp Tyr Val Asp Gly Val Glu Val His Asn
                180                 185                 190

Ala Lys Thr Lys Pro Arg Glu Glu Gln Tyr Asn Ser Thr Tyr Arg Val
                195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Glu Glu Met Thr Lys Asn Gln Val Ser Leu Thr
                260                 265                 270

Cys Leu Val Lys Gly Phe Tyr Pro Ser Asp Ile Ala Val Glu Trp Glu
            275                 280                 285

Ser Asn Gly Gln Pro Glu Asn Asn Tyr Lys Thr Thr Pro Pro Val Leu
        290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

Lys Gly Ser Asp Ser Ser Pro Leu Leu Gln Phe Gly Gly Gln Val Arg
        355                 360                 365

Gln Arg Tyr Leu Tyr Thr Asp Asp Ala Cys Gln Thr Glu Ala His Leu
            370                 375                 380

Glu Ile Arg Glu Asp Gly Thr Val Gly Gly Ala Ala Asp Gln Ser Pro
385                 390                 395                 400

Glu Ser Leu Leu Gln Leu Lys Ala Leu Lys Pro Gly Val Ile Gln Ile
                405                 410                 415

Leu Gly Val Lys Thr Ser Arg Phe Leu Cys Gln Lys Pro Asp Gly Ala
                420                 425                 430

Leu Tyr Gly Ser Leu His Phe Asp Pro Glu Ala Cys Ser Phe Arg Glu
            435                 440                 445

Leu Leu Leu Glu Asp Gly Tyr Asn Val Tyr Gln Ser Glu Ala His Gly
        450                 455                 460

Leu Pro Leu His Leu Pro Cys Asn Arg Ser Pro His Arg Asp Pro Ala
465                 470                 475                 480

Ser Arg Gly Pro Ala Arg Phe Leu Pro Leu Pro Gly Leu Pro Pro Ala
                485                 490                 495

Leu Pro Glu Pro Pro Gly Ile Leu Ala Pro Gln Pro Pro Asp Val Gly
            500                 505                 510

Ser Ser Asp Pro Leu Ala Met Val Gly Gly Ser Gln Ala Arg Ser Pro
        515                 520                 525

Ser Tyr Ala Ser
        530

<210> SEQ ID NO 145
<211> LENGTH: 216
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 145

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
                20                  25                  30

Gly Gly Gly Ser Gly Gly Gly Asp Ser Ser Pro Leu Leu Gln Phe Gly
                35                  40                  45

Gly Gln Val Arg Gln Arg Tyr Leu Tyr Thr Asp Ala Gln Glu Thr
    50                  55                  60

Glu Ala His Leu Glu Ile Arg Glu Asp Gly Thr Val Gly Gly Ala Ala
65                  70                  75                  80

His Gln Ser Pro Glu Ser Leu Leu Glu Leu Lys Ala Leu Lys Pro Gly
                85                  90                  95

Val Ile Gln Ile Leu Gly Val Lys Thr Ser Arg Phe Leu Cys Gln Lys
                100                 105                 110

Pro Asp Gly Ala Leu Tyr Gly Ser Leu His Phe Asp Pro Glu Ala Cys
                115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Arg Ser Pro His
145                 150                 155                 160

Cys Asp Pro Ala Pro Gln Gly Pro Ala Arg Phe Leu Pro Leu Pro Gly
                165                 170                 175

Leu Pro Pro Ala Leu Pro Glu Pro Pro Gly Ile Leu Ala Pro Gln Pro
                180                 185                 190

Pro Asp Val Gly Ser Ser Asp Pro Leu Ala Met Val Gly Pro Ser Gln
                195                 200                 205

Gly Arg Ser Pro Ser Tyr Ala Ser
                210                 215

<210> SEQ ID NO 146
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
                20                  25                  30

Gly Gly Gly Ser Gly Gly Gly Asp Ser Ser Pro Leu Leu Gln Phe Gly
                35                  40                  45

Gly Gln Val Arg Gln Arg Tyr Leu Tyr Thr Asp Ala Gln Glu Thr
    50                  55                  60

Glu Ala His Leu Glu Ile Arg Glu Asp Gly Thr Val Gly Gly Ala Ala
65                  70                  75                  80

His Gln Ser Pro Glu Ser Leu Leu Glu Leu Lys Ala Leu Lys Pro Gly
                85                  90                  95

Val Ile Gln Ile Leu Gly Val Lys Thr Ser Arg Phe Leu Cys Gln Lys
                100                 105                 110
```

```
Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
130                 135                 140

Glu Ala His Gly Leu Pro Leu His Leu Pro Gly Asn Arg Ser Pro His
145                 150                 155                 160

Cys Asp Pro Ala Pro Gln Gly Pro Ala Arg Phe Leu Pro Leu Pro Gly
                165                 170                 175

Leu Pro Pro Ala Leu Pro Glu Pro Pro Gly Ile Leu Ala Pro Gln Pro
                180                 185                 190

Pro Asp Val Gly Ser Ser Asp Pro Leu Ala Met Val Gly Pro Ser Gln
                195                 200                 205

Gly Arg Ser Pro Ser Tyr Ala Ser
        210                 215

<210> SEQ ID NO 147
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
                20                  25                  30

Gly Gly Gly Ser Gly Gly Gly Asp Ser Ser Pro Leu Leu Gln Phe Gly
            35                  40                  45

Gly Gln Val Arg Gln Arg Tyr Leu Tyr Thr Asp Asp Ala Gln Glu Thr
        50                  55                  60

Glu Ala His Leu Glu Ile Arg Glu Asp Gly Thr Val Gly Gly Ala Ala
65                  70                  75                  80

His Gln Ser Pro Glu Ser Leu Leu Glu Leu Lys Ala Leu Lys Pro Gly
                85                  90                  95

Val Ile Gln Ile Leu Gly Val Lys Thr Ser Arg Phe Leu Cys Gln Lys
                100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
130                 135                 140

Glu Ala His Gly Leu Pro Leu His Leu Pro Gly Asn Arg Ser Pro His
145                 150                 155                 160

Cys Asp Pro Ala Pro Gln Gly Pro Ala Arg Phe Leu Pro Leu Pro Gly
                165                 170                 175

Leu Pro Pro Ala Leu Pro Glu Pro Pro Gly Ile Leu Ala Pro Gln Pro
                180                 185                 190

Pro Asp Val Gly Ser Ser Asp Pro Leu Ala Met Val Gly Pro Ser Gln
                195                 200                 205

Gly Arg Ser Pro Ser Tyr Ala Ser
        210                 215

<210> SEQ ID NO 148
<211> LENGTH: 227
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 148

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Ser Gly
            20                  25                  30

Gly Gly Gly Ser Gly Gly Gly Gly Ser Gly Gly Gly Ser Gly Gly
        35                  40                  45

Gly Gly Asp Ser Ser Pro Leu Leu Gln Phe Gly Gly Gln Val Arg Gln
    50                  55                  60

Arg Tyr Leu Tyr Thr Asp Asp Ala Gln Glu Thr Glu Ala His Leu Glu
65                  70                  75                  80

Ile Arg Glu Asp Gly Thr Val Gly Gly Ala Ala His Gln Ser Pro Glu
                85                  90                  95

Ser Leu Leu Glu Leu Lys Ala Leu Lys Pro Gly Val Ile Gln Ile Leu
            100                 105                 110

Gly Val Lys Thr Ser Arg Phe Leu Cys Gln Lys Pro Asp Gly Ala Leu
        115                 120                 125

Tyr Gly Ser Leu His Phe Asp Pro Glu Ala Cys Ser Phe Arg Glu Leu
    130                 135                 140

Leu Leu Glu Asp Gly Tyr Asn Val Tyr Gln Ser Glu Ala His Gly Leu
145                 150                 155                 160

Pro Leu His Leu Pro Gly Asn Arg Ser Pro His Cys Asp Pro Ala Pro
                165                 170                 175

Gln Gly Pro Ala Arg Phe Leu Pro Leu Pro Gly Leu Pro Pro Ala Leu
            180                 185                 190

Pro Glu Pro Pro Gly Ile Leu Ala Pro Gln Pro Pro Asp Val Gly Ser
        195                 200                 205

Ser Asp Pro Leu Ala Met Val Gly Pro Ser Gln Gly Arg Ser Pro Ser
    210                 215                 220

Tyr Ala Ser
225

<210> SEQ ID NO 149
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Ser Gly
            20                  25                  30

Gly Gly Gly Ser Gly Gly Gly Gly Ser Gly Gly Gly Ser Gly Gly
        35                  40                  45

Gly Gly Asp Ser Ser Pro Leu Leu Gln Phe Gly Gly Gln Val Arg Gln
    50                  55                  60

Arg Tyr Leu Tyr Thr Asp Asp Ala Gln Glu Thr Glu Ala His Leu Glu
65                  70                  75                  80

Ile Arg Glu Asp Gly Thr Val Gly Gly Ala Ala His Gln Ser Pro Glu

```
                    85                  90                  95
Ser Leu Leu Glu Leu Lys Ala Leu Lys Pro Gly Val Ile Gln Ile Leu
                100                 105                 110

Gly Val Lys Thr Ser Arg Phe Leu Cys Gln Lys Pro Asp Gly Ala Leu
            115                 120                 125

Tyr Gly Ser Leu His Phe Asp Pro Glu Ala Cys Ser Phe Arg Glu Leu
        130                 135                 140

Leu Leu Glu Asp Gly Tyr Asn Val Tyr Gln Ser Glu Ala His Gly Leu
145                 150                 155                 160

Pro Leu His Leu Pro Gly Asn Arg Ser Pro His Cys Asp Pro Ala Pro
                165                 170                 175

Gln Gly Pro Ala Arg Phe Leu Pro Leu Pro Gly Leu Pro Pro Ala Leu
            180                 185                 190

Pro Glu Pro Pro Gly Ile Leu Ala Pro Gln Pro Pro Asp Val Gly Ser
        195                 200                 205

Ser Asp Pro Leu Ser
    210

<210> SEQ ID NO 150
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Asp Leu Ser Lys Gln Met Glu Glu Ala Val Arg Leu Phe Ile Glu
1               5                  10                  15

Trp Leu Lys Asn Gly Gly Ser Gly Gly Gly Ser Gly Gly Gly Gly
            20                  25                  30

Ser Gly Gly Gly Gly Ser Gly Gly Gly Asp Ser Ser Pro Leu Leu
        35                  40                  45

Gln Phe Gly Gly Gln Val Arg Gln Arg Tyr Leu Tyr Thr Asp Asp Ala
50                  55                  60

Gln Glu Thr Glu Ala His Leu Glu Ile Arg Glu Asp Gly Thr Val Gly
65                  70                  75                  80

Gly Ala Ala His Gln Ser Pro Glu Ser Leu Leu Glu Leu Lys Ala Leu
                85                  90                  95

Lys Pro Gly Val Ile Gln Ile Leu Gly Val Lys Thr Ser Arg Phe Leu
            100                 105                 110

Cys Gln Lys Pro Asp Gly Ala Leu Tyr Gly Ser Leu His Phe Asp Pro
        115                 120                 125

Glu Ala Cys Ser Phe Arg Glu Leu Leu Leu Glu Asp Gly Tyr Asn Val
    130                 135                 140

Tyr Gln Ser Glu Ala His Gly Leu Pro Leu His Leu Pro Gly Asn Arg
145                 150                 155                 160

Ser Pro His Cys Asp Pro Ala Pro Gln Gly Pro Ala Arg Phe Leu Pro
                165                 170                 175

Leu Pro Gly Leu Pro Pro Ala Leu Pro Glu Pro Pro Gly Ile Leu Ala
            180                 185                 190

Pro Gln Pro Pro Asp Val Gly Ser Ser Asp Pro Leu Ala Met Val Gly
        195                 200                 205

Pro Ser Gln Gly Arg Ser Pro Ser Tyr Ala Ser
    210                 215
```

<210> SEQ ID NO 151
<211> LENGTH: 169
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 151

Gly Gly Gln Val Arg Gln Arg Tyr Leu Tyr Thr Asp Asp Ala Gln Glu
1               5                   10                  15

Thr Glu Ala His Leu Glu Ile Arg Glu Asp Gly Thr Val Gly Gly Ala
            20                  25                  30

Ala His Gln Ser Pro Glu Ser Leu Leu Glu Leu Lys Ala Leu Lys Pro
        35                  40                  45

Gly Val Ile Gln Ile Leu Gly Val Lys Thr Ser Arg Phe Leu Cys Gln
    50                  55                  60

Lys Pro Asp Gly Ala Leu Tyr Gly Ser Leu His Phe Asp Pro Glu Ala
65                  70                  75                  80

Cys Ser Phe Arg Glu Leu Leu Leu Glu Asp Gly Tyr Asn Val Tyr Gln
                85                  90                  95

Ser Glu Ala His Gly Leu Pro Leu His Leu Pro Gly Asn Arg Ser Pro
            100                 105                 110

His Cys Asp Pro Ala Pro Gln Gly Pro Ala Arg Phe Leu Pro Leu Pro
        115                 120                 125

Gly Leu Pro Pro Ala Leu Pro Glu Pro Pro Gly Ile Leu Ala Pro Gln
    130                 135                 140

Pro Pro Asp Val Gly Ser Ser Asp Pro Leu Ala Met Val Gly Pro Ser
145                 150                 155                 160

Gln Gly Arg Ser Pro Ser Tyr Ala Ser
                165

<210> SEQ ID NO 152
<211> LENGTH: 207
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 152

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Gly Gln Val Arg Gln Arg Tyr Leu Tyr
        35                  40                  45

Thr Asp Asp Ala Gln Glu Thr Glu Ala His Leu Glu Ile Arg Glu Asp
    50                  55                  60

Gly Thr Val Gly Gly Ala Ala His Gln Ser Pro Glu Ser Leu Leu Glu
65                  70                  75                  80

Leu Lys Ala Leu Lys Pro Gly Val Ile Gln Ile Leu Gly Val Lys Thr
                85                  90                  95

Ser Arg Phe Leu Cys Gln Lys Pro Asp Gly Ala Leu Tyr Gly Ser Leu
            100                 105                 110

His Phe Asp Pro Glu Ala Cys Ser Phe Arg Glu Leu Leu Leu Glu Asp
        115                 120                 125

Gly Tyr Asn Val Tyr Gln Ser Glu Ala His Gly Leu Pro Leu His Leu
            130                 135                 140

Pro Gly Asn Arg Ser Pro His Cys Asp Pro Ala Pro Gln Gly Pro Ala
145                 150                 155                 160

Arg Phe Leu Pro Leu Pro Gly Leu Pro Pro Ala Leu Pro Glu Pro Pro
                165                 170                 175

Gly Ile Leu Ala Pro Gln Pro Pro Asp Val Gly Ser Ser Asp Pro Leu
            180                 185                 190

Ala Met Val Gly Pro Ser Gln Gly Arg Ser Pro Ser Tyr Ala Ser
        195                 200                 205

<210> SEQ ID NO 153
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gly Val Ser Thr Ser Glu Ala Lys Phe Glu Gln Asp Ser Ala Ile Leu
1               5                   10                  15

Trp Tyr Gly Val Glu Phe Ala Lys Leu His Thr Ser Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Glu Thr
    50                  55                  60

Glu Ala His Leu Glu Ile Arg Glu Asp Gly Thr Val Gly Gly Ala Ala
65                  70                  75                  80

His Gln Ser Pro Glu Ser Leu Leu Glu Leu Lys Ala Leu Lys Pro Gly
                85                  90                  95

Val Ile Gln Ile Leu Gly Val Lys Thr Ser Arg Phe Leu Cys Gln Lys
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Arg Ser Pro His
145                 150                 155                 160

Cys Asp Pro Ala Pro Gln Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ala Met Val Gly Pro Ser Gln
        195                 200                 205

Gly Arg Ser Pro Ser Tyr Ala Ser
    210                 215

<210> SEQ ID NO 154
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

```
His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Asp Ala Gln Glu Thr
    50                  55                  60

Glu Ala His Leu Glu Ile Arg Glu Asp Gly Thr Val Gly Gly Ala Ala
65                  70                  75                  80

His Gln Ser Pro Glu Ser Leu Leu Glu Leu Lys Ala Leu Lys Pro Gly
                85                  90                  95

Val Ile Gln Ile Leu Gly Val Lys Thr Ser Arg Phe Leu Cys Gln Lys
                100                 105                 110

Pro Asp Gly Ala Leu Tyr Gly Ser Leu His Phe Asp Pro Glu Ala Cys
            115                 120                 125

Ser Phe Arg Glu Leu Leu Leu Glu Asp Gly Tyr Asn Val Tyr Gln Ser
130                 135                 140

Glu Ala His Gly Leu Pro Leu His Leu Pro Gly Asn Arg Ser Pro His
145                 150                 155                 160

Cys Asp Pro Ala Pro Gln Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ala Met Val Gly Gly Ser Gln
            195                 200                 205

Gly Arg Ser Pro Ser Tyr Ala Ser
    210                 215

<210> SEQ ID NO 155
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 155
cattctgaag gcactttac tagcgatgtt tctagctacc tggaaggcca ggctgcgaaa        60
gaattcatcg cgtggctggt taaaggcggt tctggtggtg gtggttctgg cggtggcgac      120
tcgagcccgc tgctgcaatt tggcggccag gtgcgtcagc gttatctgta taccgatgat      180
gcgcaggaaa ccgaagcgca tctggaaatt cgtgaagatg gcaccgtggg cggtgcggcg      240
catcagagcc cggaaagcct gctggaactg aaagcgctga accgggcgt gattcagatt       300 ctgggcgtga aaccagccg ttttctgtgc cagaaaccgg atggcgcgct gtatggcagc      360
ctgcattttg atccggaagc gtgcagcttt cgtgaactgc tgctggaaga tggctataac      420
gtgtatcaga gcgaagcgca tggcctgccg ctgcatctgc cgggcaaccg tagcccgcat      480
tgcgatccgg caccgcaggg tccggcgcgt tttctgccgc tgccgggtct gccgccggca      540
ctgccggaac cgccgggtat tctggccccg cagccgccgg atgttggtag cagcgatccg      600
ctggcgatgg tgggtggtag ccagggtcgt agcccgagct atgcgagc                  648

<210> SEQ ID NO 156
<211> LENGTH: 227
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 156

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Ser Gly
            20                  25                  30

Gly Gly Gly Ser Gly Gly Gly Ser Gly Gly Gly Ser Gly Gly
        35                  40                  45

Gly Gly Asp Ser Ser Pro Leu Leu Gln Phe Gly Gly Gln Val Arg Gln
    50                  55                  60

Arg Tyr Leu Tyr Thr Asp Asp Ala Gln Glu Thr Glu Ala His Leu Glu
65              70                  75                  80

Ile Arg Glu Asp Gly Thr Val Gly Gly Ala Ala His Gln Ser Pro Glu
                85                  90                  95

Ser Leu Leu Glu Leu Lys Ala Leu Lys Pro Gly Val Ile Gln Ile Leu
            100                 105                 110

Gly Val Lys Thr Ser Arg Phe Leu Cys Gln Lys Pro Asp Gly Ala Leu
        115                 120                 125

Tyr Gly Ser Leu His Phe Asp Pro Glu Ala Cys Ser Phe Arg Glu Leu
    130                 135                 140

Leu Leu Glu Asp Gly Tyr Asn Val Tyr Gln Ser Glu Ala His Gly Leu
145             150                 155                 160

Pro Leu His Leu Pro Gly Asn Arg Ser Pro His Cys Asp Pro Ala Pro
                165                 170                 175

Gln Gly Pro Ala Arg Phe Leu Pro Leu Pro Gly Leu Pro Pro Ala Leu
            180                 185                 190

Pro Glu Pro Pro Gly Ile Leu Ala Pro Gln Pro Pro Asp Val Gly Ser
        195                 200                 205

Ser Asp Pro Leu Ala Met Val Gly Gly Ser Gln Gly Arg Ser Pro Ser
    210                 215                 220

Tyr Ala Ser
225
```

<210> SEQ ID NO 157
<211> LENGTH: 681
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 157

```
catggtgagg gtacgtttac ttctgatctg tctaaacaga tggaagaaga agctgttcgc      60
ctgttcattg aatggctgaa aaatggtggt tctggtggtg gtggttctgg cggtggcggt     120
tctggcggcg gtggtagcgg tggcggcggt gactcgagcc cgctgctgca gtttggcggc     180
caggtgcgtc agcgttatct gtataccgat gatgcgcagg aaaccgaagc gcatctggaa     240
attcgtgaag atggcaccgt gggcggtgcg gcgcatcaga gcccggaaag cctgctggaa     300
ctgaaagcgc tgaaaccggg cgtgattcag attctgggcg tgaaaaccag ccgttttctg     360
tgccagaaac cggatggcgc gctgtatggc agcctgcatt ttgatccgga agcgtgcagc     420
tttcgtgaac tgctgctgga agatggctat aacgtgtatc agagcgaagc gcatggcctg     480
```

-continued

```
ccgctgcatc tgccgggcaa ccgtagcccg cattgcgatc cggcaccgca gggtccggcg    540
cgttttctgc cgctgccggg tctgccgccg gcactgccgg aaccgccggg tattctggcc    600
ccgcagccgc cggatgttgg tagcagcgat ccgctggcga tggtgggtgg tagccagggt    660
cgtagcccga gctatgcgag c                                              681
```

<210> SEQ ID NO 158
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Ser Gly Gly Gly Gly
        35                  40                  45

Ser Gly Gly Gly Ser Asp Lys Thr His Thr Cys Pro Pro Cys Pro
    50                  55                  60

Ala Pro Glu Ala Ala Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser His Glu Asp Pro Glu Val Lys Phe Asn Trp Tyr
            100                 105                 110

Val Asp Gly Val Glu Val His Asn Ala Lys Thr Lys Pro Arg Glu Glu
        115                 120                 125

Gln Tyr Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Ala Leu Pro Ala Pro Ile Glu Lys Thr Ile Ser Lys Ala Lys Gly Gln
                165                 170                 175

Pro Arg Glu Pro Gln Val Tyr Thr Leu Pro Pro Ser Arg Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Lys Leu Thr Val Asp Lys Ser Arg Trp Gln Gln Gly Asn Val
                245                 250                 255

Phe Ser Cys Ser Val Met His Glu Ala Leu His Asn His Tyr Thr Gln
            260                 265                 270

Lys Ser Leu Ser Leu Ser Pro Gly Lys Gly Ser Asp Ser Ser Pro Leu
        275                 280                 285

Leu Gln Phe Gly Gly Gln Val Arg Gln Arg Tyr Leu Tyr Thr Asp Asp
    290                 295                 300

Ala Cys Gln Thr Glu Ala His Leu Glu Ile Arg Glu Asp Gly Thr Val
305                 310                 315                 320
```

```
Gly Gly Ala Ala Asp Gln Ser Pro Glu Ser Leu Leu Gln Leu Lys Ala
            325                 330                 335

Leu Lys Pro Gly Val Ile Gln Ile Leu Gly Val Lys Thr Ser Arg Phe
        340                 345                 350

Leu Cys Gln Lys Pro Asp Gly Ala Leu Tyr Gly Ser Leu His Phe Asp
        355                 360                 365

Pro Glu Ala Cys Ser Phe Arg Glu Leu Leu Leu Glu Asp Gly Tyr Asn
370                 375                 380

Val Tyr Gln Ser Glu Ala His Gly Leu Pro Leu His Leu Pro Cys Asn
385                 390                 395                 400

Arg Ser Pro His Arg Asp Pro Ala Ser Arg Gly Pro Ala Arg Phe Leu
                405                 410                 415

Pro Leu Pro Gly Leu Pro Pro Ala Leu Pro Glu Pro Gly Ile Leu
        420                 425                 430

Ala Pro Gln Pro Pro Asp Val Gly Ser Ser Asp Pro Leu Ala Met Val
        435                 440                 445

Gly Gly Ser Gln Ala Arg Ser Pro Ser Tyr Ala
        450                 455
```

<210> SEQ ID NO 159
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Ser Gly Gly Gly Gly
        35                  40                  45

Ser Gly Gly Gly Gly Ser Asp Lys Thr His Thr Cys Pro Pro Cys Pro
50                  55                  60

Ala Pro Glu Ala Ala Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser His Glu Asp Pro Glu Val Lys Phe Asn Trp Tyr
            100                 105                 110

Val Asp Gly Val Glu Val His Asn Ala Lys Thr Lys Pro Arg Glu Glu
        115                 120                 125

Gln Tyr Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Ala Leu Pro Ala Pro Ile Glu Lys Thr Ile Ser Lys Ala Lys Gly Gln
                165                 170                 175

Pro Arg Glu Pro Gln Val Tyr Thr Leu Pro Pro Ser Arg Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220
```

```
Tyr Lys Thr Thr Pro Pro Val Leu Asp Ser Asp Gly Ser Phe Phe Leu
225                 230                 235                 240

Tyr Ser Lys Leu Thr Val Asp Lys Ser Arg Trp Gln Gln Gly Asn Val
            245                 250                 255

Phe Ser Cys Ser Val Met His Glu Ala Leu His Asn His Tyr Thr Gln
        260                 265                 270

Lys Ser Leu Ser Leu Ser Pro Gly Lys Gly Ser Asp Ser Ser Pro Leu
    275                 280                 285

Leu Gln Phe Gly Gly Gln Val Arg Gln Arg Tyr Leu Tyr Thr Asp Asp
290                 295                 300

Ala Cys Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Lys Pro Asp Gly Ala Leu Tyr Gly Ser Leu His Phe Asp
        355                 360                 365

Pro Glu Ala Cys Ser Phe Arg Glu Leu Leu Leu Glu Asp Gly Tyr Asn
    370                 375                 380

Val Tyr Gln Ser Glu Ala His Gly Leu Pro Leu His Leu Pro Cys Asn
385                 390                 395                 400

Arg Ser Pro His Arg Asp Pro Ala Ser Arg Gly Pro Ala Arg Phe Leu
                405                 410                 415

Pro Leu Pro Gly Leu Pro Pro Ala Leu Pro Glu Pro Gly Ile Leu
            420                 425                 430

Ala Pro Gln Pro Pro Asp Val Gly Ser Ser Asp Pro Leu Ala Met Val
            435                 440                 445

Gly Gly Ser Gln Ala Arg Ser Pro Ser Tyr
    450                 455

<210> SEQ ID NO 160
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Ser Gly Gly Gly Gly
        35                  40                  45

Ser Gly Gly Gly Gly Ser Asp Lys Thr His Thr Cys Pro Pro Cys Pro
    50                  55                  60

Ala Pro Glu Ala Ala Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser His Glu Asp Pro Glu Val Lys Phe Asn Trp Tyr
            100                 105                 110

Val Asp Gly Val Glu Val His Asn Ala Lys Thr Lys Pro Arg Glu Glu
```

```
            115                 120                 125
Gln Tyr Asn Ser Thr Tyr Arg Val Val Ser Val Leu Thr Val Leu His
        130                 135                 140

Gln Asp Trp Leu Asn Gly Lys Glu Tyr Lys Cys Lys Val Ser Asn Lys
145                 150                 155                 160

Ala Leu Pro Ala Pro Ile Glu Lys Thr Ile Ser Lys Ala Lys Gly Gln
                165                 170                 175

Pro Arg Glu Pro Gln Val Tyr Thr Leu Pro Pro Ser Arg Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Lys Leu Thr Val Asp Lys Ser Arg Trp Gln Gln Gly Asn Val
                245                 250                 255

Phe Ser Cys Ser Val Met His Glu Ala Leu His Asn His Tyr Thr Gln
            260                 265                 270

Lys Ser Leu Ser Leu Ser Pro Gly Lys Gly Ser Asp Ser Ser Pro Leu
        275                 280                 285

Leu Gln Phe Gly Gln Val Arg Gln Arg Tyr Leu Tyr Thr Asp Asp
    290                 295                 300

Ala Cys Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Lys Pro Asp Gly Ala Leu Tyr Gly Ser Leu His Phe Asp
        355                 360                 365

Pro Glu Ala Cys Ser Phe Arg Glu Leu Leu Leu Glu Asp Gly Tyr Asn
    370                 375                 380

Val Tyr Gln Ser Glu Ala His Gly Leu Pro Leu His Leu Pro Cys Asn
385                 390                 395                 400

Arg Ser Pro His Arg Asp Pro Ala Ser Arg Gly Pro Ala Arg Phe Leu
                405                 410                 415

Pro Leu Pro Gly Leu Pro Pro Ala Leu Pro Glu Pro Pro Gly Ile Leu
            420                 425                 430

Ala Pro Gln Pro Pro Asp Val Gly Ser Ser Asp Pro Leu Ala Met Val
        435                 440                 445

Gly Gly Ser Gln Ala Arg Ser Pro Ser
    450                 455

<210> SEQ ID NO 161
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly Pro Ser
             20                  25                  30

Ser Gly Ala Pro Pro Ser Gly Gly Gly Ser Gly Gly Gly Gly
         35                  40                  45

Ser Gly Gly Gly Gly Ser Asp Lys Thr His Thr Cys Pro Pro Cys Pro
 50                  55                  60

Ala Pro Glu Ala Ala Gly Gly Pro Ser Val Phe Leu Phe Pro Pro Lys
 65                  70                  75                  80

Pro Lys Asp Thr Leu Met Ile Ser Arg Thr Pro Glu Val Thr Cys Val
                 85                  90                  95

Val Val Asp Val Ser His Glu Asp Pro Glu Val Lys Phe Asn Trp Tyr
                100                 105                 110

Val Asp Gly Val Glu Val His Asn Ala Lys Thr Lys Pro Arg Glu Glu
             115                 120                 125

Gln Tyr Asn Ser Thr Tyr Arg Val Val Ser Val Leu Thr Val Leu His
         130                 135                 140

Gln Asp Trp Leu Asn Gly Lys Glu Tyr Lys Cys Lys Val Ser Asn Lys
145                 150                 155                 160

Ala Leu Pro Ala Pro Ile Glu Lys Thr Ile Ser Lys Ala Lys Gly Gln
                165                 170                 175

Pro Arg Glu Pro Gln Val Tyr Thr Leu Pro Pro Ser Arg Glu Glu Met
             180                 185                 190

Thr Lys Asn Gln Val Ser Leu Thr Cys Leu Val Lys Gly Phe Tyr Pro
         195                 200                 205

Ser Asp Ile Ala Val Glu Trp Glu Ser Asn Gly Gln Pro Glu Asn Asn
210                 215                 220

Tyr Lys Thr Thr Pro Pro Val Leu Asp Ser Asp Gly Ser Phe Phe Leu
225                 230                 235                 240

Tyr Ser Lys Leu Thr Val Asp Lys Ser Arg Trp Gln Gln Gly Asn Val
                245                 250                 255

Phe Ser Cys Ser Val Met His Glu Ala Leu His Asn His Tyr Thr Gln
             260                 265                 270

Lys Ser Leu Ser Leu Ser Pro Gly Lys Gly Ser Asp Ser Ser Pro Leu
         275                 280                 285

Leu Gln Phe Gly Gly Gln Val Arg Gln Arg Tyr Leu Tyr Thr Asp Asp
290                 295                 300

Ala Cys Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
             340                 345                 350

Leu Cys Gln Lys Pro Asp Gly Ala Leu Tyr Gly Ser Leu His Phe Asp
         355                 360                 365

Pro Glu Ala Cys Ser Phe Arg Glu Leu Leu Glu Asp Gly Tyr Asn
370                 375                 380

Val Tyr Gln Ser Glu Ala His Gly Leu Pro Leu His Leu Pro Cys Asn
385                 390                 395                 400

Arg Ser Pro His Arg Asp Pro Ala Ser Arg Gly Pro Ala Arg Phe Leu
                405                 410                 415

Pro Leu Pro Gly Leu Pro Pro Ala Leu Pro Glu Pro Pro Gly Ile Leu
             420                 425                 430

Ala Pro Gln Pro Pro Asp Val Gly Ser Ser Asp Pro Leu Ala Met Val
```

```
                435                 440                 445
Gly Gly Ser Gln Ala Arg Ser Pro Ser Tyr Ala Ser Pro
    450                 455                 460

<210> SEQ ID NO 162
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Ser Gly Gly Gly Gly
        35                  40                  45

Ser Gly Gly Gly Gly Ser Asp Lys Thr His Thr Cys Pro Pro Cys Pro
    50                  55                  60

Ala Pro Glu Ala Ala Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser His Glu Asp Pro Glu Val Lys Phe Asn Trp Tyr
            100                 105                 110

Val Asp Gly Val Glu Val His Asn Ala Lys Thr Lys Pro Arg Glu Glu
        115                 120                 125

Gln Tyr Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Ala Leu Pro Ala Pro Ile Glu Lys Thr Ile Ser Lys Ala Lys Gly Gln
                165                 170                 175

Pro Arg Glu Pro Gln Val Tyr Thr Leu Pro Pro Ser Arg Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Lys Leu Thr Val Asp Lys Ser Arg Trp Gln Gln Gly Asn Val
                245                 250                 255

Phe Ser Cys Ser Val Met His Glu Ala Leu His Asn His Tyr Thr Gln
            260                 265                 270

Lys Ser Leu Ser Leu Ser Pro Gly Lys Gly Ser Asp Ser Ser Pro Leu
        275                 280                 285

Leu Gln Phe Gly Gly Gln Val Arg Gln Arg Tyr Leu Tyr Thr Asp Asp
    290                 295                 300

Ala Cys Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335
```

```
Leu Lys Pro Gly Val Ile Gln Ile Leu Gly Val Lys Thr Ser Arg Phe
            340                 345                 350

Leu Cys Gln Lys Pro Asp Gly Ala Leu Tyr Gly Ser Leu His Phe Asp
        355                 360                 365

Pro Glu Ala Cys Ser Phe Arg Glu Leu Leu Leu Glu Asp Gly Tyr Asn
370                 375                 380

Val Tyr Gln Ser Glu Ala His Gly Leu Pro Leu His Leu Pro Cys Asn
385                 390                 395                 400

Arg Ser Pro His Arg Asp Pro Ala Ser Arg Gly Pro Ala Arg Phe Leu
                405                 410                 415

Pro Leu Pro Gly Leu Pro Pro Ala Leu Pro Glu Pro Gly Ile Leu
            420                 425                 430

Ala Pro Gln Pro Pro Asp Val Gly Ser Ser Asp Pro Leu Ala Met Val
            435                 440                 445

Gly Gly Ser Gln Ala Arg Ser Pro Ser Tyr Ala Ala Pro
            450                 455                 460

<210> SEQ ID NO 163
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Cys Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 164
<211> LENGTH: 209
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

```
His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Cys Asp Pro Ala Pro Arg Gly
145                 150                 155                 160

Pro Ala Arg Phe Leu Pro Leu Pro Gly Leu Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 165
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
```

Ser Leu His Phe Asp Pro Glu Ala Cys Ser Phe Arg Glu Leu Leu
            115                 120                 125

Glu Asp Gly Tyr Asn Val Tyr Gln Ser Glu Ala His Gly Leu Pro Leu
    130                 135                 140

His Leu Pro Gly Asn Lys Ser Pro His Cys Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser

<210> SEQ ID NO 166
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
    130                 135                 140

His Leu Pro Gly Asn Lys Ser Pro His Cys Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser

<210> SEQ ID NO 167
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
130                 135                 140

Glu Ala His Gly Leu Pro Leu His Leu Pro Gly Asn Lys Ser Pro His
145                 150                 155                 160

Cys Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
    210                 215

<210> SEQ ID NO 168
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Gly Asp Ser Ser Pro Leu Leu Gln Phe Gly
        35                  40                  45

Gly Gln Val Arg Gln Arg Tyr Leu Tyr Thr Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

-continued

Pro Asp Gly Ala Leu Tyr Gly Ser Leu His Phe Asp Pro Glu Ala Cys
        115                 120                 125

Ser Phe Arg Glu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Cys Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
            195                 200                 205

Gly Arg Ser Pro Ser Tyr Ala Ser
    210                 215

<210> SEQ ID NO 169
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Cys Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 170
<211> LENGTH: 178
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 170

Gly Asp Ser Ser Pro Leu Leu Gln Phe Gly Gly Gln Val Arg Gln Arg
1               5                   10                  15

Tyr Leu Tyr Thr Asp Asp Ala Gln Gln Thr Glu Ala His Leu Glu Ile
                20                  25                  30

Arg Glu Asp Gly Thr Val Gly Gly Ala Ala Asp Gln Ser Pro Glu Ser
                35                  40                  45

Leu Leu Gln Leu Lys Ala Leu Lys Pro Gly Val Ile Gln Ile Leu Gly
            50                  55                  60

Val Lys Thr Ser Arg Phe Leu Cys Gln Arg Pro Asp Gly Ala Leu Tyr
65                  70                  75                  80

Gly Ser Leu His Phe Asp Pro Glu Ala Cys Ser Phe Arg Glu Leu Leu
                85                  90                  95

Leu Glu Asp Gly Tyr Asn Val Tyr Gln Ser Glu Ala His Gly Leu Pro
                100                 105                 110

Leu His Leu Pro Gly Asn Lys Ser Pro His Cys Asp Pro Ala Pro Arg
            115                 120                 125

Gly Pro Ala Arg Phe Leu Pro Leu Pro Gly Leu Pro Pro Ala Leu Pro
        130                 135                 140

Glu Pro Pro Gly Ile Leu Ala Pro Gln Pro Pro Asp Val Gly Ser Ser
145                 150                 155                 160

Asp Pro Leu Ser Met Val Gly Pro Ser Gln Gly Arg Ser Pro Ser Tyr
                165                 170                 175

Ala Ser

<210> SEQ ID NO 171
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
                20                  25                  30

Gly Gly Gly Ser Gly Gly Gly Asp Ser Ser Pro Leu Leu Gln Phe Gly
            35                  40                  45

Gly Gln Val Arg Gln Arg Tyr Leu Tyr Thr Asp Asp Ala Gln Gln Thr
        50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
                100                 105                 110

Pro Asp Gly Ala Leu Tyr Gly Ser Leu His Phe Asp Pro Glu Ala Cys
            115                 120                 125

Ser Phe Arg Glu Leu Leu Leu Glu Asp Gly Tyr Asn Val Tyr Gln Ser
        130                 135                 140
```

```
Glu Ala His Gly Leu Pro Leu His Leu Pro Gly Asn Lys Ser Pro His
145                 150                 155                 160

Cys Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser
        195                 200
```

<210> SEQ ID NO 172
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

```
His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ser Gly
            20                  25                  30

Gly Gly Gly Ser Gly Gly Asp Ser Ser Pro Leu Leu Gln Phe Gly
        35                  40                  45

Gly Gln Val Arg Gln Arg Tyr Leu Tyr Thr Asp Asp Ala Gln Gln Thr
    50                  55                  60

Glu Ala His Leu Glu Ile Arg Glu Asp Gly Thr Val Gly Gly Ala Ala
65                  70                  75                  80

Asp Gln Ser Pro Glu Ser Leu Leu Gln Leu Lys Ala Leu Lys Pro Gly
                85                  90                  95

Val Ile Gln Ile Leu Gly Val Lys Thr Ser Arg Phe Leu Cys Gln Arg
            100                 105                 110

Pro Asp Gly Ala Leu Tyr Gly Ser Leu His Phe Asp Pro Glu Ala Cys
        115                 120                 125

Ser Phe Arg Glu Leu Leu Leu Glu Asp Gly Tyr Asn Val Tyr Gln Ser
    130                 135                 140

Glu Ala His Gly Leu Pro Leu His Leu Pro Gly Asn Lys Ser Pro His
145                 150                 155                 160

Cys Asp Pro Ala Pro Arg Gly Pro Ala Arg Phe Leu Pro Leu Pro Gly
                165                 170                 175

Leu Pro Pro Ala Leu Pro Glu Pro Pro Gly Ile Leu Ala Pro Gln Pro
            180                 185                 190

Pro Asp Val Gly Ser Ser Asp Pro Leu Ser Met Val Gly Pro Ser Gln
        195                 200                 205

Gly Arg Ser Pro Ser Tyr Ala Ser
    210                 215
```

<210> SEQ ID NO 173
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

```
Gly Gly Gly Gly Ser
1               5
```

```
<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Ser Gly Gly Gly Gly Ser Gly Gly Gly
1               5                   10

<210> SEQ ID NO 175
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Gly Gly Gly Gly Ser Gly Gly Gly Gly Ser Gly Gly Gly Gly Ser
1               5                   10                  15

Gly Gly Gly Gly
            20

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Gly Gly Gly Ser Gly Gly Gly
1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ser Gly Gly Gly Gly Ser Gly Gly Gly
1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Ser Gly Gly Gly Gly Cys
1               5

<210> SEQ ID NO 179
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 179

Gly Ser Gly Gly Gly Gly Cys Gly Gly Gly
1               5                   10

<210> SEQ ID NO 180
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Gly Ser Gly Gly Gly Gly Ser Gly Gly Gly Ser Gly Gly Gly
1               5                   10                  15

Gly Ser

<210> SEQ ID NO 181
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Gly Gly Gly Ser Gly Gly Gly Ser Gly Gly Gly Ser Gly
1               5                   10                  15

Gly Gly Gly

<210> SEQ ID NO 182
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ser Gly Gly Gly Gly Ser Gly Gly Gly Ser Gly Gly Gly Gly
1               5                   10                  15

<210> SEQ ID NO 183
<211> LENGTH: 4
<212> TYPE: PRT
<213> ORGANISM: Homo sapiens

<400> SEQUENCE: 183

His Pro Ile Pro
1

<210> SEQ ID NO 184
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 184

His His His His His His
1               5
```

```
<210> SEQ ID NO 185
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Asp Ser Ser Pro Leu Leu Gln Phe Gly Gly Gln Val Arg Gln Arg Tyr
1               5                   10                  15

Leu Tyr Thr Asp Asp Ala Gln Glu Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Glu Leu Lys Ala Leu Lys Pro Gly Val Ile Gln Ile Leu Gly Val
    50                  55                  60

Lys Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asp Gly Tyr Asn Val Tyr Gln Ser Glu Ala His Gly Leu Pro Leu
            100                 105                 110

His Leu Pro Gly Asn Arg Ser Pro His Cys Asp Pro Ala Pro Gln Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 186
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Asp Ser Ser Pro Leu Leu Gln Phe Gly Gly Gln Val Arg Gln Arg Tyr
1               5                   10                  15

Leu Tyr Thr Asp Asp Ala Gln Glu Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Glu Leu Lys Ala Leu Lys Pro Gly Val Ile Gln Ile Leu Gly Val
    50                  55                  60

Lys Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asp Gly Tyr Asn Val Tyr Gln Ser Glu Ala His Gly Leu Pro Leu
            100                 105                 110

His Leu Pro Gly Asn Arg Ser Pro His Cys Asp Pro Ala Pro Gln Gly
```

```
                115                 120                 125
Pro Ala Arg Phe Leu Pro Leu Pro Gly Leu Pro Pro Ala Leu Pro Glu
        130                 135                 140
Pro Pro Gly Ile Leu Ala Pro Gln Pro Pro Asp Val Gly Ser Ser Asp
145                 150                 155                 160
Pro Leu Ala Met Val Gly Gly Ser Gln Gly Arg Ser Pro Ser Tyr Ala
                165                 170                 175
Ser
```

<210> SEQ ID NO 187
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

```
Asp Ser Ser Pro Leu Leu Gln Phe Gly Gly Gln Val Arg Gln Arg Tyr
1               5                   10                  15
Leu Tyr Thr Asp Asp Ala Cys Gln Thr Glu Ala His Leu Glu Ile Arg
                20                  25                  30
Glu Asp Gly Thr Val Gly Gly Ala Ala Asp Gln Ser Pro Glu Ser Leu
            35                  40                  45
Leu Gln Leu Lys Ala Leu Lys Pro Gly Val Ile Gln Ile Leu Gly Val
        50                  55                  60
Lys Thr Ser Arg Phe Leu Cys Gln Arg Pro Asp Gly Thr Leu Tyr Gly
65                  70                  75                  80
Ser Leu His Phe Asp Pro Glu Ala Cys Ser Phe Arg Glu Leu Leu Leu
                85                  90                  95
Glu Asp Gly Tyr Asn Val Tyr Gln Ser Glu Ala His Gly Leu Pro Leu
            100                 105                 110
His Leu Pro Cys Asn Arg Ser Pro His Arg Asp Pro Ala Ser Arg Gly
            115                 120                 125
Pro Ala Arg Phe Leu Pro Leu Pro Gly Leu Pro Pro Ala Leu Pro Glu
        130                 135                 140
Pro Pro Gly Ile Leu Ala Pro Gln Pro Pro Asp Val Gly Ser Ser Asp
145                 150                 155                 160
Pro Leu Ala Met Val Gly Gly Ser Gln Ala Arg Ser Pro Ser Tyr Ala
                165                 170                 175
Ser
```

<210> SEQ ID NO 188
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

```
Asp Ser Ser Pro Leu Leu Gln Phe Gly Gly Gln Val Arg Gln Arg Tyr
1               5                   10                  15
Leu Tyr Thr Asp Asp Ala Cys Gln Thr Glu Ala His Leu Glu Ile Arg
                20                  25                  30
Glu Asp Gly Thr Val Gly Gly Ala Ala Asp Gln Ser Pro Glu Ser Leu
            35                  40                  45
```

```
Leu Gln Leu Lys Ala Leu Lys Pro Gly Val Ile Gln Ile Leu Gly Val
     50                  55                  60

Lys Thr Ser Arg Phe Leu Cys Gln Lys Pro Asp Gly Ala Leu Tyr Gly
 65                  70                  75                  80

Ser Leu His Phe Asp Pro Glu Ala Cys Ser Phe Arg Glu Leu Leu Leu
                 85                  90                  95

Glu Asp Gly Tyr Asn Val Tyr Gln Ser Glu Ala His Gly Leu Pro Leu
                100                 105                 110

His Leu Pro Cys Asn Arg Ser Pro His Arg Asp Pro Ala Ser Arg Gly
            115                 120                 125

Pro Ala Arg Phe Leu Pro Leu Pro Gly Leu Pro Pro Ala Leu Pro Glu
            130                 135                 140

Pro Pro Gly Ile Leu Ala Pro Gln Pro Pro Asp Val Gly Ser Ser Asp
145                 150                 155                 160

Pro Leu Ala Met Val Gly Gly Ser Gln Ala Arg Ser Pro Ser Tyr Ala
                165                 170                 175

Ser
```

METHODS OF TREATING METABOLIC DISORDERS WITH DUAL FUNCTION FIBROBLAST GROWTH FACTOR 21 PROTEINS

CROSS-REFERENCE TO RELATED APPLICATIONS

This application is a divisional of U.S. application Ser. No. 13/626,207 filed on Sep. 25, 2012, now U.S. Pat. No. 9,458,214, which claims the benefit of U.S. Provisional Application No. 61/539,290 filed on Sep. 26, 2011, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Apr. 29, 2016, is named PAT054621-US-NP_SL.txt and is 343,718 bytes in size.

FIELD OF THE INVENTION

The present invention relates to new proteins comprising fibroblast growth factor 21 (FGF21) and other metabolic regulators known to improve metabolic profiles in subjects to whom they are administered.

BACKGROUND OF THE INVENTION

The fibroblast growth factor (FGF) family is characterized by 22 genetically distinct, homologous ligands, which are grouped into seven subfamilies. FGF-21 is most closely related to, and forms a subfamily with, FGF-19 and FGF-23. This FGF subfamily regulates diverse physiological processes uncommon to classical FGFs, namely energy and bile acid homeostasis, glucose and lipid metabolism, and phosphate as well as vitamin D homeostasis. Moreover, unlike other FGFs, this subfamily acts in an endocrine fashion (Moore, D. D. (2007) Science 316, 1436-8)(Beenken et al. (2009) Nature Reviews Drug Discovery 8, 235).

FGF21 is a 209 amino acid polypeptide containing a 28 amino acid leader sequence (SEQ ID NO:132). Human FGF21 has about 79% amino acid identity to mouse FGF21 and about 80% amino acid identity to rat FGF21. Fibroblast growth factor 21 (FGF21) has been described as a treatment for ischemic vascular disease, wound healing, and diseases associated with loss of pulmonary, bronchia or alveolar cell function (Nishimura et al. (2000) Biochimica et Biophysica Acta, 1492:203-206; patent publication WO01/36640; and patent publication WO01/18172). Although FGF-21 activates FGF receptors and downstream signaling molecules, including FRS2a and ERK, direct interaction of FGFRs and FGF-21 has not been detected. Studies have identified β-klotho, which is highly expressed in liver, adipocytes and pancreas, as a determinant of the cellular response to FGF-21 and a cofactor which mediates FGF-21 signaling through FGFRs (Kurosu, H. et al. (2007) J Biol Chem 282, 26687-95). FGF21 is a potent agonist of the FGFR1(IIIc), FGFR2 (IIIc) and FGFR3(IIIc) β-klotho signaling complexes.

FGF-21 has been shown to induce insulin-independent glucose uptake. FGF-21 has also been shown to ameliorate hyperglycemia in a range of diabetic rodent models. In addition, transgenic mice over-expressing FGF-21 were found to be resistant to diet-induced metabolic abnormalities, and demonstrated decreased body weight and fat mass, and enhancements in insulin sensitivity (Badman, M. K. et al. (2007) Cell Metab 5, 426-37). Administration of FGF-21 to diabetic non-human primates caused a decline in fasting plasma glucose, triglycerides, insulin and glucagon levels, and led to significant improvements in lipoprotein profiles, including a nearly 80% increase in HDL cholesterol (Kharitonenkov, A. et al. (2007) Endocrinology 148, 774-81). Recent studies investigating the molecular mechanisms of FGF21 action have identified FGF21 as an important endocrine hormone that helps to control adaptation to the fasting state (Badman et al. (2009) Endocrinology 150, 4931) (Inagaki et al. (2007) Cell Metabolism 5, 415). This provides a previously missing link downstream of PPARa, by which the liver communicates with the rest of the body in regulating the biology of energy homeostasis (Galman et al. (2008) Cell Metabolism 8, 169)(Lundasen et al. (2007) Biochemical and Biophysical Research Communications 360, 437).

FGF21 regulates adipocyte homeostasis through activation of an AMPK/SIRT1/PGC1a pathway to inhibit PPARγ expression and increase mitochondrial function (Chau et al. (2010) PNAS 107, 12553). FGF21 also increases glucose uptake by skeletal muscle as measured in cultured human myotubes and isolated mouse tissue (Mashili et al. (2011) Diabetes Metab Res Rev 27, 286-97). FGF21 treatment of rodent islet cells leads to improved function and survival through activation of ERK1/2 and Akt pathways (Wente et al. (2006) Diabetes 55, 2470). FGF21 treatment also results in altered gene expression for lipogenesis and fatty acid oxidation enzymes in rodent livers, likely through HNF4a and Foxa2 signaling. However, recent studies (Wei et al. (2012) PNAS 109, 3143-48) indicate that treatment of diet-induced obese mice with FGF21 induces bone loss, due to a diminished inactivation of PPARγ (via reduced sumoylation); a shift of mesenchymal stem cell differentiation from osteoblasts to adipocytes is seen in the presence of increased PPARγ activity in the bone following FGF21 treatment.

A difficulty associated with using FGF-21 directly as a biotherapeutic is that its half-life is very short (Kharitonenkov, A. et al. (2005) Journal of Clinical Investigation 115: 1627-1635). In mice, the half-life of human FGF21 is 0.5 to 1 hours, and in cynomolgus monkeys, the half-life is 2 to 3 hours. FGF21 may be utilized as a multi-use, sterile pharmaceutical formulation. However, it has been determined that preservatives, e.g., m-cresol, have an adverse effect on its stability under these conditions.

Another potent metabolic regulator already represented in the clinic is Glucagon-Like Peptide-1 (GLP-1) (Knudsen et al. (2004) Journal of Medicinal Chemistry 47, 4128). GLP-1 is a 36 amino acid incretin secreted by L-cells of the mammalian gut, acting on both alpha and beta cells to stimulate insulin secretion and inhibit glucagon release in a glucose-dependent manner (Hare et al. (2010) Diabetes 59, 1765; Meier et al. (2005) Diabetes-Metabolism Research and Reviews 21, 91). GLP-1 binds to and activates the GLP-1 receptor (GLP-1R), a seven-transmembrane helix protein of the class II family of G-protein coupled receptors (GPCRs) (Mayo et al. (2003) Pharmacological Reviews 55:167). As a GLP-1 receptor agonist, GLP-1 has an important role in decreasing post-prandial blood glucose levels by stimulating insulin secretion from the pancreas in order to increase glucose absorption in the peripheral tissues and inhibiting glucagon secretion, resulting in reduced hepatic glucose release.

A second clinically important GLP-1 receptor agonist is Exendin-4. Exendin-4 is a 39 residue polypeptide produced in the salivary glands of the Gila Monster lizard (Goke et al.

(1993) Diabetes 46:433-439; Fehmann et al. (1995) Endocrine Rev. 16:390-410). Although it is the product of a uniquely non-mammalian gene and appears to be expressed only in the salivary gland, Exendin-4 shares a 52% amino acid sequence homology with GLP-1, and in mammals interacts with the GLP-1 receptor (Goke, et al.; Thorens et al. (1993) Diabetes 42:1678-1682). In vitro, Exendin-4 has been shown to promote insulin secretion by insulin producing cells and, given in equimolar quantities, is more potent than GLP-1 at causing insulin release from insulin producing cells. Furthermore, Exendin-4 potently stimulates insulin release to reduce plasma glucose levels in both rodents and humans and is longer acting than GLP-1; however, because it does not occur naturally in mammals, Exendin-4 has certain potential antigenic properties in mammals that GLP-1 lacks.

The ability of GLP-1 and Exendin-4 analogues (e.g., Liraglutide and Byetta) to improve glucose control in humans is established in the clinic (Idris (2010) Diabetes Obesity & Metabolism 12, 89; Monami et al (2009) European Journal of Endocrinology 160, 909). GLP-1 has also been reported to increase beta cell mass both through induced proliferation and inhibition of apoptosis (Egan, A et al (2003) Diabetes-Metabolism Research and Reviews 19, 115; Farilla, L. et al. (2003) Endocrinology 144, 5149; Xu, G. et al. (1999) Diabetes 48, 2270). It also acts as an intestinal hormone to inhibit acid secretion and gastric emptying in the stomach while providing a satiety signal that decreases appetite (Vilsboll et al. (2009) Best Practice & Research Clinical Endocrinology & Metabolism 23, 453). These effects likely account for beneficial weight loss observed with administration of GLP-1 analogues to type 2 diabetes patients. GLP-1 has also been shown to be cardioprotective in postischemic rodent hearts (Ossum et al. (2009) Pharmacological Research 60, 411; Sonne, D. P. et al. (2008) Regulatory Peptides 146, 243; Nikolaidis, L. A. et al. (2004) Circulation 109, 962).

Additionally, GLP-1 can reduce the differentiation of human mesenchymal stem cells (hMSCs) to adipocytes by reducing the expression of PPARγ, and GLP-1 promotes cellular proliferation and cytoprotection of hMSCs (Sanz et al. (2010) Am J Physiol Endocrinol Metab 298, E634-E643).

In developing an FGF21 protein, including a variant or analogue thereof, for use as a therapeutic in the treatment of type 1 and type 2 diabetes mellitus and other metabolic conditions, an increase in half-life and stability would be desirable. FGF21 proteins having enhanced half-life and stability would allow for less frequent dosing of patients being administered the protein. Clearly, there is a need to develop a stable aqueous protein formulation for the therapeutic protein FGF21.

Furthermore, a significant challenge in the development of protein pharmaceuticals, such as metabolic regulators FGF21, GLP-1, and Exendin-4, is to cope with their physical and chemical instabilities. The compositional variety and characteristics of proteins define specific behaviors such as folding, conformational stability, and unfolding/denaturation. Such characteristics should be addressed when aiming to stabilize proteins in the course of developing pharmaceutical formulation conditions utilizing aqueous protein solutions (Wang, W., Int. J. of Pharmaceutics, 18, (1999)). A desired effect of stabilizing therapeutic proteins of interest, e.g., the proteins of the present invention, is increasing resistance to proteolysis and enzymatic degradation, thereby improving protein stability and reducing protein aggregation.

SUMMARY OF THE INVENTION

The invention relates to the identification of new proteins, e.g., fusion proteins, which comprise fibroblast growth factor 21 (FGF21) and other metabolic regulators, e.g., GLP-1 and Exendin-4, and which have improved pharmaceutical properties over the constituent agents under pharmaceutical formulation conditions, e.g., are more stable, possess the ability to improve metabolic parameters for subjects to whom they are administered, are less susceptible to proteolysis and enzymatic degradation, are less likely to aggregate and form complexes and are less likely to be immunogenic. The proteins of the invention possess both FGF21 receptor agonist and GLP-1 receptor agonist activity; they comprise truncations and variants of FGF21, and further comprise one or more of, e.g., glucagon-like peptide-1 (GLP-1), Exendin-4, or other metabolic regulators or variants thereof.

Also disclosed are methods for treating FGF21-associated and GLP-1 associated disorders, as well as other metabolic, endocrine, and cardiovascular disorders, such as obesity, type 1 and type 2 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, metabolic syndrome, acute myocardial infarction, hypertension, cardiovascular disease, atherosclerosis, peripheral arterial disease, stroke, heart failure, coronary heart disease, kidney disease, diabetic complications, neuropathy, gastroparesis, disorders associated with severe inactivating mutations in the insulin receptor, lipodystrophies including HIV-associated lypodistrophy and other metabolic disorders, and in reducing the mortality and morbidity of critically ill patients.

The proteins of the present invention may be used as a regularly administered (e.g., daily, more preferably weekly, biweekly, or monthly) injectable, either alone or in combination with oral anti-diabetic agents, which will improve the glycemic control, body weight and lipid profile of type 1 and type 2 diabetes mellitus patients. The proteins may also be used for the treatment of obesity or other FGF21- or GLP-1-associated conditions.

The proteins of the invention, e.g., GLP-1-FGF21 variant and Exendin-4-FGF21 variant fusion proteins of the invention, overcome the significant hurdles of physical instabilities associated with protein therapeutics, including, for instance, with the administration of the wild-type FGF21, as they are more stable, less susceptible to proteolysis and enzymatic degradation, less likely to aggregate and form complexes and less likely to be immunogenic than wild-type FGF21 under pharmaceutical formulation conditions.

In a first aspect, the invention provides Fibroblast Growth Factor 21 (FGF21) proteins, e.g., fusion proteins, comprising one or more of the sequences listed in Table 1, and further described herein. The proteins of the invention can further comprise GLP-1 and/or Exendin-4 proteins, whether wild-type, truncated, or mutated versions, or variants thereof. The FGF21 sequences listed in Table 1 are variants of the wild-type FGF21 sequence, e.g., the wild-type FGF21 sequence with NCBI reference number NP_061986.1, and found in such issued patents as, e.g., U.S. Pat. No. 6,716,626B1, assigned to Chiron Corporation. The GLP-1 and Exendin-4 sequences listed in Table 1 are variants of the wild-type GLP-1 and Exendin-4 sequences, e.g., those sequences with NCBI reference numbers NP_002045 and AAB22006.1, respectively, and can be found in such patent publications as, e.g., WO98/19698 and WO87/06941A, assigned to Eli Lilly and Co. and the General Hospital Corp., respectively (GLP-1) and U.S. Pat. No. 5,424,286, assigned to Amylin (Exendin-4).

Other embodiments are drawn to polynucleotides encoding the dual function proteins of the invention, a vector containing said polynucleotides and a host cell carrying said vector.

Provided herein are methods used to generate the proteins of the invention, wherein such methods involve modification of the wild-type FGF21 protein, via, e.g., the site-specific incorporation of amino acids at positions of interest within the wild-type FGF21 protein, as well as the fusion between the FGF21 portion of the molecule to other metabolic regulators, such as glucagon-like peptide-1 (GLP-1) and Exendin-4, or conjugates with polymers modified with GLP-1 and/or Exendin-4. Said modifications and fusions enhance the biological properties of the proteins of the invention relative to the wild-type versions of the proteins (e.g., FGF21, GLP-1, and Exendin-4), as well as, in some cases, serving as points of attachment for, e.g., labels and protein half-life extension agents, and for purposes of affixing said variants to the surface of a solid support. Related embodiments of the invention are methods to produce cells capable of producing said proteins of the invention, and of producing vectors containing DNA encoding said variants and fusions.

In various embodiments, the proteins of the invention can comprise one or more fragments of the FGF21, Exendin-4, and/or GLP-1 sequences, including fragments as small as 8-12 amino acid residues in length, wherein the polypeptide is capable of lowering blood glucose in a mammal. In various embodiments, the proteins of the invention can comprise one or more variants of the FGF21, Exendin-4, and/or GLP-1 sequences, e.g., with one or more amino acid deletions, insertions, additions, or substitutions relative to the wild-type sequences thereof.

In some embodiments, the proteins of the invention can be covalently linked to one or more polymers, such as polyethylene glycol (PEG) or polysialic acid, whether at the position of site-specific amino acid modifications made relative to the wild-type FGF21, GLP-1, or Exendin-4, or at the position of amino acids commonly shared with the wild-type versions of those proteins. The PEG group is attached in such a way so as enhance, and/or not to interfere with, the biological function of the constituent portions of the fusion proteins of the invention, e.g., the GLP-1 protein variants or FGF21 protein variants. In other embodiments, the polypeptides of the invention can be fused to a heterologous amino acid sequence, optionally via a linker, such as GS, GGGGSGGGGSGGGGS (SEQ ID NO:8), or SGGGGSGGG (SEQ ID NO:128). The heterologous amino acid sequence can be an IgG constant domain or fragment thereof (e.g., the Fc region), Human Serum Albumin (HSA), or albumin-binding polypeptides. Such fusion proteins disclosed herein can also form multimers.

In some embodiments, a heterologous amino acid sequence (e.g., HSA, Fc, etc.) is fused to the amino-terminal of the proteins of the invention. In other embodiments, the fusion heterologous amino acid sequence (e.g., HSA, Fc, etc.) is fused to the carboxyl-terminal of the proteins of the invention. In still other, more preferred embodiments, the heterologous amino acid sequence (e.g., HSA, Fc, etc.) is situated in the middle of the dual function proteins of the invention, i.e., between the C-terminal residue of the GLP-1 or Exendin-4 sequence and the N-terminal residue of the FGF21 sequence. Said preferred embodiment, e.g., leaves a free N-terminus for maximum GLP-1 (Exendin-4) activity and a free, intact C-terminus for maximum FGF21 activity.

In some embodiments, the GLP-1 receptor agonist is fused to the N-terminus of heavy and light chain of an antibody and FGF21 is simultaneously fused to the C-terminus of heavy and light chain of the same antibody (i.e., a fusobody, as described herein). Said preferred embodiment leaves a free N-terminus for maximum GLP-1 (Exendin-4) activity and a free, intact C-terminus for maximum FGF21 activity. A preferred embodiment uses the antibody sequence described in PCT publication WO2011/076781.

In some embodiments, the GLP-1 or Exendin-4 peptide is chemically attached to FGF21. In some embodiments, said peptides are attached to an FGF21 amino acid residue side chain. In other embodiments, said peptides are attached to the N-terminus of FGF21 through native chemical ligation or other methods known to the art. The preferred embodiment leaves a free N-terminus of GLP-1 (Exendin-4) for maximal activity and a free, intact C-terminus of FGF21 for maximal activity.

In some embodiments, the GLP-1 or Exendin-4 peptide is covalently attached to a polymer molecule that in turn is attached to the FGF21 protein variant. In a preferred embodiment, the GLP-1 or Exendin-4 peptide is attached to a PEG polymer that is simultaneously attached to a FGF21 protein variant. Said preferred embodiment leaves a free N-terminus for maximum GLP-1 (Exendin-4) activity and a free, intact C-terminus for maximum FGF21 activity. In some embodiments of the invention, a GLP-1 receptor agonist peptide is connected to a FGF21 variant through a PEG linker or other polymer linker that simultaneously provides half-life extension as well as a covalent connection for the two receptor agonists.

Yet another embodiment is drawn to methods of treating a patient exhibiting one or more FGF21-associated disorders or GLP-1-associated disorders, such as obesity, type 2 diabetes mellitus, type 1 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, metabolic syndrome, acute myocardial infarction, hypertension, cardiovascular disease, atherosclerosis, peripheral arterial disease, stroke, heart failure, coronary heart disease, kidney disease, diabetic complications, neuropathy, gastroparesis, disorders associated with inactivating mutations in the insulin receptor, lipodystrophies including HIV-associated lipodystrophy and other metabolic disorders, comprising administering to said patient in need of such treatment a therapeutically effective amount of one or more proteins of the invention or a pharmaceutical composition thereof.

The invention also provides pharmaceutical compositions comprising the dual function proteins of the invention disclosed herein and a pharmaceutically acceptable formulation agent. Such pharmaceutical compositions can be used in a method for treating a metabolic disorder, and the method comprises administering to a human patient in need thereof a pharmaceutical composition of the invention. Non-limiting examples of metabolic disorders that can be treated include type 1 and type 2 diabetes mellitus and obesity.

These and other aspects of the invention will be elucidated in the following detailed description of the invention.

BRIEF DESCRIPTION OF THE DRAWINGS

FIG. 1A shows the mutations added to slow processing by DPP-4 protease (GLP-1 peptide (circles) or dual function proteins with wild-type (V231; open squares), G0 (V251; open circles), A8G (V258; open triangles), A8S (V232; triangles), or E9P (V271; squares) GLP-1). FIG. 1B shows Exendin-4 fusions (GLP-1 peptide (squares) or dual function proteins with Exendin-4 1-39 (V234; triangles), 1-30 (V267; circles) or 1-30/E16G/E17Q (V268; open triangles)).

FIGS. 6A-6C show levels of basal glucose (AUC), alanine aminotransferase (ALT), and serum total cholesterol, respectively. FIGS. 6D-6F show levels of D12 body weight, hepatic lipids, and serum triglycerides, respectively.

Figure 1A:
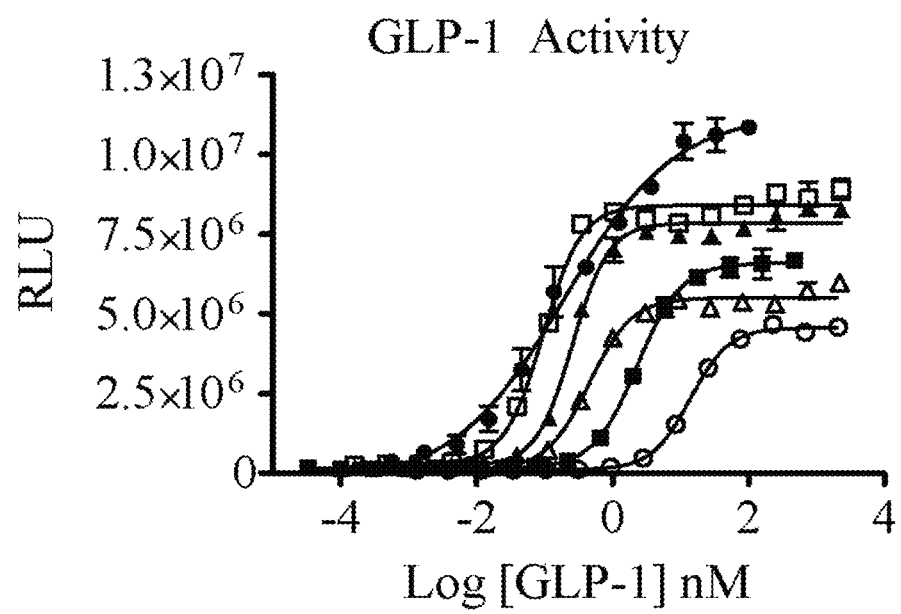
FIGS. 1A and 1B show the activity of GLP-1-FGF21-PEG fusion proteins with different N-terminal mutations, and Exendin-4-FGF21-PEG fusion proteins.

PEG (V253; triangles), V253+FGF21(V76)-PEG (open diamonds), Exendin-4(1-39)-Fc-FGF21(V103) (V211; open circles), Exendin-4(1-39)-Fc (V201; open triangles), and V201+FGF21(V101) (diamonds).

DETAILED DESCRIPTION OF THE INVENTION

The proteins of the present invention represent modified versions of the full-length, wild-type FGF21 polypeptide, as known in the art. FGF21 wild-type sequence will serve as a reference sequence (SEQ ID NO:1), for instance, when comparisons between the FGF21 wild-type sequence and the protein variants are necessary. The FGF21 wild-type sequence has NCBI reference sequence number NP_061986.1, and can be found in such issued patents as, e.g., U.S. Pat. No. 6,716,626B1, assigned to Chiron Corporation (SEQ ID NO:1).

```
Met Asp Ser Asp Glu Thr Gly Phe Glu His Ser Gly Leu Trp Val Ser
1               5                   10                  15
Val Leu Ala Gly Leu Leu Leu Gly Ala Cys Gln Ala His Pro Ile Pro
                20                  25                  30
Asp Ser Ser Pro Leu Leu Gln Phe Gly Gly Gln Val Arg Gln Arg Tyr
            35                  40                  45
Leu Tyr Thr Asp Asp Ala Gln Gln Thr Glu Ala His Leu Glu Ile Arg
        50                  55                  60
Glu Asp Gly Thr Val Gly Gly Ala Ala Asp Gln Ser Pro Glu Ser Leu
65                  70                  75                  80
Leu Gln Leu Lys Ala Leu Lys Pro Gly Val Ile Gln Ile Leu Gly Val
                85                  90                  95
Lys Thr Ser Arg Phe Leu Cys Gln Arg Pro Asp Gly Ala Leu Tyr Gly
                100                 105                 110
Ser Leu His Phe Asp Pro Glu Ala Cys Ser Phe Arg Glu Leu Leu Leu
            115                 120                 125
Glu Asp Gly Tyr Asn Val Tyr Gln Ser Glu Ala His Gly Leu Pro Leu
        130                 135                 140
His Leu Pro Gly Asn Lys Ser Pro His Arg Asp Pro Ala Pro Arg Gly
145                 150                 155                 160
Pro Ala Arg Phe Leu Pro Leu Pro Gly Leu Pro Pro Ala Leu Pro Glu
                165                 170                 175
Pro Pro Gly Ile Leu Ala Pro Gln Pro Pro Asp Val Gly Ser Ser Asp
                180                 185                 190
Pro Leu Ser Met Val Gly Pro Ser Gln Gly Arg Ser Pro Ser Tyr Ala
            195                 200                 205
Ser
209
```

The corresponding mRNA sequence coding for the full-length FGF21 polypeptide (NCBI reference sequence number NM_019113.2) is shown below (SEQ ID NO:2):

```
  1 ctgtcagctg aggatccagc cgaaagagga gccaggcact caggccacct gagtctactc
 61 acctggacaa ctggaatctg gcaccaattc taaaccactc agcttctccg agctcacacc
121 ccggagatca cctgaggacc cgagccattg atggactcgg acgagaccgg gttcgagcac
181 tcaggactgt gggtttctgt gctggctggt cttctgctgg gagcctgcca ggcacacccc
241 atccctgact ccagtcctct cctgcaattc gggggccaag tccggcagcg gtacctctac
301 acagatgatg cccagcagac agaagcccac ctggagatca gggaggatgg gacggtgggg
361 ggcgctgctg accagagccc cgaaagtctc ctgcagctga aagccttgaa gccgggagtt
421 attcaaatct gggagtcaa gacatccagg ttcctgtgcc agcggccaga tggggccctg
481 tatggatcgc tccactttga ccctgaggcc tgcagcttcc gggagctgct tcttgaggac
541 ggatacaatg tttaccagtc cgaagcccac ggcctcccgc tgcacctgcc agggaacaag
```

```
601 tccccacacc gggaccctgc accccgagga ccagctcgct tcctgccact accaggcctg 661 cccccgcac tcccggagcc acccggaatc ctggccccc agcccccga tgtgggctcc 721 tcggaccctc tgagcatggt gggaccttcc cagggccgaa gccccagcta cgcttcctga 781 agccagaggc tgtttactat gacatctcct ctttatttat taggttattt atcttattta 841 ttttttattt tttcttactt gagataataa agagttccag aggagaaaaa aaaaaaaaa 901 aaaaaaaaaa aaaaaaaaaa aaaaaaaaa aaaaaaaaaa
```

The mature FGF21 sequence lacks a leader sequence and may also include other modifications of a polypeptide such as proteolytic processing of the amino terminus (with or without a leader sequence) and/or the carboxyl terminus, cleavage of a smaller polypeptide from a larger precursor, N-linked and/or O-linked glycosylation, and other post-translational modifications understood by those with skill in the art. A representative example of a mature FGF21 sequence has the following sequence (SEQ ID NO:3, which represents amino acid positions 29-209 of full-length FGF21 protein sequence (NCBI reference sequence number NP_061986.1)):

```
His Pro Ile Pro Asp Ser Ser Pro Leu Leu Gln Phe Gly Gly Gln Val
                  5                  10                 15
Arg Gln Arg Tyr Leu Tyr Thr Asp Asp Ala Gln Gln Thr Glu Ala His
             20                  25                 30
Leu Glu Ile Arg Glu Asp Gly Thr Val Gly Gly Ala Ala Asp Gln Ser
         35                  40                  45
Pro Glu Ser Leu Leu Gln Leu Lys Ala Leu Lys Pro Gly Val Ile Gln
     50                  55                  60
Ile Leu Gly Val Lys Thr Ser Arg Phe Leu Cys Gln Arg Pro Asp Gly
 65                  70                  75                  80
Ala Leu Tyr Gly Ser Leu His Phe Asp Pro Glu Ala Cys Ser Phe Arg
             85                  90                  95
Glu Leu Leu Leu Glu Asp Gly Tyr Asn Val Tyr Gln Ser Glu Ala His
            100                 105                 110
Gly Leu Pro Leu His Leu Pro Gly Asn Lys Ser Pro His Arg Asp Pro
            115                 120                 125
Ala Pro Arg Gly Pro Ala Arg Phe Leu Pro Leu Pro Gly Leu Pro Pro
    130                 135                 140
Ala Leu Pro Glu Pro Pro Gly Ile Leu Ala Pro Gln Pro Pro Asp Val
145                 150                 155                 160
Gly Ser Ser Asp Pro Leu Ser Met Val Gly Pro Ser Gln Gly Arg Ser
                165                 170                 175
Pro Ser Tyr Ala Ser
            180
```

The corresponding cDNA sequence coding for the mature FGF21 polypeptide (SEQ ID NO:3) is shown below (SEQ ID NO:4):

```
  1 cacccatcc ctgactccag tcctctcctg caattcgggg gccaagtccg gcagcggtac 61 ctctacacag atgatgccca gcagacagaa gcccacctgg agatcaggga ggatgggacg 121 gtggggggcg ctgctgacca gagccccgaa agtctcctgc agctgaaagc cttgaagccg 181 ggagttattc aaatcttggg agtcaagaca tccaggttcc tgtgccagcg gccagatggg 240
gccctgtatg gatcgctcca ctttgaccct gaggcctgca gcttccggga gctgcttctt 301 gaggacggat acaatgttta ccagtccgaa gccacggcc tcccgctgca cctgccaggg 360
aacaagtccc cacaccggga ccctgcaccc cgaggaccag ctcgcttcct gccactacca 421 ggcctgcccc ccgcactccc ggagccacc ggaatcctgg ccccccagcc ccccgatgtg
```

```
                                             -continued
481 ggctcctcgg accctctgag catggtggga ccttcccagg gccgaagccc cagctacgct 541 tcctga
```

The proteins of the invention of the present invention represent modified versions of the full-length, wild-type GLP-1 polypeptide, as known in the art. GLP-1 wild-type sequence will serve as a reference sequence (SEQ ID NO:5), for instance, when comparisons between the GLP-1 wild-type sequence and the protein variants are necessary.

The GLP-1 wild-type sequence is post-translationally modified, and otherwise derived from, preproglucagon wild-type sequence. Preproglucagon sequence (SEQ ID NO:5) has NCBI reference sequence number NP_002045, and can be found in such patent publications as, e.g., WO98/19698 and WO87/06941A, assigned to Eli Lilly and Co. and the General Hospital Corp., respectively. As described, for example, in Goke, et al. (1991) European Journal of Clinical Investigation 21, 135, GLP-1 is a 37mer that is derived from preproglucagon (GLP-1 constitutes residues 92-138 of preproglucagon, and is underlined in SEQ ID NO:5, below). GLP-1 is further processed into an active 31mer, by cleavage of the six N-term residues.

```
  1 MKSIYFVAGL FVMLVQGSWQ RSLQDTEEKS RSFSASQADP LSDPDQMNED KRHSQGTFTS

61 DYSKYLDSRR AQDFVQWLMN TKRNRNNIAK RHDEFERHAE GTFTSDVSSY LEGQAAKEFI

121 AWLVKGRGRR DFPEEVAIVE ELGRRHADGS FSDEMNTILD NLAARDFINW LIQTKITDRK
```

An example of the processed, wild-type GLP-1 sequence is as follows (SEQ ID NO:129):

```
  1 HDEFERHAEG TFTSDVSSYL EGQAAKEFIA WLVKGRG
```

An example of the active GLP-1 sequence is as follows (SEQ ID NO:30):

```
  1 HAEGTFTSDV SSYLEGQAAK EFIAWLVKGR G
```

The corresponding mRNA sequence coding for the preproglucagon GLP-1 wild-type sequence (SEQ ID NO:5) is shown below (SEQ ID NO:6):

```
   1 gcatagaatg cagatgagca aagtgagtgg gagagggaag tcatttgtaa caaaaactca 61 ttatttacag atgagaaatt tatattgtca gcgtaatatc tgtgaggcta aacagagctg 121 gagagtatat aaaagcagtg cgccttggtg cagaagtaca gagcttagga cacagagcac 181 atcaaaagtt cccaaagagg gcttgctctc tcttcacctg ctctgttcta cagcacacta 241 ccagaagaca gcagaaatga aaagcattta ctttgtggct ggattatttg taatgctggt 301 acaaggcagc tggcaacgtt cccttcaaga cacagaggag aaatccagat cattctcagc 361 ttcccaggca gacccactca gtgatcctga tcagatgaac gaggacaagc gccattcaca 421 gggcacattc accagtgact acagcaagta tctggactcc aggcgtgccc aagatttgt 481 gcagtggttg atgaatacca agaggaacag gaataacatt gccaaacgtc acgatgaatt 541 tgagagacat gctgaaggga cctttaccag tgatgtaagt tcttatttgg aaggccaagc 601 tgccaaggaa ttcattgctt ggctggtgaa aggccgagga aggcgagatt tcccagaaga 661 ggtcgccatt gttgaagaac ttggccgcag acatgctgat ggttctttct ctgatgagat 721 gaacaccatt cttgataatc ttgccgccag ggactttata aactggttga ttcagaccaa 781 aatcactgac aggaaataac tatatcacta ttcaagatca tcttcacaac atcacctgct 841 agccacgtgg gatgtttgaa atgttaagtc ctgtaaattt aagaggtgta ttctgaggcc 901 acattgcttt gcatgccaat aaataaattt tcttttagtg ttgtgtagcc aaaaattaca 961 aatggaataa agttttatca aaatattgct aaaatatcag ctttaaaata tgaaagtgct 1021 agattctgtt attttcttct tattttggat gaagtacccc aacctgttta catttagcga
```

-continued
```
1081 taaaattatt tttctatgat ataatttgta aatgtaaatt attccgatct gacatatctg 1141 cattataata ataggagaat agaagaactg gtagccacag tggtgaaatt ggaaagagaa 1201 ctttcttcct gaaacctttg tcttaaaaat actcagcttt caatgtatca aagatacaat 1261 taaataaaat tttcaagctt ctttaccaaa aaaaaaa
```

The proteins of the invention of the present invention represent modified versions of the full-length, wild-type Exendin-4 polypeptide, as known in the art. Exendin-4 wild-type sequence will serve as a reference sequence (SEQ ID NO:7), for instance, when comparisons between the Exendin-4 wild-type sequence and the protein variants are necessary.

The Exendin-4 wild-type sequence has NCBI reference sequence number GenBank: AAB22006.1, and can be found in such issued patents as, e.g., U.S. Pat. No. 5,424,286, assigned to Amylin Pharmaceuticals, Inc. and Eli Lilly and Co. An example of the wild-type sequence is as follows (SEQ ID NO:7):

```
1 HGEGTFTSDL SKQMEEEAVR LFIEWLKNGG PSSGAPPPS
```

The proteins of the invention may comprise protein variants or mutants of the wild-type proteins listed herein, e.g., FGF21 variants, GLP-1 variants, and/or Exendin-4 variants. As used herein, the terms "protein variant," "human variant," "polypeptide or protein variant," "variant," "mutant," as well as any like terms or specific versions thereof (e.g., "FGF21 protein variant," "human GLP-1 variant," "Exendin-4 polypeptide or protein variant," "variant," "FGF21 mutant," etc.) define protein or polypeptide sequences that comprise modifications, truncations, other variants of naturally occurring (i.e., wild-type) protein or polypeptide counterparts or corresponding native sequences. "Variant FGF21" or "FGF21 mutant," for instance, is described relative to the wild-type (i.e., naturally occurring) FGF21 protein as described herein.

Representative dual function protein sequences of the invention are listed in Table 1. The descriptions of said agonists include the individual constituent agonists and, where applicable a linker. If a variant is used as a constituent agonist, the changes or substitutions made are numbered relative to their wild-type counterparts. By way of example, "Dual Function 1—Protein" (SEQ ID NO:9) contains residues 7-35 of the wild-type GLP-1 sequence as described herein (i.e., a GLP-1 receptor agonist), a linker sequence, and an FGF21 variant (i.e., an FGF21 receptor agonist) with a number of listed changes to the FGF21 wild-type sequence (SEQ ID NO:1) as described herein.

TABLE 1

Dual Function Protein and Nucleotides of the invention

| SEQ ID NO: | Variant NO: | Sequence | Long Name | Short Name |
|---|---|---|---|---|
| 9 | V272 | HSEGTFTSDV SSYLEGQAAK EFIAWLVKGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEDGYN VYQSEAHGLP LHLPGNRSPH CDPAPQGPAR FLPLPGLPPA LPEPPGILAP QPPDVGSSDP LAMVGPSQGR SPSYAS | GLP-1(7-35; A8S)-GSGGGGSGGG-FGF21(33-209; Q56E-D74H-Q82E-R105K-K150R-R154C-40 kDa branched PEG-R159Q-S195A) | GLP-1(A8S)-L10-FGF21 (V76)-40KPEGb |
| 10 | | CATTCTGAAG GCACTTTTAC TAGCGATGTT TCTAGCTACC TGGAAGGCCA GGCTGCGAAA GAATTCATCG CGTGGCTGGT TAAAGGCGGT TCTGGTGGTG GTGGTTCTGG CGGTGCCGAT AGCAGCCCGC TGCTGCAGTT TGGCGGCCAG GTGCGTCAGC GTTATCTGTA TACCGATGAT GCGCAGGAAA CCGAAGCGCA TCTGGAAATT CGTGAAGATG GCACCGTGGG CGGTGCGGCG CATCAGAGCC CGGAAAGCCT GCTGGAACTG AAAGCGCTGA AACCGGGCGT GATTCAGATT CTGGGCGTGA AAACCAGCCG TTTTCTGTGC CAGAAACCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACCG TAGCCCGCAT TGCGATCCGG CACCGCAGGG TCCGGCGCGT TTTCTGCCGC TGCCGGGTCT GCCGCCGGCA CTGCCGGAAC CGCCGGGTAT TCTGGCCCCG | GLP-1(7-35; A8S)-GSGGGGSGGG-FGF21(33-209; Q56E-D74H-Q82E-R105K-K150R-R154C-R159Q-S195A) | GLP-1(A8S)-L10-FGF21 (V76) |

TABLE 1 -continued

Dual Function Protein and Nucleotides of the invention

| SEQ ID NO: | Variant NO: | Sequence | Long Name | Short Name |
|---|---|---|---|---|
|  |  | CAGCCGCCGG ATGTTGGTAG CAGCGATCCG CTGGCGATGG TGGGTCCGAG CCAGGGTCGT AGCCCGAGCT ATGCGAGCTA A |  |  |
| 11 | V277 | HGEGTFTSDL SKQMEEEAVR LFIEWLKNGG SGGGGSGGGG SGGGGSGGGG DSSPLLQFGG QVRQRYLYTD DAQETEAHLE IREDGTVGGA AHQSPESLLE LKALKPGVIQ ILGVKTSRFL CQKPDGALYG SLHFDPEACS FRELLLEDGY NVYQSEAHGL PLHLPGNRSP HCDPAPQGPA RFLPLPGLPP ALPEPPGILA PQPPDVGSSD PLAMVGPSQG RSPSYAS | Exendin4(1-30)-SGGGGSGGGGS GGGGSGGGG-FGF21(33-209; Q56E-D74H-Q82E-R105K-K150R-R154C-40 kDa branched PEG-R159Q-S195A) | Ex(1-30)-L20-FGF21(V76)-40KPEGb |
| 12 |  | CATGGTGAGG GTACGTTTAC TTCTGATCTG TCTAAACAGA TGGAAGAAGA AGCTGTTCGC CTGTTCATTG AATGGCTGAA AAATGGTGGT TCTGGTGGTG GTGGTTCTGG CGGTGGCGGT TCTGGCGGCG GTGGTAGCGG TGGCGGCGGT GATAGCAGCC CGCTGCTGCA GTTTGGCGGC CAGGTGCGTC AGCGTTATCT GTATACCGAT GATGCGCAGG AAACCGAAGC GCATCTGGAA ATTCGTGAAG ATGGCACCGT GGGCGGTGCG GCGCATCAGA GCCCGGAAAG CCTGCTGGAA CTGAAAGCGC TGAAACCGGG CGTGATTCAG ATTCTGGGCG TGAAAACCAG CCGTTTTCTG TGCCAGAAAC CGGATGCGCT GCTGTATGGC AGCCTGCATT TTGATCCGGA AGCGTGCAGC TTTCGTGAAC TGCTGCTGGA AGATGGCTAT AACGTGTATC AGAGCGAAGC GCATGGCCTG CCGCTGCATC TGCCGGGCAA CCGTAGCCCG CATTGCGATC CGGCACCGCA GGGTCCGGCG CGTTTTCTGC CGCTGCCGGG TCTGCCGCCG GCACTGCCGG AACCGCCGGG TATTCTGGCC CCGCAGCCGC CGGATGTTGG TAGCAGCGAT CCGCTGGCGA TGGTGGGTCC GAGCCAGGGT CGTAGCCCGA GCTATGCGAG CTAA | Exendin4(1-30)-SGGGGSGGGGS GGGGSGGGG-FGF21(33-209; Q56E-D74H-Q82E-R105K-K150R-R154C-R159Q-S195A) | Ex(1-30)-L20-FGF21(V76) |
| 13 | V220 | HSEGTFTSDV SSYLEGQAAK EFIAWLVKGG SGDSSPLLQF GGQVRQRYLY TDDAQQTEAH LEIREDGTVG GAADQSPESL LQLKALKPGV IQILGVKTSR FLCQRPDGAL YGSLHFDPEA CSFRELLLED GYNVYQSEAH GLPLHLPGNK SPHRDPAPRG PARFLPLPGL PPALPEPPGI LAPQPPDVGS SDPLSMVGPS QGRSPSYAS | GLP-1(7-35; A8S)-GSG-FGF21(33-209) | GLP-1(A8S)-L3-FGF21 |
| 14 |  | CATTCTGAAG GCACTTTTAC TAGCGATGTT TCTAGCTACC TGGAAGGCCA GGCTGCGAAA GAATTCATCG CGTGGCTGGT TAAAGGCGGT TCTGGTGATA GCAGCCCGCT GCTGCAGTTT GGCGGCCAGG TGCGTCAGCG TTATCTGTAT ACCGATGATG CGCAGCAGAC CGAAGCGCAT CTGGAAATTC GTGAAGATGG CACCGTGGGC GGTGCGGCGG ATCAGAGCCC GGAAAGCCTG CTGCAGCTGA AAGCGCTGAA ACCGGGCGTG ATTCAGATTC TGGGCGTGAA AACCAGCCGT TTTCTGTGCC AGCGTCCGGA TGCGCGCTG TATGGCAGCC TGCATTTTGA TCCGGAAGCG TGCAGCTTTC GTGAACTGCT GCTGGAAGAT GGCTATAACG TGTATCAGAG CGAAGCGCAT GGCCTGCCGC TGCATCTGCC GGGCAACAAA AGCCCGCATC GTGATCCGGC ACCGCGTGGT CCGGCGCGTT TTCTGCCGCT GCCGGGTCTG CCGCCGGCAC TGCCGGAACC GCCGGGTATT CTGGCCCCGC AGCCGCCGGA TGTTGGTAGC AGCGATCCGC TGTCTATGGT GGGTCCGAGC CAGGGTCGTA GCCCGAGCTA TGCGAGCTAA | GLP-1(7-35; A8S)-GSG-FGF21(33-209) | GLP-1(A8S)-L3-FGF21 |

TABLE 1 -continued

Dual Function Protein and Nucleotides of the invention

| SEQ ID NO: | Variant NO: | Sequence | Long Name | Short Name |
|---|---|---|---|---|
| 15 | V219 | HAEGTFTSDV SSYLEGQAAK EFIAWLVKGG SGDSSPLLQF GGQVRQRYLY TDDAQQTEAH LEIREDGTVG GAADQSPESL LQLKALKPGV IQILGVKTSR FLCQRPDGAL YGSLHFDPEA CSFRELLLED GYNVYQSEAH GLPLHLPGNK SPHRDPAPRG PARFLPLPGL PPALPEPPGI LAPQPPDVGS SDPLSMVGPS QGRSPSYAS | GLP-1(7-35)-GSG-FGF21 (33-209) | GLP-1-L3-FGF21 |
| 16 | | CATGCGGAAG GCACTTTTAC TAGCGATGTT TCTAGCTACC TGGAAGGCCA GGCTGCGAAA GAATTCATCG CGTGGCTGGT TAAAGGCGGT TCTGGTGATA GCAGCCCGCT GCTGCAGTTT GGCGGCCAGG TGCGTCAGCG TTATCTGTAT ACCGATGATG CGCAGCAGAC CGAAGCGCAT CTGGAAATTC GTGAAGATGG CACCGTGGGC GGTGCGGCGG ATCAGAGCCC GGAAAGCCTG CTGCAGCTGA AAGCGCTGAA ACCGGGCGTG ATTCAGATTC TGGGCGTGAA AACCAGCCGT TTTCTGTGCC AGCGTCCGGA TGGCGCGCTG TATGGCAGCC TGCATTTTGA TCCGGAAGCG TGCAGCTTTC GTGAACTGCT GCTGGAAGAT GGCTATAACG TGTATCAGAG CGAAGCGCAT GGCCTGCCGC TGCATCTGCC GGGCAACAAA AGCCCGCATC GTGATCCGGC ACCGCGTGGT CCGGCGCGTT TTCTGCCGCT GCCGGGTCTG CCGCCGGCAC TGCCGGAACC GCCGGGTATT CTGGCCCCGC AGCCGCCGGA TGTTGGTAGC AGCGATCCGC TGTCTATGGT GGGTCCGAGC CAGGGTCGTA GCCCGAGCTA TGCGAGCTAA | GLP-1(7-35)-GSG-FGF21 (33-209) | GLP-1-L3-FGF21 |
| 17 | V295 | HGEGTFTSDL SKQMEEEAVR LFIEWLKNGG PSSGAPPPSG GGDSSPLLQF GGQVRQRYLY TDDAQQTEAH LEIREDGTVG GAADQSPESL LQLKALKPGV IQILGVKTSR FLCQRPDGAL YGSLHFDPEA CSFRELLLED GYNVYQSEAH GLPLHLPGNK SPHRDPAPRG PARFLPLPGL PPALPEPPGI LAPQPPDVGS SDPLSMVGPS QGRSPSYAS | Exendin4(1-39)-GGG-FGF21(33-209) | Ex(1-39)-L3-FGF21 |
| 18 | | CATGGTGAGG GTACGTTTAC TTCTGATCTG TCTAAACAGA TGGAAGAAGA AGCTGTTCGC CTGTTCATTG AATGGCTGAA AAATGGTGGT CCGTCCTCCG GCGCTCCTCC GCCTTCTGGT GGTGGCGACT CGAGCCCGCT GCTGCAGTTT GGCGGCCAGG TGCGTCAGCG TTATCTGTAT ACCGATGATG CGCAGCAGAC CGAAGCGCAT CTGGAAATTC GTGAAGATGG CACCGTGGGC GGTGCGGCGG ATCAGAGCCC GGAAAGCCTG CTGCAGCTGA AAGCGCTGAA ACCGGGCGTG ATTCAGATTC TGGGCGTGAA AACCAGCCGT TTTCTGTGCC AGCGTCCGGA TGGCGCGCTG TATGGCAGCC TGCATTTTGA TCCGGAAGCG TGCAGCTTTC GTGAACTGCT GCTGGAAGAT GGCTATAACG TGTATCAGAG CGAAGCGCAT GGCCTGCCGC TGCATCTGCC GGGCAACAAA AGCCCGCATC GTGATCCGGC ACCGCGTGGT CCGGCGCGTT TTCTGCCGCT GCCGGGTCTG CCGCCGGCAC TGCCGGAACC GCCGGGTATT CTGGCCCCGC AGCCGCCGGA TGTTGGTAGC AGCGATCCGC TGTCTATGGT GGGTCCGAGC CAGGGTCGTA GCCCGAGCTA TGCGAGCTAA | Exendin4(1-39)-GGG-FGF21 (33-209) | Ex(1-39)-L3-FGF21 |
| 19 | V224 | HSEGTFTSDV SSYLEGQAAK EFIAWLVKGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH RDPAPRGPAR FLPLPGLPPA LPEPPGILAP QPPDVGSSDP LSMVGPSQGR SPSYAS | GLP-1(7-35; A8S)-GSGGGGSGGG-FGF21 (33-209) | GLP-1(A8S)-L10-FGF21 |
| 20 | | CATTCTGAAG GCACTTTTAC TAGCGATGTT TCTAGCTACC TGGAAGGCCA GGCTGCGAAA GAATTCATCG CGTGGCTGGT TAAAGGCGGT TCTGGTGGTG GTGGTTCTGG CGGTGGCGAC | GLP-1(7-35; A8S)-GSGGGGSGGG-FGF21 | GLP-1(A8S)-L10-FGF21 |

TABLE 1 -continued

Dual Function Protein and Nucleotides of the invention

| SEQ ID NO: | Variant NO: | Sequence | Long Name | Short Name |
|---|---|---|---|---|
| | | TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT CGTGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | (33-209) | |
| 21 | V223 | HAEGTFTSDV SSYLEGQAAK EFIAWLVKGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH RDPAPRGPAR FLPLPGLPPA LPEPPGILAP QPPDVGSSDP LSMVGPSQGR SPSYAS | GLP-1(7-35)-GSGGGGSGGG-FGF21 (33-209) | GLP-1-L10-FGF21 |
| 22 | | CATGCGGAAG GCACTTTTAC TAGCGATGTT TCTAGCTACC TGGAAGGCCA GGCTGCGAAA GAATTCATCG CGTGGCTGGT TAAAGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT CGTGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35)-GSGGGGSGGG-FGF21 (33-209) | GLP-1-L10-FGF21 |
| 23 | V234 | HGEGTFTSDL SKQMEEEAVR LFIEWLKNGG PSSGAPPPSG GGGSGGGDSS PLLQFGGQVR QRYLYTDDAQ QTEAHLEIRE DGTVGGAADQ SPESLLQLKA LKPGVIQILG VKTSRFLCQR PDGALYGSLH FDPEACSFRE LLLEDGYNVY QSEAHGLPLH LPGNKSPHRD PAPRGPARFL PLPGLPPALP EPPGILAPQP PDVGSSDPLS MVGPSQGRSP SYAS | Exendin4 (1-39)-GGGGSGGG-FGF21(33-209) | Ex(1-39)-L8-FGF21 |
| 24 | | CATGGTGAGG GTACGTTTAC TTCTGATCTG TCTAAACAGA TGGAAGAAGA AGCTGTTCGC CTGTTCATTG AATGGCTGAA AAATGGTGGT CCGTCCTCCG GCGCTCCTCC GCCTTCTGGT GGTGGTGGTT CTGGCGGTGG CGACTCGAGC CCGCTGCTGC AGTTTGGCGG CCAGGTGCGT CAGCGTTATC TGTATACCGA TGATGCGCAG CAGACCGAAG CGCATCTGGA AATTCGTGAA GATGGCACCG TGGGCGGTGC GGCGGATCAG AGCCCGGAAA GCCTGCTGCA GCTGAAAGCG CTGAAACCGG GCGTGATTCA GATTCTGGGC GTGAAAACCA GCCGTTTTCT GTGCCAGCGT CCGGATGGCG CGCTGTATGG CAGCCTGCAT | Exendin4 (1-39)-GGGGSGGG-FGF21(33-209) | Ex(1-39)-L8-FGF21 |

TABLE 1 -continued

Dual Function Protein and Nucleotides of the invention

| SEQ ID NO: | Variant NO: | Sequence | Long Name | Short Name |
|---|---|---|---|---|
| | | TTTGATCCGG AAGCGTGCAG CTTTCGTGAA CTGCTGCTGG AAGATGGCTA TAACGTGTAT CAGAGCGAAG CGCATGGCCT GCCGCTGCAT CTGCCGGGCA ACAAAAGCCC GCATCGTGAT CCGGCACCGC GTGGTCCGGC GCGTTTTCTG CCGCTGCCGG GTCTGCCGCC GGCACTGCCG GAACCGCCGG GTATTCTGGC CCCGCAGCCG CCGGATGTTG GTAGCAGCGA TCCGCTGTCT ATGGTGGGTC CGAGCCAGGG TCGTAGCCCG AGCTATGCGA GCTAA | | |
| 25 | V193 | HSEGTFTSDV SSYLEGQAAK EFIAWLVKGG SGGGGSGGGG SGGGGSADKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SREEMTKNQV SLTCLVKGFY PSDIAVEWES NGQPENNYKT TPPVLDSDGS FFLYSKLTVD KSRWQQGNVF SCSVMHEALH NHYTQKSLSL SPGKGGGGSG GGGSGGGGSD SSPLLQFGGQ VRQRYLYTDD ACQTEAHLEI REDGTVGGAA DQSPESLLQL KALKPGVIQI LGVKTSRFLC QKPDGALYGS LHFDPEACSF RELLLEDGYN VYQSEAHGLP LHLPCNRSPH RDPASRGPAR FLPLPGLPPA LPEPPGILAP QPPDVGSSDP LAMVGGSQAR SPSYAS | GLP-1(7-35; A8S)-S(GGGGS)₃A-Fc-(GGGGS)₃-FGF21(33-209; Q55C-R105K-G148C-K150R-P158S-S195A-P199G-G202A) | GLP-1(A8S)-L17-Fc-L15-FGF21(V103) |
| 26 | V194 | HSEGTFTSDV SSYLEGQAAK EFIAWLVKGG SGGGGSGGGG SGGGGSADKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SREEMTKNQV SLTCLVKGFY PSDIAVEWES NGQPENNYKT TPPVLDSDGS FFLYSKLTVD KSRWQQGNVF SCSVMHEALH NHYTQKSLSL SPGKGGGGSG GGGSGGGGSD SSPLLQFGGQ VRQRYLYTDD ACQTEAHLEI REDGTVGGAA DQSPESLLQL KALKPGVIQI LGVKTSRFLC QKPDGALYGS LHFDPEACSF RELLLEDGYN VYQSEAHGLP LHLPCNRSPH RDPASRGPAR FLPLPGLPPA LPEPPGILAP QPPDVGSSDP LAMVGPSQAR SPSYES | GLP-1(7-35; A8S)-S(GGGGS)₃A-Fc-(GGGGS)₃-FGF21(33-209; Q55C-R105K-G148C-K150R-P158S-S195A-G202A-A208E) | GLP-1(A8S)-L17-Fc-L15-FGF21(V194) |
| 27 | V195 | HSEGTFTSDV SSYLEGQAAK EFIAWLVKGG SGGGGSGGGG SGGGGSADKT HTCPPCPAPE AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SREEMTKNQV SLTCLVKGFY PSDIAVEWES NGQPENNYKT TPPVLDSDGS FFLYSKLTVD KSRWQQGNVF SCSVMHEALH NHYTQKSLSL SPGKGGGGSG GGGSGGGGSD SSPLLQFGGQ VRQRYLYTDD ACQTEAHLEI REDGTVGGAA DQSPESLLQL KALKPGVIQI LGVKTSRFLC QKPDGALYGS LHFDPEACSF RELLLEDGYN VYQSEAHGLP LHLPCNRSPH RDPASRGPAR FLPLPGLPPA LPEPPGILAP QPPDVGSSDP LAMVGPSQAR SPSYDS | GLP-1(7-35; A8S)-S(GGGGS)₃A-Fc-(GGGGS)₃-FGF21(33-209; Q55C-R105K-G148C-P158S-K150R-S195A-G202A-A208D) | GLP-1(A8S)-L17-Fc-L15-FGF21(V195) |
| 28 | V296 | HGEGTFTSDV SSYLEGQAAK EFIAWLVKGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEDGYN VYQSEAHGLP LHLPCNRSPH CDPAPQGPAR FLPLPGLPPA LPEPPGILAP QPPDVGSSDP LAMVGPSQGR SPSYAS | GLP-1(7-35; A8G)-GSGGGGSGGG-FGF21(33-209; Q56E-D74H-Q82E-R105K-K150R-R154C-40 kDa branched | GLP-1(A8G)-L10-FGF21(V76)-40KPEGb |

TABLE 1 -continued

Dual Function Protein and Nucleotides of the invention

| SEQ ID NO: | Variant NO: | Sequence | Long Name | Short Name |
|---|---|---|---|---|
| | | | PEG-R159Q-S195A) | |
| 29 | | CATGGTGAAG GCACTTTTAC TAGCGATGTT TCTAGCTACC TGGAAGGCCA GGCTGCGAAA GAATTCATCG CGTGGCTGGT TAAAGGCGGT TCTGGTGGTG GTGGTTCTGG CGGTGGCGAT AGCAGCCCGC TGCTGCAGTT TGGCGGCCAG GTGCGTCAGC GTTATCTGTA TACCGATGAT GCGCAGGAAA CCGAAGCGCA TCTGGAAATT CGTGAAGATG GCACCGTGGG CGGTGCGGCG CATCAGAGCC GGAAAGCCT GCTGGAACTG AAAGCGCTGA AACCGGGCGT GATTCAGATT CTGGGCGTGA AACCAGCCG TTTTCTGTGC CAGAAACCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACCG TAGCCCGCAT TGCGATCCGG CACCGCAGGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGGCGATGG TGGGTCCGAG CCAGGGTCGT AGCCCGAGCT ATGCGAGCTA A | GLP-1(7-35; A8G)-GSGGGGSGGG-FGF21(33-209; Q56E-D74H-Q82E-R105K-K150R-R154C-R159Q-S195A) | GLP-1(A8G)-L10-FGF21 (V76) |
| 34 | V294 | HSEGTFTSDV SSYLEGQAAK EFIAWLVKGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH UDPAPRGPAR FLPLPGLPPA LPEPPGILAP QPPDVGSSDP LSMVGPSQGR SPSYAS | GLP-1(7-35; A8S)-GSGGGGSGGG-FGF21(33-209; R154Pcl-40 kDa branched PEG) | GLP-1(A8S)-L10-FGF21-154Pcl-40KPEGb |
| 35 | | CATTCTGAAG GCACTTTTAC TAGCGATGTT TCTAGCTACC TGGAAGGCCA GGCTGCGAAA GAATTCATCG CGTGGCTGGT TAAAGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT TAGGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35; A8S)-GSGGGGSGGG-FGF21(33-209; R154TAG) | GLP-1(A8S)-L10-FGF21-154TAG |
| 38 | V298 | HGEGTFTSDL SKQMEEEAVR LFIEWLKNGG PSSGAPPPSG GGGSGGGDSS PLLQFGGQVR QRYLYTDDAQ QTEAHLEIRE DGTVGGAADQ SPESLLQLKA LKPGVIQILG VKTSRFLCQR PDGALYGSLH FDPEACSFRE LLLEDGYNVY QSEAHGLPLH LPGNKSPHUD PAPRGPARFL PLPGLPPALP EPPGILAPQP PDVGSSDPLS MVGPSQGRSP SYAS | Exendin4 (1-39)-GGGGSGGG-FGF21(33-209; R154TAG)-40 kDa branched PEG | Ex(1-39)-L8-FGF21 (154Pcl)-40KPEGb |
| 39 | | CATGGTGAGG GTACGTTTAC TTCTGATCTG TCTAAACAGA TGGAAGAAGA AGCTGTTCGC CTGTTCATTG AATGGCTGAA AAATGGTGGT CCGTCCTCCG GCGCTCCTCC GCCTTCTGGT GGTGGTGGTT CTGGCGGTGG CGACTCGAGC FGF21(33-209; | Exendin4 (1-39)-GGGGSGGG-FGF21(33-209; | Ex(1-39)-L8-FGF21 (154TAG) |

TABLE 1 -continued

Dual Function Protein and Nucleotides of the invention

| SEQ ID NO: | Variant NO: | Sequence | Long Name | Short Name |
|---|---|---|---|---|
| | | CCGCTGCTGC AGTTTGGCGG CCAGGTGCGT CAGCGTTATC TGTATACCGA TGATGCGCAG CAGACCGAAG CGCATCTGGA AATTCGTGAA GATGGCACCG TGGGCGGTGC GGCGGATCAG AGCCCGGAAA GCCTGCTGCA GCTGAAAGCG CTGAAACCGG GCGTGATTCA GATTCTGGGC GTGAAAACCA GCCGTTTTCT GTGCCAGCGT CCGGATGGCG CGCTGTATGG CAGCCTGCAT TTTGATCCGG AAGCGTGCAG CTTTCGTGAA CTGCTGCTGG AAGATGGCTA TAACGTGTAT CAGAGCGAAG CGCATGGCCT GCCGCTGCAT CTGCCGGGCA ACAAAAGCCC GCATTAGGAT CCGGCACCGC GTGGTCCGGC GCGTTTTCTG CCGCTGCCGG GTCTGCCGCC GGCACTGCCG GAACCGCCGG GTATTCTGGC CCCGCAGCCG CCGGATGTTG GTAGCAGCGA TCCGCTGTCT ATGGTGGGTC CGAGCCAGGG TCGTAGCCCG AGCTATGCGA GCTAA | R154TAG) | |
| 40 | V235 | HSEGTFTSDV SSYLEGQAAK EFIAWLVKGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH CDPAPRGPAR FLPLPGLPPA LPEPPGILAP QPPDVGSSDP LSMVGPSQGR SPSYAS | GLP-1(7-35; A8S)- GSGGGGSGGG- FGF21(33- 209; R154C- 40 kDa branched PEG) | GLP-1(A8S)- L8- FGF21 (154C)- 40KPEGb |
| 41 | | CATTCTGAAG GCACTTTTAC TAGCGATGTT TCTAGCTACC TGGAAGGCCA GGCTGCGAAA GAATTCATCG CGTGGCTGGT TAAAGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT TGCGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35; A8S)- GSGGGGSGGG- FGF21(33- 209; R154C) | GLP-1(A8S)- L8- FGF21(154C) |
| 42 | V239 | HAEGTFTSDV SSYLEGQAAK EFIAWLVKGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH CDPAPRGPAR FLPLPGLPPA LPEPPGILAP QPPDVGSSDP LSMVGPSQGR SPSYAS | GLP-1(7-35)- GSGGGGSGGG- FGF21(33- 209; R154C- 40 kDa branched PEG) | GLP-1- L8- FGF21 (154C)- 40KPEGb |
| 43 | | CATGCGGAAG GCACTTTTAC TAGCGATGTT TCTAGCTACC TGGAAGGCCA GGCTGCGAAA GAATTCATCG CGTGGCTGGT TAAAGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC | GLP-1(7- 35)- GSGGGGSGGG- FGF21(33- 209; R154C) | GLP-1- L8- FGF21 (154C) |

TABLE 1 -continued

Dual Function Protein and Nucleotides of the invention

| SEQ ID NO: | Variant NO: | Sequence | Long Name | Short Name |
|---|---|---|---|---|
| | | GTGTATCAGA GCGAAGCGCA TGGCCTGCCG CTGCATCTGC CGGGCAACAA AAGCCCGCAT TGCGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | | |
| 44 | V299 | HGEGTFTSDL SKQMEEEAVR LFIEWLKNGG PSSGAPPPSG GGGSGGGDSS PLLQFGGQVR QRYLYTDDAQ QTEAHLEIRE DGTVGGAADQ SPESLLQLKA LKPGVIQILG VKTSRFLCQR PDGALYGSLH FDPEACSFRE LLLEDGYNVY QSEAHGLPLH LPGNKSPHCD PAPRGPARFL PLPGLPPALP EPPGILAPQP PDVGSSDPLS MVGPSQGRSP SYAS | Exendin4 (1-39)- GGGGSGGG- FGF21(33- 209; R154C- 40 kDa branched PEG) | Ex(1- 39)-L8- FGF21 (154C)- 40KPEGb |
| 45 | | CATGGTGAGG GTACGTTTAC TTCTGATCTG TCTAAACAGA TGGAAGAAGA AGCTGTTCGC CTGTTCATTG AATGGCTGAA AAATGGTGGT CCGTCCTCCG GCGCTCCTCC GCCTTCTGGT GGTGGTGGTT CTGGCGGTGG CGACTCGAGC CCGCTGCTGC AGTTTGGCGG CCAGGTGCGT CAGCGTTATC TGTATACCGA TGATGCGCAG CAGACCGAAG CGCATCTGGA AATTCGTGAA GATGGCACCG TGGGCGGTGC GGCGGATCAG AGCCCGGAAA GCCTGCTGCA GCTGAAAGCG CTGAAACCGG GCGTGATTCA GATTCTGGGC GTGAAAACCA GCCGTTTTCT GTGCCAGCGT CCGGATGGCG CGCTGTATGG CAGCCTGCAT TTTGATCCGG AAGCGTGCAG CTTTCGTGAA CTGCTGCTGG AAGATGGCTA TAACGTGTAT CAGAGCGAAG CGCATGGCCT GCCGCTGCAT CTGCCGGGCA ACAAAAGCCC GCATTGCGAT CCGGCACCGC GTGGTCCGGC GCGTTTTCTG CCGCTGCCGG GTCTGCCGCC GGCACTGCCG GAACCGCCGG GTATTCTGGC CCCGCAGCCG CCGGATGTTG GTAGCAGCGA TCCGCTGTCT ATGGTGGGTC CGAGCCAGGG TCGTAGCCCG AGCTATGCGA GCTAA | Exendin4 (1-39)- GGGGSGGG- FGF21(33- 209; R154C) | Ex(1- 39)-L8- FGF21 (154C) |
| 46 | V271 | HAPGTFTSDV SSYLEGQAAK EFIAWLVKGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH CDPAPRGPAR FLPLPGLPPA LPEPPGILAP QPPDVGSSDP LSMVGPSQGR SPSYAS | GLP-1(7-35; E9P)- GSGGGGSGGG- FGF21(33- 209; R154C- 40 kDa branched PEG) | GLP- 1(E9P)- L10- FGF21 (154C)- 40KPEGb |
| 47 | | CATGCGCCGG GCACTTTTAC TAGCGATGTT TCTAGCTACC TGGAAGGCCA GGCTGCGAAA GAATTCATCG CGTGGCTGGT TAAAGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT TGCGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35; E9P)- GSGGGGSGGG- FGF21(33- 209; R154C) | GLP- 1(E9P)- L10- FGF21 (154C) |

TABLE 1 -continued

Dual Function Protein and Nucleotides of the invention

| SEQ ID NO: | Variant NO: | Sequence | Long Name | Short Name |
|---|---|---|---|---|
| 48 | V251 | GHAEGTFTSD VSSYLEGQAA KEFIAWLVKG GSGGGGSGGG DSSPLLQFGG QVRQRYLYTD DAQQTEAHLE IREDGTVGGA ADQSPESLLQ LKALKPGVIQ ILGVKTSRFL CQRPDGALYG SLHFDPEACS FRELLLEDGY NVYQSEAHGL PLHLPGNKSP HCDPAPRGPA RFLPLPGLPP ALPEPPGILA PQPPDVGSSD PLSMVGPSQG RSPSYAS | GLP-1(6-35; 6G)-GSGGGGSGGG-FGF21(33-209; R154C-40 kDa branched PEG) | G-GLP-1-L10-FGF21(154C)-40KPEGb |
| 49 | | GGTCATGCGG AAGGCACTTT TACTAGCGAT GTTTCTAGCT ACCTGGAAGG CCAGGCTGCG AAAGAATTCA TCGCGTGGCT GGTTAAAGGC GGTTCTGGTG GTGGTGGTTC TGGCGGTGGC GACTCGAGCC CGCTGCTGCA GTTTGGCGGC CAGGTGCGTC AGCGTTATCT GTATACCGAT GATGCGCAGC AGACCGAAGC GCATCTGGAA ATTCGTGAAG ATGGCACCGT GGGCGGTGCG GCGGATCAGA GCCCGGAAAG CCTGCTGCAG CTGAAAGCGC TGAAACCGGG CGTGATTCAG ATTCTGGGCG TGAAAACCAG CCGTTTTCTG TGCCAGCGTC CGGATGGCGC GCTGTATGGC AGCCTGCATT TTGATCCGGA AGCGTGCAGC TTTCGTGAAC TGCTGCTGGA AGATGGCTAT AACGTGTATC AGAGCGAAGC GCATGCCCTG CCGCTGCATC TGCCGGGCAA CAAAAGCCCG CATTGCGATC CGGCACCGCG TGGTCCGGCG CGTTTTCTGC CGCTGCCGGG TCTGCCGCCG GCACTGCCGG AACCGCCGGG TATTCTGGCC CCGCAGCCGC CGGATGTTGG TAGCAGCGAT CCGCTGTCTA TGGTGGGTCC GAGCCAGGGT CGTAGCCCGA GCTATGCGAG CTAA | GLP-1(6-35; 6G)-GSGGGGSGGG-FGF21(33-209) | G-GLP-1-L10-FGF21(154C) |
| 50 | V265 | HSEGTFTADA SSYLEGQAAK EFIAWLVKGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH CDPAPRGPAR FLPLPGLPPA LPEPPGILAP QPPDVGSSDP LSMVGPSQGR SPSYAS | GLP-1(7-35; A8S-S14A-V16A)-GSGGGGSGGG-FGF21(33-209; R154C-40 kDa branched PEG) | GLP-1(A8S; 14/16)-L10-FGF21(154C)-40KPEGb |
| 51 | | CATTCTGAAG GCACTTTTAC TGCTGATGCT TCTAGCTACC TGGAAGGCCA GGCTGCGAAA GAATTCATCG CGTGGCTGGT TAAAGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT TGCGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35; A8S-S14A-V16A)-GSGGGGSGGG-FGF21(33-209; R154C) | GLP-1(A8S; 14/16)-L10-FGF21(154C) |
| 52 | V270 | HSEGTFTSDA AAYLEGQAAK EFIAWLVKGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH CDPAPRGPAR FLPLPGLPPA LPEPPGILAP QPPDVGSSDP LSMVGPSQGR SPSYAS | GLP-1(7-35; A8S-V16A-S17A-S18A)-GSGGGGSGGG-FGF21(33-209; R154C-40 kDa branched PEG) | GLP-1(A8S; 16/17/18)-L10-FGF21(154C)-40KPEGb |

TABLE 1 -continued

Dual Function Protein and Nucleotides of the invention

| SEQ ID NO: | Variant NO: | Sequence | Long Name | Short Name |
|---|---|---|---|---|
| 53 | | CATTCTGAAG GCACTTTTAC TAGCGATGCT GCTGCTTACC TGGAAGGCCA GGCTGCGAAA GAATTCATCG CGTGGCTGGT TAAAGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT TGCGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35; A8S-V16A-S17A-S18A)-GSGGGGSGGG-FGF21(33-209; R154C) | GLP-1(A8S)-16/17/18)-L10-(1FGF21 54C) |
| 54 | V266 | HSEGTFTSDV SSYAEGAAAK EFIAWLVKGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH CDPAPRGPAR FLPLPGLPPA LPEPPGILAP QPPDVGSSDP LSMVGPSQGR SPSYAS | GLP-1(7-35; A8S-L20A-Q23A)-GSGGGGSGGG-FGF21(33-209; R154C-40 kDa branched PEG) | GLP-1(A8S; 20/23)-L10-FGF21(154C)-40KPEGb |
| 55 | | CATTCTGAAG GCACTTTTAC TAGCGATGTT TCTAGCTACG CTGAAGGCGC TGCTGCGAAA GAATTCATCG CGTGGCTGGT TAAAGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT TGCGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35; A8S-L20A-Q23A)-GSGGGGSGGG-FGF21(33-209; R154C) | GLP-1(A8S; 20/23)-L10-FGF21(154C) |
| 58 | V300 | HSEGTFTSDS SPLLQFGGQV RQRYLYTDDA QQTEAHLEIR EDGTVGGAAD QSPESLLQLK ALKPGVIQIL GVKTSRFLCQ RPDGALYGSL HFDPEACSFR ELLLEDGYNV YQSEAHGLPL HLPGNKSPHC DPAPRGPARF LPLPGLPPAL PEPPGILAPQ PPDVGSSDPL SMVGPSQGRS PSYAS | GLP-1(7-14; A8S)-FGF21(33-209; R154C-40 kDa branched PEG) | GLP-1(A8S; 7-14)-L0-FGF21(154C)-40KPEGb |
| 59 | | CATTCTGAAG GCACTTTTAC TAGCGATAGC AGCCCGCTGC TGCAGTTTGG CGGCCAGGTG CGTCAGCGTT ATCTGTATAC CGATGATGCG CAGCAGACCG AAGCGCATCT GGAAATTCGT GAAGATGGCA CCGTGGGCGG TGCGGCGGAT CAGAGCCCGG AAAGCCTGCT GCAGCTGAAA GCGCTGAAAC CGGGCGTGAT TCAGATTCTG GGCGTGAAAA CCAGCCGTTT TCTGTGCCAG CGTCCGGATG GCGCGCTGTA TGGCAGCCTG | GLP-1(7-14; A8S)-FGF21(33-209; R154C) | GLP-1(A8S; 7-14)-L0-FGF21(154C) |

TABLE 1 -continued

Dual Function Protein and Nucleotides of the invention

| SEQ ID NO: | Variant NO: | Sequence | Long Name | Short Name |
|---|---|---|---|---|
| | | CATTTTGATC CGGAAGCGTG CAGCTTTCGT GAACTGCTGC TGGAAGATGG CTATAACGTG TATCAGAGCG AAGCGCATGG CCTGCCGCTG CATCTGCCGG GCAACAAAAG CCCGCATTGC GATCCGGCAC CGCGTGGTCC GGCGCGTTTT CTGCCGCTGC CGGGTCTGCC GCCGGCACTG CCGGAACCGC CGGGTATTCT GGCCCCGCAG CCGCCGGATG TTGGTAGCAG CGATCCGCTG TCTATGGTGG GTCCGAGCCA GGGTCGTAGC CCGAGCTATG CGAGCTAA | | |
| 60 | V262 | HSEGTFTSDV SSGGGGSGGG DSSPLLQFGG QVRQRYLYTD DAQQTEAHLE IREDGTVGGA ADQSPESLLQ LKALKPGVIQ ILGVKTSRFL CQRPDGALYG SLHFDPEACS FRELLLEDGY NVYQSEAHGL PLHLPGNKSP HCDPAPRGPA RFLPLPGLPP ALPEPPGILA PQPPPDVGSSD PLSMVGPSQG RSPSYAS | GLP-1(7-18; A8S)- GGGGSGGG- FGF21(33- 209; R154C- 40 kDa branched PEG) | GLP- 1(A8S; 7-18)- L8- FGF21 (154C)- 40KPEGb |
| 61 | | CATTCTGAAG GCACTTTTAC TAGCGATGTT TCTTCTGGTG GTGGTGGTTC TGGCGGTGGC GACTCGAGCC CGCTGCTGCA GTTTGGCGGC CAGGTGCGTC AGCGTTATCT GTATACCGAT GATGCGCAGC AGACCGAAGC GCATCTGGAA ATTCGTGAAG ATGGCACCGT GGGCGGTGCG GCGGATCAGA GCCCGGAAAG CCTGCTGCAG CTGAAAGCGC TGAAACCGGG CGTGATTCAG ATTCTGGGCG TGAAAACCAG CCGTTTTCTG TGCCAGCGTC CGGATGGCGC GCTGTATGGC AGCCTGCATT TTGATCCGGA AGCGTGCAGC TTTCGTGAAC TGCTGCTGGA AGATGGCTAT AACGTGTATC AGAGCGAAGC GCATGGCCTG CCGCTGCATC TGCCGGGCAA CAAAAGCCCG CATTGCGATC CGGCACCGCG TGGTCCGGCG CGTTTTCTGC CGCTGCCGGG TCTGCCGCCG GCACTGCCGG AACCGCCGGG TATTCTGGCC CCGCAGCCGC CGGATGTTGG TAGCAGCGAT CCGCTGTCTA TGGTGGGTCC GAGCCAGGGT CGTAGCCCGA GCTATGCGAG CTAA | GLP-1(7-18; A8S)- GGGGSGGG- FGF21(33- 209; R154C) | GLP- 1(A8S; 7-18)- L8- FGF21 (154C) |
| 62 | V261 | HSEGTFTSDV SSYLESGGGG SGGGDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHCDPAP RGPARFLPLP GLPPALPEPP GILAPQPPPDV GSSDPLSMVG PSQGRSPSYA S | GLP-1(7-21; A8S)- SGGGGSGGG- FGF21(33- 209; R154C- 40 kDa branched PEG) | GLP- 1(A8S; 7-21)- L9- FGF21 (154C)- 40KPEGb |
| 63 | | CATTCTGAAG GCACTTTTAC TAGCGATGTT TCTAGCTACC TGGAATCGG TGGTGGTGGT TCTGGCGGTG CGACTCGAG CCCGCTGCTG CAGTTTGGCG GCCAGGTGCG TCAGCGTTAT CTGTATACCG ATGATGCGCA GCAGACCGAA GCGCATCTGG AAATTCGTGA AGATGGCACC GTGGGCGGTG CGGCGGATCA GAGCCCGGAA AGCCTGCTGC AGCTGAAAGC GCTGAAACCG GGCGTGATTC AGATTCTGGG CGTGAAAACC AGCCGTTTTC TGTGCCAGCG TCCGGATGGC GCGCTGTATG GCAGCCTGCA TTTTGATCCG GAAGCGTGCA GCTTTCGTGA ACTGCTGCTG GAAGATGGCT ATAACGTGTA TCAGAGCGAA GCGCATGGCC TGCCGCTGCA TCTGCCGGGC AACAAAAGCC CGCATTGCGA TCCGGCACCG CGTGGTCCGG CGCGTTTTCT GCCGCTGCCG GGTCTGCCGC CGGCACTGCC GGAACCGCCG GGTATTCTGG CCCCGCAGCC GCCGGATGTT GGTAGCAGCG ATCCGCTGTC TATGGTGGGT CCGAGCCAGG GTCGTAGCCC GAGCTATGCG AGCTAA | GLP-1(7-21; A8S)- SGGGGSGGG- FGF21(33- 209; R154C) | GLP- 1(A8S; 7-21)- L9- FGF21 (154C) |
| 66 | V260 | HSEGTFTSDV SSYLEGQAAK EFISGGGGSG GGDSSPLLQF GGQVRQRYLY TDDAQQTEAH | GLP-1(7-29; A8S)- | GLP- 1(A8S; |

TABLE 1 -continued

Dual Function Protein and Nucleotides of the invention

| SEQ ID NO: | Variant NO: | Sequence | Long Name | Short Name |
|---|---|---|---|---|
| | | LEIREDGTVG GAADQSPESL LQLKALKPGV IQILGVKTSR FLCQRPDGAL YGSLHFDPEA CSFRELLLED GYNVYQSEAH GLPLHLPGNK SPHCDPAPRG PARFLPLPGL PPALPEPPGI LAPQPPDVGS SDPLSMVGPS QGRSPSYAS | SGGGGSGGG- FGF21(33- 209; R154C- 40 kDa branched PEG) | 7-29)- L9- FGF21 (154C)- 40KPEGb |
| 67 | | CATTCTGAAG GCACTTTTAC TAGCGATGTT TCTAGCTACC TGGAAGGCCA GGCTGCGAAA GAATTCATCT CTGGTGGTGG TGGTTCTGGC GGTGGCGACT CGAGCCCGCT GCTGCAGTTT GGCGGCCAGG TGCGTCAGCG TTATCTGTAT ACCGATGATG CGCAGCAGAC CGAAGCGCAT CTGGAAATTC GTGAAGATGG CACCGTGGGC GGTGCGGCGG ATCAGAGCCC GGAAAGCCTG CTGCAGCTGA AAGCGCTGAA ACCGGGCGTG ATTCAGATTC TGGGCGTGAA AACCAGCCGT TTTCTGTGCC AGCGTCCGGA TGGCGCGCTG TATGGCAGCC TGCATTTTGA TCCGGAAGCG TGCAGCTTTC GTGAACTGCT GCTGGAAGAT GGCTATAACG TGTATCAGAG CGAAGCGCAT GGCCTGCCGC TGCATCTGCC GGGCAACAAA AGCCCGCATT GCGATCCGGC ACCGCGTGGT CCGGCGCGTT TTCTGCCGCT GCCGGGTCTG CCGCCGGCAC TGCCGGAACC GCCGGGTATT CTGGCCCCGC AGCCGCCGGA TGTTGGTAGC AGCGATCCGC TGTCTATGGT GGGTCCGAGC CAGGGTCGTA GCCCGAGCTA TGCGAGCTAA | GLP-1(7-29; A8S)- SGGGGSGGG- FGF21(33- 209) | GLP- 1(A8S; 7-29)- L9- FGF21 (154C) |
| 68 | V259 | HSEGTFTSDV SSYLEGQAAK EFIAWLSGGG GSGGGDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHCDPA PRGPARFLPL PGLPPALPEP PGILAPQPPD VGSSDPLSMV GPSQGRSPSY AS | GLP-1(7-32; A8S)- SGGGGSGGG- FGF21(33- 209; R154C- 40 kDa branched PEG) | GLP- 1(A8S; 7-32)- L9- FGF21 (154C)- 40KPEGb |
| 69 | | CATTCTGAAG GCACTTTTAC TAGCGATGTT TCTAGCTACC TGGAAGGCCA GGCTGCGAAA GAATTCATCG CGTGGCTGTC TGGTGGTGGT GGTTCTGGCG GTGGCGACTC GAGCCCGCTG CTGCAGTTTG GCGGCCAGGT GCGTCAGCGT TATCTGTATA CCGATGATGC GCAGCAGACC GAAGCGCATC TGGAAATTCG TGAAGATGGC ACCGTGGGCG GTGCGGCGGA TCAGAGCCCG GAAAGCCTGC TGCAGCTGAA AGCGCTGAAA CCGGGCGTGA TTCAGATTCT GGGCGTGAAA ACCAGCCGTT TTCTGTGCCA GCGTCCGGAT GGCGCGCTGT ATGGCAGCCT GCATTTTGAT CCGGAAGCGT GCAGCTTTCG TGAACTGCTG CTGGAAGATG GCTATAACGT GTATCAGAGC GAAGCGCATG GCCTGCCGCT GCATCTGCCG GGCAACAAAA GCCCGCATTG CGATCCGGCA CCGCGTGGTC CGGCGCGTTT TCTGCCGCTG CCGGGTCTGC CGCCGGCACT GCCGGAACCG CCGGGTATTC TGGCCCCGCA GCCGCCGGAT GTTGGTAGCA GCGATCCGCT GTCTATGGTG GGTCCGAGCC AGGGTCGTAG CCCGAGCTAT GCGAGCTAA | GLP-1(7-32; A8S)- SGGGGSGGG- FGF21(33- 209; R154C) | GLP- 1(A8S; 7-32)- L9- FGF21 (154C) |
| 70 | V263 | HSEGTFTSDV CSYLEGQAAK EFIAWLVKGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH RDPAPRGPAR FLPLPGLPPA LPEPPGILAP QPPDVGSSDP LSMVGPSQGR SPSYAS | GLP-1(7-35; A8S-S17C- 40 kDa branched PEG)- GSGGGGSGGG- FGF21(33-209) | GLP- 1(A8S- S17C)- 40KPEGb- L10- FGF21 |
| 71 | | CATTCTGAAG GCACTTTTAC TAGCGATGTT TGTAGCTACC TGGAAGGCCA GGCTGCGAAA GAATTCATCG CGTGGCTGGT TAAAGGCGGT TCTGGTGGTG GTGGTTCTGG CGGTGGCGAC | GLP-1(7-35; A8S-S17C)- GSGGGGSGGG- FGF21(33- | GLP- 1(A8S- S17C)- L10- |

TABLE 1 -continued

Dual Function Protein and Nucleotides of the invention

| SEQ ID NO: | Variant NO: | Sequence | Long Name | Short Name |
|---|---|---|---|---|
| | | TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT CGTGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | 209) | FGF21 |
| 72 | V269 | HSEGTFTSDV SSYLEGCAAK EFIAWLVKGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH RDPAPRGPAR FLPLPGLPPA LPEPPGILAP QPPDVGSSDP LSMVGPSQGR SPSYAS | GLP-1(7-35; A8S-Q23C-40 kDa branched PEG)- GSGGGGSGGG- FGF21(33- 209) | GLP- 1(A8S- Q23C)- 40KPEGb- L10- FGF21 |
| 73 | | CATTCTGAAG GCACTTTTAC TAGCGATGTT TCTAGCTACC TGGAAGGCTG TGCTGCGAAA GAATTCATCG CGTGGCTGGT TAAAGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT CGTGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35; A8S-Q23C)- GSGGGGSGGG- FGF21(33- 209) | GLP- 1(A8S- Q23C)- L10- FGF21 |
| 74 | V243 | HSEGTFTSDV SSYLEGQAAC EFIAWLVKGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH RDPAPRGPAR FLPLPGLPPA LPEPPGILAP QPPDVGSSDP LSMVGPSQGR SPSYAS | GLP-1(7-35; A8S-K26C-40 kDa branched PEG)- GSGGGGSGGG- FGF21(33- 209) | GLP- 1(A8S- K26C)- L10- FGF21- 40KPEGb |
| 75 | | CATTCTGAAG GCACTTTTAC TAGCGATGTT TCTAGCTACC TGGAAGGCCA GGCTGCGTGT GAATTCATCG CGTGGCTGGT TAAAGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC | GLP-1(7-35; A8S-K26C)- GSGGGGSGGG- FGF21(33- 209) | GLP- 1(A8S- K26C)- L10- FGF21 |

TABLE 1 -continued

Dual Function Protein and Nucleotides of the invention

| SEQ ID NO: | Variant NO: | Sequence | Long Name | Short Name |
|---|---|---|---|---|
| | | GTGTATCAGA GCGAAGCGCA TGGCCTGCCG CTGCATCTGC CGGGCAACAA AAGCCCGCAT CGTGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | | |
| 76 | V264 | HSEGTFTSDV SSYLEGQAAK CFIAWLVKGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH RDPAPRGPAR FLPLPGLPPA LPEPPGILAP QPPDVGSSDP LSMVGPSQGR SPSYAS | GLP-1(7-35; A8S-E27C-40 kDa branched PEG)-GSGGGGSGGG-FGF21(33-209) | GLP-1(A8S-E27C)-40KPEGb-L10-FGF21 |
| 77 | | CATTCTGAAG GCACTTTTAC TAGCGATGTT TCTAGCTACC TGGAAGGCCA GGCTGCGAAA TGTTTCATCG CGTGGCTGGT TAAAGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT CGTGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35; A8S-E27C)-GSGGGGSGGG-FGF21(33-209) | GLP-1(A8S-E27C)-L10-FGF21 |
| 78 | V244 | HSEGTFTSDV SSYLEGQAAK EFIAWLVCGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH RDPAPRGPAR FLPLPGLPPA LPEPPGILAP QPPDVGSSDP LSMVGPSQGR SPSYAS | GLP-1(7-35; A8S-K34C-40 kDa branched PEG)-GSGGGGSGGG-FGF21(33-209) | GLP-1(A8S-K34C)-L10-FGF21-40KPEGb |
| 79 | | CATTCTGAAG GCACTTTTAC TAGCGATGTT TCTAGCTACC TGGAAGGCCA GGCTGCGAAA GAATTCATCG CGTGGCTGGT TTGTGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT CGTGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35; A8S-K34C)-GSGGGGSGGG-FGF21(33-209) | GLP-1(A8S-K34C)-L10-FGF21 |

TABLE 1 -continued

Dual Function Protein and Nucleotides of the invention

| SEQ ID NO: | Variant NO: | Sequence | Long Name | Short Name |
|---|---|---|---|---|
| 80 | V250 | HSEGTFTSDV SSYLEGQAAK EFIAWLVKGG SGGGGCGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH RDPAPRGPAR FLPLPGLPPA LPEPPGILAP QPPDVGSSDP LSMVGPSQGR SPSYAS | GLP-1(7-35; A8S)- GSGGGGC(40 kDa branched PEG)GGG- FGF21(33-209) | GLP-1(A8S)-L10-C-FGF2140 KPEGb |
| 81 | | CATTCTGAAG GCACTTTTAC TAGCGATGTT TCTAGCTACC TGGAAGGCCA GGCTGCGAAA GAATTCATCG CGTGGCTGGT TAAAGGCGGT TCTGGTGGTG GTGGTTGTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT CGTGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35; A8S)- GSGGGGCGGG- FGF21(33-209) | GLP-1(A8S)-L10-C-FGF21 |
| 82 | V240 | HAEGTFTSDV SSYLEGQAAC EFIAWLVKGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH RDPAPRGPAR FLPLPGLPPA LPEPPGILAP QPPDVGSSDP LSMVGPSQGR SPSYAS | GLP-1(7-35; K26C-40 kDa branched PEG)- GSGGGGSGGG- FGF21(33-209) | GLP-1(K26C)-L10-FGF21-40KPEGb |
| 83 | | CATGCGGAAG GCACTTTTAC TAGCGATGTT TCTAGCTACC TGGAAGGCCA GGCTGCGTGT GAATTCATCG CGTGGCTGGT TAAAGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT CGTGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35; K26C)- GSGGGGSGGG- FGF21(33-209) | GLP-1(K26C)-L10-FGF21 |
| 84 | V241 | HAEGTFTSDV SSYLEGQAAK EFIAWLVCGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH RDPAPRGPAR FLPLPGLPPA LPEPPGILAP QPPDVGSSDP LSMVGPSQGR SPSYAS | GLP-1(7-35; K34C-40 kDa branched PEG)- GSGGGGSGGG- FGF21(33-209) | GLP-1-(K34C)-L10-5G521-40KPEGb |

TABLE 1 -continued

Dual Function Protein and Nucleotides of the invention

| SEQ ID NO: | Variant NO: | Sequence | Long Name | Short Name |
|---|---|---|---|---|
| 85 | | CATGCGGAAG GCACTTTTAC TAGCGATGTT TCTAGCTACC TGGAAGGCCA GGCTGCGAAA GAATTCATCG CGTGGCTGGT TTGTGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT CGTGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35; K34C)-GSGGGGSGGG-FGF21(33-209) | GLP-1(K34C)-L10-FGF21 |
| 86 | V242 | HAEGTFTSDV SSYLEGQAAK EFIAWLVKGG SGGGGCGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH RDPAPRGPAR FLPLPGLPPA LPEPPGILAP QPPDVGSSDP LSMVGPSQGR SPSYAS | GLP-1(7-35)-GSGGGGC(40 kDa branched PEG)GGG-FGF21(33-209) | GLP-1-L10-C-FGF21-40KPEGb |
| 87 | | CATGCGGAAG GCACTTTTAC TAGCGATGTT TCTAGCTACC TGGAAGGCCA GGCTGCGAAA GAATTCATCG CGTGGCTGGT TAAAGGCGGT TCTGGTGGTG GTGGTTGTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT CGTGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35)-GSGGGGCGGG-FGF21(33-209) | GLP-1-L10-C-FGF21 |
| 88 | V267 | HGEGTFTSDL SKQMEEEAVR LFIEWLKNGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH CDPAPRGPAR FLPLPGLPPA LPEPPGILAP QPPDVGSSDP LSMVGPSQGR SPSYAS | Exendin4(1-30)-SGGGGSGGG-FGF21(33-209; R154C-40 kDa branched PEG) | Ex(1-30)-L9-FGF21(154C)-40KPEGb |
| 89 | | CATGGTGAGG GTACGTTTAC TTCTGATCTG TCTAAACAGA TGGAAGAAGA AGCTGTTCGC CTGTTCATTG AATGGCTGAA AAATGGTGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT | Exendin4(1-30)-SGGGGSGGG-FGF21(33-209; R154C) | Ex(1-30)-L9-FGF21(154C) |

TABLE 1 -continued

Dual Function Protein and Nucleotides of the invention

| SEQ ID NO: | Variant NO: | Sequence | Long Name | Short Name |
|---|---|---|---|---|
| | | CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AGCCCGCAT TGCGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | | |
| 90 | V268 | HGEGTFTSDL SKQMEGEAVR LFIEWLKNGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH CDPAPRGPAR FLPLPGLPPA LPEPPGILAP QPPDVGSSDP LSMVGPSQGR SPSYAS | Exendin4(1-30; E16G-E17Q)-SGGGGSGGG-FGF21(33-209; R154C-40 kDa branched PEG) | Ex(1-30; GQ)-L9-FGF21(154C)-40KPEGb |
| 91 | | CATGGTGAGG GTACGTTTAC TTCTGATCTG TCTAAACAGA TGGAAGGGCA AGCTGTTCGC CTGTTCATTG AATGGCTGAA AAATGGTGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AGCCCGCAT TGCGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | Exendin4(1-30; E16G-E17Q)-SGGGGSGGG-FGF21(33-209; R154C) | Ex(1-30; GQ)-L9-FGF21(154C) |
| 92 | V301 | HSEGTFTSDV SSYLEGQAAK EFIAWLVCGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH UDPAPRGPAR FLPLPGLPPA LPEPPGILAP QPPDVGSSDP LSMVGPSQGR SPSYAS | GLP-1(7-35; A8S-K34C)-GSGGGGSGGG-FGF21(33-209; R154Pcl) | GLP-1(A8S-K34C)-FGF21(154Pcl)- |
| 93 | | CATTCTGAAG GCACTTTTAC TAGCGATGTT TCTAGCTACC TGGAAGGCCA GGCTGCGAAA GAATTCATCG CGTGGCTGGT TTGTGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AGCCCGCAT TAGGATCCGG CACCGCGTGG TCCGGCGCGT TTTCTGCCGC TGCCGGGTCT GCCGCCGGCA CTGCCGGAAC CGCCGGGTAT TCTGGCCCCG | GLP-1(7-35; A8S-K34C)-GSGGGGSGGG-FGF21(33-209; R154TAG) | GLP-1(A8S-K34C)-L10-FGF21(154TAG) |

TABLE 1 -continued

Dual Function Protein and Nucleotides of the invention

| SEQ ID NO: | Variant NO: | Sequence | Long Name | Short Name |
|---|---|---|---|---|
| | | CAGCCGCCGG ATGTTGGTAG CAGCGATCCG CTGTCTATGG TGGGTCCGAG CCAGGGTCGT AGCCCGAGCT ATGCGAGCTA A | | |
| 94 | V302 | HAEGTFTSDV SSYLEGQAAK EFIAWLVCGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH UDPAPRGPAR FLPLPGLPPA LPEPPGILAP QPPDVGSSDP LSMVGPSQGR SPSYAS | GLP-1(7-35; K34C)- GSGGGGSGGG- FGF21(33- 209; R154Pcl) | GLP-1(K34C)- L10- FGF21 (154Pcl) |
| 95 | | CATGCGGAAG GCACTTTTAC TAGCGATGTT TCTAGCTACC TGGAAGGCCA GGCTGCGAAA GAATTCATCG CGTGGCTGGT TTGTGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT TAGGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35; K34C)- GSGGGGSGGG- FGF21(33- 209; R154TAG) | GLP-1(K34C)- L10- FGF21 (154TAG) |
| 96 | V303 | HSEGTFTSDV SSYLEGQAAK EFIAWLVUGG SGGGGSGGGD SSPLLQFGGQ VRQRYLYTDD AQQTEAHLEI REDGTVGGAA DQSPESLLQL KALKPGVIQI LGVKTSRFLC QRPDGALYGS LHFDPEACSF RELLLEDGYN VYQSEAHGLP LHLPGNKSPH CDPAPRGPAR FLPLPGLPPA LPEPPGILAP QPPDVGSSDP LSMVGPSQGR SPSYAS | GLP-1(7-35; A8S- K34Pcl)- GSGGGGSGGG- FGF21(33- 209; R154C) | GLP-1(A8S- K34Pcl)- L10-FGF21 (154C) |
| 97 | | CATTCTGAAG GCACTTTTAC TAGCGATGTT TCTAGCTACC TGGAAGGCCA GGCTGCGAAA GAATTCATCG CGTGGCTGGT TTAGGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGCAGA CCGAAGCGCA TCTGGAAATT CGTGAAGATG GCACCGTGGG CGGTGCGGCG GATCAGAGCC CGGAAAGCCT GCTGCAGCTG AAAGCGCTGA AACCGGGCGT GATTCAGATT CTGGGCGTGA AAACCAGCCG TTTTCTGTGC CAGCGTCCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACAA AAGCCCGCAT TGCGATCCGG CACCGCGTGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGTCTATGG TGGGTCCGAG CCAGGGTCGT AGCCCGAGCT ATGCGAGCTA A | GLP-1(7-35; A8S- K34TAG)- GSGGGGSGGG- FGF21(33- 209; R154C) | GLP-1(A8S- K34TAG)- L10-FGF21 (154C) |
| 98 | V281 | HSEGTFTSDV SSYLEGQAAK EFIAWLVKGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEDGYN VYQSEAHGLP LHLPGNRSPH RDPAPQGPAR FLPLPGLPPA | GLP-1(7- 35; A8S)- GSGGGGSGGG- FGF21(33- 209; Q56E- D74H-Q82E- | GLP-1 (A8S)- L10- FGF21 (V76- 154R) |

TABLE 1 -continued

Dual Function Protein and Nucleotides of the invention

| SEQ ID NO: | Variant NO: | Sequence | Long Name | Short Name |
|---|---|---|---|---|
| | | LPEPPGILAP QPPDVGSSDP LAMVGPSQGR SPSYAS | R105K-K150R-R159Q-S195A) | |
| 99 | | CATTCTGAAG GCACTTTTAC TAGCGATGTT TCTAGCTACC TGGAAGGCCA GGCTGCGAAA GAATTCATCG CGTGGCTGGT TAAAGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGGAAA CCGAAGCGCA TCTGGAAATT CGTGAAGATG GCACCGTGGG CGGTGCGGCG CATCAGAGCC CGGAAAGCCT GCTGGAACTG AAAGCGCTGA AACCGGGCGT GATTCAGATT CTGGGCGTGA AAACCAGCCG TTTTCTGTGC CAGAAACCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACCG TAGCCCGCAT CGTGATCCGG CACCGCAGGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGGCGATGG TGGGTCCGAG CCAGGGTCGT AGCCCGAGCT ATGCGAGCTA A | GLP-1(7-35; A8S)-GSGGGGSGGG-FGF21(33-209; Q56E-D74H-Q82E-R105K-K150R-R159Q-S195A) | GLP-1(A8S)-L10-FGF21(V76-154R) |
| 100 | V304 | HSEGTFTSDV SSYLEGQAAK EFIAWLVKGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEEGYN VYQSEAHGLP LHLPGNRSPH RDPAPQGPAR FLPLPGLPPA LPEPPGILAP QPPDVGSSDP LAMVGPSQGR SPSYAS | GLP-1(7-35; A8S)-GSGGGGSGGG-FGF21(33-209; Q56E-D74H-Q82E-R105K-D130E-K150R-R159Q-S195A) | GLP-1(A8S)-L10-FGF21(V76-154R-130E) |
| 101 | | CATTCTGAAG GCACTTTTAC TAGCGATGTT TCTAGCTACC TGGAAGGCCA GGCTGCGAAA GAATTCATCG CGTGGCTGGT TAAAGGCGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGGAAA CCGAAGCGCA TCTGGAAATT CGTGAAGATG GCACCGTGGG CGGTGCGGCG CATCAGAGCC CGGAAAGCCT GCTGGAACTG AAAGCGCTGA AACCGGGCGT GATTCAGATT CTGGGCGTGA AAACCAGCCG TTTTCTGTGC CAGAAACCGG ATGGCGCGCT GTATGGCAGC CTGCATTTTG ATCCGGAAGC GTGCAGCTTT CGTGAACTGC TGCTGGAAGA AGGCTATAAC GTGTATCAGA GCGAAGCGCA TGGCCTGCCG CTGCATCTGC CGGGCAACCG TAGCCCGCAT CGTGATCCGG CACCGCAGGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGGCGATGG TGGGTCCGAG CCAGGGTCGT AGCCCGAGCT ATGCGAGCTA A | GLP-1(7-35; A8S)-GSGGGGSGGG-FGF21(33-209; Q56E-D74H-Q82E-R105K-D130E-K150R-R159Q-S195A) | GLP-1(A8S)-L10-FGF21(V76-154R-130E) |
| 102 | V273 | HSEGTFTSDV SSYLEGQAAK EFIAWLVCGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEEGYN VYQSEAHGLP LHLPGNRSPH RDPAPQGPAR FLPLPGLPPA LPEPPGILAP QPPDVGSSDP LAMVGPSQGR SPSYAS | GLP-1(7-35; A8S-K34C-40 kDa branched PEG)-GSGGGGSGGG-FGF21(33-209; Q56E-D74H-Q82E-R105K-D130E- | GLP-1(A8S-K34C)-L10-FGF21(V76-154R)-40KPEGb |

TABLE 1 -continued

Dual Function Protein and Nucleotides of the invention

| SEQ ID NO: | Variant NO: | Sequence | Long Name | Short Name |
|---|---|---|---|---|
| | | | K150R-R159Q-S195A) | |
| 103 | | CATTCTGAAG GCACTTTTAC TAGCGATGTT TCTAGCTACC TGGAAGGCCA GGCTGCGAAA GAATTCATCG CGTGGCTGGT TTGTGGCGGT TCTGGTGGTG GTGGTTCTGG CGGTGGCGAC TCGAGCCCGC TGCTGCAGTT GGCGGCCAG GTGCGTCAGC GTTATCTGTA TACCGATGAT GCGCAGGAAA CCGAAGCGCA TCTGGAAATT CGTGAAGATG GCACCGTGGG CGGTGCGGCG CATCAGAGCC CGGAAAGCCT GCTGGAACTG AAAGCGCTGA AACCGGGCGT GATTCAGATT CTGGGCGTGA AAACCAGCCG TTTTCTGTGC CAGAAACCGG ATGGCGCGCT GTATGGCAGC CTGCATTTTG ATCCGGAAGC GTGCAGCTTT CGTGAACTGC TGCTGGAAGA AGGCTATAAC GTGTATCAGA GCGAAGCGCA TGGCCTGCCG CTGCATCTGC CGGGCAACCG TAGCCCGCAT CGTGATCCGG CACCGCAGGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGGCGATGG TGGGTCCGAG CCAGGGTCGT AGCCCGAGCT ATGCGAGCTA A | GLP-1(7-35; A8S-K34C)-GSGGGGSGGG-FGF21(33-209; Q56E-D74H-Q82E-R105K-D130E-K150R-R159Q-S195A) | GLP-1(A8S-K34C)-L10-FGF21(V76-154R) |
| 104 | V305 | HSEGTFTSDV SSYLEGQAAK EFIAWLVCGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEDGYN VYQSEAHGLP LHLPGNRSPH RDPAPQGPAR FLPLPGLPPA LPEPPGILAP QPPDVGSSDP LAMVGPSQAR SPSYAS | GLP-1(7-35; A8S-K34C-40 kDa branched PEG)-GSGGGGSGGG-FGF21(33-209; Q56E-D74H-Q82E-R105K-K150R-R159Q-S195A-G202A) | GLP-1(A8S-K34C)-L10-FGF21(V76-154R-202A)-40KPEGb |
| 105 | | CATTCTGAAG GCACTTTTAC TAGCGATGTT TCTAGCTACC TGGAAGGCCA GGCTGCGAAA GAATTCATCG CGTGGCTGGT TTGTGGCGGT TCTGGTGGTG GTGGTTCTGG CGGTGGCGAC TCGAGCCCGC TGCTGCAGTT GGCGGCCAG GTGCGTCAGC GTTATCTGTA TACCGATGAT GCGCAGGAAA CCGAAGCGCA TCTGGAAATT CGTGAAGATG GCACCGTGGG CGGTGCGGCG CATCAGAGCC CGGAAAGCCT GCTGGAACTG AAAGCGCTGA AACCGGGCGT GATTCAGATT CTGGGCGTGA AAACCAGCCG TTTTCTGTGC CAGAAACCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACCG TAGCCCGCAT CGTGATCCGG CACCGCAGGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGGCGATGG TGGGTCCGAG CCAGGGCGCGT AGCCCGAGCT ATGCGAGCTA A | GLP-1(7-35; A8S-K34C)-GSGGGGSGGG-FGF21(33-209; Q56E-D74H-Q82E-R105K-K150R-R159Q-S195A-G202A) | GLP-1(A8S-K34C)-L10-FGF21(V76-154R-202A) |
| 108 | V306 | HGEGTFTSDL SKQMEEEAVR LFIEWLKNGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLEEGYN VYQSEAHGLP LHLPGNRSPH RDPAPQGPAR FLPLPGLPPA LPEPPGILAP QPPDVGSSDP LAMVGPSQGR SPSYAS | Exendin4(1-30)-SGGGGSGGGG-FGF21(33-209; Q56E-D74H-Q82E-R105K-D130E-K150R- | Ex(1-30)-L9-FGF21(V76-154R) |

TABLE 1 -continued

Dual Function Protein and Nucleotides of the invention

| SEQ ID NO: | Variant NO: | Sequence | Long Name | Short Name |
|---|---|---|---|---|
| | | | R159Q-S195A) | |
| 109 | | CATGGTGAGG GTACGTTTAC TTCTGATCTG TCTAAACAGA TGGAAGAAGA AGCTGTTCGC CTGTTCATTG AATGGCTGAA AAATGGTGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGGAAA CCGAAGCGCA TCTGGAAATT CGTGAAGATG GCACCGTGGG CGGTGCGGCG CATCAGAGCC CGGAAAGCCT GCTGGAACTG AAAGCGCTGA AACCGGGCGT GATTCAGATT CTGGGCGTGA AAACCAGCCG TTTTCTGTGC CAGAAACCGG ATGGCGCGCT GTATGGCAGC CTGCATTTTG ATCCGGAAGC GTGCAGCTTT CGTGAACTGC TGCTGGAAGA AGGCTATAAC GTGTATCAGA GCGAAGCGCA TGGCCTGCCG CTGCATCTGC CGGGCAACCG TAGCCCGCAT CGTGATCCGG CACCGCAGGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGGCGATGG TGGGTCCGAG CCAGGGTCGT AGCCCGAGCT ATGCGAGCTA A | Exendin4(1-30)-SGGGGSGGG-FGF21(33-209; Q56E-D74H-Q82E-R105K-D130E-K150R-R159Q-S195A) | Ex(1-30)-L9-FGF21 (V76-154R) |
| 110 | V274 | HGEGTFTSDL SKQMEEEAVR LFIEWLCNGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEEGYN VYQSEAHGLP LHLPGNRSPH RDPAPQGPAR FLPLPGLPPA LPEPPGILAP QPPDVGSSDP LAMVGPSQGR SPSYAS | Exendin4(1-30; K27C-40 kDa branched PEG)-SGGGGSGGG-FGF21(33-209; Q56E-D74H-Q82E-R105K-D130E-K150R-R159Q-S195A) | Ex(1-30; K27C)-L9-FGF21 (V76-154R-130E)-40KPEGb |
| 111 | | CATGGTGAGG GTACGTTTAC TTCTGATCTG TCTAAACAGA TGGAAGAAGA AGCTGTTCGC CTGTTCATTG AATGGCTGTG TAATGGTGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGGAAA CCGAAGCGCA TCTGGAAATT CGTGAAGATG GCACCGTGGG CGGTGCGGCG CATCAGAGCC CGGAAAGCCT GCTGGAACTG AAAGCGCTGA AACCGGGCGT GATTCAGATT CTGGGCGTGA AAACCAGCCG TTTTCTGTGC CAGAAACCGG ATGGCGCGCT GTATGGCAGC CTGCATTTTG ATCCGGAAGC GTGCAGCTTT CGTGAACTGC TGCTGGAAGA AGGCTATAAC GTGTATCAGA GCGAAGCGCA TGGCCTGCCG CTGCATCTGC CGGGCAACCG TAGCCCGCAT CGTGATCCGG CACCGCAGGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGGCGATGG TGGGTCCGAG CCAGGGTCGT AGCCCGAGCT ATGCGAGCTA A | Exendin4(1-30; K27C)-SGGGGSGGG-FGF21(33-209; Q56E-D74H-Q82E-R105K-D130E-K150R-R159Q-S195A) | Ex(1-30; K27C)-L9-FGF21 (V76-154R-130E) |
| 112 | V307 | HGEGTFTSDL SKQMEEEAVR LFIEWLKCGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEEGYN VYQSEAHGLP LHLPGNRSPH RDPAPQGPAR FLPLPGLPPA LPEPPGILAP QPPDVGSSDP LAMVGPSQGR SPSYAS | Exendin4(1-30; N28C-40 kDa branched PEG)-SGGGGSGGG-FGF21(33-209; Q56E-D74H-Q82E-R105K- | Ex(1-30; N28C)-L9-FGF21 (V76-154R-130E)-40KPEGb |

TABLE 1 -continued

Dual Function Protein and Nucleotides of the invention

| SEQ ID NO: | Variant NO: | Sequence | Long Name | Short Name |
|---|---|---|---|---|
| | | | D130E-K150R-R159Q-S195A) | |
| 113 | | CATGGTGAGG GTACGTTTAC TTCTGATCTG TCTAAACAGA TGGAAGAAGA AGCTGTTCGC CTGTTCATTG AATGGCTGAA ATGTGGTGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGGAAA CCGAAGCGCA TCTGGAAATT CGTGAAGATG GCACCGTGGG CGGTGCGGCG CATCAGAGCC CGGAAAGCCT GCTGGAACTG AAAGCGCTGA AACCGGGCGT GATTCAGATT CTGGGCGTGA AAACCAGCCG TTTTCTGTGC CAGAAACCGG ATGGCGCGCT GTATGGCAGC CTGCATTTTG ATCCGGAAGC GTGCAGCTTT CGTGAACTGC TGCTGGAAGA AGGCTATAAC GTGTATCAGA GCGAAGCGCA TGGCCTGCCG CTGCATCTGC CGGGCAACCG TAGCCCGCAT CGTGATCCGG CACCGCAGGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGGCGATGG TGGGTCCGAG CCAGGGTCGT AGCCCGAGCT ATGCGAGCTA A | Exendin4(1-30; N28C)-SGGGGSGGG-FGF21(33-209; Q56E-D74H-Q82E-R105K-D130E-K150R-R159Q-S195A) | Ex(1-30; N28C)-L9-FGF21 (V76-154R-130E) |
| 114 | V308 | HGEGTFTSDL SKQMEEEAVR LFIEWLCNGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEDGYN VYQSEAHGLP LHLPGNRSPH RDPAPQGPAR FLPLPGLPPA LPEPPGILAP QPPDVGSSDP LAMVGPSQAR SPSYAS | Exendin4(1-30; K27C-40 kDa branched PEG)-SGGGGSGGG-FGF21(33-209; Q56E-D74H-Q82E-R105K-K150R-R159Q-S195A-G202A) | Ex(1-30; K27C)--L9-FGF21 (V76-154R-202A)-40KPEGb |
| 115 | | CATGGTGAGG GTACGTTTAC TTCTGATCTG TCTAAACAGA TGGAAGAAGA AGCTGTTCGC CTGTTCATTG AATGGCTGTG TAATGGTGGT TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGGAAA CCGAAGCGCA TCTGGAAATT CGTGAAGATG GCACCGTGGG CGGTGCGGCG CATCAGAGCC CGGAAAGCCT GCTGGAACTG AAAGCGCTGA AACCGGGCGT GATTCAGATT CTGGGCGTGA AAACCAGCCG TTTTCTGTGC CAGAAACCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACCG TAGCCCGCAT CGTGATCCGG CACCGCAGGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGGCGATGG TGGGTCCGAG CCAGGCGCGT AGCCCGAGCT ATGCGAGCTA A | Exendin4(1-30; K27C)-SGGGGSGGG-FGF21(33-209; Q56E-D74H-Q82E-R105K-K150R-R159Q-S195A-G202A) | Ex(1-30; K27C)-L9-FGF21 (V76-154R-202A) |
| 116 | V309 | HGEGTFTSDL SKQMEEEAVR LFIEWLKCGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEDGYN VYQSEAHGLP LHLPGNRSPH RDPAPQGPAR FLPLPGLPPA LPEPPGILAP QPPDVGSSDP LAMVGPSQAR SPSYAS | Exendin4(1-30; N28C-40 kDa branched PEG)-SGGGGSGGG-FGF21(33-209; Q56E- | Ex(1-30; N28C)-L9-FGF21 (V76-154R-202A)-40KPEGb |

TABLE 1 -continued

Dual Function Protein and Nucleotides of the invention

| SEQ ID NO: | Variant NO: | Sequence | Long Name | Short Name |
|---|---|---|---|---|
| | | | D74H-Q82E-R105K-K150R-R159Q-S195A-G202A) | |
| 117 | | CATGGTGAGG GTACGTTTAC TTCTGATCTG TCTAAACAGA TGGAAGAAGA AGCTGTTCGC CTGTTCATTG AATGGCTGAA ATGTGGTGG TCTGGTGGTG GTGGTTCTGG CGGTGGCGAC TCGAGCCCGC TGCTGCAGTT TGGCGGCCAG GTGCGTCAGC GTTATCTGTA TACCGATGAT GCGCAGGAAA CCGAAGCGCA TCTGGAAATT CGTGAAGATG GCACCGTGGG CGGTGCGGCG CATCAGAGCC CGGAAAGCCT GCTGGAACTG AAAGCGCTGA AACCGGGCGT GATTCAGATT CTGGGCGTGA AAACCAGCCG TTTTCTGTGC CAGAAACCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACCG TAGCCCGCAT CGTGATCCGG CACCGCAGGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGGCGATGG TGGGTCCGAG CCAGGCGCGT AGCCCGAGCT ATGCGAGCTA A | Exendin4(1-30; N28C)-SGGGGSGGG-FGF21(33-209; Q56E-D74H-Q82E-R105K-K150R-R159Q-S195A-G202A) | Ex(1-30; N28C)-L9-FGF21 (V76-154R-202A) |
| 118 | V276 | HSEGTFTSDV SSYLEGQAAK EFIAWLVKGG GSGGGGSGGG GSGGGGSGGG DSSPLLQFGG QVRQRYLYTD DAQETEAHLE IREDGTVGGA AHQSPESLLE LKALKPGVIQ ILGVKTSRFL CQKPDGALYG SLHFDPEACS FRELLLEDGY NVYQSEAHGL PLHLPGNRSP HCDPAPQGPA RFLPLPGLPP ALPEPPGILA PQPPDVGSSD PLAMVGPSQG RSPSYAS | GLP-1(7-35; A8S)-GGS(GGGGS)3-FGF21(33-209; Q56E-D74H-Q82E-R105K-K150R-R154C-40 kDa branched PEG-R159Q-S195A) | GLP-1(A8S)-L20-FGF21(V76)-40KPEGb |
| 119 | | CATTCTGAAG GCACTTTTAC TAGCGATGTT TCTAGCTACC TGGAAGGCCA GGCTGCGAAA GAATTCATCG CGTGGCTGGT TAAAGGCGGT GGTAGCGGTG GCGGCGGTTC TGGTGGTGGT GGTTCTGGCG GTGGCGGTAG CGGTGGCGGC GATAGCAGCC CGCTGCTGCA GTTTGGCGGC CAGGTGCGTC AGCGTTATCT GTATACCGAT GATGCGCAGG AAACCGAAGC GCATCTGGAA ATTCGTGAAG ATGGCACCGT GGGCGGTGCG GCGCATCAGA GCCCGGAAAG CCTGCTGGAA CTGAAAGCGC TGAAACCGGG CGTGATTCAG ATTCTGGGCG TGAAAACCAG CCGTTTTCTG TGCCAGAAAC CGGATGGCGC GCTGTATGGC AGCCTGCATT TTGATCCGGA AGCGTGCAGC TTTCGTGAAC TGCTGCTGGA AGATGGCTAT AACGTGTATC AGAGCGAAGC GCATGGCCTG CCGCTGCATC TGCCGGGCAA CCGTAGCCCG CATTGCGATC CGGCACCGCA GGGTCCGGCG CGTTTTCTGC CGCTGCCGGG TCTGCCGCCG GCACTGCCGG AACCGCCGGG TATTCTGGCC CCGCAGCCGC CGGATGTTGG TAGCAGCGAT CCGCTGGCGA TGGTGGGTCC GAGCCAGGGT CGTAGCCCGA GCTATGCGAG CTAA | GLP-1(7-35; A8S)-GGS(GGGGS)3-FGF21(33-209; Q56E-D74H-Q82E-R105K-K150R-R154C-R159Q-S195A) | GLP-1(A8S)-L20-FGF21(V76) |
| 120 | V197 | HGEGTFTSDL SKQMEEEAVR LFIEWLKNGG GGGGSDKTHT CPPCPAPEAA GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR EEMTKNQVSL | Exendin4(1-30)-(GGGGS)-Fc-(GGGGS)3-FGF21(33-209; Q55C-R105K- | Exendin (1-30)-L5-Fc-L15-FGF21 (V103)) |

TABLE 1 -continued

Dual Function Protein and Nucleotides of the invention

| SEQ ID NO: | Variant NO: | Sequence | Long Name | Short Name |
|---|---|---|---|---|
| | | TCLVKGFYPS DIAVEWESNG QPENNYKTTP PVLDSDGSFF LYSKLTVDKS RWQQGNVFSC SVMHEALHNH YTQKSLSLSP GKGGGGSGGG GSGGGGSDSS PLLQFGGQVR QRYLYTDDAC QTEAHLEIRE DGTVGGAADQ SPESLLQLKA LKPGVIQILG VKTSRFLCQK PDGALYGSLH FDPEACSFRE LLLEDGYNVY QSEAHGLPLH LPCNRSPHRD PASRGPARFL PLPGLPPALP EPPGILAPQP PDVGSSDPLA MVGGSQARSP SYAS | | G148C- K150R- P158S- S195A- P199G- G202A) |
| 121 | V196 | HGEGTFTSDL SKQMEEEAVR LFIEWLKNGG GGGGSGGGGS GGGGSDKTHT CPPCPAPEAA GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR EEMTKNQVSL TCLVKGFYPS DIAVEWESNG QPENNYKTTP PVLDSDGSFF LYSKLTVDKS RWQQGNVFSC SVMHEALHNH YTQKSLSLSP GKGGGGSGGG GSGGGGSDSS PLLQFGGQVR QRYLYTDDAC QTEAHLEIRE DGTVGGAADQ SPESLLQLKA LKPGVIQILG VKTSRFLCQK PDGALYGSLH FDPEACSFRE LLLEDGYNVY QSEAHGLPLH LPCNRSPHRD PASRGPARFL PLPGLPPALP EPPGILAPQP PDVGSSDPLA MVGGSQARSP SYAS | Exendin4(1- 30)-(GGGGS)₃- Fc-(GGGGS)₃- FGF21(33- 209; Q55C- R105K- G148C- K150R- P158S- S195A- P199G- G202A) | Ex(1- 30)-L15- Fc-L15- FGF21 (V103) |
| 122 | V199 | HGEGTFTSDL SKQMEEEAVR LFIEWLKNGG PSSGAPPPSG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG KGGGGSGGGG SGGGGSDSSP LLQFGGQVRQ RYLYTDDACQ TEAHLEIRED GTVGGAADQS PESLLQLKAL KPGVIQILGV KTSRFLCQKP DGALYGSLHF DPEACSFREL LLEDGYNVYQ SEAHGLPLHL PCNRSPHRDP ASRGPARFLP LPGLPPALPE PPGILAPQPP DVGSSDPLAM VGGSQARSPS YAS | Exendin4(1- 39)-(GGGGS)- Fc-(GGGGS)₃- FGF21(33- 209; Q55C- R105K- G148C- K150R- P158S- S195A- P199G- G202A) | Ex(1- 39)-L5- Fc-L15- FGF21 (V103) |
| 123 | V198 | HGEGTFTSDL SKQMEEEAVR LFIEWLKNGG PSSGAPPPSG GGGSGGGGSG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG KGGGGSGGGG SGGGGSDSSP LLQFGGQVRQ RYLYTDDACQ TEAHLEIRED GTVGGAADQS PESLLQLKAL KPGVIQILGV KTSRFLCQKP DGALYGSLHF DPEACSFREL LLEDGYNVYQ SEAHGLPLHL PCNRSPHRDP ASRGPARFLP LPGLPPALPE PPGILAPQPP DVGSSDPLAM VGGSQARSPS YAS | Exendin4(1- 39)-(GGGGS)₃- Fc-(GGGGS)₃- FGF21(33- 209; Q55C- R105K- G148C- K150R- P158S- S195A- P199G- G202A) | Ex(1- 39)- L15-Fc- L15- FGF21 (V103) |
| 124 | V203 | HSEGTFTSDV SSYLEGQAAK EFIAWLVKGG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG KGGGGSGGGG SGGGGSDSSP LLQFGGQVRQ RYLYTDDACQ TEAHLEIRED GTVGGAADQS PESLLQLKAL KPGVIQILGV KTSRFLCQKP DGALYGSLHF | GLP-1(7-35; A8S)- (GGGGS)-Fc- (GGGGS)₃- FGF21(33- 209; Q55C- R105K- G148C- K150R- P158S- S195A- P199G- | GLP- 1(A8S)- L5-Fc- L15- FGF21 (V103) |

TABLE 1 -continued

Dual Function Protein and Nucleotides of the invention

| SEQ ID NO: | Variant NO: | Sequence | Long Name | Short Name |
|---|---|---|---|---|
| | | DPEACSFREL LLEDGYNVYQ SEAHGLPLHL PCNRSPHRDP ASRGPARFLP LPGLPPALPE PPGILAPQPP DVGSSDPLAM VGGSQARSPS YAS | G202A) | |
| 125 | V202 | HSEGTFTSDV SSYLEGQAAK EFIAWLVKGG GGGSGGGGSG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG KGGGGSGGGG SGGGGSDSSP LLQFGGQVRQ RYLYTDDACQ TEAHLEIRED GTVGGAADQS PESLLQLKAL KPGVIQILGV KTSRFLCQKP DGALYGSLHF DPEACSFREL LLEDGYNVYQ SEAHGLPLHL PCNRSPHRDP ASRGPARFLP LPGLPPALPE PPGILAPQPP DVGSSDPLAM VGGSQARSPS YAS | GLP-1(7-35; A8S)- (GGGGS)₃-Fc- (GGGGS)₃- FGF21(33- 209; Q55C- R105K- G148C- K150R- P158S- S195A- P199G- G202A) | GLP- 1(A8S)- L15-Fc- L15- FGF21 (V103) |
| 126 | V310 | HGEGTFTSDL SKQMEEEAVR LFIEWLKNGG PSSGAPPPSG GGGSGGGGSG GGGSGGGGDS SPLLQFGGQV RQRYLYTDDA QETEAHLEIR EDGTVGGAAH QSPESLLELK ALKPGVIQIL GVKTSRFLCQ KPDGALYGSL HFDPEACSFR ELLLEDGYNV YQSEAHGLPL HLPGNRSPHC DPAPQGPARF LPLPGLPPAL PEPPGILAPQ PPDVGSSDPL AMVGPSQGRS PSYAS | Exendin4(1- 39)- (GGGGS)₃GGGG -FGF21(33- 209; Q56E- D74H-Q82E- R105K- K150R-R154C-40 kDa branched PEG- R159Q- S195A) | Ex(1- 39)- L19- FGF21 (V76)- 40KPEGb |
| 127 | | CATGGTGAGG GTACGTTTAC TTCTGATCTG TCTAAACAGA TGGAAGAAGA AGCTGTTCGC CTGTTCATTG AATGGCTGAA AAATGGTGGT CCGTCCTCCG GCGCTCCTCC GCCTTCTGGT GGTGGTGGTT CTGGCGGTGG CGGTTCTGGC GGCGGTGGTA GCGGTGGCGG CGGTGATAGC AGCCCGCTGC TGCAGTTTGG CGGCCAGGTG CGTCAGCGTT ATCTGTATAC CGATGATGCG CAGGAAACCG AAGCGCATCT GGAAATTCGT GAAGATGGCA CCGTGGGCGG TGCGGCGCAT CAGAGCCCGG AAAGCCTGCT GGAACTGAAA GCGCTGAAAC CGGGCGTGAT TCAGATTCTG GGCGTGAAAA CCAGCCGTTT TCTGTGCCAG AAACCGGATG GCGCGCTGTA TGGCAGCCTG CATTTTGATC CGGAAGCGTG CAGCTTTCGT GAACTGCTGC TGGAAGATGG CTATAACGTG TATCAGAGCG AAGCGCATGG CCTGCCGCTG CATCTGCCGG GCAACCGTAG CCCGCATTGC GATCCGGCAC CGCAGGGTCC GGCGCGTTTT CTGCCGCTGC CGGGTCTGCC GCCGGCACTG CCGGAACCGC CGGGTATTCT GGCCCCGCAG CCGCCGGATG TTGGTAGCAG CGATCCGCTG GCGATGGTGG GTCCGAGCCA GGGTCGTAGC CCGAGCTATG CGAGCTAA | Exendin4(1- 39)- (GGGGS)₃GGGG- FGF21(33- 209; Q56E- D74H-Q82E- R105K- K150R- R154C- R159Q- S195A) | Ex(1- 39)- L19- FGF21 (V76) |
| 31 | V206 | HGEGTFTSDL SKQMEEEAVR LFIEWLKNGG PSSGAPPPSD KTHTCPPCPA PEAAGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGKDSSP LLQFGGQVRQ RYLYTDDACQ TEAHLEIRED GTVGGAADQS PESLLQLKAL KPGVIQILGV KTSRFLCQKP DGALYGSLHF DPEACSFREL LLEDGYNVYQ SEAHGLPLHL PCNRSPHRDP | Exendin4(1- 39)-Fc- FGF21(33- 209; Q55C- R105K- G148C- K150R- P158S- S195A- P199G- G202A) | Ex(1- 39)-L0- Fc-L0- FGF21 (V103) |

TABLE 1 -continued

Dual Function Protein and Nucleotides of the invention

| SEQ ID NO: | Variant NO: | Sequence | Long Name | Short Name |
|---|---|---|---|---|
|  |  | ASRGPARFLP LPGLPPALPE PPGILAPQPP DVGSSDPLAM VGGSQARSPS YAS |  |  |
| 32 | V208 | HGEGTFTSDL SKQMEEEAVR LFIEWLKNGG PSSGAPPPSD KTHTCPPCPA PEAAGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGKGSDS SPLLQFGGQV RQRYLYTDDA CQTEAHLEIR EDGTVGGAAD QSPESLLQLK ALKPGVIQIL GVKTSRFLCQ RPDGTLYGSL HFDPEACSFR ELLLEDGYNV YQSEAHGLPL HLPCNRSPHR DPASRGPARF LPLPGLPPAL PEPPGILAPQ PPDVGSSDPL AMVGGSQARS PSYAS | Exendin4(1-39)-Fc-GS-FGF21(33-209; Q55C-A109T-G148C-K150R-P158S-S195A-P199G-G202A) | Ex(1-39)-L0-Fc-L2-FGF21 (V101) |
| 33 |  | CACGGAGAAG GCACCTTTAC ATCGGACTTG TCGAAGCAGA TGGAGGAAGA AGCGGTGAGG CTCTTCATCG AGTGGCTCAA GAATGGAGGA CCCTCAAGCG GAGCGCCTCC TCCTTCCGAC AAAACCCATA CATGTCCGCC TTGTCCCGCA CCAGAAGCAG CGGGTGGGCC CTCGGTGTTC CTGTTCCCGC CAAAACCGAA GGACACACTT ATGATTTCAC GCACACCGGA AGTGACTTGC GTCGTGGTGG ATGTATCGCA CGAGGACCCC GAGGTCAAAT TCAACTGGTA TGTCGATGGA GTGGAGGTGC ACAATGCAAA GACCAAGCCG AGGGAAGAAC AATACAATAG CACGTACCGA GTCGTGTCCG TCTTGACGGT CCTTCACCAG GACTGGCTGA ACGGAAAGGA GTACAAGTGC AAAGTGAGCA ATAAGGCCCT CCCTGCCCCG ATTGAGAAAA CCATTTCCAA GGCCAAAGGT CAGCCTAGAG AACCTCAAGT GTATACTCTT CCGCCCCTCA CGCGAAGAGA TGACGAAAAAC CAAGTGTCGC TTACGTGTCT TGTCAAAGGT TTCTACCCCT CGGACATCGC CGTAGAGTGG GAGTCGAACG GCCAGCCGGA GAACAACTAC AAGACCACGC CCCCTGTCTT GGATAGCGAC GGATCGTTTT TCCTCTACTC GAAACTCACA GTAGATAAGT CCCGATGGCA ACAGGGTAAT GTCTTTAGCT GCAGCGTGAT GCACGAGGCG CTTCACAATC ATTACACACA AAAATCACTG TCGCTTAGCC CGGGAAAGGG TTCAGATTCG TCGCCCCTGT TGCAGTTTGG TGGACAGGTC AGACAGCGCT ACCTTTACAC GGATGACGCC TGCCAGACAG AGGCACACCT CGAAATCAGA GAGGACGGTA CGGTCGGGGG TGCGGCCGAT CAGAGCCCCG AGTCGCTTCT CCAGTTGAAG GCCCTTAAGC CAGGAGTCAT CCAGATTTTG GGAGTAAAGA CCTCACGGTT TCTCTGTCAG CGTCCAGATG GGACACTGTA CGGCTCATTG CATTTCGATC CCGAAGCGTG CTCGTTCCGG GAGTTGCTGC TTGAGGACGG ATATAACGTC TATCAGAGCG AAGCGCATGG CCTCCCCCTT CACCTCCCCG TGTAACAGGTC GCCGCATCGG GATCCGGCCT CGAGGGGTCC CGCGAGATTT CTTCCGTTGC CCGGGTTGCC TCCCGCGCTG CCCGAGCCTC CCGGGATCCT CGCGCCACAG CCTCCTGATG TAGGGTCCTC GGACCCTTTG GCGATGGTAG GTGGATCACA AGCACGGTCC CCGAGCTATG CATCA | Exendin4(1-39)-Fc-GS-FGF21(33-209; Q55C-A109T-G148C-K150R-P158S-S195A-P199G-G202A) | Ex(1-39)-L0-Fc-L2-FGF21 (V101) |
| 36 | V209 | HGEGTFTSDL SKQMEEEAVR LFIEWLKNGG PSSGAPPPSG GGGSGGGGSG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY | Exendin4(1-39)-(GGGGS)3-Fc-GS-FGF21(33-209; Q55C-A109T-G148C-K150R- | Ex(1-39)-L15-Fc-L2-FGF21 (V101) |

TABLE 1 -continued

Dual Function Protein and Nucleotides of the invention

| SEQ ID NO: | Variant NO: | Sequence | Long Name | Short Name |
|---|---|---|---|---|
| | | TQKSLSLSPG KGSDSSPLLQ FGGQVRQRYL YTDDACQTEA HLEIREDGTV GGAADQSPES LLQLKALKPG VIQILGVKTS RFLCQRPDGT LYGSLHFDPE ACSFRELLLE DGYNVYQSEA HGLPLHLPCN RSPHRDPASR GPARFLPLPG LPPALPEPPG ILAPQPPDVG SSDPLAMVGG SQARSPSYAS | P158S-S195A-P199G-G202A) | |
| 37 | | CACGGAGAAG GCACCTTTAC ATCGGACTTG TCGAAGCAGA TGGAGGAAGA AGCGGTGAGG CTCTTCATCG AGTGGCTCAA GAATGGAGGA CCCTCAAGCG GAGCGCCTCC TCCTTCCGGA GGAGGTGGGT CGGCGGTGG AGGCTCCGGA GGGGGAGGGA GCGACAAAAC CCATACATGT CCGCCTTGTC CCGCACCAGA AGCAGCGGGT GGGCCCTCGG TGTTCCTGTT CCCGCCAAAA CCGAAGGACA CACTTATGAT TTCACGCACA CCGGAAGTGA CTTGCGTCGT GGTGGATGTA TCGCACGAGG ACCCCGAGGT CAAATTCAAC TGGTATGTCG ATGGAGTGGA GGTGCACAAT GCAAAGACCA AGCCGAGGGA AGAACAATAC AATAGCACGT ACCGAGTCGT GTCCGTCTTG ACGGTCCTTC ACCAGGACTG GCTGAACGGA AAGGAGTACA AGTGCAAAGT GAGCAATAAG GCCCTCCCTG CCCCGATTGA GAAAACCATT TCCAAGGCCA AGGTCAGCC TAGAGAACCT CAAGTGTATA CTCTTCCGCC CTCACGCGAA GAGATGACGA AAAACCAAGT GTCGCTTACG TGTCTTGTCA AAGGTTTCTA CCCCTCGGAC ATCGCCGTAG AGTGGGAGTC GAACGGCCAG CCGGAGAACA ACTACAAGAC CACGCCCCCT GTCTTGGATA GCGACGGATC GTTTTTCCTC TACTCGAAAC TCACAGTAGA TAAGTCCCGA TGGCAACAGG GTAATGTCTT TAGCTGCAGC GTGATGCACG AGGCGCTTCA CAATCATTAC ACACAAAAAT CACTGTCGCT TAGCCCGGGA AAGGGTTCAG ATTCGTCGCC CCTGTTGCAG TTTGGTGGAC AGGTCAGACA GCGCTACCTT TACACGGATG ACGCCTGCCA GACAGAGGCA CACCTCGAAA TCAGAGAGGA CGGTACGGTC GGGGGTGCGG CCGATCAGAG CCCCGAGTCG CTTCTCCAGT TGAAGGCCCT TAAGCCAGGA GTCATCCAGA TTTTGGGAGT AAAGACCTCA CGGTTTCTCT GTCAGCGTCC AGATGGGACA CTGTACGGCT CATTGCATTT CGATCCCGAA GCGTGCTCGT TCCGGGAGTT GCTGCTTGAG GACGGATATA ACGTCTATCA GAGCGAAGCG CATGGCCTCC CCCTTCACCT CCCGTGTAAC AGGTCGCCGC ATCGGGATCC GGCCTCGAGG GGTCCCGCGA GATTCTTCC GTTGCCCGGG TTGCCTCCCG CGCTGCCCGA GCCTCCCGGG ATCCTCGCGC CACAGCCTCC TGATGTAGGG TCCTCGGACC CTTTGGCGAT GGTAGGTGGA TCACAAGCAC GGTCCCCGAG CTATGCATCA | Exendin4(1-39)-(GGGGS)3-Fc-GS-FGF21(33-209; Q55C-A109T-G148C-K150R-P158S-S195A-P199G-G202A) | Ex(1-39)-L15-Fc-L2-FGF21 (V101) |
| 133 | V210 | HGEGTFTSDL SKQMEEEAVR LFIEWLKNGG PSSGAPPPSD KTHTCPPCPA PEAAGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGKGSDS SPLLQFGGQV RQRYLYTDDA CQTEAHLEIR EDGTVGGAAD QSPESLLQLK ALKPGVIQIL GVKTSRFLCQ KPDGALYGSL HFDPEACSFR ELLLEDGYNV YQSEAHGLPL HLPCNRSPHR DPASRGPARF LPLGLPPAL PEPPGILAPQ PPDVGSSDPL AMVGGSQARS PSYAS | Exendin4(1-39-Fc-GS-FGF21(33-209; Q55C-R105K-G148C-K150R-P158S-S195A-P199G-G202A) | Ex(1-39)-L0-Fc-L2-FGF21 (V103) |
| 56 | | CACGGAGAAG GCACCTTTAC ATCGGACTTG TCGAAGCAGA TGGAGGAAGA AGCGGTGAGG CTCTTCATCG AGTGGCTCAA GAATGGAGGA | Exendin4(1-39-Fc-GS-FGF21(33- | Ex(1-39)-L0-Fc-L2- |

TABLE 1 -continued

Dual Function Protein and Nucleotides of the invention

| SEQ ID NO: | Variant NO: | Sequence | Long Name | Short Name |
|---|---|---|---|---|
| | | CCCTCAAGCG GAGCGCCTCC TCCTTCCGAC AAAACCCATA CATGTCCGCC TTGTCCCGCA CCAGAAGCAG CGGGTGGGCC CTCGGTGTTC CTGTTCCCGC CAAAACCGAA GGACACACTT ATGATTTCAC GCACACCGGA AGTGACTTGC GTCGTGGTGG ATGTATCGCA CGAGGACCCC GAGGTCAAAT TCAACTGGTA TGTCGATGGA GTGGAGGTGC ACAATGCAAA GACCAAGCCG AGGGAAGAAC AATACAATAG CACGTACCGA GTCGTGTCCG TCTTGACGGT CCTTCACCAG GACTGGCTGA ACGGAAAGGA GTACAAGTGC AAAGTGAGCA ATAAGGCCCT CCCTGCCCCG ATTGAGAAAA CCATTTCCAA GGCCAAAGGT CAGCCTAGAG AACCTCAAGT GTATACTCTT CCGCCCTCAC GCGAAGAGAT GACGAAAAAC CAAGTGTCGC TTACGTGTCT TGTCAAAGGT TTCTACCCCT CGGACATCGC CGTAGAGTGG GAGTCGAACG GCCAGCCGGA GAACAACTAC AAGACCACGC CCCCTGTCTT GGATAGCGAC GGATCGTTTT TCCTCTACTC GAAACTCACA GTAGATAAGT CCCGATGGCA ACAGGGTAAT GTCTTTAGCT GCAGCGTGAT GCACGAGGCG CTTCACAATC ATTACACACA AAAATCACTG TCGCTTAGCC CGGGGAAAGGG TTCAGATTCG TCGCCCCTGT TGCAGTTTGG TGGACAGGTC AGACAGCGCT ACCTTTACAC GGATGACGCC TGCCAGACAG AGGCACACCT CGAAATCAGA GAGGACGGTA CGGTCGGGGG TGCGGCCGAT CAGAGCCCCG AGTCGCTTCT CCAGTTGAAG GCCCTTAAGC CAGGAGTCAT CCAGATTTTG GGAGTAAAGA CCTCACGGTT TCTCTGTCAG AAACCAGATG GGGCACTGTA CGGCTCATTG CATTTCGATC CCGAAGCGTG CTCGTTCCGG GAGTTGCTGC TTGAGGACGG ATATAACGTC TATCAGAGCG AAGCGCATGG CCTCCCCCTT CACCTCCCGT GTAACAGGTC GCCGCATCGG GATCCGGCCT CGAGGGGTCC CGCGAGATTT CTTCCGTTGC CCGGGTTGCC TCCCGCGCTG CCCGAGCCTC CCGGGATCCT CGCGCCACAG CCTCCTGATG TAGGGTCCTC GGACCCTTTG GCGATGGTAG GTGGATCACA AGCACGGTCC CCGAGCTATG CATCA | 209; Q55C-R105K-G148C-K150R-P158S-S195A-P199G-G202A) | FGF21 (V103) |
| 134 | V211 | HGEGTFTSDL SKQMEEEAVR LFIEWLKNGG PSSGAPPPSG GGGSGGGGSG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG KGSDSSPLLQ FGGQVRQRYL YTDDACQTEA HLEIREDGTV GGAADQSPES LLQLKALKPG VIQILGVKTS RFLCQKPDGA LYGSLHFDPE ACSFRELLLE DGYNVYQSEA HGLPLHLPCN RSPHRDPASR GPARFLPLPG LPPALPEPPG ILAPQPPDVG SSDPLAMVGG SQARSPSYAS | Exendin4(1-39)-(GGGGS)₃Fc-GS-FGF21(33-209; Q55C-R105K-G148C-K150R-P158S-S195A-P199G-G202A) | Ex(1-39)-L15-Fc-L2-FGF21 (V103) |
| 57 | | CACGGAGAAG GCACCTTTAC ATCGGACTTG TCGAAGCAGA TGGAGGAAGA AGCCGGTGAGG CTCTTCATCG AGTGGCTCAA GAATGGAGGA CCCTCAAGCG GAGCGCCTCC TCCTTCCGGA GGAGGTGGGT CGGGCGGTGG AGGCTCCGGA GGGGGAGGGA GCGACAAAAC CCATACATGT CCGCCTTGTC CCGCACCAGA AGCAGCGGGT GGGCCCTCGG TGTTCCTGTT CCCGCCAAAA CCGAAGGACA CACTTATGAT TTCACGCACA CCGGAAGTGA CTTGCGTCGT GGTGGATGTA TCGCACGAGG ACCCCGAGGT CAAATTCAAC TGGTATGTCG ATGGAGTGGA GGTGCACAAT GCAAAGACCA AGCCGAGGGA AGAACAATAC AATAGCACGT ACCGAGTCGT GTCCGTCTTG | Exendin4(1-39)-(GGGGS)₃Fc-GS-FGF21 (33-209; Q55C-R105K-G148C-K150R-P158S-S195A-P199G-G202A) | Ex(1-39)-L15-Fc-L2-FGF21 (V103) |

TABLE 1 -continued

Dual Function Protein and Nucleotides of the invention

| SEQ ID NO: | Variant NO: | Sequence | Long Name | Short Name |
|---|---|---|---|---|
| | | ACGGTCCTTC ACCAGGACTG GCTGAACGGA AAGGAGTACA AGTGCAAAGT GAGCAATAAG GCCCTCCCTG CCCCGATTGA GAAAACCATT TCCAAGGCCA AAGGTCAGCC TAGAGAACCT CAAGTGTATA CTCTTCCGCC CTCACGCGAA GAGATGACGA AAAACCAAGT GTCGCTTACG TGTCTTGTCA AAGGTTTCTA CCCCTCGGAC ATCGCCGTAG AGTGGGAGTC GAACGGCCAG CCGGAGAACA ACTACAAGAC CACGCCCCCT GTCTTGGATA GCGACGGATC GTTTTTCCTC TACTCGAAAC TCACAGTAGA TAAGTCCCGA TGGCAACAGG GTAATGTCTT TAGCTGCAGC GTGATGCACG AGGCGCTTCA CAATCATTAC ACACAAAAAT CACTGTCGCT TAGCCCGGGA AAGGGTTCAG ATTCGTCGCC CCTGTTGCAG TTTGGTGGAC AGGTCAGACA GCGCTACCTT TACACGGATG ACGCCTGCCA GACAGAGGCA CACCTCGAAA TCAGAGAGGA CGGTACGGTC GGGGGTGCGG CCGATCAGAG CCCCGAGTCG CTTCTCCAGT TGAAGGCCCT TAAGCCAGGA GTCATCCAGA TTTTGGGAGT AAAGACCTCA CGGTTTCTCT GTCAGAAACC AGATGGGGCA CTGTACGGCT CATTGCATTT CGATCCCGAA GCGTGCTCGT TCCGGGAGTT GCTGCTTGAG GACGGATATA ACGTCTATCA GAGCGAAGCG CATGGCCTCC CCCTTCACCT CCCGTGTAAC AGGTCGCCGC ATCGGGATCC GGCCTCGAGG GGTCCCGCGA GATTTCTTCC GTTGCCCGGG TTGCCTCCCG CGCTGCCCGA GCCTCCCGGG ATCCTCGCGC CACAGCCTCC TGATGTAGGG TCCTCGGACC CTTTGGCGAT GGTAGGTGGA TCACAAGCAC GGTCCCCGAG CTATGCATCA | | |
| 135 | V214 | HSEGTFTSDV SSYLEGQAAK EFIAWLVKGG GGGSGGGGSG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG KGSDSSPLLQ FGGQVRQRYL YTDDACQTEA HLEIREDGTV GGAADQSPES LLQLKALKPG VIQILGVKTS RFLCQRPDGT LYGSLHFDPE ACSFRELLLE DGYNVYQSEA HGLPLHLPCN RSPHRDPASR GPARFLPLPG LPPALPEPPG ILAPQPPDVG SSDPLAMVGG SQARSPSYAS | GLP-1(7-35; A8S)-(GGGGS)$_3$-Fc-GS-FGF21(33-209; Q55C-A109T-G148C-K150R-P158S-S195A-P199G-G202A) | GLP-1(A8S)-L15-Fc-L2-FGF21(V101) |
| 64 | | CACTCCGAAG GAACATTCAC TTCCGATGTA AGCTCGTATT TGGAAGGGCA GGCGGCTAAG GAGTTTATCG CATGGTTGGT CAAAGGTGGT GGAGGTGGGT CGGGCGGTGG AGGCTCCGGA GGGGGAGGGA GCGACAAAAC CCATACATGT CCGCCTTGTC CCGCACCAGA AGCAGCGGGT GGGCCCTCGG TGTTCCTGTT CCCGCCAAAA CCGAAGGACA CACTTATGAT TTCACGCACA CCGGAAGTGA CTTGCGTCGT GGTGGATGTA TCGCACGAGG ACCCCGAGGT CAAATTCAAC TGGTATGTCG ATGGAGTGGA GGTGCACAAT GCAAAGACCA AGCCGAGGGA AGAACAATAC AATAGCACGT ACCGAGTCGT GTCCGTCTTG ACGGTCCTTC ACCAGGACTG GCTGAACGGA AAGGAGTACA AGTGCAAAGT GAGCAATAAG GCCCTCCCTG CCCCGATTGA GAAAACCATT TCCAAGGCCA AAGGTCAGCC TAGAGAACCT CAAGTGTATA CTCTTCCGCC CTCACGCGAA GAGATGACGA AAAACCAAGT GTCGCTTACG TGTCTTGTCA AAGGTTTCTA CCCCTCGGAC ATCGCCGTAG AGTGGGAGTC GAACGGCCAG CCGGAGAACA ACTACAAGAC CACGCCCCCT GTCTTGGATA GCGACGGATC GTTTTTCCTC TACTCGAAAC TCACAGTAGA TAAGTCCCGA TGGCAACAGG GTAATGTCTT TAGCTGCAGC | GLP-1(7-35; A8S)-(GGGGS)$_3$-Fc-GS-FGF21(33-209; Q55C-A109T-G148C-K150R-P158S-S195A-P199G-G202A) | GLP-1(A8S)-L15-Fc-L2-FGF21(V101) |

TABLE 1 -continued

Dual Function Protein and Nucleotides of the invention

| SEQ ID NO: | Variant NO: | Sequence | Long Name | Short Name |
|---|---|---|---|---|
| | | GTGATGCACG AGGCGCTTCA CAATCATTAC ACACAAAAAT CACTGTCGCT TAGCCCGGGA AAGGGTTCAG ATTCGTCGCC CCTGTTGCAG TTTGGTGGAC AGGTCAGACA GCGCTACCTT TACACGGATG ACGCCTGCCA GACAGAGGCA CACCTCGAAA TCAGAGAGGA CGGTACGGTC GGGGGTGCGG CCGATCAGAG CCCCGAGTCG CTTCTCCAGT TGAAGGCCCT TAAGCCAGGA GTCATCCAGA TTTTGGGAGT AAAGACCTCA CGGTTTCTCT GTCAGCGTCC AGATGGGACA CTGTACGGCT CATTGCATTT CGATCCGAA GCGTGCTCGT TCCGGGAGTT GCTGCTTGAG GACGGATATA ACGTCTATCA GAGCGAAGCG CATGGCCTCC CCCTTCACCT CCCGTGTAAC AGGTCGCCGC ATCGGGATCC GGCCTCGAGG GGTCCCGCGA GATTTCTTCC GTTGCCCGGG TTGCCTCCCG CGCTGCCCGA GCCTCCCGGG ATCCTCGCGC ACAGCCTCC TGATGTAGGG TCCTCGGACC CTTTGGCGAT GGTAGGTGGA TCACAAGCAC GGTCCCCGAG CTATGCATCA | | |
| 136 | V216 | HSEGTFTSDV SSYLEGQAAK EFIAWLVKGG GGGSGGGGSG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG KGSDSSPLLQ FGGQVRQRYL YTDDACQTEA HLEIREDGTV GGAADQSPES LLQLKALKPG VIQILGVKTS RFLCQKPDGA LYGSLHFDPE ACSFRELLLE DGYNVYQSEA HGLPLHLPCN RSPHRDPASR GPARFLPLPG LPPALPEPPG ILAPQPPDVG SSDPLAMVGG SQARSPSYAS | GLP-1(7-35; A8S)-(GGGGS)₃-Fc-GS-FGF21(33-209; Q55C-R105K-G148C-K150R-158S-S195A-P199G-G202A) | GLP-1(A8S)-L15-Fc-L2-FGF21(V103) |
| 65 | | CACTCCGAAG GAACATTCAC TTCCGATGTA AGCTCGTATT TGGAAGGGCA GGCGGCTAAG GAGTTTATCG CATGGTTGGT CAAAGGTGGT GGAGGTGGGT CGGGCGGTGG AGGCTCCGGA GGGGGAGGGA GCGACAAAAC CCATACATGT CCGCCTTGTC CCGCACCAGA AGCAGCGGGT GGGCCCTCGG TGTTCCTGTT CCCGCCAAAA CCGAAGGACA CACTTATGAT TTCACGCACA CCGGAAGTGA CTTGCGTCGT GGTGGATGTA TCGCACGAGG ACCCCGAGGT CAAATTCAAC TGGTATGTCG ATGGAGTGGA GGTGCACAAT GCAAAGACCA AGCCGAGGGA AGAACAATAC AATAGCACGT ACCGAGTCGT GTCCGTCTTG ACGGTCCTTC ACCAGGACTG GCTGAACGGA AAGGAGTACA AGTGCAAAGT GAGCAATAAG GCCCTCCCTG CCCCGATTGA GAAAACCATT TCCAAGGCCA AAGGTCAGCC TAGAGAACCT CAAGTGTATA CTCTTCCGCC CTCACGCGAA GAGATGACGA AAAACCAAGT GTCGCTTACG TGTCTTGTCA AAGGTTTCTA CCCCTCGGAC ATCGCCGTAG AGTGGGAGTC GAACGGCCAG CCGGAGAACA ACTACAAGAC CACGCCCCCT GTCTTGGATA GCGACGGATC GTTTTTCCTC TACTCGAAAC TCACAGTAGA TAAGTCCCGA TGGCAACAGG GTAATGTCTT TAGCTGCAGC GTGATGCACG AGGCGCTTCA CAATCATTAC ACACAAAAAT CACTGTCGCT TAGCCCGGGA AAGGGTTCAG ATTCGTCGCC CCTGTTGCAG TTTGGTGGAC AGGTCAGACA GCGCTACCTT TACACGGATG ACGCCTGCCA GACAGAGGCA CACCTCGAAA TCAGAGAGGA CGGTACGGTC GGGGGTGCGG CCGATCAGAG CCCCGAGTCG CTTCTCCAGT TGAAGGCCCT TAAGCCAGGA GTCATCCAGA TTTTGGGAGT AAAGACCTCA CGGTTTCTCT GTCAGAAACC AGATGGGGCA CTGTACGGCT CATTGCATTT CGATCCGAA GCGTGCTCGT TCCGGGAGTT GCTGCTTGAG | GLP-1(7-35; A8S)-(GGGGS)₃-Fc-GS-FGF21(33-209; Q55C-R105K-G148C-K150R-P158S-S195A-P199G-G202A) | GLP-1(A8S)-L15-Fc-L2-FGF21(V103) |

TABLE 1 -continued

Dual Function Protein and Nucleotides of the invention

| SEQ ID NO: | Variant NO: | Sequence | Long Name | Short Name |
|---|---|---|---|---|
|  |  | GACGGATATA ACGTCTATCA GAGCGAAGCG CATGGCCTCC CCCTTCACCT CCCGTGTAAC AGGTCGCCGC ATCGGGATCC GGCCTCGAGG GGTCCCGCGA GATTCTTCC GTTGCCCGGG TTGCCTCCCG CGCTGCCCGA GCCTCCCGGG ATCCTCGCGC CACAGCCTCC TGATGTAGGG TCCTCGGACC CTTTGGCGAT GGTAGGTGGA TCACAAGCAC GGTCCCCGAG CTATGCATCA |  |  |
| 137 | V218 | HSEGTFTSDV SSYLEGQAAK EFIAWLVKGG GGGSGGGGSG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG KDSSPLLQFG GQVRQRYLYT DDACQTEAHL EIREDGTVGG AADQSPESLL QLKALKPGVI QILGVKTSRF LCQKPDGALY GSLHFDPEAC SFRELLLEDG YNVYQSEAHG LPLHLPCNRS PHRDPASRGP ARFLPLPGLP PALPEPPGIL APQPPDVGSS DPLAMVGGSQ ARSPSYAS | GLP-1(7-35; A8S)-(GGGGS)₃-Fc-FGF21(33-209; Q55C-R105K-G148C-K150R-P158S-S195A-P199G-G202A) | GLP-1(A8S)-L15-Fc-L0-FGF21 (V103) |
| 106 |  | CACTCCGAAG GAACATTCAC TTCCGATGTA AGCTCGTATT TGGAAGGGCA GGCGGCTAAG GAGTTTATCG CATGGTTGGT CAAAGGTGGT GGAGGTGGGT CGGCGGTGG AGGCTCCGGA GGGGGAGGGA GCGACAAAAC CCATACATGT CCGCCTTGTC CCGCACCAGA AGCAGCGGGT GGGCCCTCGG TGTTCCTGTT CCCGCCAAAA CCGAAGGACA CACTTATGAT TTCACGCACA CCGGAAGTGA CTTGCGTCGT GGTGGATGTA TCGCACGAGG ACCCCGAGGT CAAATTCAAC TGGTATGTCG ATGGAGTGGA GGTGCACAAT GCAAAGACCA AGCCGAGGGA AGAACAATAC AATAGCACGT ACCGAGTCGT GTCCGTCTTG ACGGTCCTTC ACCAGGACTG GCTGAACGGA AAGGAGTACA AGTGCAAAGT GAGCAATAAG GCCCTCCCTG CCCCGATTGA GAAAACCATT TCCAAGGCCA AAGGTCAGCC TAGAGAACCT CAAGTGTATA CTCTTCCGCC CTCACGCGAA GAGATGACGA AAAACCAAGT GTCGCTTACG TGTCTTGTCA AAGGTTTCTA CCCCTCGGAC ATCGCCGTAG AGTGGGAGTC GAACGGCCAG CCGGAGAACA ACTACAAGAC CACGCCCCCT GTCTTGGATA GCGACGGATC GTTTTTCCTC TACTCGAAAC TCACAGTAGA TAAGTCCCGA TGGCAACAGG GTAATGTCTT TAGCTGCAGC GTGATGCACG AGGCGCTTCA CAATCATTAC ACACAAAAAT CACTGTCGCT TAGCCCGGGA AAGGATTCGT CGCCCCTGTT GCAGTTTGGT GGACAGGTCA GACAGCGCTA CCTTTACACG GATGACGCCT GCCAGACAGA GGCACACCTC GAAATCAGAG AGGACGGTAC GGTCGGGGGT GCGGCCGATC AGAGCCCCGA GTCGCTTCTC CAGTTGAAGG CCCTTAAGCC AGGAGTCATC CAGATTTTGG GAGTAAAGAC CTCACGGTTT CTCTGTCAGA AACCAGATGG GGCACTGTAC GGCTCATTGC ATTTCGATCC CGAAGCGTGC TCGTTCCGGG AGTTGCTGCT TGAGGACGGA TATAACGTCT ATCAGAGCGA AGCGCATGGC CTCCCCCTTC ACCTCCCGTG TAACAGGTCG CCGCATCGGG ATCCGGCCTC GAGGGGTCCC GCGAGATTTC TTCCGTTGCC CGGGTTGCCT CCCGCGCTGC CCGAGCCTCC CGGGATCCTC GCGCCACAGC CTCCTGATGT AGGGTCCTCG GACCCTTTG CGATGGTAGG TGGATCACAA GCACGGTCCC CGAGCTATGC ATCA | GLP-1(7-35; A8S)-(GGGGS)₃-Fc-FGF21(33-209; Q55C-R105K-G148C-K150R-P158S-S195A-P199G-G202A) | GLP-1(A8S)-L15-Fc-L0-FGF21(V 103) |
| 107 | V200 | HGEGTFTSDL SKQMEEEAVR LFIEWLKNGG PSSGAPPPSG GGGSGGGGSG GGGSDKTHTC PPCPAPEAAG GPSVFLFPPK PKDTLMISRT | Exendin4(1-39)-(GGGGS)₃-Fc | Ex(1-39)-L15-Fc |

TABLE 1 -continued

Dual Function Protein and Nucleotides of the invention

| SEQ ID NO: | Variant NO: | Sequence | Long Name | Short Name |
|---|---|---|---|---|
| | | PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG K | | |
| 139 | V201 | HGEGTFTSDL SKQMEEEAVR LFIEWLKNGG PSSGAPPPSG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG K | Exendin4(1-39)-GGGGS-Fc | Ex(1-39)-L5-Fc |
| 140 | V207 | HGEGTFTSDL SKQMEEEAVR LFIEWLKNGG PSSGAPPPSD KTHTCPPCPA PEAAGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGKGGGG SGGGGSGGGG SDSSPLLQFG GQVRQRYLYT DDACQTEAHL EIREDGTVGG AADQSPESLL QLKALKPGVI QILGVKTSRF LCQKPDGALY GSLHFDPEAC SFRELLLEDG YNVYQSEAHG LPLHLPCNRS PHRDPASRGP ARFLPLPGLP PALPEPPGIL APQPPDVGSS DPLAMVGGSQ ARSPSYAS | Exendin4(1-39)-Fc-(GGGGS)₃-FGF21(33-209; Q55C-R105K-G148C-K150R-P158S-S195A-P199G-G202A) | Ex(1-39)-L0-Fc-L15-FGF21 (V103) |
| 141 | V212 | HSEGTFTSDV SSYLEGQAAK EFIAWLVKDK THTCPPCPAP EAAGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSREEMTKNQ VSLTCLVKGF YPSDIAVEWE SNGQPENNYK TTPPVLDSDG SFFLYSKLTV DKSRWQQGNV FSCSVMHEAL HNHYTQKSLS LSPGKGGGGS GGGGSGGGGS DSSPLLQFGG QVRQRYLYTD DACQTEAHLE IREDGTVGGA ADQSPESLLQ LKALKPGVIQ ILGVKTSRFL CQKPDGALYG SLHFDPEACS FRELLLEDGY NVYQSEAHGL PLHLPCNRSP HRDPASRGPA RFLPLPGLPP ALPEPPGILA PQPPDVGSSD PLAMVGGSQA RSPSYAS | GLP-1(7-35; A8S)-Fc-(GGGGS)₃-FGF21(33-209; Q55C-R105K-G148C-K150R-P158S-S195A-P199G-G202A) | GLP-1(A8S)-L0-Fc-L15-FGF21 (V103) |
| 142 | V213 | HSEGTFTSDV SSYLEGQAAK EFIAWLVKDK THTCPPCPAP EAAGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSREEMTKNQ VSLTCLVKGF YPSDIAVEWE SNGQPENNYK TTPPVLDSDG SFFLYSKLTV DKSRWQQGNV FSCSVMHEAL HNHYTQKSLS LSPGKGSDSS PLLQFGGQVR QRYLYTDDAC QTEAHLEIRE DGTVGGAADQ SPESLLQLKA LKPGVIQILG VKTSRFLCQR PDGTLYGSLH FDPEACSFRE LLLEDGYNVY QSEAHGLPLH LPCNRSPHRD PASRGPARFL PLPGLPPALP EPPGILAPQP PDVGSSDPLA MVGGSQARSP SYAS | GLP-1(7-35; A8S)-Fc-GS-FGF21(33-209; Q55C-A109T-G148C-K150R-P158S-S195A-P199G-G202A) | GLP-1(A8S)-L0-Fc-L2-FGF21 (V101) |
| 143 | V215 | HSEGTFTSDV SSYLEGQAAK EFIAWLVKDK THTCPPCPAP EAAGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSREEMTKNQ VSLTCLVKGF YPSDIAVEWE SNGQPENNYK TTPPVLDSDG | GLP-1(7-35; A8S)-Fc-GS-FGF21(33-209; Q55C-R105K-G148C- | GLP-1(A8S)-L0-Fc-L2-FGF21 (V103) |

TABLE 1 -continued

Dual Function Protein and Nucleotides of the invention

| SEQ ID NO: | Variant NO: | Sequence | Long Name | Short Name |
|---|---|---|---|---|
| | | SFFLYSKLTV DKSRWQQGNV FSCSVMHEAL HNHYTQKSLS LSPGKGSDSS PLLQFGGQVR QRYLYTDDAC QTEAHLEIRE DGTVGGAADQ SPESLLQLKA LKPGVIQILG VKTSRFLCQK PDGALYGSLH FDPEACSFRE LLLEDGYNVY QSEAHGLPLH LPCNRSPHRD PASRGPARFL PLPGLPPALP EPPGILAPQP PDVGSSDPLA MVGGSQARSP SYAS | K150R-P158S-S195A-P199G-G202A) | |
| 144 | V217 | HGEGTFTSDL SKQMEEEAVR LFIEWLKNGG PSSGAPPPSG GGGSGGGGSG GGGSTDTLLL WVLLLWVPGS TGHGEGTFTS DLSKQMEEEA VRLFIEWLKN GGPSSGAPPP SGGGGSGGGG SGGGGSDKTH TCPPCPAPEA AGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PGKGSDSSPL LQFGGQVRQR YLYTDDACQT EAHLEIREDG TVGGAADQSP ESLLQLKALK PGVIQILGVK TSRFLCQKPD GALYGSLHFD PEACSFRELL LEDGYNVYQS EAHGLPLHLP CNRSPHRDPA SRGPARFLPL PGLPPALPEP PGILAPQPPD VGSSDPLAMV GGSQARSPSY AS | Exendin4(1-39)-(GGGGS)<sub>3</sub>-Exendin4(1-39)-(GGGGS)3-Fc-GS-FGF21(33-209; Q55C-R105K-G148C-K150R-P158S-5195A-P199G-G202A) | Ex(1-39)-L15-Ex(1-39)-L15-Fc-L2-FGF21 (V103) |
| 145 | V278 | HSEGTFTSDV SSYLEGQAAK EFIAWLVKGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEDGYN VYQSEAHGLP LHLPGNRSPH CDPAPQGPAR FLPLPGLPPA LPEPPGILAP QPPDVGSSDP LAMVGPSQGR SPSYAS | GLP-1(7-35; A8S)-GSGGGGSGGG-FGF21(33-209; Q56E-D74H-Q82E-R105K-K150R-R154C-bis-maleimide dimer 40 kDa branched PEG-R159Q-5195A) | GLP-1(A8S)-L10-FGF21 (V76) Dimer-40KPEGb |
| 146 | V279 | HSEGTFTSDV SSYLEGQAAK EFIAWLVKGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEDGYN VYQSEAHGLP LHLPGNRSPH CDPAPQGPAR FLPLPGLPPA LPEPPGILAP QPPDVGSSDP LAMVGPSQGR SPSYAS | GLP-1(7-35; A8S)-GSGGGGSGGG-FGF21(33-209; Q56E-D74H-Q82E-R105K-K150R-R154C-bis-maleimide dimer 20 kDa branched PEG-R159Q-S195A) | GLP-1(A8S)-L10-FGF21 (V76) Dimer-20KPEGb |
| 147 | V280 | HSEGTFTSDV SSYLEGQAAK EFIAWLVKGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEDGYN VYQSEAHGLP LHLPGNRSPH CDPAPQGPAR FLPLPGLPPA LPEPPGILAP QPPDVGSSDP LAMVGPSQGR SPSYAS | GLP-1(7-35; A8S)-GSGGGGSGGG-FGF21(33-209; Q56E-D74H-Q82E-R105K-K150R-R154C-R159Q-S195A) | GLP-1(A8S)-L10-FGF21 (V76) |
| 148 | V283 | HGEGTFTSDL SKQMEEEAVR LFIEWLKNGG SGGGGSGGGG SGGGGSGGGG DSSPLLQFGG | Exendin4(1-30)- | Ex(1-30 - |

TABLE 1 -continued

Dual Function Protein and Nucleotides of the invention

| SEQ ID NO: | Variant NO: | Sequence | Long Name | Short Name |
|---|---|---|---|---|
| | | QVRQRYLYTD DAQETEAHLE IREDGTVGGA AHQSPESLLE LKALKPGVIQ ILGVKTSRFL CQKPDGALYG SLHFDPEACS FRELLLEDGY NVYQSEAHGL PLHLPGNRSP HCDPAPQGPA RFLPLPGLPP ALPEPPGILA PQPPDVGSSD PLAMVGPSQG RSPSYAS | S(GGGGS)₃GGG G-FGF21(33-209; Q56E-D74H-Q82E-R105K-K150R-R154C-R159Q-S195A) | L20-FGF21 (V76) |
| 149 | V284 | HGEGTFTSDL SKQMEEEAVR LFIEWLKNGG SGGGGSGGGG SGGGGSGGGG DSSPLLQFGG QVRQRYLYTD DAQETEAHLE IREDGTVGGA AHQSPESLLE LKALKPGVIQ ILGVKTSRFL CQKPDGALYG SLHFDPEACS FRELLLEDGY NVYQSEAHGL PLHLPGNRSP HCDPAPQGPA RFLPLPGLPP ALPEPPGILA PQPPDVGSSD PLS | Exendin4(1-30)-S(GGGGS)₃GGGG-FGF21(33-195; Q56E-D74H-Q82E-R105K-K150R-R154C-40 kDa branched PEG-R159Q) | Ex(1-30)-L20-FGF21 (V76; CΔ14)-40KPEGb |
| 150 | V285 | DLSKQMEEEA VRLFIEWLKN GGSGGGGSGG GGSGGGGSGG GGDSSPLLQF GGQVRQRYLY TDDAQETEAH LEIREDGTVG GAAHQSPESL LELKALKPGV IQILGVKTSR FLCQKPDGAL YGSLHFDPEA CSFRELLLED GYNVYQSEAH GLPLHLPGNR SPHCDPAPQG PARFLPLPGL PPALPEPPGI LAPQPPDVGS SDPLAMVGPS QGRSPSYAS | Exendin4(9-30)-S(GGGGS)₃GGGG-FGF21(33-209; Q56E-D74H-Q82E-R105K-K150R-R154C-40 kDa branched PEG-R159Q-S195A) | Ex(9-30)-L20-FGF21 (V76)-40KPEGb |
| 151 | V289 | GGQVRQRYLY TDDAQETEAH LEIREDGTVG GAAHQSPESL LELKALKPGV IQILGVKTSR FLCQKPDGAL YGSLHFDPEA CSFRELLLED GYNVYQSEAH GLPLHLPGNR SPHCDPAPQG PARFLPLPGL PPALPEPPGI LAPQPPDVGS SDPLAMVGPS QGRSPSYAS | FGF21(42-209; Q56E-D74H-Q82E-R105K-K150R-R154C-40 kDa branched PEG-R159Q-S195A) | FGF21(V 76; NΔ9) 40KPEGb |
| 152 | V290 | HSEGTFTSDV SSYLEGQAAK EFIAWLVKGG SGGGGSGGGG QVRQRYLYTD DAQETEAHLE IREDGTVGGA AHQSPESLLE LKALKPGVIQ ILGVKTSRFL CQKPDGALYG SLHFDPEACS FRELLLEDGY NVYQSEAHGL PLHLPGNRSP HCDPAPQGPA RFLPLPGLPP ALPEPPGILA PQPPDVGSSD PLAMVGPSQG RSPSYAS | GLP-1(7-35; A8S)-GSGGGGSGGG-FGF21(42-209; Q56E-D74H-Q82E-R105K-K150R-R154C-40 kDa branched PEG-R159Q-S195A) | GLP-1(A8S)-L10-FGF21 (V76; NΔ9)-40KPEGb |
| 153 | V291 | GVSTSEAKFE QDSAILWYGV EFAKLHTSGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEDGYN VYQSEAHGLP LHLPGNRSPH CDPAPQGPAR FLPLPGLPPA LPEPPGILAP QPPDVGSSDP LAMVGPSQGR SPSYAS | GLP-1(7-35; A8S scramble)-GSGGGGSGGG-FGF21(33-209; Q56E-D74H-Q82E-R105K-K150R-R154C-40 kDa branched | GLP-1(A8S; scramble)-L10-FGF21 (V76)-40KPEGb |

TABLE 1 -continued

Dual Function Protein and Nucleotides of the invention

| SEQ ID NO: | Variant NO: | Sequence | Long Name | Short Name |
|---|---|---|---|---|
| | | | PEG-R159Q-S195A) | |
| 154 | V311 | HSEGTFTSDV SSYLEGQAAK EFIAWLVKGG SGGGGSGGGD SSPLLQFGGQ VRQRYLYTDD AQETEAHLEI REDGTVGGAA HQSPESLLEL KALKPGVIQI LGVKTSRFLC QKPDGALYGS LHFDPEACSF RELLLEDGYN VYQSEAHGLP LHLPGNRSPH CDPAPQGPAR FLPLPGLPPA LPEPPGILAP QPPDVGSSDP LAMVGGSQGR SPSYAS | GLP-1(7-35; A8S)-GSGGGGSGGG-FGF21(33-209; Q56E-D74H-Q82E-R105K-K150R-R154C-40 kDa branched PEG-R159Q-S195A-P199G) | GLP-1(A8S)-L10-FGF21 (V76-P199G)-40KPEGb |
| 155 | | CATTCTGAAG GCACTTTTAC TAGCGATGTT TCTAGCTACC TGGAAGGCCA GGCTGCGAAA GAATTCATCG CGTGGCTGGT TAAAGGCGGT TCTGGTGGTG GTGGTTCTGG CGGTGGCGAC TCGAGCCCGC TGCTGCAATT TGGCGGCCAA GTGCGTCAGC GTTATCTGTA TACCGATGAT GCGCAGGAAA CCGAAGCGCA TCTGGAAATT CGTGAAGATG GCACCGTGGG CGGTGCGGCG CATCAGAGCC CGGAAAGCCT GCTGGAACTG AAAGCGCTGA AACCGGGCGT GATTCAGATT CTGGGCGTGA AAACCAGCCG TTTTCTGTGC CAGAAACCGG ATGGCGCGCT GTATGGCAGC CTGCATTTTG ATCCGGAAGC GTGCAGCTTT CGTGAACTGC TGCTGGAAGA TGGCTATAAC GTGTATCAGA GCGAAGCGCA TGGCCTGCCG CTGCATCTGC CGGGCAACCG TAGCCCGCAT TGCGATCCGG CACCGCAGGG TCCGGCGCGT TTTCTGCCGC TGCCGGGTCT GCCGCCGGCA CTGCCGGAAC CGCCGGGTAT TCTGGCCCCG CAGCCGCCGG ATGTTGGTAG CAGCGATCCG CTGGCGATGG TGGGTGGTAG CCAGGGTCGT AGCCCGAGCT ATGCGAGC | GLP-1(7-35; A8S)-GSGGGGSGGG-FGF21(33-209; Q56E-D74H-Q82E-R105K-K150R-R154C-40 kDa branched PEG-R159Q-S195A-P199G) | GLP-1(A8S)-L10-FGF21 (V76-P199G)-40KPEGb |
| 156 | V312 | HGEGTFTSDL SKQMEEEAVR LFIEWLKNGG SGGGGSGGGG SGGGGSGGGG DSSPLLQFGG QVRQRYLYTD DAQETEAHLE IREDGTVGGA AHQSPESLLE LKALKPGVIQ ILGVKTSRFL CQKPDGALYG SLHFDPEACS FRELLLEDGY NVYQSEAHGL PLHLPGNRSP HCDPAPQGPA RFLPLPGLPP ALPEPPGILA PQPPDVGSSD PLAMVGGSQG RSPSYAS | Exendin4(1-30)-S(GGGGS)₃GGGG-FGF21(33-209; Q56E-D74H-Q82E-R105K-K150R-R154C-40 kDa branched PEG-R159Q-S195A-P199G) | Ex(1-30)-L20-FGF21 (V76-P199G)-40KPEGb |
| 157 | | CATGGTGAGG GTACGTTTAC TTCTGATCTG TCTAAACAGA TGGAAGAAGA AGCTGTTCGC CTGTTCATTG AATGGCTGAA AAATGGTGGT TCTGGTGGTG GTGGTTCTGG CGGTGGCGGT TCTGGCGGCG GTGGTAGCGG TGGCGGCGGT GACTCGAGCC CGCTGCTGCA GTTTGGCGGC CAGGTGCGTC AGCGTTATCT GTATACCGAT GATGCGCAGG AAACCGAAGC GCATCTGGAA ATTCGTGAAG ATGGCACCGT GGGCGGTGCG GCGCATCAGA GCCCGGAAAG CCTGCTGGAA CTGAAAGCGC TGAAACCGGG CGTGATTCAG ATTCTGGGCG TGAAAACCAG CCGTTTTCTG TGCCAGAAAC CGGATGGCGC GCTGTATGGC AGCCTGCATT TTGATCCGGA AGCGTGCAGC TTTCGTGAAC TGCTGCTGGA AGATGGCTAT AACGTGTATC AGAGCGAAGC GCATGGCCTG CCGCTGCATC TGCCGGGCAA CCGTAGCCCG CATTGCGATC CGGCACCGCA GGGTCCGGCG CGT | Exendin4(1-30)-S(GGGGS)₃GGGG-FGF21(33-209; Q56E-D74H-Q82E-R105K-K150R-R154C-40 kDa branched PEG-R159Q-S195A-P199G) | Ex(1-30)-L20-FGF21 (V76-P199G)-40KPEGb |

TABLE 1 -continued

Dual Function Protein and Nucleotides of the invention

| SEQ ID NO: | Variant NO: | Sequence | Long Name | Short Name |
|---|---|---|---|---|
| | | CGTTTTCTGC CGCTGCCGGG TCTGCCGCCG GCACTGCCGG AACCGCCGGG TATTCTGGCC CCGCAGCCGC CGGATGTTGG TAGCAGCGAT CCGCTGGCGA TGGTGGGTGG TAGCCAGGGT CGTAGCCCGA GCTATGCGAG C | | |
| 158 | V313 | HGEGTFTSDL SKQMEEEAVR LFIEWLKNGG PSSGAPPPSG GGGSGGGGSG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG KGSDSSPLLQ FGGQVRQRYL YTDDACQTEA HLEIREDGTV GGAADQSPES LLQLKALKPG VIQILGVKTS RFLCQKPDGA LYGSLHFDPE ACSFRELLLE DGYNVYQSEA HGLPLHLPCN RSPHRDPASR GPARFLPLPG LPPALPEPPG ILAPQPPDVG SSDPLAMVGG SQARSPSYA | Exendin4(1-39)-(GGGGS)$_3$-Fc-GS-FGF21(33-208; Q55C-R105K-G148C-K150R-P158S-P174L-S195A-P199G-G202A) | Ex(1-39)-L15-Fc-L2-FGF21(V103; CA1) |
| 159 | V314 | HGEGTFTSDL SKQMEEEAVR LFIEWLKNGG PSSGAPPPSG GGGSGGGGSG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG KGSDSSPLLQ FGGQVRQRYL YTDDACQTEA HLEIREDGTV GGAADQSPES LLQLKALKPG VIQILGVKTS RFLCQKPDGA LYGSLHFDPE ACSFRELLLE DGYNVYQSEA HGLPLHLPCN RSPHRDPASR GPARFLPLPG LPPALPEPPG ILAPQPPDVG SSDPLAMVGG SQARSPSY | Exendin4(1-39)-(GGGGS)$_3$-Fc-GS-FGF21(33-207; Q55C-R105K-G148C-K150R-P158S-P174L-S195A-P199G-G202A) | Ex(1-39)-L15-Fc-L2-FGF21(V103; CA2) |
| 160 | V315 | HGEGTFTSDL SKQMEEEAVR LFIEWLKNGG PSSGAPPPSG GGGSGGGGSG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG KGSDSSPLLQ FGGQVRQRYL YTDDACQTEA HLEIREDGTV GGAADQSPES LLQLKALKPG VIQILGVKTS RFLCQKPDGA LYGSLHFDPE ACSFRELLLE DGYNVYQSEA HGLPLHLPCN RSPHRDPASR GPARFLPLPG LPPALPEPPG ILAPQPPDVG SSDPLAMVGG SQARSPS | Exendin4(1-39)-(GGGGS)$_3$-Fc-GS-FGF21(33-206; Q55C-R105K-G148C-K150R-P158S-P174L-S195A-P199G-G202A) | Ex(1-39)-L15-Fc-L2-FGF21(V103; CA3) |
| 161 | V316 | HGEGTFTSDL SKQMEEEAVR LFIEWLKNGG PSSGAPPPSG GGGSGGGGSG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG KGSDSSPLLQ FGGQVRQRYL YTDDACQTEA HLEIREDGTV GGAADQSPES LLQLKALKPG VIQILGVKTS RFLCQKPDGA LYGSLHFDPE ACSFRELLLE DGYNVYQSEA HGLPLHLPCN RSPHRDPASR GPARFLPLPG LPPALPEPPG ILAPQPPDVG SSDPLAMVGG SQARSPSYAS P | Exendin4(1-39)-(GGGGS)$_3$-Fc-GS-FGF21(33-209; Q55C-R105K-G148C-K150R-P158S-P174L-S195A-P199G-G202A)-P | Ex(1-39)-L15-Fc-L2-FGF21(V103)+P210 |

TABLE 1 -continued

Dual Function Protein and Nucleotides of the invention

| SEQ ID NO: | Variant NO: | Sequence | Long Name | Short Name |
|---|---|---|---|---|
| 162 | V317 | HGEGTFTSDL SKQMEEEAVR LFIEWLKNGG PSSGAPPPSG GGGSGGGGSG GGGSDKTHTC PPCPAPEAAG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG KGSDSSPLLQ FGGQVRQRYL YTDDACQTEA HLEIREDGTV GGAADQSPES LLQLKALKPG VIQILGVKTS RFLCQKPDGA LYGSLHFDPE ACSFRELLLE DGYNVYQSEA HGLPLHLPCN RSPHRDPASR GPARFLPLPG LPPALPEPPG ILAPQPPDVG SSDPLAMVGG SQARSPSYAA P | Exendin4(1-39)-(GGGGS)3-Fc-GS-FGF21 (33-209; Q55C-R105K-G148C-K150R-P158S-P174L-S195A-P199G-G202A-S209A)-p | Ex(1-39)-L15-Fc-L2-FGF21 (V103-S209A)+P210 |
| 163 | V225 | HAEGTFTSDVSSYLEGQAAKEFIAWLVKGGSG DSSPLLQFGGQVRQRYLYTDDAQQTEAHLEIR EDGTVGGAADQSPESLLQLKALKPGVIQILGV KTSRFLCQRPDGALYGSLHFDPEACSFRELLL EDGYNVYQSEAHGLPLHLPGNKSPHCDPAPRG PARFLPLPGLPPALPEPPGILAPQPPDVGSSD PLSMVGPSQGRSPSYAS | GLP-1(7-35)-SG-FGF21(33-209; R154C) | GLP-1-L2-FGF21 (154C) |
| 164 | V226 | HSEGTFTSDVSSYLEGQAAKEFIAWLVKGGSG DSSPLLQFGGQVRQRYLYTDDAQQTEAHLEIR EDGTVGGAADQSPESLLQLKALKPGVIQILGV KTSRFLCQRPDGALYGSLHFDPEACSFRELLL EDGYNVYQSEAHGLPLHLPGNKSPHCDPAPRG PARFLPLPGLPPALPEPPGILAPQPPDVGSSD PLSMVGPSQGRSPSYAS | GLP-1(7-35; A8S)-SG-FGF21(33-209; R154C) | GLP-1(A8S)-L2-FGF21 (154C) |
| 165 | V229 | HAEGTFTSDVSSYLEGQAAKEFIAWLVKGGSG DSSPLLQFGGQVRQRYLYTDDAQQTEAHLEIR EDGTVGGAADQSPESLLQLKALKPGVIQILGV KTSRFLCQRPDGALYGSLHFDPEACSFRELLL EDGYNVYQSEAHGLPLHLPGNKSPHCDPAPRG PARFLPLPGLPPALPEPPGILAPQPPDVGSSD PLSMVGPSQGRSPSYAS | GLP-1(7-35)-SG-FGF21(33-209; R154C-40 kDa linear PEG) | GLP-1-L2-FGF21 (154C)-40KPEG1 |
| 166 | V230 | HSEGTFTSDVSSYLEGQAAKEFIAWLVKGGSG DSSPLLQFGGQVRQRYLYTDDAQQTEAHLEIR EDGTVGGAADQSPESLLQLKALKPGVIQILGV KTSRFLCQRPDGALYGSLHFDPEACSFRELLL EDGYNVYQSEAHGLPLHLPGNKSPHCDPAPRG PARFLPLPGLPPALPEPPGILAPQPPDVGSSD PLSMVGPSQGRSPSYAS | GLP-1(7-35; A8S)-SG-FGF21(33-209; R154C-40 kDa linear PEG) | GLP-1(A8S)-L2-FGF21 (154C)-40KPEG1 |
| 167 | V231 | HAEGTFTSDVSSYLEGQAAKEFIAWLVKGGSG GGGSGGGDSSPLLQFGGQVRQRYLYTDDAQQT EAHLEIREDGTVGGAADQSPESLLQLKALKPG VIQILGVKTSRFLCQRPDGALYGSLHFDPEAC SFRELLLEDGYNVYQSEAHGLPLHLPGNKSPH CDPAPRGPARFLPLPGLPPALPEPPGILAPQP PDVGSSDPLSMVGPSQGRSPSYAS | GLP-1(7-35)-SGGGGSGGG-FGF21(33-209; R154C-40 kDa linear PEG) | GLP-1-L8-FGF21 (154C)-40KPEG1 |
| 168 | V232 | HSEGTFTSDVSSYLEGQAAKEFIAWLVKGGSG GGGSGGGDSSPLLQFGGQVRQRYLYTDDAQQT EAHLEIREDGTVGGAADQSPESLLQLKALKPG VIQILGVKTSRFLCQRPDGALYGSLHFDPEAC SFRELLLEDGYNVYQSEAHGLPLHLPGNKSPH CDPAPRGPARFLPLPGLPPALPEPPGILAPQP PDVGSSDPLSMVGPSQGRSPSYAS | GLP-1(7-35; A8S)-SGGGGSGGG-FGF21(33-209; R154C-40 kDa linear PEG) | GLP-1(A8S)-L8-FGF21(154C)-40KPEG1 |
| 169 | V237 | HAEGTFTSDVSSYLEGQAAKEFIAWLVKGGSG DSSPLLQFGGQVRQRYLYTDDAQQTEAHLEIR EDGTVGGAADQSPESLLQLKALKPGVIQILGV KTSRFLCQRPDGALYGSLHFDPEACSFRELLL EDGYNVYQSEAHGLPLHLPGNKSPHCDPAPRG PARFLPLPGLPPALPEPPGILAPQPPDVGSSD PLSMVGPSQGRSPSYAS | GLP-1(7-35)-SG-FGF21(33-209; R154C-40 kDa branched PEG) | GLP-1-L2-FGF21 (154C)-40KPEGb |

TABLE 1 -continued

Dual Function Protein and Nucleotides of the invention

| SEQ ID NO: | Variant NO: | Sequence | Long Name | Short Name |
|---|---|---|---|---|
| 170 | V238 | GDSSPLLQFGGQVRQRYLYTDDAQQTEAHLEI REDGTVGGAADQSPESLLQLKALKPGVIQILG VKTSRFLCQRPDGALYGSLHFDPEACSFRELL LEDGYNVYQSEAHGLPLHLPGNKSPHCDPAPR GPARFLPLPGLPPALPEPPGILAPQPPDVGSS DPLSMVGPSQGRSPSYAS | G-FGF21(33-209; R154C-40 kDa branched PEG) | FGF21 (R154C)-40KPEGb |
| 171 | V253 | HSEGTFTSDVSSYLEGQAAKEFIAWLVKGGSG GGGSGGGDSSPLLQFGGQVRQRYLYTDDAQQT EAHLEIREDGTVGGAADQSPESLLQLKALKPG VIQILGVKTSRFLCQRPDGALYGSLHFDPEAC SFRELLLEDGYNVYQSEAHGLPLHLPGNKSPH CDPAPRGPARFLPLPGLPPALPEPPGILAPQP PDVGSSDPLS | GLP-1(7-35; A8S)-SGGGGSGGG-FGF21(33-194; R154C-40 kDa branched PEG) | GLP-1(A8S)-L8-FGF21-(C414; 154C)-40KPEGb |
| 172 | V258 | HGEGTFTSDVSSYLEGQAAKEFIAWLVKGGSG GGGSGGGDSSPLLQFGGQVRQRYLYTDDAQQT EAHLEIREDGTVGGAADQSPESLLQLKALKPG VIQILGVKTSRFLCQRPDGALYGSLHFDPEAC SFRELLLEDGYNVYQSEAHGLPLHLPGNKSPH CDPAPRGPARFLPLPGLPPALPEPPGILAPQP PDVGSSDPLSMVGPSQGRSPSYAS | GLP-1(7-35; A8G)-SGGGGSGGG-FGF21(33-209; R154C-40 kDa branched PEG) | GLP-1(A8G)-L8-FGF21 (154C)-40KPEGb |

The variants or mutants used in the proteins of the invention, e.g., variants of wild-type FGF21, GLP-1, and/or Exendin-4 feature at least one substituted, added, and/or removed amino acid relative to the wild-type protein. Additionally, the variants may include N- and/or C-terminal truncations relative to the wild-type proteins. Generally speaking, a variant possesses some modified property, structural or functional, of the wild-type protein. For example, the variant may have enhanced or improved physical stability in concentrated solutions (e.g., less hydrophobic mediated aggregation), enhanced or improved plasma stability when incubated with blood plasma or reduced risk for immunogenicity or enhanced or improved bioactivity while maintaining a favorable bioactivity profile.

Acceptable amino acid substitutions and modifications which constitute differences between the portions of the proteins of the invention and their wild-type comparator proteins include, but are not limited to, one or more amino acid substitutions, including substitutions with pyrrolysine, pyrroline-carboxy-lysine (Pcl) and non-naturally occurring amino acid analogs, and truncations. Thus, the proteins of the invention (e.g., the fusion proteins of the invention) include, but are not limited to, site-directed mutants, truncated polypeptides, proteolysis-resistant mutants, aggregation-reducing mutants, combination mutants, and fusion proteins, as described herein.

One skilled in the art of expression of proteins will recognize that methionine or methionine-arginine sequence can be introduced at the N-terminus of any of the proteins of the invention, for expression in E. coli, and are contemplated within the context of this invention.

One skilled in the art of expression of proteins will recognize that additional tags or fusion domains for the purposes of modulating expression levels, purification, or stabilization can be introduced to the N-terminus of any of the proteins of the invention, with or without an additional peptide to target digestion by a specific protease for later removal of that tag or fusion domain, for expression in any host cell, and are contemplated within the context of this invention.

One skilled in the art of expression of proteins will recognize that leader peptides targeting the expressed protein to the periplasm or extracellular space can be introduced at the N-terminus of any of the proteins of the invention, for expression in E. coli or other bacterial hosts, and are contemplated within the context of this invention.

One skilled in the art of expression of proteins will recognize that leader peptides targeting the expressed protein to the ER, secretory vesicles, or extracellular space can be introduced at the N-terminus of any of the proteins of the invention, for expression in eukaryotic host cells, and are contemplated within the context of this invention.

The proteins of the invention may possess increased compatibility with pharmaceutical preservatives (e.g., m-cresol, phenol, benzyl alcohol), thus enabling the preparation of a preserved pharmaceutical formulation that maintains the physiochemical properties and biological activity of the protein during storage. Accordingly, variants with enhanced pharmaceutical stability relative to wild-type, have improved physical stability in concentrated solutions under both physiological and preserved pharmaceutical formulation conditions, while maintaining biological potency. By way of non-limiting example, the proteins of the invention may be more resistant to proteolysis and enzymatic degradation; may have improved stability; and may be less likely to aggregate, than their wild-type counterparts or corresponding native sequence. As used herein, these terms are not mutually exclusive or limiting, it being entirely possible that a given variant has one or more modified properties of the wild-type protein.

The invention also encompasses nucleic acid molecules encoding the proteins of the invention, comprising, for example, an FGF21 amino acid sequence that is at least about 95% identical to the amino acid sequence of SEQ ID NO:3, but wherein specific residues conferring a desirable property to the FGF21 protein variant, e.g., improved potency to FGF21-receptors, proteolysis-resistance, increased half-life or aggregation-reducing properties and combinations thereof have not been further modified. In other words, with the exception of residues in the FGF21 mutant sequence that have been modified in order to confer proteolysis-resistance, aggregation-reducing, or other properties, about 5% (alternately 4%, alternately 3%, alternately 2%, alternately 1%) of all other amino acid residues in the FGF21 mutant sequence can be modified. Such FGF21 mutants possess at least one activity of the wild-type FGF21 polypeptide.

Similarly, the invention also comprises nucleic acid molecules encoding the GLP-1 and Exendin-4 portions of the molecule, whose amino acid sequences are at least about 85%, identical, and more preferably at least about 90 to 95% identical, to the amino acid sequence of SEQ ID NO:30 and 7, respectively, but wherein specific residues conferring a desirable property to the dual function protein variant, e.g., proteolysis-resistance, increased half-life or aggregation-reducing properties and combinations thereof have not been further modified.

The invention also encompasses a nucleic acid molecule comprising a nucleotide sequence that is at least about 85%, identical, and more preferably, at least about 90 to 95% identical to the nucleotide sequence of SEQ ID NO:2, SEQ ID NO:4, SEQ ID NO:6, and the cDNA sequence encoding wild-type Exendin-4, but wherein the nucleotides encoding amino acid residues conferring the encoded protein's proteolysis-resistance, aggregation-reducing or other properties have not been further modified. In other words, with the exception of nucleotides that encode residues in the FGF21, GLP-1, or Exendin-4 mutant sequences that have been modified in order to confer proteolysis-resistance, aggregation-reducing, or other properties, about 15%, and more preferably about 10 to 5% of all other nucleotides in the mutant sequence can be modified. Such nucleic acid molecules encode proteins possessing at least one activity of their wild-type counterparts.

Provided herein are methods used to generate the proteins of the invention, wherein such methods involve site-specific modification and non-site-specific modification of the wild-type versions of the proteins (e.g., the FGF21 wild-type protein as described herein), e.g., truncations of the wild-type proteins, and the site-specific incorporation of amino acids at positions of interest within the wild-type proteins. Said modifications enhance the biological properties of the proteins of the invention relative to the wild-type proteins, as well as, in some cases, serving as points of attachment for, e.g., labels and protein half-life extension agents, and for purposes of affixing said variants to the surface of a solid support. Related embodiments of the invention are methods of producing cells capable of producing said dual function proteins of the invention, and of producing vectors containing DNA encoding said variants.

In certain embodiments, such modifications, e.g., site-specific modifications, are used to attach conjugates, e.g., PEG groups to proteins, polypeptides, and/or peptides of the invention, for purposes of, e.g., extending half-life or otherwise improving the biological properties of said proteins, polypeptides, and/or peptides. Said techniques are described further herein.

In other embodiments, such modifications, e.g., site-specific modifications are used to attach other polymers, small molecules and recombinant protein sequences that extend half-life of the protein of the invention. One such embodiment includes the attachment of fatty acids or specific albumin binding compounds to proteins, polypeptides, and/or peptides. In other embodiments, the modifications are made at a particular amino acid type and may be attached at one or more sites on the protein.

In other embodiments, such modifications, e.g., site-specific modifications are used as means of attachment for the production of wild-type and/or variant multimers, e.g., dimers (homodimers or heterodimers) or trimers or tetramers. These multimeric protein molecules may additionally have groups such as PEG, sugars, and/or PEG-cholesterol conjugates attached or be fused either amino-terminally or carboxy-terminally to other proteins such as Fc, Human Serum Albumin (HSA), etc.

In other embodiments, such site-specific modifications are used to produce proteins, polypeptides and/or peptides wherein the position of the site-specifically incorporated pyrrolysine, pyrroline-carboxy-lysine, or pyrrolysine analogue or non-naturally occurring amino acids (para-acetyl-Phe, para-azido-Phe) allows for controlled orientation and attachment of such proteins, polypeptides and/or peptides onto a surface of a solid support or to have groups such as PEG, sugars and/or PEG-cholesterol conjugates attached.

In other embodiments, such site-specific modifications are used to site-specifically cross-link proteins, polypeptides and/or peptides thereby forming hetero-oligomers including, but not limited to, heterodimers and heterotrimers. In other embodiments, such site-specific modifications are used to site-specifically cross-link proteins, polypeptides and/or peptides thereby forming protein-protein conjugates, protein-polypeptide conjugates, protein-peptide conjugates, polypeptide-polypeptide conjugates, polypeptide-peptide conjugates or peptide-peptide conjugates. In other embodiments, a site specific modification may include a branching point to allow more than one type of molecule to be attached at a single site of a protein, polypeptide or peptide.

In other embodiments, the modifications listed herein can be done in a non-site-specific manner and result in protein-protein conjugates, protein-polypeptide conjugates, protein-peptide conjugates, polypeptide-polypeptide conjugates, polypeptide-peptide conjugates or peptide-peptide conjugates of the invention.

Definitions

Various definitions are used throughout this document. Most words have the meaning that would be attributed to those words by one skilled in the art. Words specifically defined either below or elsewhere in this document have the meaning provided in the context of the present invention as a whole and as are typically understood by those skilled in the art.

As used herein, the term "FGF21" refers to a member of the fibroblast growth factor (FGF) protein family. An amino acid sequence of FGF21 (GenBank Accession No. NP_061986.1) is set forth as SEQ ID NO:1, the corresponding polynucleotide sequence of which is set forth as SEQ ID NO:2 (NCBI reference sequence number NM_019113.2). "FGF21 variant," "FGF21 mutant," and similar terms describe modified version of the FGF21 protein, e.g., with constituent amino acid residues deleted, added, modified, or substituted.

As used herein, the term "FGF21 receptor" refers to a receptor for FGF21 (Kharitonenkov, A, et al. (2008) Journal of Cellular Physiology 215:1-7; Kurosu, H et al. (2007) JBC 282:26687-26695; Ogawa, Y et al. (2007) PNAS 104:7432-7437). The term "FGF21 polypeptide" refers to a naturally-occurring polypeptide expressed in humans. For purposes of this disclosure, the term "FGF21 polypeptide" can be used interchangeably to refer to any full-length FGF21 polypeptide, e.g., SEQ ID NO:1, which consists of 209 amino acid residues and which is encoded by the nucleotide sequence of SEQ ID NO:2; any mature form of the polypeptide, which consists of 181 amino acid residues, and in which the 28 amino acid residues at the amino-terminal end of the full-length FGF21 polypeptide (i.e., which constitute the signal peptide) have been removed.

"Variant 76," or "V76," as used herein, is an FGF21 protein variant, featuring a 40 kDa branched PEG linked through Cys154, and eight point mutations relative to the 177 amino acid wild-type protein, for example, SEQ ID NO: 185 or SEQ ID NO: 186 which is v76 with a P199G mutation. Synthesis of the variant is described in greater detail herein.

"Variant 101," or "V101," as used herein, is an FGF21 protein variant, featuring an engineered disulfide bridge, and eight point mutations relative to the 177 amino acid wild-type protein, for example, SEQ ID NO: 187, expressed as a fusion to human IgG1 Fc-domain with a GS linker. Synthesis of the variant is described in greater detail herein.

"Variant 103," or "V103," as used herein, is an FGF21 protein variant, featuring an engineered disulfide bridge, and eight point mutations relative to the 177 amino acid wild-type protein, for example, SEQ ID NO: 188, expressed as a fusion to human IgG1 Fc-domain with a GS linker. Synthesis of the variant is described in greater detail herein.

"Variant 188," or "V188," as used herein, is an FGF21 protein variant, featuring an engineered disulfide bridge, and eight point mutations relative to the 177 amino acid wild-type protein, expressed as a fusion to human IgG1 Fc-domain with a (SGGGG)$_3$ linker. Synthesis of the variant is described in greater detail herein "GLP-1-FGF21-PEG dual agonists," "dual function proteins," "dual function fusion proteins," "dual activity proteins," "fusion products," "dual FGF21 receptor agonist and GLP-1 receptor agonist," "dual FGF21 receptor agonist and GLP-1 receptor agonist proteins of the invention," "GLP-1-FGF21 fusion proteins," "fusion proteins of the invention," "fusions of the invention," and similar terms define protein or polypeptide fusions comprising at least an FGF21 polypeptide or protein variant, mutant, or truncated version, fused or linked to another metabolic regulator such as GLP-1 or Exendin-4. They comprise a single molecule with dual activity or dual function vis-à-vis the receptors of their respective constituents, i.e., they show the ability to agonize the FGF21 receptor and the GLP-1 receptor. The constituent sequences of said fusion proteins may comprise modifications, truncations, other variants of naturally occurring (i.e., wild-type) protein or polypeptide counterparts, and may employ any number of various other modifications, e.g., PEG groups for half-life extension.

A particularly preferred embodiment of the GLP-1-FGF21-PEG fusion protein of the invention incorporates V76 (as defined herein) as the FGF21 variant. Said preferred embodiment is also referred to herein as "GLP-1(A8S)-FGF21-PEG" and features a substitution from alanine to serine at position 8 relative to the wild-type GLP-1 sequence (SEQ ID NO:5129) and substitution from arginine to cysteine at position 154 relative to the wild-type FGF21 sequence (SEQ ID:1). The sequence of GLP-1(A8S)-FGF21 (V76)-PEG is as follows (SEQ ID NO:9).

```
  1 HSEGTFTSDV SSYLEGQAAK EFIAWLVKGG SGGGGSGGGD SSPLLQFGGQ VRQRYLYTDD
 61 AQETEAHLEI REDGTVGGAA HQSPESLLEL KALKPGVIQI LGVKTSRFLC QKPDGALYGS
121 LHFDPEACSF RELLLEDGYN VYQSEAHGLP LHLPGNRSPH CDPAPQGPAR FLPLPGLPPA
181 LPEPPGILAP QPPDVGSSDP LAMVGPSQGR SPSYAS
```

The term "isolated nucleic acid molecule" refers to a nucleic acid molecule of the present invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecules or other contaminants that are found in its natural environment that would interfere with its use in polypeptide production or its therapeutic, diagnostic, prophylactic or research use.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "operably linked" is used herein to refer to an arrangement of flanking sequences wherein the flanking sequences so described are configured or assembled so as to perform their usual function. Elements of fusions proteins may be operably linked to one another so as to allow the fusion protein to function as if it were a naturally occurring, endogenous protein, and/or to combine disparate elements of said fusion proteins in a synergistic fashion.

On a nucleotide level, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "amino acid," as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission.

The term "naturally occurring" when used in connection with biological materials such as nucleic acid molecules, polypeptides, host cells, and the like, refers to materials which are found in nature and are not manipulated by man. Similarly, "non-naturally occurring" as used herein refers to a material that is not found in nature or that has been structurally modified or synthesized by man. When used in connection with nucleotides, the term "naturally occurring" refers to the bases adenine (A), cytosine (C), guanine (G), thymine (T), and uracil (U). When used in connection with amino acids, the term "naturally occurring" refers to the 20 conventional amino acids (i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y)), as well as selenocysteine, pyrrolysine (Pyl, or O), and pyrroline-carboxy-lysine (Pcl, or Z).

Pyrrolysine (Pyl) is an amino acid naturally found within methylamine methyltransferases of methanogenic archaea of the family *Methanosarcina*. Pyrrolysine is a lysine analogue co-translationally incorporated at in-frame UAG codons in the respective mRNA, and it is considered the 22nd natural amino acid.

As described at least in PCT patent publication WO2010/48582 (applicant IRM, LLC), attempts to biosynthesize pyrrolysine (Pyl) in *E. coli* resulted in the formation of a "demethylated pyrrolysine," referred to herein as pyrroline-carboxy-lysine, or Pcl. "Pcl," as used herein, refers to either Pcl-A or Pcl-B.

The terms "non-natural amino acid" and "unnatural amino acid," as used herein, are interchangeably intended to represent amino acid structures that cannot be generated biosynthetically in any organism using unmodified or modified genes from any organism, whether the same or different. The terms refer to an amino acid residue that is not present in the naturally occurring (wild-type) FGF21 protein sequence or the sequences of the present invention. These include, but are not limited to, modified amino acids and/or amino acid analogues that are not one of the 20 naturally occurring amino acids, selenocysteine, pyrrolysine (Pyl), or pyrroline-carboxy-lysine (Pcl, e.g., as described in PCT patent publication WO2010/48582). Such non-natural amino acid residues can be introduced by substitution of naturally occurring amino acids, and/or by insertion of non-natural amino acids into the naturally occurring (wild-type) FGF21 protein sequence or the sequences of the invention. The non-natural amino acid residue also can be incorporated such that a desired functionality is imparted to the FGF21 molecule, for example, the ability to link a functional moiety (e.g., PEG). When used in connection with amino acids, the symbol "U" shall mean "non-natural amino acid" and "unnatural amino acid," as used herein.

In addition, it is understood that such "unnatural amino acids" typically require a modified tRNA and a modified tRNA synthetase (RS) for incorporation into a protein. These "selected" orthogonal tRNA/RS pairs are generated by a selection process as developed by Schultz et al. or by random or targeted mutation. As way of example, pyrroline-carboxy-lysine is a "natural amino acid" as it is generated biosynthetically by genes transferred from one organism into the host cells and as it is incorporated into proteins by using natural tRNA and tRNA synthetase genes, while p-aminophenylalanine (See, Generation of a bacterium with a 21 amino acid genetic code, Mehl R A, Anderson J C, Santoro S W, Wang L, Martin A B, King D S, Horn D M, Schultz P G. J Am Chem Soc. 2003 Jan. 29; 125(4):935-9) is an "unnatural amino acid" because, although generated biosynthetically, it is incorporated into proteins by a "selected" (i.e. not "naturally-occurring") orthogonal tRNA/tRNA synthetase pair.

Modified encoded amino acids include, but are not limited to, hydroxyproline, γ-carboxyglutamate, 0-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. The term "amino acid" also includes naturally occurring amino acids that are metabolites in certain organisms but are not encoded by the genetic code for incorporation into proteins. Such amino acids include, but are not limited to, ornithine, D-ornithine, and D-arginine.

The term "amino acid analogue," as used herein, refers to compounds that have the same basic chemical structure as a naturally occurring amino acid, by way of example only, an α-carbon that is bound to a hydrogen, a carboxyl group, an amino group, and an R group. Amino acid analogues include the natural and unnatural amino acids which are chemically blocked, reversibly or irreversibly, or their C-terminal carboxy group, their N-terminal amino group and/or their side-chain functional groups are chemically modified. Such analogues include, but are not limited to, methionine sulfoxide, methionine sulfone, S-(carboxymethyl)-cysteine, S-(carboxymethyl)-cysteine sulfoxide, S-(carboxymethyl)-cysteine sulfone, aspartic acid-(beta-methyl ester), N-ethylglycine, alanine carboxamide, homoserine, norleucine, and methionine methyl sulfonium.

The term "amino acid mimetics," as used herein, refers to chemical compounds that have a structure that is different from the general chemical structure of an amino acid, but functions in a manner similar to a naturally occurring amino acid.

The term "biologically active variant" refers to any polypeptide variant used in the dual function proteins of the invention, e.g., as a constituent protein of the fusions, that possesses an activity of its wild-type (e.g., naturally-occurring) protein or polypeptide counterpart, such as the ability to modulate blood glucose, HbA1c,☐ insulin, triglyceride, or cholesterol levels; increase pancreatic function; reduce lipid levels in liver; reduce body weight; and to improve glucose tolerance, energy expenditure, or insulin sensitivity, regardless of the type or number of modifications that have been introduced into the polypeptide variant. Polypeptide variants possessing a somewhat decreased level of activity relative to their wild-type versions can nonetheless be considered to be biologically active polypeptide variants. A non-limiting representative example of a biologically active polypeptide variant of the invention is an FGF21 variant, which is modified after, and possesses similar or enhanced biological properties relative to, wild-type FGF21.

The terms "effective amount" and "therapeutically effective amount" each refer to the amount of a fusion protein of the invention used to support an observable level of one or more biological activities of the wild-type polypeptide or protein counterparts, such as the ability to lower blood glucose, insulin, triglyceride or cholesterol levels; reduce liver triglyceride or lipid levels; reduce body weight; or improve glucose tolerance, energy expenditure, or insulin sensitivity. For example, a "therapeutically-effective amount" administered to a patient exhibiting, suffering, or prone to suffer from FGF21-associated disorders or GLP-1-associated disorders (such as type 1 or type 2 diabetes mellitus, obesity, or metabolic syndrome), is such an amount which induces, ameliorates or otherwise causes an improvement in the pathological symptoms, disease progression, physiological conditions associated with or resistance to succumbing to the afore mentioned disorders. For the purposes of the present invention a "subject" or "patient" is preferably a human, but can also be an animal, more specifically, a companion animal (e.g., dogs, cats, and the like), farm animals (e.g., cows, sheep, pigs, horses, and the like) and laboratory animals (e.g., rats, mice, guinea pigs, and the like).

The term "pharmaceutically acceptable carrier" or "physiologically acceptable carrier" as used herein refers to one or more formulation materials suitable for accomplishing or enhancing the delivery of a fusion protein of the invention.

The term "antigen" refers to a molecule or a portion of a molecule that is capable of being bound by an antibody, and additionally that is capable of being used in an animal to produce antibodies that are capable of binding to an epitope of that antigen. An antigen may have one or more epitopes.

The term "native Fc" refers to molecule or sequence comprising the sequence of a non-antigen-binding fragment resulting from digestion of whole antibody or produced by other means, whether in monomeric or multimeric form, and can contain the hinge region. The original immunoglobulin source of the native Fc is preferably of human origin and can be any of the immunoglobulins, although IgG1 and IgG2 are preferred. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgA2). One example of a native Fc is a disulfide-bonded dimer resulting from papain digestion of an IgG (see Ellison et al., 1982, Nucleic Acids Res. 10: 4071-9). The term "native Fc" as used herein is generic to the monomeric, dimeric, and multimeric forms. The term "Fc variant" refers to a molecule or sequence that is modified from a native Fc but still comprises a binding site for the salvage receptor, FcRn (neonatal Fc receptor). International Publication Nos. WO 97/34631 and WO 96/32478 describe exemplary Fc variants, as well as interaction with the salvage receptor, and are hereby incorporated by reference. Thus, the term "Fc variant" can comprise a molecule or sequence that is humanized from a non-human native Fc. Furthermore, a native Fc comprises regions that can be removed because they provide structural features or biological activity that are not required for the fusion molecules of the Proteins of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "Fc domain" encompasses native Fc and Fc variants and sequences as defined above. As with Fc variants and native Fc molecules, the term "Fc domain" includes molecules in monomeric or multimeric form, whether digested from whole antibody or produced by other means. In some embodiments of the present invention, an Fc domain can be fused to FGF21 or a FGF21 mutant (including a truncated form of FGF21 or a FGF21 mutant) via, for example, a covalent bond between the Fc domain and the FGF21 sequence. Such fusion proteins can form multimers via the association of the Fc domains and both these fusion proteins and their multimers are an aspect of the present invention.

As used in the present text, the term "fusobody" refers to an antibody-like soluble protein comprising two heterodimers, each heterodimer consisting of one heavy and one light chains of amino acids, stably associated together, for example, via one or more disulfide bond(s). Each heavy or light chain comprises constant regions of an antibody, referred hereafter respectively as the heavy and light chain constant regions of the fusobody. The heavy chain constant region comprises at least $C_H1$ region of an antibody and may further comprise $C_H2$ and $C_H3$ regions, including the hinge region. The light chain constant region comprises $C_L$ region of an antibody. In a fusobody, the variable regions of an antibody are replaced by heterologous soluble binding domains. By way of non-limiting example, a fusobody of the invention can comprise a dual function fusion protein of the invention, wherein the GLP-1 receptor agonist is fused to the N-terminus of heavy and light chain of an antibody and FGF21 is simultaneously fused to the C-terminus of heavy and light chain of the same antibody.

The term "heterologous" means that these domains are not naturally found associated with constant regions of an antibody. In particular, such heterologous binding domains do not have the typical structure of an antibody variable domain consisting of 4 framework regions, FR1, FR2, FR3 and FR4 and the 3 complementarity determining regions (CDRs) in-between. Each arm of the fusobody therefore comprises a first single chain polypeptides comprising a first binding domain covalently linked at the N-terminal part of a constant $C_H1$ heavy chain region of an antibody, and a second single chain polypeptide comprising a second binding domain covalently linked at the N-terminal part of a constant $C_L$ light chain of an antibody. The covalent linkage may be direct, for example via peptidic bound or indirect, via a linker, for example a peptidic linker. The two heterodimers of the fusobody are covalently linked, for example, by at least one disulfide bridge at their hinge region, like an antibody structure. Examples of molecules with a fusobody structure have been described in the art, in particular, fusobodies comprising ligand binding region of heterodimeric receptor (see for example international patent publications WO01/46261 and WO11/076781).

The term "polyethylene glycol" or "PEG" refers to a polyalkylene glycol compound or a derivative thereof, with or without coupling agents or derviatization with coupling or activating moieties.

The term "Exenatide" indicates a synthetic version of exendin-4, Exenatide, marketed as Byetta and Bydureon, is a glucagon-like peptide-1 agonist (GLP-1 agonist) medication approved in April 2005 for the treatment of diabetes mellitus type 2. It belongs to the group of incretin mimetics and is manufactured by Amylin Pharmaceuticals.

Exendin-4 is a 39 residue polypeptide produced in the salivary glands of the Gila Monster lizard (Goke et al. (1993) Diabetes 46:433-439; Fehmann et al. (1995) Endocrine Rev. 16:390-410). Although it is the product of a uniquely non-mammalian gene and appears to be expressed only in the salivary gland, Exendin-4 shares a 52% amino acid sequence homology with GLP-1 and in mammals interacts with the GLP-1 receptor (Goke, et al.; Thorens et al. (1993) Diabetes 42:1678-1682).

The term "FGF21-associated disorders," "GLP-1-associated disorders," "Exendin-4-associated disorders," and terms similarly used herein, includes obesity, type 1 and type 2 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, metabolic syndrome, acute myocardial infarction, hypertension, cardiovascular disease, atherosclerosis, peripheral arterial disease, stroke, heart failure, coronary heart disease, kidney disease, diabetic complications, neuropathy, gastroparesis, disorders associated with severe inactivating mutations in the insulin receptor, lipodystrophies including HIV-associated lipodystrophy, and other metabolic disorders.

The term "disorders associated with severe inactivating mutations in the insulin receptor," and terms similarly used herein, describe conditions in subjects afflicted with mutations in the insulin receptor (or possible proteins directly downstream from it) which cause severe insulin resistance but are often (though not always) seen without the obesity common in Type 2 diabetes mellitus. In many ways, subjects afflicted with these conditions manifest hybrid symptoms of Type 1 diabetes mellitus and Type 2 diabetes mellitus. Subjects thereby afflicted fall into several categories of roughly increasing severity, including: Type A Insulin Resistance, Type C Insulin Resistance (AKA HAIR-AN Syndrome), Rabson-Mendenhall Syndrome and finally Donohue's Syndrome or Leprechaunism. These disorders are associated with very high endogenous insulin levels, and very often, hyperglycemia. Subjects thereby afflicted also present with various clinical features associated with "insulin toxicity," including hyperandrogenism, polycystic ovarian syndrome (PCOS), hirsuitism, and acanthosis nigricans (excessive growth and pigmentation) in the folds of the skin.

"Lipodystrophies, including HIV-associated lipodystrophy" are disorders of adipose tissue characterized by a selective loss of body fat. Patients with lipodystrophy have a tendency to develop insulin resistance, hyperinsulinemia, hyperglycemia, hypertriglyceridemia and fatty liver. There are numerous forms of lipodystrophy that are inherited (genetic) or acquired. The genetic forms of lipodystrophy include congenital generalized lipodystrophy (the Berardinelli-Seip syndrome) and several types of familial partial lipodystrophy (the Dunnigan type, the Kobberling type, the mandibuloacral dysplasis type). The acquired forms of lipodystrophy include acquired generalized lipodystrophy (the Lawrence syndrome), acquired partial lipodystrophy (the Barraquer-Simons syndrome), and lipodystrophy induced by protease inhibitors and nucleoside reverse transcriptase inhibitors used to treat HIV.

"Type 2 diabetes mellitus" is a condition characterized by excess glucose production in spite of the availability of insulin, and circulating glucose levels remain excessively high as a result of inadequate glucose clearance.

"Type 1 diabetes mellitus" is a condition characterized by high blood glucose levels caused by total lack of insulin. This occurs when the body's immune system attacks the insulin-producing beta cells in the pancreas and destroys them. The pancreas then produces little or no insulin.

"Glucose intolerance" or Impaired Glucose Tolerance (IGT) is a pre-diabetic state of dysglycemia that is associated with increased risk of cardiovascular pathology. The pre-diabetic condition prevents a subject from moving glucose into cells efficiently and utilizing it as an efficient fuel source, leading to elevated glucose levels in blood and some degree of insulin resistance.

"Hyperglycemia" is defined as an excess of sugar (glucose) in the blood.

"Hypoglycemia", also called low blood sugar, occurs when your blood glucose level drops too low to provide enough energy for your body's activities.

"Hyperinsulinemia" is defined as a higher-than-normal level of insulin in the blood.

"Insulin resistance" is defined as a state in which a normal amount of insulin produces a subnormal biologic response.

"Obesity," in terms of the human subject, can be defined as that body weight over 20 percent above the ideal body weight for a given population (R. H. Williams, Textbook of Endocrinology, 1974, p. 904-916).

"Diabetic complications" are problems, caused by high blood glucose levels, with other body functions such as kidneys, nerves (neuropathies), feet (foot ulcers and poor circulation) and eyes (e.g. retinopathies). Diabetes also increases the risk for heart disease and bone and joint disorders. Other long-term complications of diabetes include skin problems, digestive problems, sexual dysfunction and problems with teeth and gums.

"Metabolic syndrome" can be defined as a cluster of at least three of the following signs: abdominal fat—in most men, a 40-inch waist or greater; high blood sugar—at least 110 milligrams per deciliter (mg/dl) after fasting; high triglycerides—at least 150 mg/dL in the bloodstream; low HDL—less than 40 mg/dl; and, blood pressure of 130/85 mmHg or higher.

"Pancreatitis" is inflammation of the pancreas.

"Dyslipidemia" is a disorder of lipoprotein metabolism, including lipoprotein overproduction or deficiency. Dyslipidemias may be manifested by elevation of the total cholesterol, low-density lipoprotein (LDL) cholesterol and triglyceride concentrations, and a decrease in high-density lipoprotein (HDL) cholesterol concentration in the blood.

"Nonalcoholic fatty liver disease (NAFLD)" is a liver disease, not associated with alcohol consumption, characterized by fatty change of hepatocytes.

"Nonalcoholic steatohepatitis (NASH)" is a liver disease, not associated with alcohol consumption, characterized by fatty change of hepatocytes, accompanied by intralobular inflammation and fibrosis.

"Hypertension" or high blood pressure that is a transitory or sustained elevation of systemic arterial blood pressure to a level likely to induce cardiovascular damage or other adverse consequences. Hypertension has been arbitrarily defined as a systolic blood pressure above 140 mmHg or a diastolic blood pressure above 90 mmHg.

"Cardiovascular diseases" are diseases related to the heart or blood vessels.

"Acute myocardial infarction" occurs when there is interruption of the blood supply to a part of the heart. The resulting ischemia and oxygen shortage, if left untreated for a sufficient period of time, can cause damage or death (infarction) of the heart muscle tissue (myocardium).

"Peripheral arterial disease" occurs when plaque builds up in the arteries that carry blood to the head, organs and limbs. Over time, plaque can harden and narrow the arteries which limits the flow of oxygen-rich blood to organs and other parts of the body.

"Atherosclerosis" is a vascular disease characterized by irregularly distributed lipid deposits in the intima of large and medium-sized arteries, causing narrowing of arterial lumens and proceeding eventually to fibrosis and calcification. Lesions are usually focal and progress slowly and intermittently. Limitation of blood flow accounts for most clinical manifestations, which vary with the distribution and severity of lesions.

"Stroke" is any acute clinical event, related to impairment of cerebral circulation, that lasts longer than 24 hours. A stroke involves irreversible brain damage, the type and severity of symptoms depending on the location and extent of brain tissue whose circulation has been compromised.

"Heart failure", also called congestive heart failure, is a condition in which the heart can no longer pump enough blood to the rest of the body.

"Coronary heart disease", also called coronary artery disease, is a narrowing of the small blood vessels that supply blood and oxygen to the heart.

"Kidney disease" or nephropathy is any disease of the kidney. Diabetic nephropathy is a major cause of morbidity and mortality in people with type 1 or type 2 diabetes mellitus.

"Neuropathies" are any diseases involving the cranial nerves or the peripheral or autonomic nervous system.

"Gastroparesis" is weakness of gastric peristalsis, which results in delayed emptying of the bowels.

"Click chemistry" is a term that was introduced by K. B. Sharpless in 2001 to describe reactions that are high yielding, wide in scope, create only byproducts that can be removed without chromatography, are stereospecific, simple to perform, and can be conducted in easily removable or benign solvents.

The critically ill patients encompassed by the present invention generally experience an unstable hypermetabolic state. This unstable metabolic state is due to changes in substrate metabolism, which may lead to relative deficiencies in some nutrients. Generally there is an increased oxidation of both fat and muscle.

Moreover, critically ill patients are preferably patients that experience systemic inflammatory response syndrome or respiratory distress. A reduction in morbidity means reducing the likelihood that a critically ill patient will develop additional illnesses, conditions, or symptoms or reducing the severity of additional illnesses, conditions, or symptoms. For example reducing morbidity may correspond to a decrease in the incidence of bacteremia or sepsis or complications associated with multiple organ failure.

As used herein, the singular forms "a," "an" and "the" include plural references unless the content clearly dictates otherwise. Thus, for example, reference to "an antibody" includes a mixture of two or more such antibodies.

As used herein, the term "about" refers to +1-20%, more preferably, +1-10%, or still more preferably, +1-5% of a value.

The terms "polypeptide" and "protein", are used interchangeably and refer to a polymeric form of amino acids of any length, which can include coded and non-coded amino acids, naturally and non-naturally occurring amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "individual", "subject", "host" and "patient" are used interchangeably and refer to any subject for whom diagnosis, treatment, or therapy is desired, particularly humans. Other subjects may include cattle, dogs, cats, guinea pigs, rabbits, rats, mice, horses, and the like. In some preferred embodiments the subject is a human.

As used herein, the term "sample" refers to biological material from a patient. The sample assayed by the present invention is not limited to any particular type.

Samples include, as non-limiting examples, single cells, multiple cells, tissues, tumors, biological fluids, biological molecules, or supernatants or extracts of any of the foregoing. Examples include tissue removed for biopsy, tissue removed during resection, blood, urine, lymph tissue, lymph fluid, cerebrospinal fluid, mucous, and stool samples. The sample used will vary based on the assay format, the detection method and the nature of the tumors, tissues, cells or extracts to be assayed. Methods for preparing samples are well known in the art and can be readily adapted in order to obtain a sample that is compatible with the method utilized.

As used herein, the term "biological molecule" includes, but is not limited to, polypeptides, nucleic acids, and saccharides.

As used herein, the term "modulating" refers to a change in the quality or quantity of a gene, protein, or any molecule that is inside, outside, or on the surface of a cell. The change can be an increase or decrease in expression or level of the molecule. The term "modulates" also includes changing the quality or quantity of a biological function/activity including, without limitation, the ability to lower blood glucose, insulin, triglyceride, or cholesterol levels; to reduce liver lipid or liver triglyceride levels; to reduce body weight; and to improve glucose tolerance, energy expenditure, or insulin sensitivity.

As used herein, the term "modulator" refers to a composition that modulates one or more physiological or biochemical events associated with an FGF21-associated disorder, such as type 1 or type 2 diabetes mellitus or a metabolic condition like obesity. Said events include but are not limited to the ability to lower blood glucose, insulin, triglyceride, or cholesterol levels; to reduce liver lipid or liver triglyceride levels; to reduce body weight; and to improve glucose tolerance, energy expenditure, or insulin sensitivity.

A "gene product" is a biopolymeric product that is expressed or produced by a gene. A gene product may be, for example, an unspliced RNA, an mRNA, a splice variant mRNA, a polypeptide, a post-translationally modified polypeptide, a splice variant polypeptide etc. Also encompassed by this term are biopolymeric products that are made using an RNA gene product as a template (i.e. cDNA of the RNA). A gene product may be made enzymatically, recombinantly, chemically, or within a cell to which the gene is native. In some embodiments, if the gene product is proteinaceous, it exhibits a biological activity. In some embodiments, if the gene product is a nucleic acid, it can be translated into a proteinaceous gene product that exhibits a biological activity.

"Modulation of FGF21 activity," "Modulation of GLP-1 activity," and "Modulation of Exendin-4 activity," as used herein, refers to an increase or decrease in FGF21, GLP-1, or Exendin-4 activity, respectively, that can be a result of, for example, interaction of an agent with an FGF21, GLP-1, or Exendin-4 polynucleotide or polypeptide, inhibition of FGF21, GLP-1, or Exendin-4 transcription and/or translation (e.g., through antisense or siRNA interaction with the FGF21, GLP-1, or Exendin-4 gene or FGF21, GLP-1, or Exendin-4 transcript, through modulation of transcription factors that facilitate FGF21, GLP-1, or Exendin-4 expression), and the like. For example, modulation of a biological activity refers to an increase or a decrease in a biological activity. FGF21, GLP-1, or Exendin-4 activity can be assessed by means including, without limitation, assaying blood glucose, insulin, triglyceride, or cholesterol levels in a subject, assessing FGF21, GLP-1, or Exendin-4 polypeptide levels, or by assessing FGF21, GLP-1, or Exendin-4 transcription levels.

Comparisons of FGF21, GLP-1, or Exendin-4 activity can also be accomplished by, e.g., measuring levels of an FGF21, GLP-1, or Exendin-4 downstream biomarker, and measuring increases in FGF21, GLP-1, or Exendin-4 signaling. FGF21, GLP-1, or Exendin-4 activity can also be assessed by measuring: cell signaling; kinase activity; glucose uptake into adipocytes; blood insulin, triglyceride, or cholesterol level fluctuations; liver lipid or liver triglyceride level changes; interactions between FGF21, GLP-1, or Exendin-4 and a receptor; or phosphorylation of an FGF21, GLP-1, or Exendin-4 receptor. In some embodiments phosphorylation of an FGF21, GLP-1, or Exendin-4 receptor can be tyrosine phosphorylation. In some embodiments modulation of FGF21, GLP-1, or Exendin-4 activity can cause modulation of an FGF21, GLP-1, or Exendin-4-related phenotype.

A "FGF21, GLP-1, or Exendin-4 downstream biomarker," as used herein, is a gene or gene product, or measurable indicia of a gene or gene product. In some embodiments, a gene or activity that is a downstream marker of FGF21, GLP-1, or Exendin-4 exhibits an altered level of expression. In some embodiments, an activity of the downstream marker is altered in the presence of an FGF21, GLP-1, or Exendin-4 modulator. In some embodiments, the downstream markers exhibit altered levels of expression when FGF21, GLP-1, or Exendin-4 signaling is perturbed with dual function protein of the present invention. For example, FGF21 downstream markers include, without limitation, glucose or 2-deoxy-glucose uptake, pERK and other phosphorylated or acetylated proteins or NAD levels.

As used herein, the term "up-regulates" refers to an increase, activation or stimulation of an activity or quantity. For example, FGF21, GLP-1, or Exendin-4 modulators, such as the dual function proteins of the invention, may increase or agonize the activity of an FGF21, GLP-1, or Exendin-4 receptor. In one embodiment, one or more of FGFR-1(IIIc), FGFR-2(IIIc), or FGFR-3(IIIc) and/or β-klotho may be up-regulated in response to a dual function protein of the invention. Up-regulation can also refer to an FGF21, GLP-1, or Exendin-4-related activity, such as e.g., the ability to lower blood glucose, insulin, triglyceride, or cholesterol levels; to reduce liver lipid or triglyceride levels; to reduce body weight; to improve glucose tolerance, energy expenditure, or insulin sensitivity; or to cause phosphorylation of an FGF21, GLP-1, or Exendin-4 receptor; or to increase an FGF21, GLP-1, or Exendin-4 downstream marker. For example, the FGFR21 receptor can be one or more of FGFR-1(IIIc), FGFR-2(IIIc), or FGFR-3(IIIc) and/or β-klotho. Up-regulation may range anywhere from 25% to 500% as compared to a control.

As used herein, the term "N-terminus" refers to at least the first 20 amino acids of a protein.

As used herein, the terms "N-terminal domain" and "N-terminal region" are used interchangeably and refer to a fragment of a protein that begins at the first amino acid of the protein and ends at any amino acid in the N-terminal half of the protein. For example, the N-terminal domain of FGF21 is from amino acid 1 of SEQ ID NO:1 to any amino acid between about amino acids 10 and 105 of SEQ ID NO:1.

As used herein, the term "C-terminus" refers to at least the last 20 amino acids of a protein.

As used herein, the terms "C-terminal domain" and "C-terminal region" are used interchangeably and refer to a fragment of a protein that begins at any amino acid in the C-terminal half of the protein and ends at the last amino acid of the protein. For example, the C-terminal domain of FGF21 begins at any amino acid from amino acid 105 to about amino acid 200 of SEQ ID NO:1 and ends at amino acid 209 of SEQ ID NO:1.

The term "domain" as used herein refers to a structural part of a biomolecule that contributes to a known or suspected function of the biomolecule. Domains may be co-extensive with regions or portions thereof and may also incorporate a portion of a biomolecule that is distinct from a particular region, in addition to all or part of that region.

As used herein, the term "signal domain" (also called "signal sequence" or "signal peptide") refers to a peptide domain that resides in a continuous stretch of amino acid sequence at the N-terminal region of a precursor protein (often a membrane-bound or secreted protein) and is involved in post-translational protein transport. In many cases the signal domain is removed from the full-length protein by specialized signal peptidases after the sorting process has been completed. Each signal domain specifies a particular destination in the cell for the precursor protein. The signal domain of FGF21 is amino acids 1-28 of SEQ ID NO:1.

As used herein, the term "receptor binding domain" refers to any portion or region of a protein that contacts a membrane-bound receptor protein, resulting in a cellular response, such as a signaling event.

As used herein, the term "ligand binding domain" refers to any portion or region of a fusion protein of the invention retaining at least one qualitative binding activity of a corresponding native sequence.

The term "region" refers to a physically contiguous portion of the primary structure of a biomolecule. In the case of proteins, a region is defined by a contiguous portion of the amino acid sequence of that protein. In some embodiments a "region" is associated with a function of the biomolecule.

The term "fragment" as used herein refers to a physically contiguous portion of the primary structure of a biomolecule. In the case of proteins, a portion is defined by a contiguous portion of the amino acid sequence of that protein and refers to at least 3-5 amino acids, at least 8-10 amino acids, at least 11-15 amino acids, at least 17-24 amino acids, at least 25-30 amino acids, and at least 30-45 amino acids. In the case of oligonucleotides, a portion is defined by a contiguous portion of the nucleic acid sequence of that oligonucleotide and refers to at least 9-15 nucleotides, at least 18-30 nucleotides, at least 33-45 nucleotides, at least 48-72 nucleotides, at least 75-90 nucleotides, and at least 90-130 nucleotides. In some embodiments, portions of biomolecules have a biological activity. In the context of the present invention, FGF21 polypeptide fragments do not comprise the entire FGF21 polypeptide sequence set forth in SEQ ID NO:1.

A "native sequence" polypeptide is one that has the same amino acid sequence as a polypeptide derived from nature. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

As used herein, the phrase "homologous nucleotide sequence," or "homologous amino acid sequence," or variations thereof, refers to sequences characterized by a homology, at the nucleotide level or amino acid level, of at least a specified percentage and is used interchangeably with "sequence identity." Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than humans, including, but not limited to, mammals. Homologous nucleotide sequences also include, but are not limited to, naturally occurring allelic variations and mutations of the nucleotide sequences set forth herein. Homologous amino acid sequences include those amino acid sequences which contain conservative amino acid substitutions and which polypeptides have the same binding and/or activity. In some embodiments, a nucleotide or amino acid sequence is homologous if it has at least 60% or greater, up to 99%, identity with a comparator sequence. In some embodiments, a nucleotide or amino acid sequence is homologous if it shares one or more, up to 60, nucleotide/amino acid substitutions, additions, or deletions with a comparator sequence. In some embodiments, the homologous amino acid sequences have no more than 5 or no more than 3 conservative amino acid substitutions.

Percent homology or identity can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489). In some embodiments, homology between the probe and target is between about 75% to about 85%. In some embodiments, nucleic acids have nucleotides that are at least about 95%, about 97%, about 98%, about 99% and about 100% homologous to SEQ ID NO:2, or a portion thereof.

Homology may also be at the polypeptide level. In some embodiments, constituent polypeptides of the dual function proteins of the invention may be at least 95% homologous to their full-length wild-type counterparts or corresponding native sequences, or to portions thereof. The degree or percentage identity of dual function proteins of the invention, or portions thereof, and different amino acid sequences is calculated as the number of exact matches in an alignment of the two sequences divided by the length of the "invention sequence" or the "foreign sequence", whichever is shortest. The result is expressed as percent identity.

As used herein, the term "mixing" refers to the process of combining one or more compounds, cells, molecules, and the like together in the same area. This may be performed, for example, in a test tube, petri dish, or any container that allows the one or more compounds, cells, or molecules, to be mixed.

As used herein, the term "substantially purified" refers to a compound (e.g., either a polynucleotide or a polypeptide or an antibody) that is removed from its natural environment and is at least 60% free, at least 75% free, and at least 90% free from other components with which it is naturally associated.

The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, lipid aggregates and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles.

Naturally occurring disulfide bonds, as provided by cysteine residues, generally increase thermodynamic stability of proteins. Successful examples of increased thermodynamic stability, as measured in increase of the melting temperature, are multiple disulfide-bonded mutants of the enzymes T4 lysozyme (Matsumura et al., PNAS 86:6562-6566 (1989)) and barnase (Johnson et al., J. Mol. Biol. 268:198-208 (1997)). An aspect of the present invention is an enhancement of the physical stability of FGF21 in the presence of a preservative, achieved by the presence of disulfide bonds within the variants, which constrain the flexibility of wild-type FGF21 and thereby limit access of the preservative to the hydrophobic core of the protein. Enhancement of the physical stability of FGF21 within the proteins of the present invention, due to the presence of disulfide bonds within the variants, can confer additional protection to said proteins, whether or not in the presence of a preservative, including but not limited to protection against fluctuations in environmental conditions such as pH and temperature.

Improvements of the Dual Function Proteins of the Invention Over Wild Type Protein Comparators and Combinations Thereof It is well known in the art that a significant challenge in the development of protein pharmaceuticals is to deal with the physical and chemical instabilities of proteins.

This is even more apparent when a protein pharmaceutical formulation is intended to be a multiple use, injectable formulation requiring a stable, concentrated and preserved solution, while maintaining a favorable bioactivity profile. Biophysical characterization of wild-type FGF21 in the literature established that a concentrated protein solution (>5 mg/ml), when exposed to stress conditions, such as high temperature or low pH, lead to accelerated association and aggregation (i.e., poor physical stability and biopharmaceutical properties). Exposure of a concentrated protein solution of FGF21 to pharmaceutical preservatives (e.g., m-cresol) also had a negative impact on physical stability.

Therefore, an embodiment of the present invention is to enhance physical stability of concentrated solutions, while maintaining chemical stability and biological potency, under both physiological and preserved formulation conditions. It is thought that association and aggregation may result from hydrophobic interactions, since, at a given protein concentration, temperature, and ionic strength have considerable impact on physical stability.

For the most part, non-conserved, presumed surface exposed amino acid residues are targeted. The local environment of these residues is analyzed and, those not deemed structurally important are selected for mutagenesis. One method to initiate specific changes is to further decrease the pI of the protein by introducing glutamic acid residues ("glutamic acid scan"). The introduction of charged substitutes can inhibit hydrophobic-mediated aggregation via charge-charge repulsion and potentially improve preservative compatibility. In addition, one skilled in the art would also recognize that with sufficient mutagenesis, the pI could be shifted into a basic pH range by the introduction of positive charge, with or without concomitant decrease in negative charge, thus allowing for charge-charge repulsion.

An additional difficulty associated with therapeutic applications of wild-type FGF21 as a biotherapeutic, for instance, is that its half-life is very short in vivo (on the order of 0.5 and 2 h, respectively, in mouse and primate). There is hence a need to develop follow-up compounds that are more efficacious either through higher potency or longer half-life. Similarly, various mechanisms have been employed to enhance serum half-life for GLP-1 (1-2 minutes due to rapid cleavage by endogenous proteases, particularly dipeptidyl peptidase-4 (DPP4)) through use of Exendin-4 or other analogues that are resistant to cleavage by DPP4 as well as further modifications and formulations for extended half-life or slow release of compound.

The proteins of the invention, e.g., dual FGF21 receptor agonist and GLP-1 receptor agonist proteins of the invention, were developed as a way to achieve the desirable effects of FGF21 and GLP-1 treatment at a higher potency and in a half-life-extended formulation. The co-administration of GLP-1 and FGF21 has been described in the literature, e.g., in patent publications WO2010/068735 and WO2009/020802, with data suggesting additive or synergistic effects of co-administration of GLP-1 and FGF21 for treatment of obesity and type 2 diabetes. However, co-localization of the two receptor agonists in a single molecule, e.g., in the form of the proteins of the invention, provides better access of both GLP-1 and FGF21 to tissues or cells and provides increased benefit over simple co-administration as separate entities. This advantage of combining two agonists into a single molecule compared to simple co-administration of each is especially advantageous for tissues in which both the GLP-1 and the FGF21 receptors are expressed in the same tissues, such as adipose, pancreatic β-cells, hepatic and hypothalamic cells. Dual FGF21 receptor agonist and GLP-1 receptor agonist proteins of the invention and other single dual activity entities have improved biological properties due to altered receptor trafficking, altered signal transduction effects and/or entropic (avidity) effects.

Because FGF21 and GLP-1 (or Exendin-4) act through different mechanisms, it is expected that they will have additive or synergistic effects when, for example, administered at the same time in the form of the dual function proteins of the invention. GLP-1 and Exendin-4 act primarily to increase insulin secretion in response to food intake while FGF21 sensitizes the body to respond better to insulin, which may provide benefit for both type 1 and type 2 diabetes in managing blood glucose levels. Beta-cell protective effects combined with the improved beta-cell function and insulin sensitivity has the potential to provide benefit even in type 1 diabetics.

Another example is weight loss: The satiety signal and slowed gastric emptying by GLP-1 or Exendin-4 are expected to lower appetite while FGF21 increases metabolism in adipose and other tissues which could increase loss of fat. These two effects could result in an additive or even synergistic weight loss with combined dosing. Expression of receptors for both FGF21 and GLP-1 in metabolically active tissues suggests that simultaneous delivery of a FGF21 receptor agonist and a GLP-1 receptor agonist to such tissues may be beneficial for treating metabolic diseases. A combination of GLP-1 and Exendin-4's cardioprotective effects and improved lipid profiles seen with FGF21 could also result in an additive benefit for cardiovascular disease associated with obesity, type 2 and type 1 diabetes.

Another likely benefit of GLP-1 and FGF21 dual agonism is an improved, i.e., reduced, side effect profile. Recent studies (Wei et al. (2012) PNAS 109, 3143-48) indicate that treatment of diet-induced obese mice with FGF21 induces bone loss, due to a diminished inactivation of PPARγ (via reduced sumoylation); a shift of mesenchymal stem cell differentiation from osteoblasts to adipocytes is seen in the presence of increased PPARγ activity in the bone following FGF21 treatment. However, it has also been reported (Sanz et al. (2010) Am J Physiol Endocrinol Metab 298, E634-E643) that GLP-1 can reduce the differentiation of human mesenchymal stem cells to adipocytes by reducing the expression of PPARγ. Therefore, as GLP-1 has the potential to be bone protective, GLP-1-FGF21 fusion proteins are likely to reduce the risk of bone loss compared to FGF21-only treatments.

Although the embodiments of the present invention concern the physical and chemical stability under both physiological and preserved pharmaceutical formulation conditions, maintaining the biological potency of the proteins of the invention as compared to, e.g., wild-type FGF21 is an important factor of consideration as well. Therefore, the biological potency of the proteins of the present invention is defined by the ability of the proteins to affect glucose uptake and/or the lowering of plasma glucose levels, as shown herein in the examples.

The proteins, polypeptides, and/or peptides of the invention administered according to this invention may be generated and/or isolated by any means known in the art. The most preferred method for producing the variant is through recombinant DNA methodologies and is well known to those skilled in the art. Such methods are described in Current Protocols in Molecular Biology (John Wiley & Sons, Inc.), which is incorporated herein by reference.

Additionally, the preferred embodiments include a biologically active peptide derived from the variant described herein. Such a peptide will contain at least one of the substitutions described and the variant will possess biological activity. The peptide may be produced by any and all means known to those skilled in the art, examples of which included but are not limited to enzymatic digestion, chemical synthesis or recombinant DNA methodologies.

It is established in the art that fragments of peptides of certain fibroblast growth factors are biologically active. See for example, Baird et al., Proc. Natl. Acad. Sci (USA) 85:2324-2328 (1988), and J. Cell. Phys. Suppl. 5:101-106 (1987). Therefore, the selection of fragments or peptides of the variant is based on criteria known in the art. For example, it is known that dipeptidyl peptidase IV (DPP-IV, or DPP-4) is a serine type protease involved in inactivation of neuropeptides, endocrine peptides, and cytokines (Damme et al. Chem. Immunol. 72: 42-56, (1999)). The N-terminus of FGF21 (HisProIlePro) contains two dipeptides that could potentially be substrates to DPP-IV, resulting in a fragment of FGF21 truncated at the N-terminus by 4 amino acids. Unexpectedly, this fragment of wild-type FGF21 has been demonstrated to retain biological activity, thus, proteins of the present invention truncated at the N-terminus by up to 4 amino acids, is an embodiment of the present invention.

The invention also encompasses polynucleotides encoding the above-described variants that may be in the form of RNA or in the form of DNA, which DNA includes cDNA, genomic DNA, and synthetic DNA. The DNA may be double-stranded or single-stranded. The coding sequences that encode the proteins of the present invention may vary as a result of the redundancy or degeneracy of the genetic code.

The polynucleotides that encode for the proteins of the invention may include the following: only the coding sequence for the variant, the coding sequence for the variant and additional coding sequence such as a functional polypeptide, or a leader or secretory sequence or a pro-protein sequence; the coding sequence for the variant and non-coding sequence, such as introns or non-coding sequence 5' and/or 3' of the coding sequence for the variant. Thus the term "polynucleotide encoding a variant" encompasses a polynucleotide that may include not only coding sequence for the variant but also a polynucleotide, which includes additional coding and/or non-coding sequence.

The invention further relates to variants of the described polynucleotides that encode for fragments, analogs and derivatives of the polypeptide that contain the indicated substitutions. The variant of the polynucleotide may be a naturally occurring allelic variant of the human FGF21 sequence, a non-naturally occurring variant, or a truncated variant as described above. Thus, the present invention also includes polynucleotides encoding the variants described above, as well as variants of such polynucleotides, which variants encode for a fragment, derivative or analog of the disclosed variant. Such nucleotide variants include deletion variants, substitution variants, truncated variants, and addition or insertion variants as long as at least one of the indicated amino acid substitutions of the first or second embodiments is present.

The polynucleotides of the invention will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences. The dual function proteins or fragments thereof can be expressed in mammalian cells, insect, yeast, bacterial or other cells under the control of appropriate promoters. Cell free translation systems can also be employed to produce such proteins using RNAs derived from DNA constructs of the present invention.

*E. coli* is a prokaryotic host useful particularly for cloning the polynucleotides of the present invention. Other microbial hosts suitable for use include *Bacillus subtilus, Salmonella typhimurium*, and various species of *Serratia, Pseudomonas, Streptococcus*, and *Staphylococcus*, although others may also be employed as a matter of choice. In these prokaryotic hosts, one can also make expression vectors, which will typically contain expression control sequences compatible with the host cell (e.g., an origin of replication).

In addition, any of a number of well-known promoters may be present, such as the lactose promoter system, a tryptophan (Trp) promoter system, a beta-lactamase promoter system, or a promoter system from phages lambda or T7. The promoters will typically control expression, optionally with an operator sequence, and have ribosome binding site sequences and the like, for initiating and completing transcription and translation.

One skilled in the art of expression of proteins will recognize that methionine or methionine-arginine sequence can be introduced at the N-terminus of the mature sequence (SEQ ID NO: 3) for expression in *E. coli* and are contemplated within the context of this invention. Thus, unless otherwise noted, proteins of the present invention expressed in *E. coli* have a methionine sequence introduced at the N-terminus.

Other microbes, such as yeast or fungi, may also be used for expression. *Pichia pastoris, Saccharomyces cerevisiae, Schizosaccharomyces pombe*, and *Pichia angusta* are examples of preferred yeast hosts, with suitable vectors having expression control sequences, such as promoters, including 3-phosphoglycerate kinase or other glycolytic enzymes, and an origin of replication, termination sequences and the like as desired. *Aspergillus niger, Trichoderma reesei*; and *Schizophyllum commune*, are examples of fungi hosts, although others may also be employed as a matter of choice.

Mammalian tissue cell culture may also be used to express and produce the polypeptides of the present invention. Eukaryotic cells are actually preferred, because a number of suitable host cell lines capable of secreting intact variants have been developed in the art, and include the CHO cell lines, various COS cell lines, NSO cells, Syrian Hamster Ovary cell lines, HeLa cells, or human embryonic kidney cell lines (i.e. HEK293, HEK293EBNA).

Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are promoters derived from SV40, adenovirus, bovine papilloma virus, cytomegalovirus, Raus sarcoma virus, and the like. Preferred polyadenylation sites include sequences derived from SV40 and bovine growth hormone.

The vectors containing the polynucleotide sequences of interest (e.g., the Proteins of the invention and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Various methods of protein purification may be employed and such methods are known in the art and described, for example, in Deutscher, Methods in Enzymology 182: 83-9 (1990) and Scopes, Protein Purification: Principles and Practice, Springer-Verlag, NY (1982). The purification step(s) selected will depend, for example, on the nature of the production process used for the Proteins of the invention.

The proteins, polypeptides, and/or peptides of the invention, e.g., the dual activity fusion proteins of the invention, should be formulated and dosed in a fashion consistent with good medical practice, taking into account the clinical condition of the patient, the site of delivery of the protein compositions, the method of administration, the scheduling of administration, and other factors known to practitioners.

The "therapeutically effective amount" of the proteins of the invention for purposes herein is thus determined by such considerations.

The pharmaceutical compositions of the proteins of the present invention may be administered by any means that achieve the generally intended purpose: to treat type 1 and type 2 diabetes mellitus, obesity, metabolic syndrome, or critically ill patients. Non-limiting permissible means of administration include, for example, by inhalation or suppository or to mucosal tissue such as by lavage to vaginal, rectal, urethral, buccal and sublingual tissue, orally, nasally, topically, intranasally, intraperitoneally, parenterally, intravenously, intramuscularly, intrasternally, by intraarticular injection, intralymphatically, interstitially, intra-arterially, subcutaneously, intrasynovial, transepithelial, and transdermally. In some embodiments, the pharmaceutical compositions are administered by lavage, orally or inter-arterially. Other suitable methods of introduction can also include rechargeable or biodegradable devices and slow or sustained release polymeric devices. The pharmaceutical compositions of this invention can also be administered as part of a combinatorial therapy with other known metabolic agents.

The dosage administered will be dependent upon the age, health, and weight of the recipient, kind of concurrent treatment, if any, frequency of treatment, and the nature of the effect desired. Compositions within the scope of the invention include all compositions wherein an FGF21 variant is present in an amount that is effective to achieve the desired medical effect for treatment type 1 or type 2 diabetes mellitus, obesity, or metabolic syndrome. While individual needs may vary from one patient to another, the determination of the optimal ranges of effective amounts of all of the components is within the ability of the clinician of ordinary skill.

The proteins of the present invention can be formulated according to known methods to prepare pharmaceutically useful compositions. A desired formulation would be one that is a stable lyophilized product that is reconstituted with an appropriate diluent or an aqueous solution of high purity with optional pharmaceutically acceptable carriers, preservatives, excipients or stabilizers [Remington's Pharmaceutical Sciences 16th edition (1980)]. The proteins of the present invention may be combined with a pharmaceutically acceptable buffer, and the pH adjusted to provide acceptable stability, and a pH acceptable for administration.

For parenteral administration, in one embodiment, the proteins of the invention are formulated generally by mixing one or more of them at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. Preferably, one or more pharmaceutically acceptable anti-microbial agents may be added. Phenol, m-cresol, and benzyl alcohol are preferred pharmaceutically acceptable anti-microbial agents.

Optionally, one or more pharmaceutically acceptable salts may be added to adjust the ionic strength or tonicity. One or more excipients may be added to further adjust the isotonicity of the formulation. Glycerin, sodium chloride, and mannitol are examples of an isotonicity adjusting excipient.

Those skilled in the art can readily optimize pharmaceutically effective dosages and administration regimens for therapeutic compositions comprising Proteins of the invention, as determined by good medical practice and the clinical condition of the individual patient. A typical dose range for the proteins of the present invention will range from about 0.01 mg per day to about 1000 mg per day (or about 0.05 mg per week to about 5000 mg per week administered once per week) for an adult. Preferably, the dosage ranges from about 0.1 mg per day to about 100 mg per day (or about 0.5 mg per week to about 500 mg per week administered once per week), more preferably from about 1.0 mg/day to about 10 mg/day (or about 5 mg per week to about 50 mg per week administered once per week). Most preferably, the dosage is about 1-5 mg/day (or about 5 mg per week to about 25 mg per week administered once per week). The appropriate dose of an FGF21 variant administered will result in lowering blood glucose levels and increasing energy expenditure by faster and more efficient glucose utilization, and thus is useful for treating type 1 and type 2 diabetes mellitus, obesity and metabolic syndrome.

In addition, because hyperglycemia and insulin resistance are common in critically ill patients given nutritional support, some intensive care units (ICUs) administer insulin to treat excessive hyperglycemia in fed critically ill patients. In fact, recent studies document the use of exogenous insulin to maintain blood glucose at a level no higher than 110 mg per deciliter reduced morbidity and mortality among critically ill patients in the surgical intensive care unit, regardless of whether they had a history of diabetes (Van den Berghe et al. N Engl J Med., 345(19):1359, (2001)). Thus, proteins of the present invention are uniquely suited to help restore metabolic stability in metabolically unstable critically ill patients. Proteins of the invention such as those containing variants of FGF21 are unique in that they stimulate glucose uptake and enhances insulin sensitivity but do not induce hypoglycemia.

In another aspect of the present invention, proteins of the invention for use as a medicament for the treatment of obesity, type 1 and type 2 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, metabolic syndrome, acute myocardial infarction, conditions associated with severe inactivating mutations in the insulin receptor, lipodystrophies including HIV-associated lipodystrophy, and other metabolic disorders is contemplated.

Having now described the present invention in detail, the same will be more clearly understood by reference to the following examples, which are included herewith for purposes of illustration only and are not intended to be limiting of the invention.

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); and Sambrook et al., Molecular Cloning: A Laboratory Manual (2nd Edition, 1989).

Site-Specific FGF21 Mutants

In some embodiments, the fusion proteins of the invention include additional mutants of GLP-1 or Exendin-4, GLP-1/Glucagon hybrid peptides, GLP-1 analogues with unnatural amino acids (to convey DPP-4 resistance, for PEGylation, or for other purposes).

In some embodiments, the proteins of the invention comprise FGF21 agonists with one or more of the following additional modifications of wild-type FGF21:

(i) additional disulfides, unnatural amino acids, or modifications to promote dimerization such as formation of a disulfide at R154C or introduction of a cysteine at another site, or dimerization through a fused Fc domain, or dimer formation through a cross-linker such as a bifunctional PEG;

(ii) fragments of FGF21;

(iii) proteins selected to have FGF21 activity (binding to beta-klotho and binding and activation of the FGFR's); and (iv) an FGF21 mimetic antibody (of various formats such as Fab, unibody, svFc etc.).

In some embodiments, the dual activity proteins of the invention comprise one or more of the following linkers: a simple amide bond, short peptides (particularly Ser/Gly repeats), additional residues from the FGF21 translated sequence, or a larger linker up to an entire protein (such as an Fc domain, an HSA-binding helix bundle, HSA, etc.). The two moieties can also be linked by other chemical means, such as through unnatural amino acids or standard chemical linkers (maleimide-Cys, NHS-Lys, "click chemistry", etc.) "Linker" for the FGF21 mimetic antibody approach could include those already listed and also an insertion into a loop with subsequent cleavage to release the GLP-1 N-terminus.

In some embodiments, the fusion protein of the invention comprises PEGylation occurring at one, two, or more specific sites. In preferred embodiments, the PEGylation occurs within the FGF21 molecule or the linker. In some embodiments, the PEGylation is not within ~10 amino acids of the N-terminus of the dual function protein, preferably not within ~10 amino acids of the start of FGF21. PEGylation attachment chemistries can include NHS-Lys, maleimide-Cys, unnatural amino acids (aldehyde, "click chemistry", Pcl, etc.) and can be combined with suitable protein variants to control the stoichiometry of the reaction.

The PEG group of the fusion proteins of the invention can be of any size (e.g., 1, 2, 3.4, 5, 10, 20, 24, 29, 30, 40 kDa), and can be linear, branched, or comb structured, with a preference for a total PEGylation of greater than or equal to 40 kDa. Optimal PEGylation achieves half-life extension sufficient for once weekly dosing. PEGylation of protein dimers, trimers, tetramers etc. may result in adequate serum half-life extension using shorter PEG polymers. Branched and comb PEG structures may be beneficial in terms of lower viscosity.

Preferred half-life extension methodologies for the fusion proteins of the invention include integrating an IgG Fc domain or HSA into the linker and may not require PEGylation. Additionally, using Fc domain fusions will result in dimerization and may result in enhanced potency in addition to half-life extension.

Other embodiments of the invention include but are not limited to the following attachments, for half-life extension: HSA-binding lipid or small molecule or micelle to either the monomeric or a dimeric version of the fusion.

In certain embodiments of the invention, other attachments may be made to proteins, polypeptides, and/or peptides of the invention, to achieve half-life extension and other improved biological properties. They can include attaching PEG-cholesterol conjugates (including micelles and liposomes) to the proteins, polypeptides, and/or peptides of the invention, and/or attaching sugars (glycosylate) to the proteins, polypeptides, and/or peptides of the invention. In still other embodiments, similar techniques are employed to add conjugates of, e.g., polysialic acid (PSA), hydroxyethyl starch (HES), albumin-binding ligands, or carbohydrate shields to proteins, polypeptides, and/or peptides.

The HESylation technique, for example, couples branched hydroxyethylstarch (HES) chains (60 kDa or 100 kDa, highly branched amylopectin fragments from corn starch) to a protein, polypeptides, and/or peptides via reductive alkylation. Polysialation conjugates proteins, polypeptides, and/or peptides of interest with polysialic acid (PSA) polymers in a manner similar to PEGylation. PSA polymers are negatively charged, non-immunogenic polymers that occur naturally in the body and are available in molecular weights of 10-50 kD.

In still other embodiments of the invention, other attachments or modifications may be made to proteins, polypeptides, and/or peptides of the invention, to achieve half-life extension and other improved biological properties. These include the creation of recombinant PEG (rPEG) groups, and their attachment to the proteins, polypeptides, and/or peptides of the invention. As developed by the company Amunix, Inc. The rPEG technology is based on protein sequences with PEG-like properties that are genetically fused to biopharmaceuticals, avoiding the extra chemical conjugation step. rPEGs are extended half-life Exenatide constructs that contain a long unstructured tail of hydrophilic amino acids, and which are capable of both increasing a protein or peptide's serum half-life and slowing its rate of absorption, thus reducing the peak-trough ratio significantly. rPEGs have an increased hydrodynamic radius and show an apparent molecular weight that is about 15-fold their actual molecular weight, mimicking the way PEGylation achieves a long serum half-life. Similar recombinant polypeptide sequences are also developed by XL-protein GmbH for the "PASylation" of proteins.

Chemically-Modified Dual Function Protein Mutants

Chemically modified forms of the fusion proteins described herein, including, e.g., truncated and variant forms of the dual function fusion proteins described herein, can be prepared by one skilled in the art, given the disclosures described herein. Such chemically modified dual function proteins are altered such that the chemically modified mutant is different from the unmodified mutant, either in the type or location of the molecules naturally attached to the mutant. Chemically modified mutants can include molecules formed by the deletion of one or more naturally-attached chemical groups.

In one embodiment, proteins of the present invention can be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable. Non-water soluble polymers conjugated to proteins of the present invention also form an aspect of the invention.

Exemplary polymers each can be of any molecular weight and can be branched or unbranched. The polymers each typically have an average molecular weight of between about 2 kDa to about 100 kDa (the term "about" indicating that in preparations of a water-soluble polymer, some molecules will weigh more and some less than the stated molecular weight). The average molecular weight of each polymer is preferably between about 5 kDa and about 50 kDa, more preferably between about 12 kDa and about 40 kDa, and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-(C1-C10), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules that can be used to prepare covalently attached dual function protein variant multimers. Also encompassed by the present invention are dual function protein variants covalently attached to polysialic acid.

In some embodiments of the present invention, a dual function protein variant is covalently, or chemically, modified to include one or more water-soluble polymers, including, but not limited to, polyethylene glycol (PEG), polyoxyethylene glycol, or polypropylene glycol. See, e.g., U.S. Pat. Nos. 4,640,835; 4,496,689; 4,301,144; 4,670,417; 4,791,192; and 4,179,337. In some embodiments of the present invention, adual function protein comprises one or more polymers, including, but not limited to, monomethoxy-polyethylene glycol, dextran, cellulose, another carbohydrate-based polymer, poly-(N-vinyl pyrrolidone)-polyethylene glycol, propylene glycol homopolymers, a polypropylene oxide/ethylene oxide co-polymer, polyoxyethylated polyols (e.g., glycerol), polyvinyl alcohol, or mixtures of such polymers.

In some embodiments of the present invention, a dual function protein is covalently-modified with PEG subunits. In some embodiments, one or more water-soluble polymers are bonded at one or more specific positions (for example, at the N-terminus) of the dual function protein mutant. In some embodiments, one or more water-soluble polymers are randomly attached to one or more side chains of a dual function protein mutant. In some embodiments, PEG is used to improve the therapeutic capacity of a dual function protein mutant. Certain such methods are discussed, for example, in U.S. Pat. No. 6,133,426, which is hereby incorporated by reference for any purpose.

In embodiments of the present invention wherein the polymer is PEG, the PEG group can be of any convenient molecular weight, and can be linear or branched.

The average molecular weight of the PEG group will preferably range from about 2 kD to about 100 kDa, and more preferably from about 5 kDa to about 50 kDa, e.g., 10, 20, 30, 40, or 50 kDa. The PEG groups will generally be attached to the dual function protein mutant via acylation or reductive alkylation through a reactive group on the PEG moiety (e.g., an aldehyde, amino, thiol, or ester group) to a reactive group on the dual function protein mutant (e.g., an aldehyde, amino, or ester group).

Branched PEG derivatives, also known as "Y-shaped" PEG derivatives, contain two linear methoxy PEG chain attached to a central core. The sterically bulky structure of these "Y-shaped" PEG derivatives will facilitate the single point attachment of the modified molecules. By way of example, three kinds of "Y-shaped" PEG derivatives are Y-NHS-40K (useful for amine PEGylation); Y-MAL-40K (useful for thiol PEGylation); and Y-ALD-40K (e.g., Y-AALD-40K and Y-PALD-40K)(useful for N-terminal PEGylation). For amine PEGylation, the "Y-shape" NHS ester will react with the amino group of lysine(s) or the N-terminal amine in biological active molecules to produce a stable amide linkage(s). This NHS ester will couple with the targeted molecules at pH 7-8.5. For thiol PEGylation, the "Y-shape" maleimide will react with the thiol groups in biological active molecules to generate a stable 3-thiosuccinimidyl ether linkage. This maleimide will couple with the targeted molecules at an approximate pH of 7.4 in the presence of other functional groups. For N-terminal PEGylation, the "Y-shape" aldehyde will preferably react with the N-terminal amine in biological active molecules to produce a stable amine linkage in the presence of a reducing reagent such as sodium cyanoborohydride. This aldehyde will couple with the N-terminal amine of the targeted molecules at pH 5-8. Reagents for performing branched PEGylation are available through, e.g., JenKem Technology.

The PEGylation of a polypeptide, including the proteins of the invention, can be specifically carried out using any of the PEGylation reactions known in the art. Such reactions are described, for example, in the following references: Francis et al., 1992, Focus on Growth Factors 3: 4-10; European Patent Nos. 0 154 316 and 0 401 384; and U.S. Pat. No. 4,179,337. For example, PEGylation can be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono C1-C10 alkoxy or aryloxy derivatives thereof (see, e.g., U.S. Pat. No. 5,252,714).

In some embodiments of the present invention, a useful strategy for the attachment of the PEG group to a polypeptide involves combining, through the formation of a conjugate linkage in solution, a peptide and a PEG moiety, each bearing a special functionality that is mutually reactive toward the other. The peptides can be easily prepared with conventional solid phase synthesis. The peptides are "pre-activated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water-soluble polymer that can be used for protein modification. Therefore, the Proteins of the invention fused to a polysaccharide polymer form embodiments of the present invention. Dextrans are polysaccharide polymers comprised of individual subunits of glucose predominantly linked by alpha 1-6 linkages. The dextran itself is available in many molecular weight ranges, and is readily available in molecular weights from about 1 kD to about 70 kD. Dextran is a suitable water-soluble polymer for use as a vehicle by itself or in combination with another vehicle (e.g., Fc). See, e.g., International Publication No. WO 96/11953. The use of dextran conjugated to therapeutic or diagnostic immunoglobulins has been reported. See, e.g., European Patent Publication No. 0 315 456, which is hereby incorporated by reference. The present invention also encompasses the use of dextran of about 1 kD to about 20 kD.

In general, chemical modification can be performed under any suitable condition used to react a protein with an activated polymer molecule. Methods for preparing chemically modified polypeptides will generally comprise the steps of: (a) reacting the polypeptide with the activated polymer molecule (such as a reactive ester or aldehyde derivative of the polymer molecule) under conditions whereby a FGF21 protein variant becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment of the present invention, chemically modified FGF21 mutants can have a single polymer molecule moiety at the amino-terminus (see, e.g., U.S. Pat. No. 5,234,784)

In another embodiment of the present invention, proteins of the invention can be chemically coupled to biotin. The biotinylated proteins of the invention are then allowed to bind to avidin, resulting in tetravalent avidin/biotin/proteins of the invention. Proteins of the invention can also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that can be alleviated or modulated by the administration of the present chemically modified dual function proteins mutants include those described herein for proteins of the invention. However, the chemically modified dual function proteins mutants disclosed herein can have additional activities, enhanced or reduced biological activity, or other characteristics, such as increased or decreased half-life, as compared to unmodified dual function proteins mutants.

Therapeutic Compositions of Dual Function Proteins and Administration Thereof

Therapeutic compositions comprising the dual function proteins of the invention are within the scope of the present invention, and are specifically contemplated in light of, e.g., the identification of several mutant dual function proteins sequences exhibiting enhanced properties. Such dual function proteins mutant pharmaceutical compositions can comprise a therapeutically effective amount of a dual function proteins protein variant in admixture with a pharmaceutically or physiologically acceptable formulation agent selected for suitability with the mode of administration.

Acceptable formulation materials preferably are nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides; preferably sodium or potassium chloride; or mannitol sorbitol), delivery vehicles, diluents, excipients and/or pharmaceutical adjuvants (see, e.g., Remington's Pharmaceutical Sciences (18th Ed., A. R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage (see, e.g., Remington's Pharmaceutical Sciences, supra). Such compositions can influence the physical state, stability, rate of in vivo release, and rate of in vivo clearance of the fusion protein of the invention.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the present invention, dual function pharmaceutical compositions can be prepared for storage by mixing the selected composition having the desired degree of purity with optional formulation agents (Remington's Pharmaceutical Sciences, supra) in the form of a lyophilized cake or an aqueous solution. Further, the dual function protein product can be formulated as a lyophilizate using appropriate excipients such as sucrose.

The pharmaceutical compositions containing the fusion proteins of the invention can be selected for parenteral delivery. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention can be in the form of a pyrogen-free, parenterally acceptable, aqueous solution comprising the desired dual function protein in a pharmaceutically acceptable vehicle. A particularly suitable vehicle for parenteral injection is sterile distilled water in which a dual function protein is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, a dual function protein of the invention can be formulated as a dry powder for inhalation. Dual function protein inhalation solutions can also be formulated with a propellant for aerosol delivery. In yet another embodiment, solutions can be nebulized. Pulmonary administration is further described in International Publication No. WO 94/20069, which describes the pulmonary delivery of chemically modified proteins.

It is also contemplated that certain formulations can be administered orally. In one embodiment of the present invention, dual function proteins of the invention that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the dual function proteins of the invention. Diluents, flavorings, low melting point waxes, vegetable oils, lubricants, suspending agents, tablet disintegrating agents, and binders can also be employed.

Another pharmaceutical composition can involve an effective quantity of the proteins of the invention in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions comprising dual function proteins of the invention will be evident to those skilled in the art, including formulations involving dual function proteins of the invention in sustained- or controlled-delivery formulations. Techniques for formulating a variety of other sustained- or controlled-delivery means, such as liposome carriers, bio-erodible microparticles or porous beads and depot injections, are also known to those skilled in the art (see, e.g., International Publication No. WO 93/15722, which describes the controlled release of porous polymeric microparticles for the delivery of pharmaceutical compositions, and Wischke & Schwendeman, 2008, Int. J Pharm. 364: 298-327, and Freiberg & Zhu, 2004, Int. J Pharm. 282: 1-18, which discuss microsphere/microparticle preparation and use).

Additional examples of sustained-release preparations include semipermeable polymer matrices in the form of shaped articles, e.g. films, or microcapsules. Sustained release matrices can include polyesters, hydrogels, polylactides (U.S. Pat. No. 3,773,919 and European Patent No. 0 058 481), copolymers of L-glutamic acid and gamma ethyl-L-glutamate (Sidman et al., 1983, Biopolymers 22: 547-56), poly(2-hydroxyethyl-methacrylate) (Langer et al., 1981, J. Biomed. Mater. Res. 15: 167-277 and Langer, 1982, Chem. Tech. 12: 98-105), ethylene vinyl acetate (Langer et al., supra) or poly-D-3-hydroxybutyric acid (European Patent No. 0 133 988). Sustained-release compositions can also include liposomes, which can be prepared by any of several methods known in the art. See, e.g., Epstein et al., 1985, Proc. Natl. Acad. Sci. U.S.A. 82: 3688-92; and European Patent Nos. 0 036 676, 0 088 046, and 0 143 949.

The pharmaceutical compositions of the invention to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

In a specific embodiment, the present invention is directed to kits for producing a single-dose administration unit. The kits can each contain both a first container having a dried protein and a second container having an aqueous formulation. Also included within the scope of this invention are kits containing single and multi-chambered pre-filled syringes (e.g., liquid syringes and lyosyringes).

Dosages of Dual Function Proteins and Administration Thereof

The effective amount of a pharmaceutical composition of the invention to be employed therapeutically will depend, for example, upon the therapeutic context and objectives. One skilled in the art will appreciate that the appropriate dosage levels for treatment will thus vary depending, in part, upon the molecule delivered, the indication for which the fusion protein variant is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg.

The frequency of dosing will depend upon the pharmacokinetic parameters of the dual function protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraarterial, intraportal, or intralesional routes; by sustained release systems (which may also be injected); or by implantation devices. Where desired, the compositions can be administered by bolus injection or continuously by infusion, or by implantation device.

Alternatively or additionally, the composition can be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

Therapeutic Uses of Dual Function Proteins

Proteins of the invention can be used to treat, diagnose, ameliorate, or prevent a number of diseases, disorders, or conditions, including, but not limited to metabolic disorders. In one embodiment, the metabolic disorder to be treated is diabetes, e.g., type 2 diabetes mellitus. In another embodiment, the metabolic disorder is obesity. Other embodiments include metabolic conditions or disorders such as type 1 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, metabolic syndrome, hypertension, cardiovascular disease, acute myocardial infarction, atherosclerosis, peripheral arterial disease, stroke, heart failure, coronary heart disease, kidney disease, diabetic complications, neuropathy, disorders associated with severe inactivating mutations in the insulin receptor, lipodystrophies including HIV-associated lipodystrophy, gastroparesis and other metabolic disorders.

In application, a disorder or condition such as type 1 or type 2 diabetes mellitus or obesity can be treated by administering a dual function protein variant as described herein to a patient in need thereof in the amount of a therapeutically effective dose. The administration can be performed as described herein, such as by IV injection, intraperitoneal injection, intramuscular injection, or orally in the form of a tablet or liquid formation. In most situations, a desired dosage can be determined by a clinician, as described herein, and can represent a therapeutically effective dose of the dual function protein polypeptide. It will be apparent to those of skill in the art that a therapeutically effective dose of dual function protein polypeptide will depend, inter alia, upon the administration schedule, the unit dose of antigen administered, whether the nucleic acid molecule or polypeptide is administered in combination with other therapeutic agents, the immune status and the health of the recipient. The term "therapeutically effective dose," as used herein, means that amount of dual function protein polypeptide that elicits the biological or medicinal response in a tissue system, animal, or human being sought by a researcher, medical doctor, or other clinician, which includes alleviation of the symptoms of the disease or disorder being treated.

Pharmaceutical Compositions

The present invention also provides pharmaceutical compositions comprising one or more of the dual function proteins of the invention or mutants described herein and a pharmaceutically acceptable carrier. In some embodiments the pharmaceutical compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington: The Science and Practice of Pharmacy (1995) Alfonso Gennaro, Lippincott, Williams, & Wilkins.

Fusion Proteins and Peptidic Compounds

In another embodiment, the proteins of the present invention can be made into a fusion protein or peptidic compound derived from the dual function proteins of the invention amino acid sequences. Such fusion proteins and peptidic compounds can be made using standard techniques known in the art. For example, peptidic compounds can be made by chemical synthesis using standard peptide synthesis techniques and then introduced into cells by a variety of means known in the art for introducing peptides into cells (e.g., liposome and the like).

The in vivo half-life of the fusion protein or peptidic compounds of the invention can be improved by making peptide modifications, such as the addition of N-linked glycosylation sites into the dual function proteins of the invention, or conjugating dual function proteins of the invention to poly(ethylene glycol)(PEG; pegylation), e.g., via lysine-monopegylation or cysteine-monopegylation. Such techniques have proven to be beneficial in prolonging the half-life of therapeutic protein drugs. It is expected that pegylation of the proteins of the invention of the invention may result in similar pharmaceutical advantages.

In addition, PEGylation can be achieved in any part of a polypeptide of the invention by the introduction of a non-natural amino acid. Certain non-natural amino acids can be introduced by the technology described in Deiters et al., J Am Chem Soc 125:11782-11783, 2003; Wang and Schultz, Science 301:964-967, 2003; Wang et al., Science 292:498-500, 2001; Zhang et al., Science 303:371-373, 2004 or in U.S. Pat. No. 7,083,970. Briefly, some of these expression systems involve site-directed mutagenesis to introduce a nonsense codon, such as an amber TAG, into the open reading frame encoding a polypeptide of the invention. Such expression vectors are then introduced into a host that can utilize a tRNA specific for the introduced nonsense codon and charged with the non-natural amino acid of choice. Particular non-natural amino acids that are beneficial for purpose of conjugating moieties to the polypeptides of the invention include those with acetylene and azido side chains. The proteins of the invention containing these novel amino acids can then be PEGylated at these chosen sites in the protein.

Similarly PEGylation can be achieved in any part of a protein of the invention by the introduction of pyrrolysine or pyrroline-carboxy-lysine as described by Ou et al. (Proc Natl Acad Sci USA. 2011 Jun. 28; 108(26):10437-42. Epub 2011 Jun. 13).

EXAMPLES

Example 1: Design of GLP-1/Proteins of the Invention

In order to test the efficacy of GLP-1 and FGF21 together, a fusion molecule was designed. Because GLP-1 requires a free N-terminus and FGF21 requires a free C-terminus for receptor binding and activation, the two were cloned in the order of N-GLP-1-linker-FGF21-C. Initial constructs were made with GLP-1 residues 7-35 and with or without several modifications to the N-terminus for DPP-4 protection (discussed below). Further modifications of GLP-1 (point mutants or deletions) were tested and scored by in vitro potency.

Linkers of 3, 8, 10, or 20 amino acids were cloned. For FGF21, residues 33-209 of the wild-type human protein were used. Constructs with and without PEGylation sites were produced. PEGylation was accomplished using maleimide-PEG reagents (40 kDa linear and branched PEGs) reactive toward an introduced Cys. The Cys was placed at position R154 of FGF21 and at several sites in the GLP-1 or Exendin-4 and linker. Constructs have also been designed for modification through incorporation of a Pcl, Pyl, Pyl analog or a reactive non-naturally occurring amino acid by introducing a TAG (amber) codon at position R154 of FGF21 or K34 of GLP-1. Additional constructs were designed for two different modifications by inclusion of the Cys at R154 or K34 and a TAG codon for incorporation of a Pcl, Pyl, Pyl analog or a reactive non-naturally occurring amino acid at the other site. Constructs were made fusing GLP-1 and FGF21 to an Fc domain of a human antibody. Variant 76 (V76) sequence of FGF21 was introduced into the fusion format.

Expression and purification of the fusions: Fusion proteins were typically expressed in E. coli by cloning the DNA sequence encoding the particular dual function variant into a vector containing coding sequences for one of several removable domains (for example, NPro or NPro variants with or without His6 tag, or His6 tag with a TEV-protease recognition peptide, or His6-Ubiquitin, or His6-Smt3) The vectors further included an inducible promoter to initiate mRNA transcription for protein expression such as the lac, T7 or arabinose promoters). Briefly, the vectors were transformed to DH10b-derived E. coli cells or BL21(DE3)-derived cells, grown under standard conditions, and induced to express protein with 0.2% arabinose or IPTG added to the culture media. Cells were harvested 3-4 hours post-induction, spun, and frozen. Pellets were thawed and resuspended for lysis by sonication and insoluble protein was isolated by centrifugation. The pellet was then solubilized in 6M guanidine, and the dissolved, clarified proteins were loaded to Ni-NTA columns. The columns were washed with denaturing and then non-denaturing buffers and eluted in a non-denaturing buffer according to standard practice. The eluates were buffer exchanged to remove imidazole, digested with specific proteases for removal of tags, (for example TEV protease, ubquitinase Usp2, or Ulp1 for specific removal of smt3), and purified by Ni-NTA. The fusion protein-containing fractions were further purified by size exclusion chromatography before PEGylation (typically with NOF Sunbright GL2-400 MA 40 kDa branched PEG maleimide). PEGylated proteins were isolated by anion exchange chromatography, placed in PBS, and concentrated or stored for various assays.

Figure 1B:
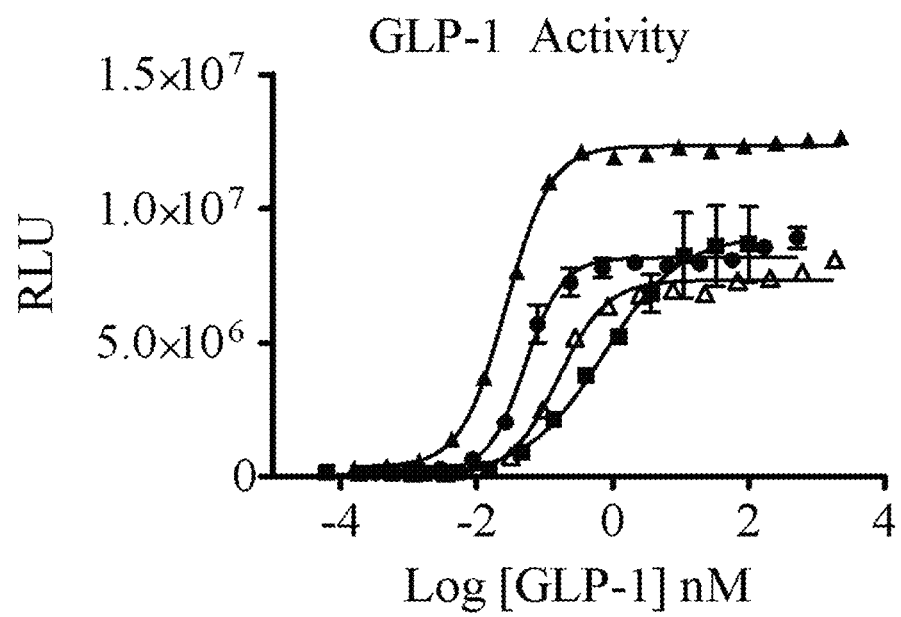

Protection of GLP-1 by mutation of the N-terminus: Because processing of the N-terminus of GLP-1 by DPP-4 is known to inactivate the peptide toward its primary receptor, several mutations reported in the literature were explored to slow this process. Constructs with the addition of an extra glycine to the N-terminus, mutation of Glu9 to Pro, or mutation of Ala8 to Gly or Ser, were all tested in a cell-based assay of GLP-1 activity. In the context of the fusion to FGF21 with a 40 kDa PEG attached to FGF21, the mutations at Ala8 retained superior activity to the other N-terminal modifications (FIG. 1a), and the A8S mutation was used in subsequent designs. In addition, the DPP-4-resistant analogue, Exendin-4 was also tested in the fusions as an alternative moiety with extended half-life in vivo (FIG. 1b). [See, e.g., J. Y. Oh et al. (2009) Bulletin of the Korean Chemical Society 30, 2471-2474; K. Adelhorst, (1994) JBC 269, 6275; B. D. Green et al. (2003) Biological Chemistry 384, 1543; J. C. Parker et al. (1998) Journal of Peptide Research 52, 398; C. F. Deacon et al. (1998) Diabetologia 41, 271; R. Burcelin et al. (1999) Metabolism-Clinical and Experimental 48, 252; U. Ritzel et al. (1998) Journal of Endocrinology 159, 93.]

Figure 2:
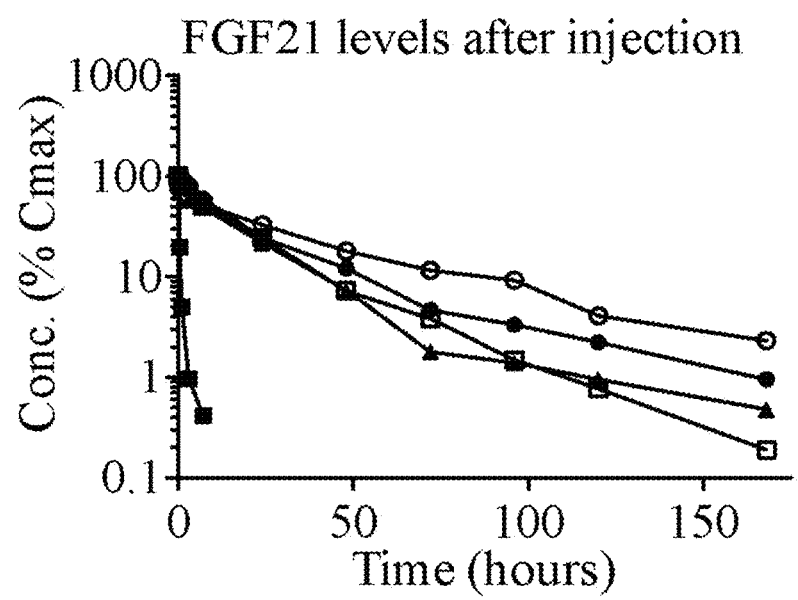
FIG. 2 shows pharmacokinetic properties (PK) of the GLP-1-FGF21-PEG fusion proteins (FGF21-PEG (V294; open squares), GLP-1(A8S)-PEG (V253; open circles) or dual function proteins with wild-type GLP-1 (V237; circles) or GLP-1(A8S) (V235; triangles) GLP-1). The PK of wild-type non-PEGylated FGF21 injected at 0.25 mg/kg is shown for comparison (squares).
Figure 3A:
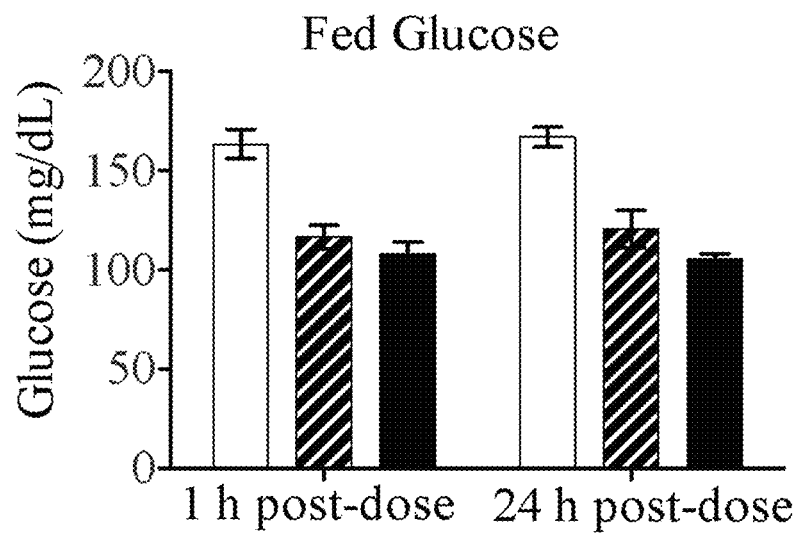
FIGS. 3A-3C show results from using the oral glucose tolerance test (OGTT) to measure the efficacy of half-life extended GLP-1-FGF21-PEG fusion proteins. Eight week C57BL/6J mice (n=5) were dosed by intraperitoneal (i.p.) injection with 1 mg/kg compound or vehicle (solid white bars; triangles). Blood glucose was measured at 1 and 24 hours post dose to assess acute effects of the GLP-1, which were similar for the wild-type GLP-1 (V239; hashed bars; squares) and GLP-1(A8S) versions (V232; black bars; circles) at 1 hour and retained slightly better by the GLP-1 (A8S) version at 24 hours. On the third night, the mice were fasted before challenge with 1.5 g/kg oral glucose at 72 hours post-dose. The mice dosed with the A8S version showed significantly improved control of blood glucose compared to those with the wild-type GLP-1 version, suggesting that the A8S mutation increased long-term levels of active GLP-1.
Figure 3B:
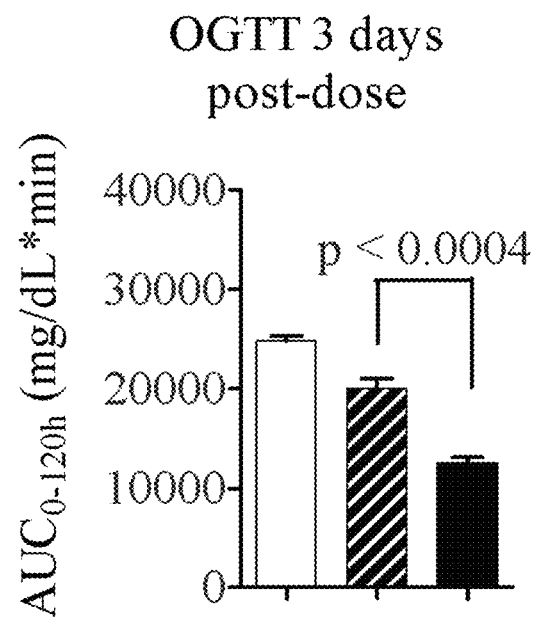
Figure 3C:
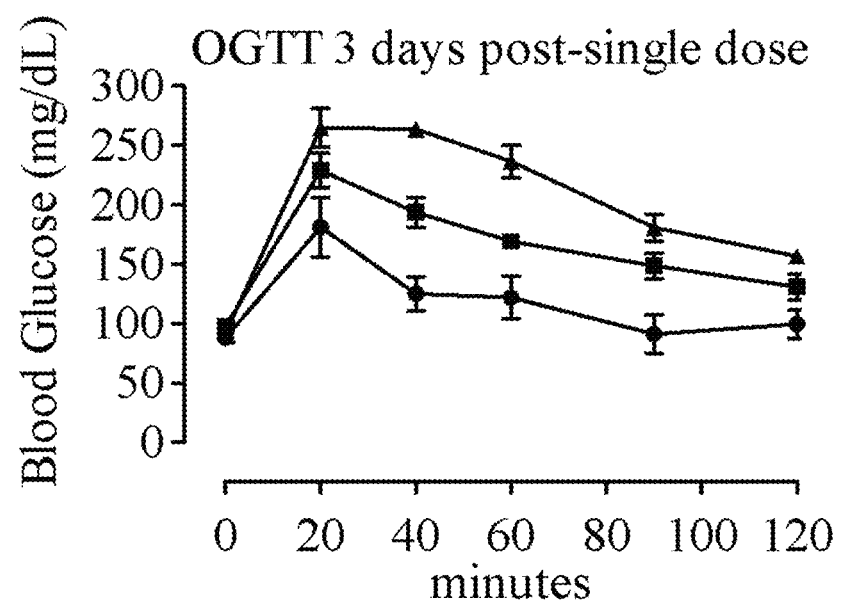

The A8S mutation was also compared to wild-type GLP-1 for pharmacokinetic properties in vivo. A fusion protein with wild-type GLP-1 (V329) and one with the GLP-1(A8S) mutation (V232) were injected intravenously into rats at 1 mg/kg, and the serum levels were measured against standard curves produced with the dosing solutions. When measured with a human FGF21-reactive ELISA kit, the molecules appeared to behave similarly to each other and to FGF21 alone with the same size (40 kDa) PEG attached (FIG. 2). To measure the half-life extension of GLP-1 activity, C57BL/6J mice were injected with the same two dual function protein variants with either wild-type GLP-1 or GLP-1(A8S). While both acutely lowered the fed glucose level after dosing, the GLP-1(A8S) variant retained greater activity in an oral glucose tolerance test (OGTT) measurement 3 days after dosing (FIG. 3). These data demonstrate that the A8S mutation increases the effective half-life of the GLP-1 moiety of the fusion while the PK of the FGF21 moiety is not much affected by the addition of GLP-1.

Design of the peptide linker between GLP-1 and FGF21: Linkers of 3, 8, 10, or 20 amino acids were tested. No significant difference in activity was observed for the variants with different linkers, although there were differences in expression yields in some fusion contexts. Additionally, constructs were tested with various lengths of GLP-1 (8 to 31 residues) or Exendin-4 (30 or more residues) and tested for in vitro activity in the GLP-1R cell-based assay.

Example 2: Test of Fusions in the Ob/Ob and Db/Db Diabetic Mouse Models

FGF21 has been shown to improve blood glucose levels, liver lipid levels, and body weight in the ob/ob mouse model of type-2 diabetes (T2D; see, e.g., A. Kharitonenkov et al. (2005) Journal of Clinical Investigation 115, 1627; T. Coskun et al. (2008) Endocrinology 149, 6018; and E. D. Berglund et al. (2009) Endocrinology 150, 4084). Likewise, GLP-1 analogues have been shown to improve glucose control, beta cell function and liver health in this genetic mouse diabetes model (Gallwitz B., Glucagon-like peptide-1 as a treatment option for type 2 diabetes and its role in restoring beta-cell mass. *Diabetes Technol Ther.* 2005, 7:651-7).

Figure 4:
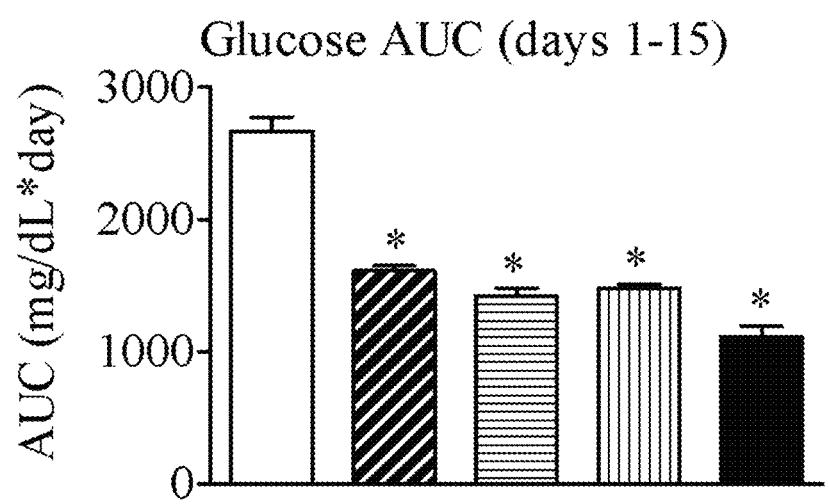
FIG. 4 shows efficacy of GLP-1-FGF21-PEG fusion proteins in ob/ob mice. Ten week old male ob/ob mice (n=8) were dosed i.p. twice weekly with the indicated compounds for two weeks. Equivalent dosing of FGF21-PEG (V238; diagonal hashed bars; squares) and GLP-1-FGF21(R154C)-PEG (V239; horizontal hashed bars; open squares) showed very similar improvements in blood glucose levels, body weight, and liver health (as measured by serum ALT levels and liver weight) when compared to the vehicle-treated group (circles). The DPP-4-resistant fusion, 0.2 mg/kg GLP-1(A8S)-FGF21(R154C)-PEG (V235; vertical hashed bars; open triangles) showed similar efficacy to other compounds, but equal dosing at 1 mg/kg GLP-1(A8S)-FGF21(R154C)-PEG (V235; black bars; triangles) gave additional lowering of blood glucose, body weight, alanine aminotransferase (ALT), and liver weight.
Figure 5A:
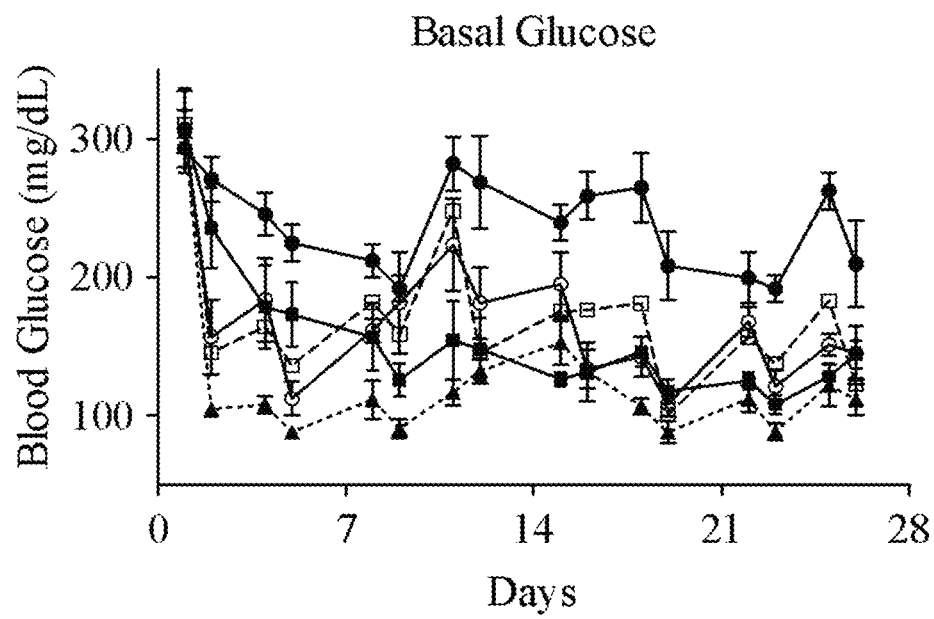
FIGS. 5A-5G show a comparison of the GLP-1(A8S)-FGF21(R154C)-PEG (V235; black bars; open triangles) fusion protein to co-administration of FGF21(R154C)-PEG+GLP-1(A8S)-PEG (vertical hashed bars; open circles), single administration of FGF21(R154C)-PEG (V238; 0.2 mg/kg (light diagonal hashed bars); 1 mg/kg (dark diagonal hashed bars; squares)), and single administration of GLP-1(A8S)-PEG (V253; 0.2 mg/kg (light horizontal hashed bars); 1 mg/kg (dark horizontal hashed bars; open squares)) in ob/ob mice. Nine week old male ob/ob mice (n=8) were dosed i.p. twice weekly with the indicated compounds or vehicle (solid white bars; circles) for four weeks. The fusion showed significantly improved efficacy compared to co-administration of FGF21(R154C)-PEG+GLP-1(A8S)-PEG. Although only moderate weight loss was observed with FGF21(R154C)-PEG and GLP-1(A8S)-FGF21(R154C)-PEG, other groups gained a substantial amount of weight, only in part due to differences in food intake.
Figure 5B:
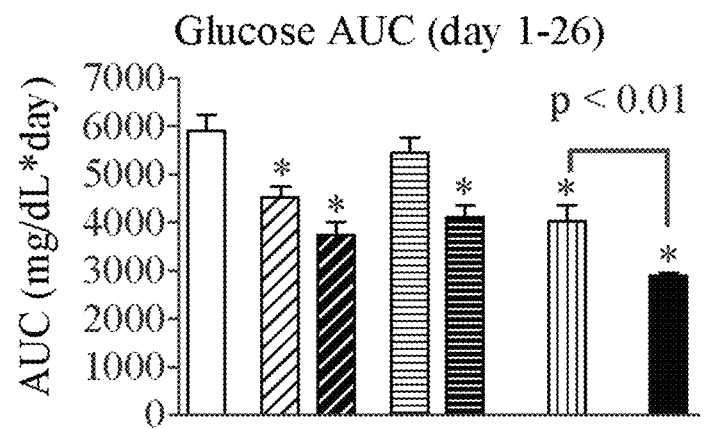
Figure 5C:
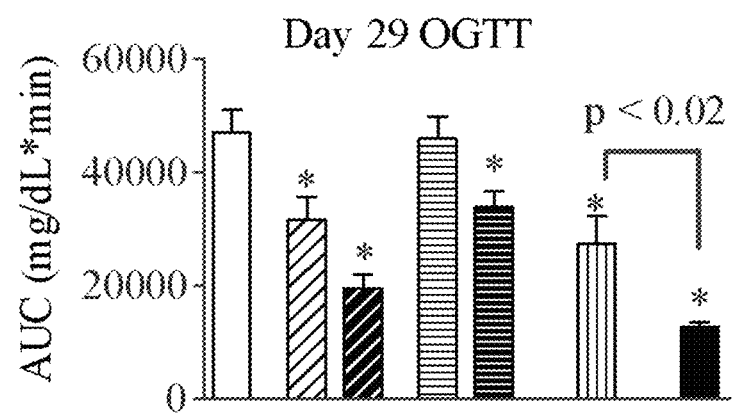
Figure 5D:
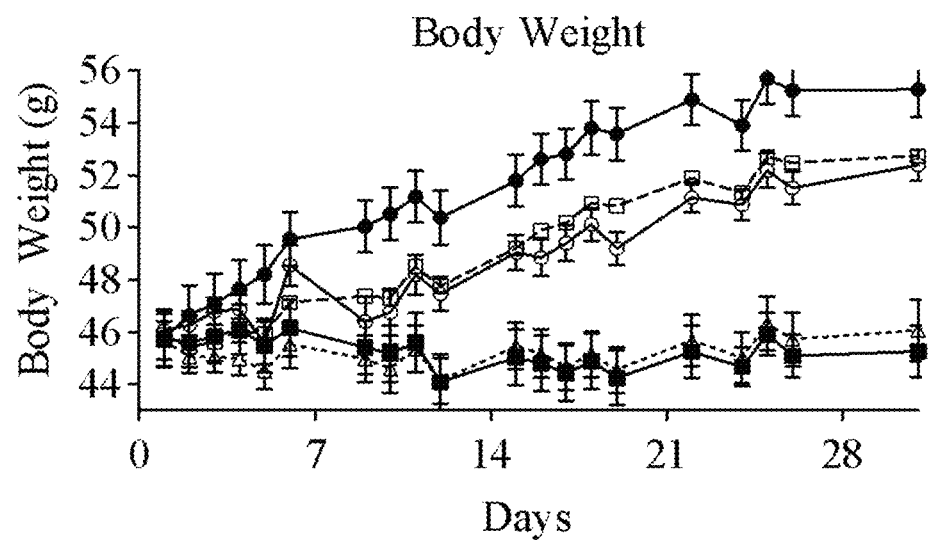
Figure 5E:
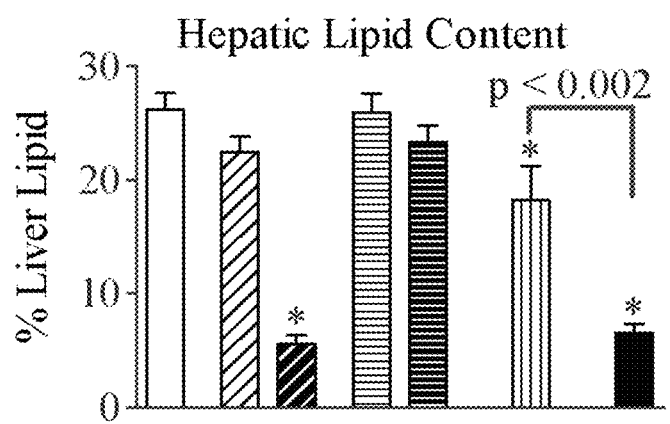
Figure 5F:
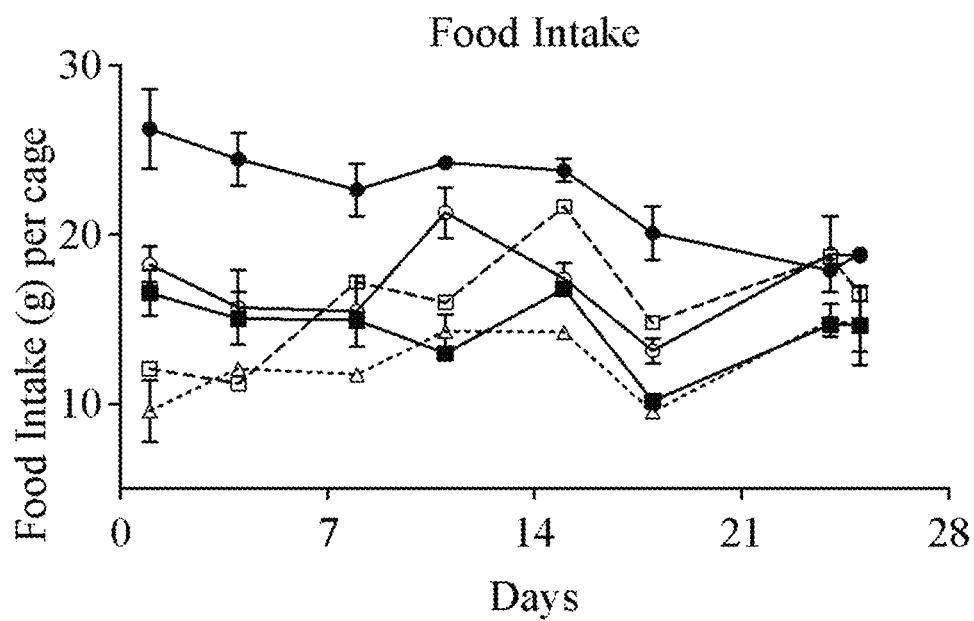
Figure 5G:
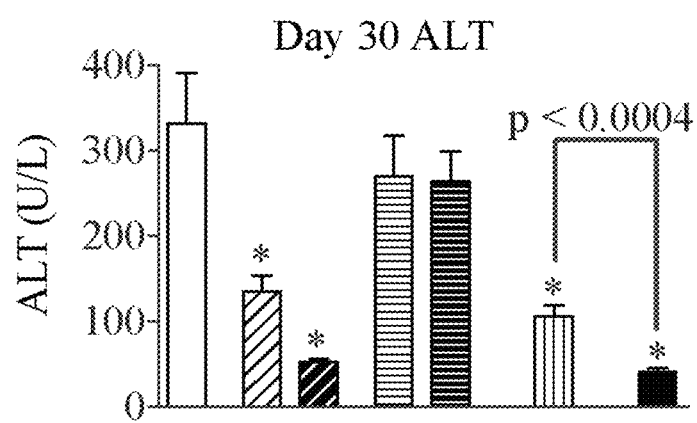
Figure 6A:
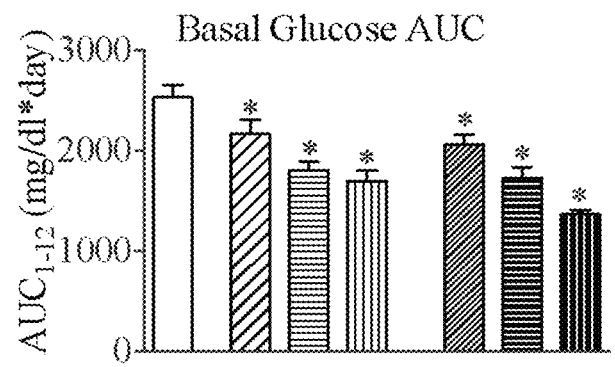
FIGS. 6A-6F show efficacy of GLP-1(A8S)-FGF21-PEG fusion proteins in ob/ob mice, comparing FGF21(R154C)-PEG (V235; dark bars) to FGF21(V76)-PEG (V272; light bars). Nine week old male ob/ob mice (n=8) were dosed i.p. twice weekly with the indicated compounds or vehicle (solid white bars) for two weeks. Both the GLP-1(A8S)-FGF21 (R154C)-PEG and the GLP-1(A8S)-FGF21(V76)-PEG fusions showed a dose response from 0.05 to 0.2 mg/kg (0.05 diagonal hashed bars; 0.1 horizontal hashed bars; 0.2 vertical hashed bars) for glucose control and body weight. At 0.2 mg/kg, GLP-1(A8S)-FGF21(V76)-PEG was more efficacious than GLP-1(A8S)-FGF21FGF21(R154C)-PEG particularly for lowering of glucose levels, body weight, serum triglycerides and cholesterol.
Figure 6B:
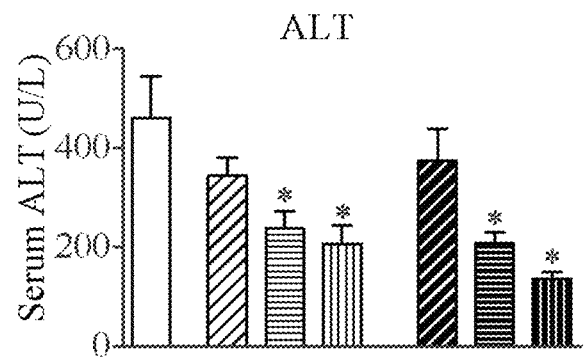
Figure 6C:
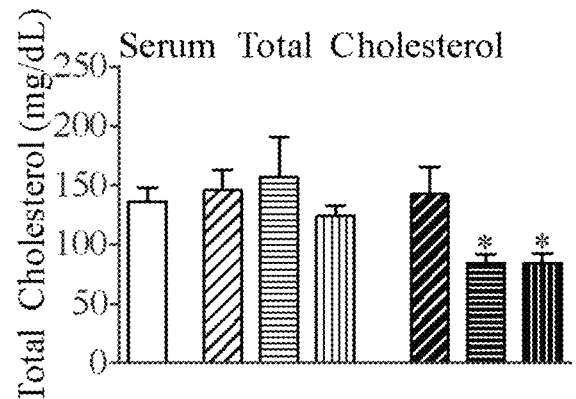
Figure 6D:
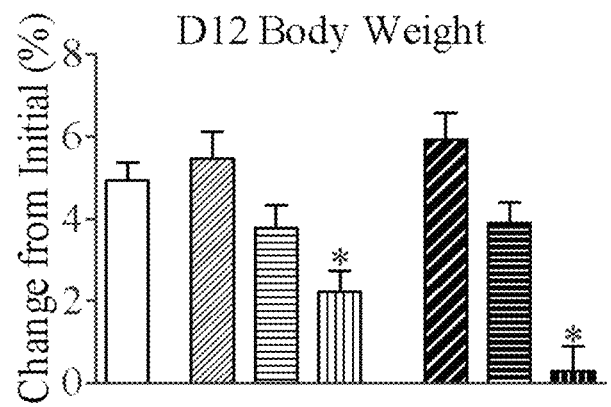
Figure 6E:
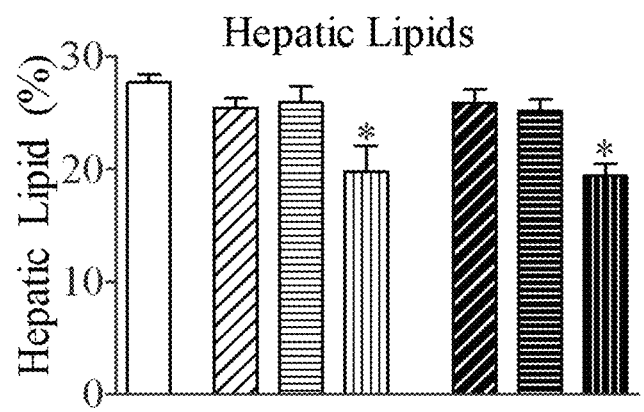
Figure 6F:
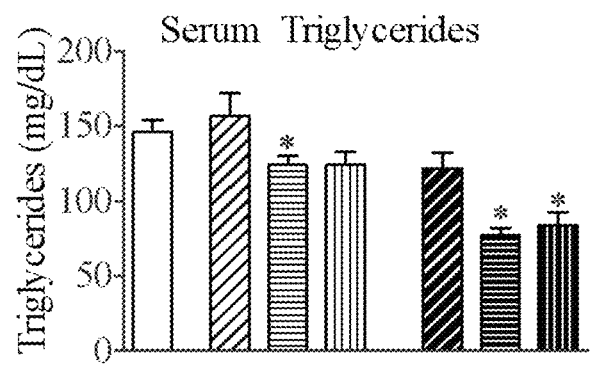

To determine if the fusion of GLP-1 to FGF21 would lead to additional efficacy, the WT GLP-1 and GLP-1(A8S) versions were tested against an equivalent FGF21 molecule each with the same 40 kDa branched PEG attached. In a two week study with twice weekly dosing, the FGF21(R154C)-PEG (V238) and GLP-1-FGF21(R154C)-PEG (V239) showed similar effects on blood glucose, body weight, and liver health (assessed by alanine aminotransferase (ALT) serum levels, weight, and appearance) (FIG. 4). Glucose measurements showed a faster improvement for the fusion than for FGF21 alone after the first dose. The two converged at time points more than a day after dosing, suggesting that the additional benefit due to GLP-1 was shorter lived than the FGF21 efficacy.

The GLP-1(A8S)-FGF21(R154C)-PEG (V235) fusion also showed similar effects at 0.2 mg/kg, rather than the 1 mg/kg used for the other compounds. This compound also generally gave more consistent results between dosing, suggesting that the DPP-4-resistance was critical to the overall improvement in efficacy as compared to the up-and-down behavior of GLP-1-FGF21(R154C)-PEG (V239). It was also observed that the GLP-1(A8S)-FGF21(R154C)-PEG (V235) at 1 mg/kg showed additional lowering of glucose, body weight, ALT/AST, and liver weight.

Additional studies were conducted to see if the improved efficacy could be replicated with co-administration of separate FGF21 and GLP-1 compounds. To make dosing of proteins similar between groups, a tool compound was made in which 14 amino acids were removed from the FGF21 C-terminus. This molecule (V253) was at least 1000× less potent in the FGF21 receptor assay but retained equal potency in the GLP-1R assay as compared to the other fusions and was unable to inhibit wild-type FGF21 activity. This compound had pharmacokinetics in rat similar to the other fusions when assessed by FGF21 levels (FIG. 2).

Results of a four week study in which ob/ob mice were treated with FGF21(V76)-PEG, GLP-1(A8S)-PEG (V253), both together, or GLP-1(A8S)-FGF21(V76)-PEG fusion (V272) are shown in FIG. 5. The fusion was significantly more efficacious than co-treatment of the individual FGF21 (V76)-PEG and GLP-1(A8S)-PEG molecules on fed glucose AUC, OGTT glucose AUC, body weight at the end of the study, hepatic lipid content, and ALT measurement (p-values <0.05 for all).

Serum exposure of human FGF21 and GLP-1 were checked in the terminal serum samples to confirm exposure in the various groups. Human FGF21 was detected in all treated groups, and a significant increase in active GLP-1 was measured in all groups treated with GLP-1 (A8S)-PEG (V253) or GLP-1(A8S)-FGF21(V76)-PEG (V272). The GLP-1(A8S)-FGF21(V76)-PEG (V272) group showed similar levels of human FGF21 to the 0.2 mg/kg FGF21 (V76)-PEG group, suggesting that the improved efficacy is not due to a higher systemic accumulation of the fusion in the animals. The GLP-1(A8S)-PEG (V253) molecule was fully active in vitro (Table 8). These data demonstrate that the efficacy of the fusion was dependent on both moieties being in a single molecule, and, e.g., benefitted from a synergy at the cellular level.

To further test GLP-1(A8S)-FGF21(V76)-PEG (V272) vs. co-administration, three studies were conducted in db/db mice. In each study, male db/db mice (8-11 weeks old were dosed i.p. twice weekly. In an initial three week study, the dual function fusion protein, GLP-1(A8S)-FGF21(V76)-PEG (V272), matched the glucose lowering of the co-administration at equal doses and surpassed the efficacy of single entity dosing. The dual function fusion protein also showed superior body weight loss.

Figure 8A:
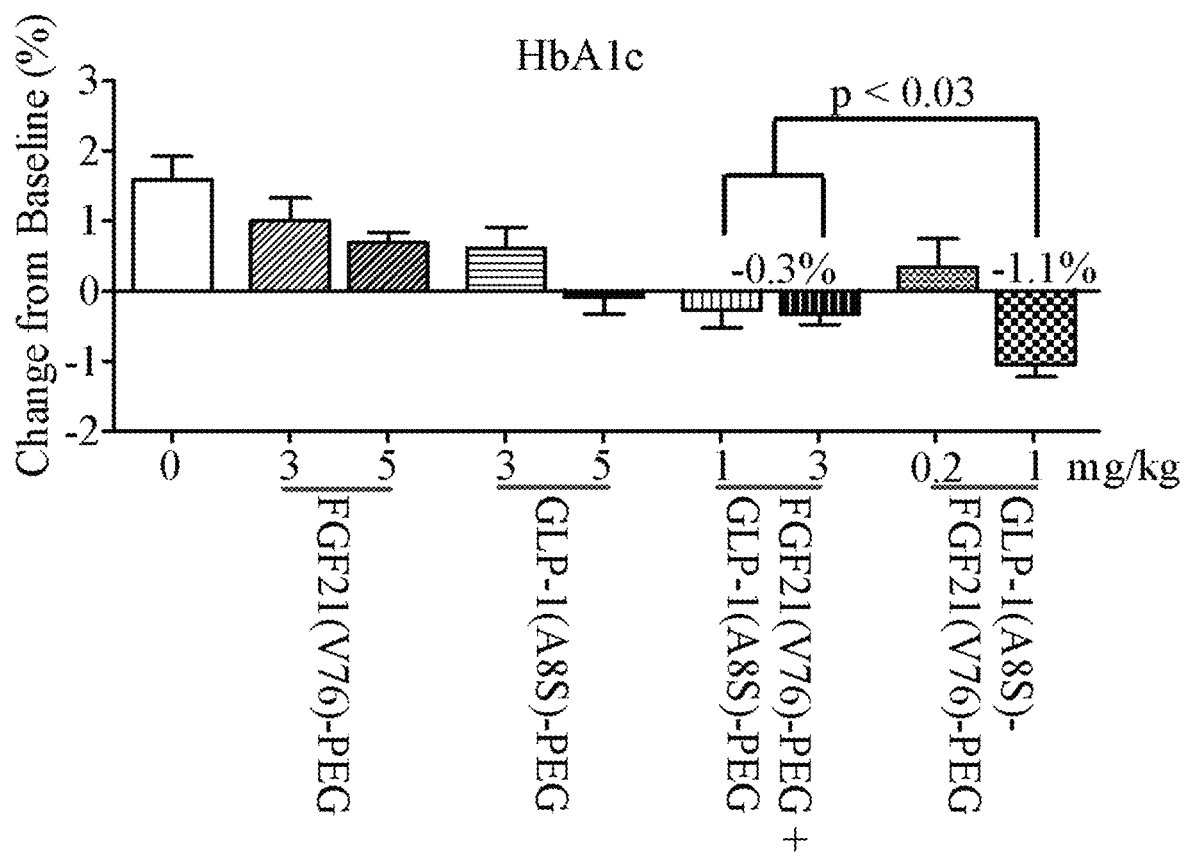
FIGS. 8A-8B show the ability of GLP-1-FGF21-PEG fusion proteins to improve glucose lowering (FIG. 8A) and body weight (FIG. 8B), relative to the combination of the individual agents. Db/db mice were dosed twice per week, for two weeks, with vehicle (white bars; open circles), a combination of individual GLP-1(A8S)-PEG (V253; 3 mg/kg (light horizontal hashed bars; open diamonds) and 5 mg/kg (dark horizontal bars; diamonds)) and FGF21(V76)-PEG (3 mg/kg (V76; light diagonal hashed bars; open squares) and 5 mg/kg (dark diagonal hashed bars; squares)), as well as with the GLP-1(A8S)-FGF21(V76)-PEG dual function fusion protein of the invention (V272; 0.2 mg/kg (smelled checked bars; open triangles); 1 mg/kg (large checked bars; triangles)). As seen in the figure, 0.2 mg/kg of the GLP-1(7-35; A8S)-FGF21(V76)-PEG dual function fusion protein (V272) is as effective as 5 mg/kg of FGF21 (V76)-PEG. Also as seen in the figure, 1.0 mg/kg of the GLP-1(7-35; A8S)-FGF21(V76)-PEG dual function fusion protein (V272) is more effective that the maximal effective combination doses of FGF21(V76)-PEG+GLP-1(7-35; A8S)-PEG (1+1 mg/kg (light horizontal hashed bars; exes) and 3+3 mg/kg (dark horizontal bars; stars), for both glycemic and body weight endpoints.
Figure 8B:
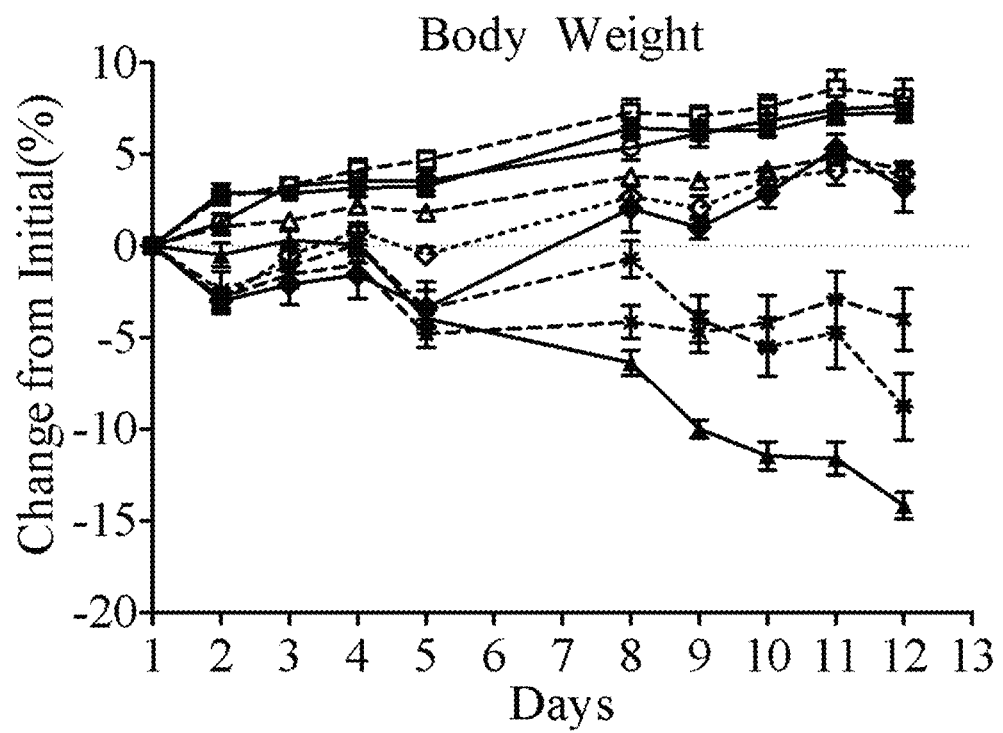

In a second two week study, GLP-1(A8S)-FGF21(V76)-PEG (V272) showed similar glucose lowering compared to FGF21(V76)-PEG at a 25-fold lower dose and GLP-1 (A8S)-PEG (V253) at a 5-fold lower dosing. In addition, GLP-1(A8S)-FGF21(V76)-PEG (V272) lowered HbA1c significantly more and lowered body weight significantly more than the mono-therapies or the maximally efficacious dose of the co-administration groups (FIG. 8, Table 2). Unexpectedly, altering the dosing ratio of the co-treatments higher than 1:1 did not improve the observed efficacy (Table 2). This suggests that dual function proteins including equal numbers of GLP-1 moieties and FGF21 moieties can achieve optimal efficacy during in vivo treatments.

TABLE 2

Therapeutic Dosages

| Treatment | Dose (mg/kg 2x/wk) | HbA1c, change from initial (%) | Body weight, day 12 (g) |
|---|---|---|---|
| Vehicle | N/A | 1.6 ± 0.9 | 42.3 ± 2.1 |
| V76 | 1 | 2.2 ± 1.0 | 43.3 ± 2.1 |
| V76 | 3 | 1.0 ± 0.9 | 42.3 ± 1.3 |
| V76 | 5 | 0.7 ± 0.4[1] | 42.1 ± 1.9 |
| V253 | 1 | 0.8 ± 0.7[1] | 42.6 ± 2.1 |
| V253 | 3 | 0.6 ± 0.8[1] | 40.9 ± 2.6 |
| V253 | 5 | −0.1 ± 0.6[1] | 40.4 ± 2.1 |
| V76 + V253 | 1 + 1 | −0.3 ± 0.6[1] | 37.7 ± 2.2[1] |
| V76 + V253 | 1 + 3 | 0.5 ± 0.6[1] | 37.7 ± 1.7[1] |
| V76 + V253 | 3 + 1 | −0.1 ± 0.5[1] | 38.9 ± 1.2[1] |
| V76 + V253 | 3 + 3 | −0.3 ± 0.4[1] | 36.0 ± 1.7[1] |
| V272 | 0.2 | 0.4 ± 1.1[1] | 41.1 ± 2.7 |
| V272 | 1 | −1.1 ± 0.5[1,2] | 33.8 ± 2.1[1,2] |

[1]p-value vs. vehicle <0.05.
[2]p-value vs. co-treatment groups <0.05

Figure 7A:
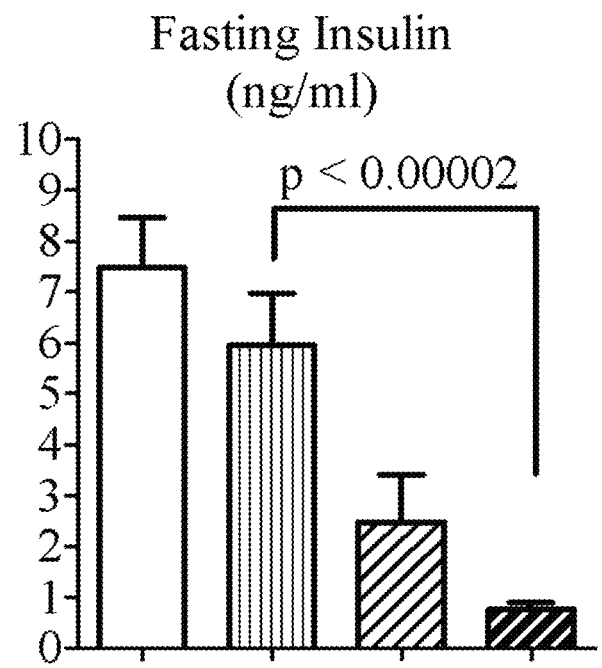
FIGS. 7A-7B show the ability of GLP-1(A8S)-FGF21 (V76)-PEG fusion proteins to improve pancreatic function and increase islet insulin content, relative to the combination of the individual agents. Db/db mice were dosed twice per week, for four weeks, with a combination of individual GLP-1(A8S)-PEG+FGF21(V76)-PEG (V76+V253; vertical hashed bars), as well as with the GLP-1(A8S)-FGF21(V76)-PEG dual function fusion protein of the invention (V272; diagonal hashed bars; light for 0.5 mg/kg and dark for 1 mg/kg), or vehicle (white bars).
Figure 7B:
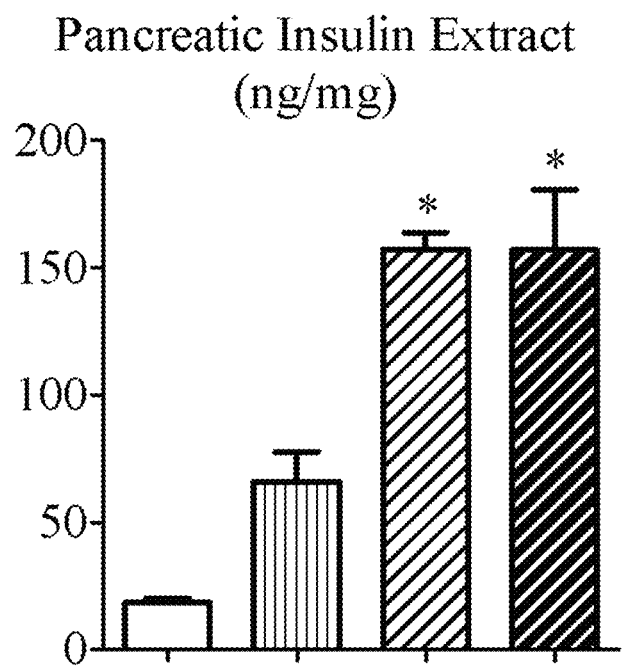

Table 2 shows efficacy of mono-therapies and co-treatments at different doses compared to dual function proteins in a db/db mouse study with 2 weeks of dosing. The reported values are averages of measurements made in eight animals with standard deviation. In a four week study, male db/db mice (n=8) were dosed twice weekly for four weeks with mono-therapies, co-treatments, or dual function fusion proteins. On day 27, the mice were fasted and the blood insulin levels were measured for all animals. At the end of the study, pancreatic insulin contents were extracted and measured (n=3). GLP-1(A8S)-FGF21(V76)-PEG (V272) showed a robust dose response from 0.1-1 mg/kg with efficacy equal to or better than FGF21(V76)-PEG or GLP-1 (A8S)-PEG (V253) alone on glucose levels, HbA1c, and body weight at more than 10-fold lower dose, and improved efficacy over the maximally efficacious dosing of the co-administration. GLP-1(A8S)-FGF21(V76)-PEG (V272) also lowered fasting insulin levels in the serum while increasing insulin content of the pancreas to a greater extent than the single or combination treatments of GLP-1(A8S)-PEG (V253) and FGF21(V76)-PEG (FIG. 7). GLP-1(A8S)-FGF21(V76)-PEG (V272)-treated animals were close to lean control mice in fed glucose, HbA1c, and body weight numbers.

To estimate metabolic rate and substrate utilization, we measured oxygen consumption and carbon dioxide production using an Oxymax indirect calorimetry system (Columbus Instruments, Columbus, Ohio). Mice were housed in the chamber with a 12-h light/12-h dark cycle in an ambient temperature of 22-24° C. $VO_2$ and $VCO_2$ rates were determined under Oxymax system settings and protocol. The system was calibrated against a standard gas mixture to measure $O_2$ consumed ($VO_2$, ml/kg/h) and $CO_2$ generated ($VCO_2$, ml/kg/h). Metabolic rate ($VO_2$) and respiratory exchange ratio (RER) (ratio of $VCO_2/VO_2$) were evaluated over a 72-h period. Calculated RER values indicated that animals treated with fusion protein relied more on lipid substrates (RER values close to 0.75-0.85) particularly during the 24-72 hours after the second dose when compared to vehicle or combination treated groups. During this period, vehicle and combination treated groups showed RER values were close to 0.9 suggesting more of carbohydrate substrate utilization for energy and to a lesser extent lipid substrate utilization for energy expenditure. The data suggest that fusion protein treatment caused an increase in fatty acid oxidation that may be contributing to its body weight reduction effect in db/db mice A dual function fusion protein, when compared to combination, showed improved beta-cell function in vivo. After four doses of either dual function protein GLP-1(A8S)-FGF21(V76)-PEG (V272) or GLP-1(A8S)-PEG (V253) plus FGF21(V76)-PEG, db/db mice were dosed orally with glucose and arginine. The glucose excursion of the dual function protein-treated group (72% lower than vehicle) was significantly lower than the combination-treated group (56% lower than vehicle). During the experiment, the amount of insulin secreted was also higher for the dual function protein-treated group (279% higher than vehicle) than for the combination-treated group (122% higher than vehicle).

Overall, the figures and tables, as well as data not shown herein, demonstrate the ability of the dual function fusion proteins of the invention, e.g., GLP-1(A8S)-FGF21(V76)-PEG (V272), to improve metabolic parameters for in vitro and in vivo rodent models of diabetes, when compared to a combination of individual GLP-1 and FGF21 (e.g., FGF21 (V76)-PEG and GLP-1(A8S)-PEG (V253)). Said improved parameters (as used herein, "metabolic parameters") include but are not limited to fed glucose (AUC), body weight, liver triglycerides, plasma HbA1c, serum triglyceride levels total cholesterol levels, oral glucose tolerance test serum glucose measurement (AUC), fasting serum insulin, pancreatic insulin content, and body fat percentage.

Example 3: Design of GLP-1/Proteins of the Invention from FGF21 Variants

A fusion was made with the following FGF21 variant sequence, which we refer to herein as "Variant 76" or "V76":

```
                                                    (SEQ ID NO: 130)
  1 DSSPLLQFGG QVRQRYLYTD DAQETEAHLE IREDGTVGGA AHQSPESLLE LKALKPGVIQ

61 ILGVKTSRFL CQKPDGALYG SLHFDPEACS FRELLLEDGY NVYQSEAHGL PLHLPGNRSP

121 HCDPAPQGPA RFLPLPGLPP ALPEPPGILA PQPPDVGSSD PLAMVGPSQG RSPSYAS
```

FGF21(V76)-PEG features a 40 kDa branched PEG linked through Cys154, and eight point mutations relative to the 177 amino acid wild-type protein (Q56E, D74H, Q82E, R105K, K150R, R154C, R159Q, S195A, all made relative to full-length FGF21 protein sequence (NCBI reference sequence number NP_061986.1)). The risk of clinical immunogenicity toward this molecule is considered low based on an EpiScreen time course assay of human T-cell responses. The molecule has a serum half-life time of more than 30 h in mouse and rat and significantly lowers glucose AUC in ob/ob mice with twice-weekly injections of 1 mg/kg.

The GLP-1(A8S)-FGF21(V76)-PEG (V272) molecule was tested against the GLP-1(A8S)-FGF21(R154C)-PEG (V235) fusion at three doses (0.05, 0.1 and 0.2 mg/kg). Both fusions showed a dose response in lowering glucose AUC, body weight, food intake, and ALT (FIG. 6). GLP-1(A8S)-FGF21(V76)-PEG (V272) was generally equal or better and showed higher efficacy for all parameters at the 0.2 mg/kg dose. GLP-1(A8S)-FGF21(V76)-PEG (V272) also showed lowering of serum triglycerides and cholesterol at both 0.1 and 0.2 mg/kg. Based on these data, the GLP-1(A8S)-FGF21(V76)-PEG (V272) molecule shows similar or improved properties to the initial fusions and is suitable for further study and development.

Ex4(1-30)-L20-FGF21(V76)-PEG (V277) also showed similar efficacy to GLP-1(A8S)-FGF21(V76)-PEG (V272) in an ob/ob 2 week study for glucose control, body weight and lipid levels.

Choice of PEGylation site for half-life extension. As seen for example in FIG. 2, PEGylation was used to extend the half-life of the molecule from a few minutes for GLP-1 or less than an hour for FGF21 to longer than 30 hours as measured in rats. To see if the two moieties of the fusion could be modulated by placement of the PEG, a series of constructs was made with the extra cysteine not in the FGF21 sequence but in that of GLP-1 or the linker. These constructs were tested for both GLP-1 and FGF21 activity in cell-based assays. Experiments reveal a stretch of positions within the fusion protein sequences at which PEGylation does not greatly impact either activity. Careful placement of the PEG at the N-terminal end of this stretch could be used to make a molecule with knocked-down GLP-1 activity while placement in the linker could be used to knock-down FGF21 activity. Such a molecule may be useful in tuning the potency of the fusion (for example, if the high potency of GLP-1 or Exendin-4 resulted in a poor therapeutic window when dosed at the efficacious level of a lower potency FGF21).

Based on these data, fusions with PEGylation at K34C of GLP-1 (V273) or K27C of Exendin-4 (V274) were prepared with FGF21(V76-C154R) whose sequence is as follows:

```
                                                    (SEQ ID NO: 131)
    DSSPLLQFGG QVRQRYLYTD DAQETEAHLE IREDGTVGGA

AHQSPESLLE LKALKPGVIQ ILGVKTSRFL CQKPDGALYG
```

-continued

```
    SLHFDPEACS FRELLLEEGY NVYQSEAHGL PLHLPGNRSP

HRDPAPQGPA RFLPLPGLPP ALPEPPGILA PQPPDVGSSD

PLAMVGPSQG RSPSYAS
```

A two week study in ob/ob mice demonstrates that, although the new fusions (V273 and V274) exhibited potency in vitro similar to the previous fusions and similar pharmacokinetics in rat, they were not as efficacious in vivo. At 0.2 mg/kg, the GLP-1 fusion variant showed no significant efficacy for glucose or body weight. The Exendin-4 fusion variant showed significant lowering of ALT and body weight and a trend toward lower AST compared to vehicle but no significant effect on blood glucose. Although these fusions may show efficacy at higher doses, the original format with PEGylation at R154C in FGF21 was chosen for further study. It is unclear if this unexpected difference indicates a special property of the GLP-1(A8S)-FGF21 (V76-154R)-PEG version of the fusion that is blocked by PEGylation at the alternate site or if there is another explanation such as the PEG blocking the GLP-1R interaction more on the native cells with native receptor levels than on the transfected cells used for the in vitro assay.

Example 4: Further Characterization of GLP-1/FGF21 Proteins of the Invention In order to further optimize and rank the GLP-1-FGF21-PEG dual activity proteins of the invention, and to gain a fuller appreciation of their improved efficacy over co-administration models, the fusions are tested in the ob/ob model of efficacy. These include but are not limited to molecules with longer or shorter linkers, additional proteins of the invention (which may include but are not limited to mutants based on Variant 76 or additional variants in development such as additional or different point mutations, insertions or deletions, dimerized molecules, alternative PEGylation strategies, molecules with additional disulfide bridges, molecules produced in different expression systems), and variants of Exendin-4 or GLP-1 to improve serum stability or activity. Candidates are also filtered by in silico immunogenicity prediction, expression levels, and quality of final products (related to solubility, aggregation and stability).

In order to further characterize the synergy of FGF21 and GLP-1 for treatment of diabetes and obesity, interaction dynamics of the two molecules are mapped, and the fusion proteins are compared to the maximally efficacious co-administration of the individual parent molecules. These experiments are conducted in models that focus on obesity and weight loss (Diet Induced Obesity in rat or mouse) and those that better model aspects of diabetes such as hyperglycemia, dislipidemia, and impaired beta cell function (ob/ob or db/db mice). The extent of synergy achieved by the dual activity proteins of the invention can be further determined by mapping the efficacy of each individual molecule, the combination of the two at different ratios, and the fusion.

Testing in cell-based assays with primary or immortalized rat islets and primary human islets is conducted to assess the efficacy of the fusion for cell proliferation, protection from apoptosis, and function, e.g., to validate the dual activity proteins of the invention in accepted models of Type 1 Diabetes (see further Van Belle, T. L. et al. Drug Discovery today: disease models. 209 pp. 41-45). Preferred in vivo models are those featuring pancreatic ablation by streptozotocin (STZ); targeted beta-cell ablation in a genetically modified and inducible mouse strain (RIP-DTA) in which the beta-cells are destroyed by supplementing the diet with doxycycline to induce targeted expression of diphtheria toxin; or the non-obese diabetic (NOD) mouse model of Type-1 diabetes with an autoimmunity mechanism. In these models, testing is possible in both prophylactic dosing to assess beta-cell protection (particularly in NOD) as well as post-challenge dosing to assess beta-cell stimulation and proliferation (particularly in STZ and RIP-DTA).

The following experiments are conducted to more fully realize the mechanism of efficacy synergy achieved by the dual activity proteins of the invention over the co-administration regimens: Cells co-transfected with both receptors (GLP-1R; FGFR1(IIIc), 2(IIIc), 3(IIIc), or 4; and beta-klotho) can be used to determine if the receptors are able to potentiate the opposing signal at the cell surface. Crosstalk between downstream signals can be detected in cells naturally expressing both receptors (e.g., beta cells). In animals, the contribution of food intake (investigated with pair-fed cohorts), increased metabolic rate (investigated in clamp and metabolic chamber experiments), and other mechanisms could be more thoroughly investigated to elucidate a mode of action for the synergistic effects of the two signals. Gene expression profiling of key tissues (liver, pancreas, adipose, intestine, heart, aorta, brain, etc.) may also be conducted in order to elucidate the unique signaling of the fusion proteins, potentially accounting for their improved efficacy.

The following experiments are conducted to understand the activity of dual function proteins of the invention to control or modify differentiation of mesenchymal stem cells (MSC): MSC can be treated with proteins of the invention alone or with compounds or mixtures of compounds known to induce osteogenesis or with compounds or mixtures of compounds known to induce adipogenesis and the resulting rates of differentiation to osteoblast-like cells or adipocyte-like cells can be measured.

Example 5: Design of GLP-1 and Exendin-4-Containing Proteins of the Invention from Fc-Fusion FGF21 Variants Constructs were made with alternative linkers (for example, SGGGGSGGGGSGGGGSA (SEQ ID NO:138), GGGGS (SEQ ID NO:173), GG, and GGGGSGGGGSGGGGS (SEQ ID NO:174)), FGF21 variants, and GLP-1-related peptides. Typically the dual function proteins containing an Fc domain were expressed in HEK293 cells. The DNA coding sequences of these fusions were cloned into vectors containg sequence encoding a leader peptide to direct the proteins for secretion and further containing sequences necessary to promote mRNA syntehsis and protein expression of the desired products. HEK293 cells were transiently transfected with the vectors. The media from these cell cultures were collected, filtered, and purified by protein A affinity chromatography. The eluates were brought to netural pH and further purified by size exclusion chromatography. The products were then concentrated and stored for various assays. Variants were tested for activity in vitro in four assays: CRE-luciferase expression induction in HEK293 transfected with GLP-1R (Table 3) and glucose stimulated insulin secretion in INS1E cells (Table 6) to measure activity through GLP-1R; ERK phosphorylation induction in HEK293 transfected with beta-klotho (Table 4) and 2-deoxyglucose uptake by 3T3L1 cells (Table 5) to measure FGF21 activity. Variants with GLP-1 (A8S) and a 15 amino acid linker were more active than variants with GLP-1 and shorter linkers. Exendin-4 (1-39) variants with all linkers tested were active. Exendin-4 (1-30)-containing variants had similar in vitro potency to Exendin-4 (1-39)-containing constructs. A variant with a tandem repeat of Exendin-4(1-39) was not as potent as variants with a single copy of a GLP-1-related peptide.

TABLE 3

GLP-1R activation in HEK293-GLP-1R-CRE-Luciferase Reporter Cells.

| Variant# | GLP-1R $EC_{50}$ (nM) |
| --- | --- |
| V193 | 0.024 |
| V194 | 0.042 |
| V195 | 0.041 |
| V196 | 0.027 |
| V197 | 0.085 |
| V198 | 0.024 |
| V199 | 0.046 |
| V202 | 0.025 |
| V203 | 0.252 |
| V206 | 0.047 |
| V207 | 0.088 |
| V208 | 0.044 |
| V209 | 0.033 |
| V210 | 0.038 |
| V211 | 0.032 |
| V212 | 5.90 |

TABLE 3-continued

GLP-1R activation in HEK293-GLP-1R-CRE-Luciferase Reporter Cells.

| Variant# | GLP-1R EC$_{50}$ (nM) |
|---|---|
| V213 | 18.4 |
| V214 | 0.023 |
| V215 | 8.99 |
| V216 | 0.025 |
| V217 | 4.53 |

TABLE 4

Activity measured in an ERK phosphorylation assay of FGF21 activity in HEK293-KLB cells.

| Variant# | βklotho pERK EC$_{50}$ (nM) | % γ-max vs. WT FGF21 | Potency (Fold over WT FGF21) |
|---|---|---|---|
| V193 | 2.1 | 101 | 1.2 |
| V194 | 9.8 | 97 | 5.8 |
| V195 | 13 | 76 | 7.6 |
| V196 | 0.87 | 58 | 0.18 |
| V197 | 0.92 | 63 | 0.19 |
| V198 | 0.94 | 67 | 0.24 |
| V199 | 1.04 | 58 | 0.27 |
| V202 | 1.78 | 67 | 0.37 |
| V203 | 1.01 | 70 | 0.21 |
| V206 | 0.51 | 83 | 0.15 |
| V207 | 1.10 | 83 | 0.34 |
| V208 | 0.53 | 54 | 0.20 |
| V209 | 0.70 | 83 | 0.21 |
| V210 | 0.84 | 88 | 0.24 |
| V211 | 0.58 | 73 | 0.17 |
| V212 | 1.24 | 89 | 0.37 |
| V213 | 1.00 | 61 | 0.37 |
| V214 | 0.55 | 50 | 0.21 |
| V215 | 0.92 | 51 | 0.34 |
| V216 | 0.85 | 56 | 0.32 |
| V217 | 2.23 | 46 | 0.83 |

TABLE 5

Activity measured in a 2-deoxyglucose uptake in 3T3L1 mouse adipocytes.

| Variant# | 2DOG EC$_{50}$ (nM) | % γ-max vs. WT FGF21 | Potency (Fold over WT FGF21) |
|---|---|---|---|
| V194 | 2.8 | 118 | 1.6 |
| V196 | 0.055 | 90 | 0.14 |
| V197 | 0.077 | 100 | 0.18 |
| V198 | 0.079 | 105 | 0.21 |
| V199 | 0.090 | 101 | 0.37 |
| V202 | 0.45 | 86 | 2.5 |
| V203 | 0.078 | 100 | 0.31 |
| V206 | 0.093 | 85 | 0.34 |
| V208 | 0.067 | 87 | 0.25 |
| V209 | 0.157 | 91 | 0.59 |
| V210 | 0.067 | 98 | 0.27 |
| V211 | 0.073 | 99 | 0.29 |
| V214 | 0.213 | 87 | 0.81 |
| V216 | 0.137 | 80 | 0.56 |

TABLE 6

Activity measured by glucose-stimulated insulin secretion (GSIS) in INS1E rat insulinoma cells.

| Variant# | GSIS EC50 (nM) (avg of 2) |
|---|---|
| V196 | 9.1 |
| V197 | 46 |
| V198 | 4.4 |
| V199 | 5.0 |
| V202 | 33 |
| V203 | 128 |
| V206 | 2.4 |
| V208 | 1.6 |
| V209 | 1.9 |
| V210 | 2.7 |
| V211 | 1.5 |
| V214 | 4.6 |
| V216 | 6.8 |

Eight ob/ob mice were dosed with variants twice per week at 0.5 mg/kg for two weeks. Blood glucose and body weight were measured during the studies, and hepatic lipids were measured at the end of the study. As seen in the following table (Table 7), treated animals had reduced blood glucose, lower body weight, and lower hepatic lipids throughout the study, when compared to vehicle-treated age-matched animals.

TABLE 7

Summary of results of treating ob/ob mice twice per week at 0.5 mg/kg for two weeks.

| Variant# | BW loss, D12 (% of Veh) | Fed AUC lowering (% of Veh) | TG FASTED (8 h, or O/N) (% of Veh) | Hepatic Lipids (% of Veh) |
|---|---|---|---|---|
| V193 | −20* | −55* | 39 | −66* |
| V195 | −7* | −30* | N/A | −10 |
| V196 | −23* | −63* | 8 | −65* |
| V197 | −16* | −53* | 52 | −85* |
| V198 | −24* | −64* | −7 | −69* |
| V199 | −24* | −64* | −7 | −69* |
| V200 | −14* | −39* | −5 | −62* |
| V201 | −22* | −60* | −10 | −58* |
| V202 | −18* | −59* | 22 | −63* |
| V203 | −8* | −33* | 68* | −73* |
| V206 | −16* | −58* | −19 | −56* |
| V207 | −22* | −64* | −10 | −55* |
| V208 | −21* | −60* | 10 | −57* |
| V209 | −28* | −66* | −11 | −62* |
| V210 | −23* | −67* | −14 | −57* |
| V211 | −28* | −68* | 0 | −52* |
| V214 | −19* | −58* | 110* | −41* |
| V216 | −21* | −62* | 29 | −51* |

*p-value vs. vehicle <0.05

Figure 9:
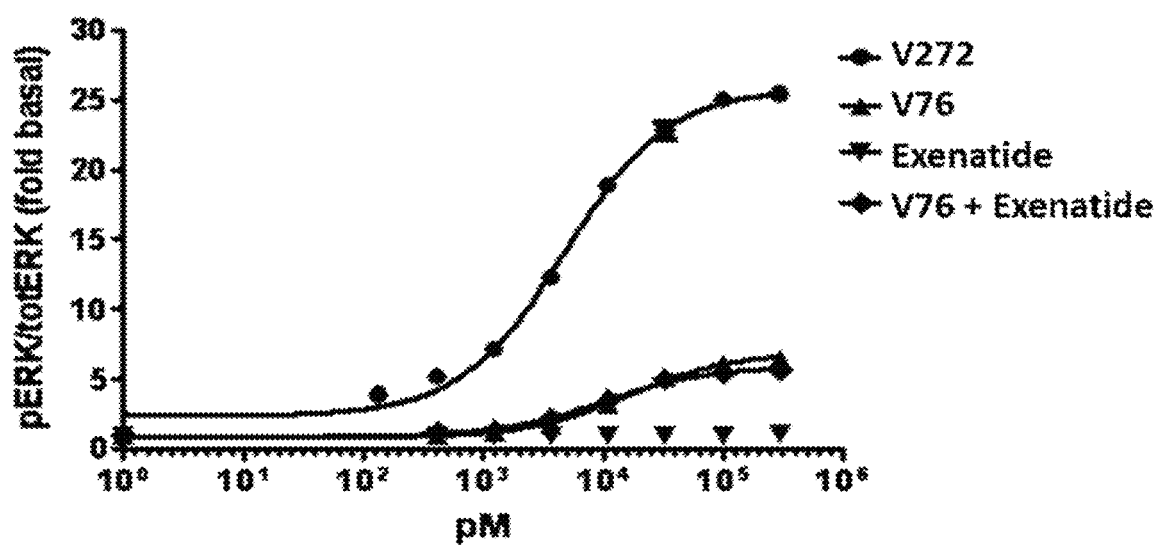
FIG. 9 shows the results of an assay for FGF21 activity. Phosphorylation of ERK is measured after treatment of HEK293-beta-klotho cells with the indicated compounds. The activity of GLP-1(A8S)-V76-PEG (V272) is significantly higher in magnitude of signal compared to the same FGF21 variant FGF21(V76)-PEG in the presence or absence of equimolar Exenatide.
Figure 10A:
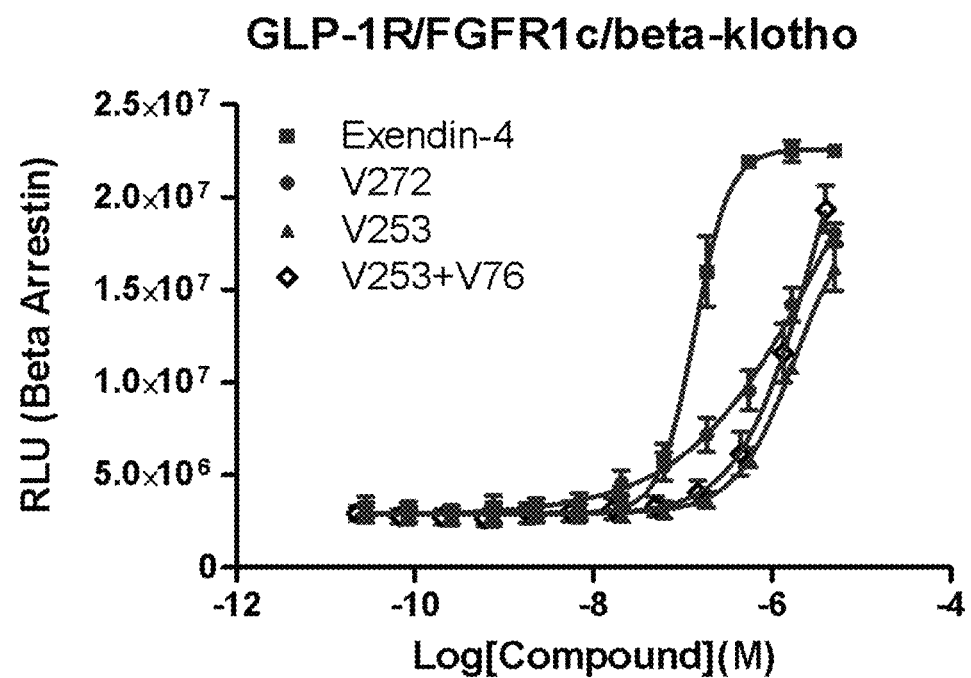
FIGS. 10A-D present results of a receptor pharmacology assay used to measure the activity of fusion proteins compared to matched single agonist proteins or peptides. HEK293 cells transfected with GLP-1R and FGFR1c/beta-klotho (FIGS. 10A and 10B) or with GLP-1R alone (FIGS. 10C and 10D) were assayed for beta-arrestin recruitment to GLP-1R after treatment with compounds for 1 hour. Molecules tested in the assay were: Exendin-4 (squares), GLP-1(A8S)-FGF21(V76)-PEG (V272; circles), GLP-1(A8S)-
Figure 10B:
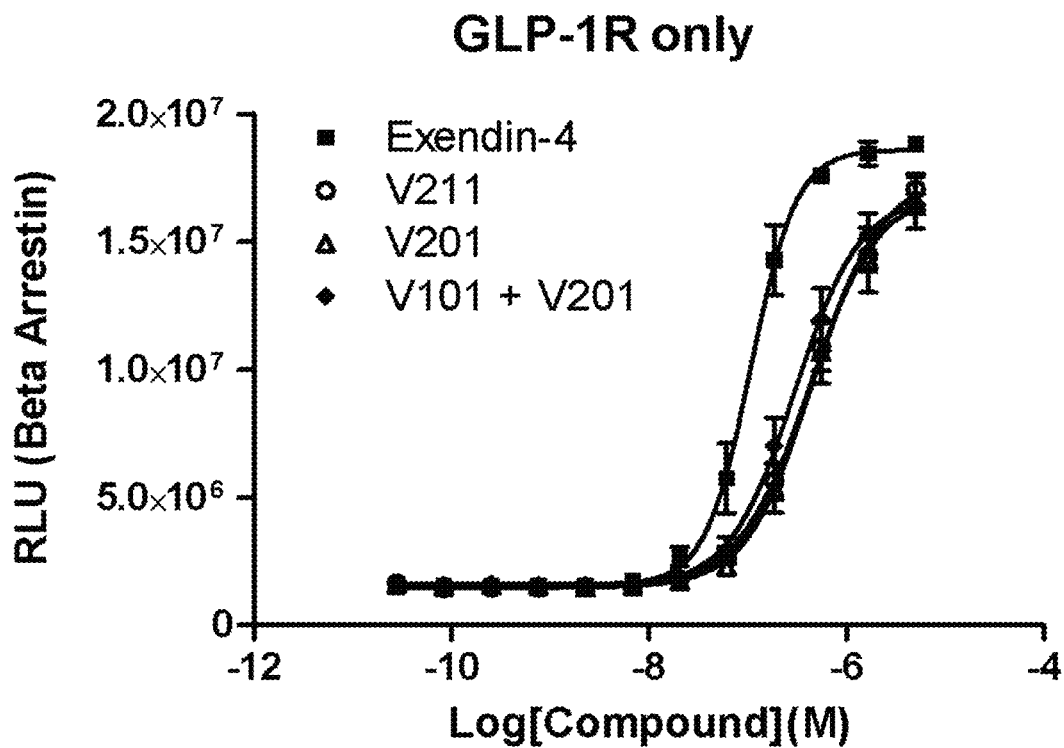
Figure 10C:
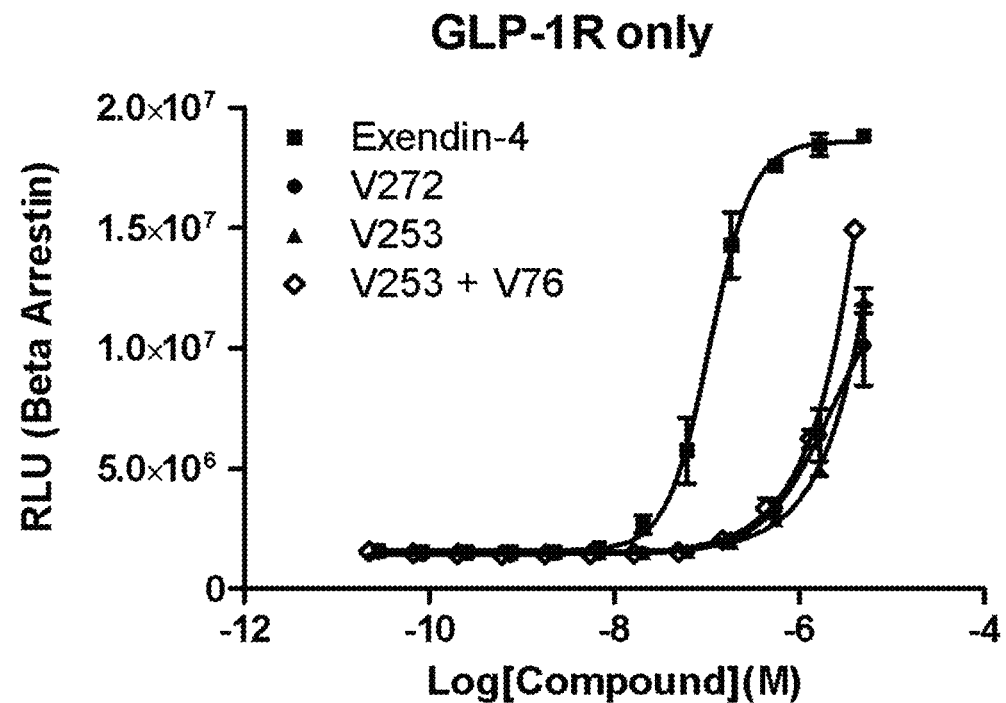
Figure 10D:
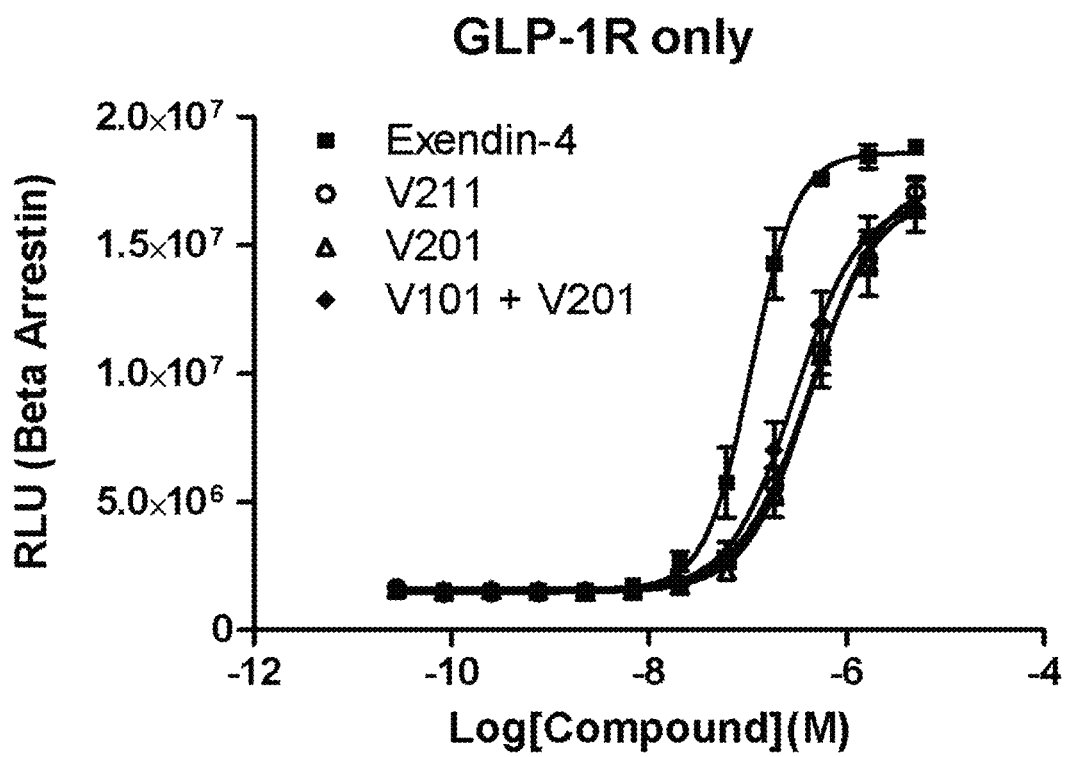

Example 6: Further Characterization of Proteins of the Invention in Receptor Pharmacology Assays As seen, for example, in FIG. 9, dual agonist proteins of the invention were compared to various forms of FGF21 and Exenatide for their ability to induce ERK phosphorylation in HEK293 transfected with beta-klotho. At 10 minutes, cells treated with GLP-1(A8S)-FGF21(V76)-PEG (V272) showed a higher potency and higher maximal proportion of phospho-ERK to total ERK when compared to cells treated with FGF21(V76)-PEG plus Exenatide. The higher maximal phospho-ERK signal shows that the dual function protein V272 is a superior agonist for signaling through FGFR1c/beta-klotho when compared to the FGF21(V76)-PEG molecule, possibly due to better interaction with the receptor (for example, the N-terminal extension causing the dual function protein to attain a more favorable structure for receptor binding or activation).

Select dual function proteins were tested for their ability to induce phospho-ERK signaling in human adipocytes. When compared to a single function FGF21 molecule (V101), the dual function proteins V208, V209, V211, V14, and V272 were more potent for stimulating phosphorylation of ERK. Because these are human cells, it may also suggest that the dual function proteins of the invention will be highly active in treatment of human disease when compared to treatments including other FGF21 mimetics, similar to what has been demonstrated for activity in rodents to date.

As seen, for example, in Table 8 and FIG. 10, dual agonist proteins of the invention were compared to Exenatide, GLP-1 peptide, Exendin-4(1-39)-L5-Fc (V201), and GLP-1(A8S)-PEG (V253) for their ability to signal through GLP-1R in HEK293 cells transfected with GLP-1R or cells co-transfected with GLP-1R, beta-klotho and FGFR1c. Cells were treated with compound for 30 minutes, and cAMP levels were measured. Table 8 shows that in cells with both the GLP-1R and the FGF21 receptor complex, the dual agonist proteins (V272 and V211) showed higher potency than the single agonists (V253 and V101) alone or in combination with Exendin-4. In cells with only GLP-1R, the potency of the single agonists alone or in combination with Exendin-4 was equal to that of the dual agonist proteins. FGF21 variants alone were inactive in the assay.

TABLE 8

Assay of cAMP induction in cells treated with dual function proteins of the invention.

| | GLP-1R/FGFR1c/beta-klotho | | | GLP-1R only | | |
|---|---|---|---|---|---|---|
| Compound | EC50 (nM) | EC50 (fold-Ex-4) | y-max (% Ex-4) | EC50 (nM) | EC50 (fold-Ex-4) | y-max (% Ex-4) |
| Ex-4 | 6.0 | 1.0 | 100 | 11 | 1.0 | 100 |
| V253 | 24 | 4.1 | 92 | 34 | 3.2 | 81 |
| V253 + V76 | 12 | 2.1 | 91 | 38 | 3.5 | 82 |
| V272 | 2.4 | 0.4 | 97 | 64 | 6.0 | 76 |
| V201 | 26 | 4.4 | 93 | 32 | 3.0 | 100 |
| V201 + V101 | 15 | 2.4 | 98 | 18 | 1.7 | 82 |
| V211 | 6.6 | 1.1 | 92 | 39 | 3.6 | 98 |

Two additional HEK293 cell lines were generated in Discoverx's PathHunder assay format which utilizes complementation of beta-galactosidase fragments on beta-arrestin and the C-terminus of GLP-1R to measure recruitment of arrestin upon receptor activation. FIGS. 10a-10d show that with a 1 hour incubation of cells with protein or peptide, GLP-1 (A8S)-FGF21(V76)-PEG (V272), Exendin-4(1-39)-L15-Fc-L15-FGF21(V103) (V211), GLP-1(A8S)-PEG (V253), and Exendin-4(1-39)-L5-Fc (V201), were less potent than Exenatide for recruitment of beta-arrestin and that no difference in behavior was noted whether cells contained GLP-1R/FGFR1c/beta-klotho or GLP-1R alone.

The receptor pharmacology studies presented here suggest that the dual function proteins of the invention will be superior in activity and efficacy when compared to combinations or co-treatments of conventional FGF21 and GLP-1/Exenatide molecules. The PEGylated dual function protein GLP-1(A8S)-FGF21(V76)-PEG (V272) unexpectedly showed higher potency and maximal signal for phospho-ERK induction when compared to the FGF21(V76)-PEG molecule. These data show that the dual function proteins are equivalent or superior for FGF21 signaling when compared to other FGF21 variants. Likewise, the dual function proteins exhibit higher potency for cAMP signaling downstream of GLP-1R when cells express both the GLP-1 and FGF21 receptors. These properties may reflect a direct interaction between the receptors or an indirect effect such as a boost in local concentration through avidity toward the two receptors. These observations suggest a mechanism for improved activity of the dual function proteins that may explain why co-treatments of individual GLP-1 and FGF21 variants have not been sufficient to match the in vivo efficacy of the dual function proteins, as presented in other examples of this invention.

Example 7: Characterization of Proteins of the Invention in Models of Type-1 Diabetes (T1D)

RIP-DTA transgenic mice (9-10 weeks old) were treated with doxycycline for 3 days to induce controlled beta-cell ablation (similar to Thorel et al., Nature 2010(464)1149-1154). The mice were then treated for three weeks, twice per week with FGF21(V76)-PEG, FGF21(V76)-PEG+GLP-1(A8S)-PEG (V253), or GLP-1(A8S)-FGF21(V76)-PEG (V272). Treated animals in all three groups showed lower basal fed glucose levels during the study. The dual function protein treatment resulted in significantly lower glucose AUC (64% reduced from vehicle) compared to combination treatment (55% reduced from vehicle). After fasting, the mice were given a glucose bolus, and glucose excursion was measured. All three treatments lowered blood glucose levels compared to vehicle-treated animals, with the dual function protein treatment resulting in a 76% reduction compared to 66% for the combination treatment. All treated groups had increased pancreatic insulin content compared to vehicle, with the dual function protein treatment resulting in a 76% greater insulin content than combination treatment.

NOD mice were treated twice per week for three weeks with GLP-1(A8S)-FGF21(154C)-PEG (V235) or GLP-1(A8S)-PEG (V253)+FGF21(154C)-PEG (V238). After two weeks, the mice were fasted and given a glucose bolus for an OGTT. The dual function protein-treated mice showed significantly lower fasted glucose (~60% of vehicle) and glucose excursion during challenge (~45%) compared to vehicle while combination-treated animals had fasted glucose levels that were not significantly different from vehicle (~70%) and similar glucose excursion during challenge compared to vehicle-treated animals. At the end of the study, the dual function protein-treated animals had significantly lower basal glucagon levels (~50%) than vehicle, while combination-treated animals had levels similar to vehicle.

Example 8. Predictive Immunogenicity Results—MHC-Associated Peptide Proteomics (MAPPs) and T-Cell Assay Results The formation of anti-drug antibodies (ADA) to mAbs and other therapeutic proteins could potentially lead to severe immunotoxicological reactions, such as IgE-mediated anaphylactic reactions (Chung et al. (2008) N Eng J Med, 358, 1109-17) or immune complex disease, e.g., vasculitis, glomerulonephritis (Descotes and Gouraud (2008) Expert Opin Drug Metab Toxicol 4, 1537-49) as well as to a loss of clinical exposure and efficacy. Some patients treated with the therapeutic proteins PEGylated megakaryocyte growth and development factor (PEG-MGDF) and erythropoietin (EPO; Eprex) developed neutralizing ADA that were cross-reactive to their respective endogenous counterparts, leading to severe thrombocytopenia with PEG- MGDF and pure red-cell aplasia with Eprex (Li et al. (2007) Blood 98, 3241-8; Casadevall et al. (2002) N Engl J Med 346, 469-75). Hence, it is important to assess the immunogenicity risk prior to human testing. Evaluating the immunogenicity risk and putting in place a solid immunogenicity risk mitigation plan for the clinical development phase will be especially important for therapeutic proteins containing modified, non-human sequences such as the FGF21 variants that are the subject of this invention.

Formation of ADA can be induced in at least two different ways. T cell-dependent and -independent pathways have been described for B cell activation. A strong, high affinity IgG response is T cell-dependent and requires involvement of CD4+T helper cells (TH cells). The immune response is analogous to a response against foreign antigens: naive TH cells are specifically activated by professional antigen presenting cells (APCs), such as dendritic cells (DCs), and in turn induce activation of drug-specific B cells.

The MHC-associated Peptide Proteomics (MAPPs) assay involves in vitro identification of HLA class II associated peptides, which are processed by professional antigen presenting cells (APCs) such as dendritic cells. Antigen uptake, processing and presentation processes are taken into account. In this approach, immature human monocyte-derived DCs of different healthy blood donors, are incubated with different biotherapeutic drug candidates in the presence of an activation stimulus. The naturally processed HLA class II-associated peptides, which are derived from the biotherapeutic protein, are identified by liquid chromatography-mass spectrometry (Kropshofer and Spindeldreher (2005) in Antigen Presenting Cells: From Mechanisms to Drug Development, eds. Kropshofer and Vogt, Wiley-VCH, Weinheim, 159-98).

T cell assays provide a format in which the potential risk for immunogenicity of whole protein therapeutics can be assessed. T cell assays evaluate the capacity of a therapeutic protein to induce a CD4+ T cell response. Using a cohort of healthy blood donors covering a broad panel of HLA class II haplotypes, purified therapeutic proteins are tested for T cell proliferation and/or cytokine secretion in vitro. This technology been used successfully to compare protein variants for the potential to induce an immune response in vivo (Jones et al. (2004) J Interferon Cytokine Res. 24, 560-72.; Jones et al. (2005) J Thromb Haemost. 3, 991-1000) and this assessment of currently approved monoclonal antibodies does show some degree of correlation between the activation of T cells observed in vitro and immunogenicity in the clinic (Perry et al. (2008) Drugs R D 9, 385-96). In the context of this invention, peripheral blood mononuclear cells (PBMCs) from a cohort of 50 healthy donors representing the world population (based on HLA allotypes) are incubated with the FGF21 variants and T cell responses are measured using proliferation assays ([$^3$]-Thymidine uptake) and IL-2 cytokine secretion (ELISpot). Subsequently, analysis of the frequency and magnitude of the CD4+ T cell responses are carried out to assess the risk of clinical immunogenicity.

The combined use of the T cell and MAPPs assays provides an effective process for evaluation of immunogenicity risk in the clinic using human cells. Modifications to a therapeutic protein candidate that results in a reduced number of peptides presented by dendritic cells and a reduced number of responding donors in the T-cell assay will be advantageous as these proteins bear a lower risk to develop immunogenicity in the clinic. An example of a protein modification that has been described to reduce immunogenicity is PEGylation. However, reduced immunogenicity does not always occur with PEGylation (Li et al. (2007) Blood 98, 3241-8).

In the MAPPs assay, all tested PEGylated GLP-1(A8S) and Exendin-4 FGF21-fusion molecules, including V272 (PEGylated) and V277 (PEGylated) and the non-PEGylated Fc-FGF21 variants containing the Q55C, G148C mutations (V101, V103 and V188), show a low number of clusters, and peptide length variants that are comparable to V76 (PEGylated) and lower than wild-type FGF21 or V76 (non-PEGylated). In the T cell assay, the frequency of T-cell responses was <10% of the study cohort and the magnitude of the responses were low for V272 (PEGylated) and V277 (PEGylated) and the non-PEGylated Fc-FGF21 variants containing the Q55C, G148C mutations (V101, V103 and V188) (Table 10). The absence of a PEG moiety or the absence of the additional disulfide bond at Q55C, G148C may contribute to the increased MAPPs and T-cell assay responses seen with wild-type FGF21 and V76 (non-PEGylated) (Tables 9 and 10). Based on the results from the MAPPs and T cell assays, the risk to develop immunogenicity in the clinic can be considered to be low for V76 (PEGylated), V272 (PEGylated), V277 (PEGylated) and the non-PEGylated Fc-FGF21 variants containing the Q55C, G148C mutations (V101, V103, V188). It is known that the addition of disulfide bonds to proteins can enhance their proteolytic stability and this feature of the Fc-FGF21 variants containing the Q55C, G148C mutations may contribute to the reduced number of peptides displayed by antigen-loaded mature dendritic cells in the MAPPs assay.

In addition, the increased MAPPs response in the assays to non-PEGylated V76 may be explained by the free cysteine leading to dimerization of the molecule and thereby impacting antigen processing and presentation. This is in line with the observation that wild type FGF21 with the introduced free cysteine showed the same tendency to dimerize and resulted in increased presentation of peptides. It is likely that additional PEGylated dual function proteins, and the GLP-1(A8S)-Fc-FGF21 variants (V202, V203, V212, V213, V214, V215, V216, V218 etc.) and the Exendin-4-Fc-FGF21 variants (V196, V197, V198, V199, V206, V207, V208, V209, V210, V211 etc.) containing the Q55C, G148C mutations, will also exhibit MAPPs and T cell assay responses that would be consistent with a low risk of developing immunogenicity in the clinic.

TABLE 9

T-cell assay summary with wild-type FGF21, V76 (non-PEGylated) and V76 (PEGylated) Experiment

| Outcome T cell assay | KLH (positive control) | FGF21-WT (non-PEGylated) | FGF21-WT- (PEGylated) | V76 (non-PEGylated) | V76 (PEGylated) |
| --- | --- | --- | --- | --- | --- |
| Proliferation % | 90 | 6 | 4 | 16 | 4 |
| ELISpot % | 82 | 10 | 8 | 10 | 4 |

TABLE 9-continued

T-cell assay summary with wild-type FGF21, V76 (non-PEGylated) and V76 (PEGylated) Experiment

| Outcome T cell assay | KLH (positive control) | FGF21-WT (non-PEGylated) | FGF21-WT- (PEGylated) | V76 (non-PEGylated) | V76 (PEGylated) |
|---|---|---|---|---|---|
| Proliferation and ELISpot % | 78 | 6 | 4 | 10 | 2 |

TABLE 10

T-cell assay summary with V76 (PEGylated), V272 (PEGylated), V277 (PEGylated), V101, V103 and V188 Experiment

| Outcome T cell assay | KLH (positive control) | V76 (PEGylated) | V272 (PEGylated) | V277 (PEGylated) | V101 | V103 | V188 |
|---|---|---|---|---|---|---|---|
| Proliferation % | 92 | 4 | 6 | 4 | 4 | 6 | 4 |
| ELISpot % | 91 | 6 | 6 | 4 | 4 | 6 | 9 |
| Proliferation and ELISpot % | 85 | 4 | 6 | 4 | 4 | 6 | 4 |

What is claimed is:

1. A method of treating a metabolic disorder by administering to a subject in need thereof a dual function fusion protein, wherein the dual function fusion protein comprises a GLP-1 receptor agonist, an FGF21 receptor agonist, and an Fc domain attached to each other via a GS linker, having an orientation of N-terminus-GLP-1 receptor agonist-linker-Fc domain-linker-FGF21 receptor agonist-C-terminus; and wherein the metabolic disorder is obesity, type 2 diabetes mellitus, dyslipidemia, nonalcoholic fatty liver disease (NAFLD), nonalcoholic steatohepatitis (NASH), insulin resistance, hyperinsulinemia, glucose intolerance, or hyperglycemia.

2. The method of claim 1, wherein the dual function fusion protein comprises the amino acid sequence of SEQ ID NO:36.

3. The method of claim 1, wherein the dual function fusion protein comprises the amino acid sequence of SEQ ID NO:134.

4. The method of claim 1, wherein the dual function fusion protein comprises the amino acid sequence of SEQ ID NO:135.

5. The method of claim 1, wherein the GLP-1 receptor agonist is selected from wild-type GLP-1, Exendin-4, GLP-1 variants, and Exendin-4 analogues.

6. The method of claim 1, wherein the FGF21 receptor agonist is selected from FGF21 variants comprising the following amino acid sequences:

(a)
(SEQ ID NO: 185)
DSSPLLQFGG QVRQRYLYTD DAQETEAHLE IREDGTVGGA

AHQSPESLLE LKALKPGVIQ ILGVKTSRFL CQKPDGALYG

SLHFDPEACS FRELLLEDGY NVYQSEAHGL PLHLPGNRSP

HCDPAPQGPA RFLPLPGLPP ALPEPPGILA PQPPDVGSSD

PLAMVGPSQG RSPSYAS;

(b)
(SEQ ID NO: 186)
DSSPLLQFGG QVRQRYLYTD DAQETEAHLE IREDGTVGGA

AHQSPESLLE LKALKPGVIQ ILGVKTSRFL CQKPDGALYG

SLHFDPEACS FRELLLEDGY NVYQSEAHGL PLHLPGNRSP

HCDPAPQGPA RFLPLPGLPP ALPEPPGILA PQPPDVGSSD

PLAMVGGSQG RSPSYAS;

(c)
(SEQ ID NO: 187)
D SSPLLQFGGQ VRQRYLYTDD ACQTEAHLEI REDGTVGGAA

DQSPESLLQL KALKPGVIQI LGVKTSRFLC QRPDGTLYGS

LHFDPEACSF RELLLEDGYN VYQSEAHGLP LHLPCNRSPH

RDPASRGPAR FLPLPGLPPA LPEPPGILAP QPPDVGSSDP

LAMVGGSQAR SPSYAS;
and (d)
(SEQ ID NO: 188)
D SSPLLQFGGQ VRQRYLYTDD ACQTEAHLEI REDGTVGGAA

DQSPESLLQL KALKPGVIQI LGVKTSRFLC QKPDGALYGS

LHFDPEACSF RELLLEDGYN VYQSEAHGLP LHLPCNRSPH

RDPASRGPAR FLPLPGLPPA LPEPPGILAP QPPDVGSSDP

LAMVGGSQAR SPSYAS.

7. The method of claim 1, wherein the metabolic disorder is obesity.

8. The method of claim 1, wherein the metabolic disorder is type 2 diabetes mellitus.

9. The method of claim 1, wherein the metabolic disorder is dyslipidemia.

10. The method of claim 1, wherein the metabolic disorder is nonalcoholic fatty liver disease (NAFLD).

11. The method of claim 1, wherein the metabolic disorder is nonalcoholic steatohepatitis (NASH).

12. The method of claim 1, wherein the metabolic disorder is insulin resistance.

13. The method of claim 1, wherein the metabolic disorder is hyperinsulinemia.

14. The method of claim 1, wherein the metabolic disorder is glucose intolerance.

15. The method of claim 1, wherein the metabolic disorder is hyperglycemia.

\* \* \* \* \*